(12) United States Patent
Park

(10) Patent No.: US 11,129,678 B2
(45) Date of Patent: Sep. 28, 2021

(54) ARTHROPLASTY JIGS WITH MATING ACCURACY

(71) Applicant: Howmedica Osteonics Corporation, Mahwah, NJ (US)

(72) Inventor: Ilwhan Park, Walnut Creek, CA (US)

(73) Assignee: Howmedica Osteonics Corporation, Mahwah, NJ (US)

(*) Notice: Subject to any disclaimer, the term of this patent is extended or adjusted under 35 U.S.C. 154(b) by 350 days.

(21) Appl. No.: 16/431,394

(22) Filed: Jun. 4, 2019

(65) Prior Publication Data

US 2019/0282302 A1 Sep. 19, 2019

Related U.S. Application Data

(60) Continuation of application No. 16/017,320, filed on Jun. 25, 2018, now Pat. No. 10,617,475, which is a continuation of application No. 15/802,137, filed on Nov. 2, 2017, now Pat. No. 10,034,714, which is a continuation of application No. 15/469,171, filed on Mar. 24, 2017, now Pat. No. 9,839,485, which is a continuation of application No. 15/242,312, filed on Aug. 19, 2016, now Pat. No. 9,636,120, which is a division of application No. 14/476,500, filed on Sep. 3, 2014, now Pat. No. 9,451,970, which is a continuation of application No. 13/731,850, filed on Dec. 31, 2012, now Pat. No. 8,961,527, which is a
(Continued)

(51) Int. Cl.
*A61B 17/58* (2006.01)
*A61B 17/60* (2006.01)
*A61F 2/00* (2006.01)
*A61B 34/10* (2016.01)
*A61B 17/15* (2006.01)
*A61B 17/16* (2006.01)
*A61B 17/17* (2006.01)

(52) U.S. Cl.
CPC .............. *A61B 34/10* (2016.02); *A61B 17/15* (2013.01); *A61B 17/155* (2013.01); *A61B 17/157* (2013.01); *A61B 17/1675* (2013.01); *A61B 17/1764* (2013.01); *A61B 17/58* (2013.01); *A61B 2034/108* (2016.02)

(58) Field of Classification Search
USPC ..................................................... 606/87–89
See application file for complete search history.

(56) References Cited

U.S. PATENT DOCUMENTS

2007/0226986 A1* 10/2007 Park .................... A61B 17/1764
29/592

* cited by examiner

*Primary Examiner* — Sameh R Boles
(74) *Attorney, Agent, or Firm* — Polsinelli PC

(57) ABSTRACT

Disclosed herein is a method of defining a mating surface in a first side of an arthroplasty jig. The mating surface is configured to matingly receive and contact a corresponding patient surface including at least one of a bone surface and a cartilage surface. The first side is oriented towards the patient surface when the mating surface matingly receives and contacts the patient surface. The method may include: a) identifying a contour line associated with the patient surface as represented in a medical image; b) evaluating via an algorithm the adequacy of the contour line for defining a portion of the mating surface associated with the contour line; c) modifying the contour line if the contour line is deemed inadequate; and d) employing the modified contour line to define the portion of the mating surface associated with the contour line.

30 Claims, 81 Drawing Sheets

Related U.S. Application Data division of application No. 12/505,056, filed on Jul. 17, 2009, now Pat. No. 8,777,875.

(60) Provisional application No. 61/083,053, filed on Jul. 23, 2008.

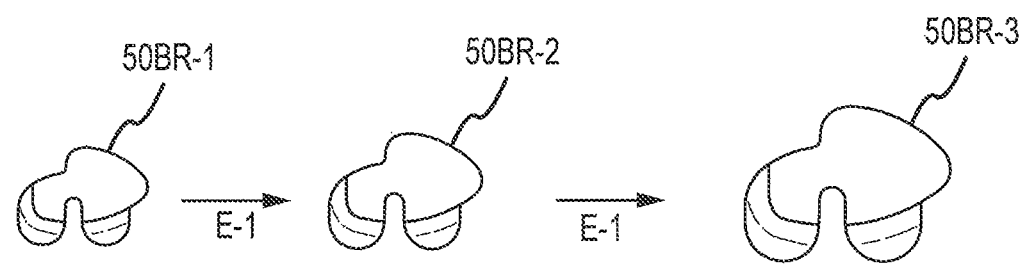
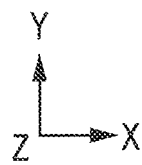
FIG.14A
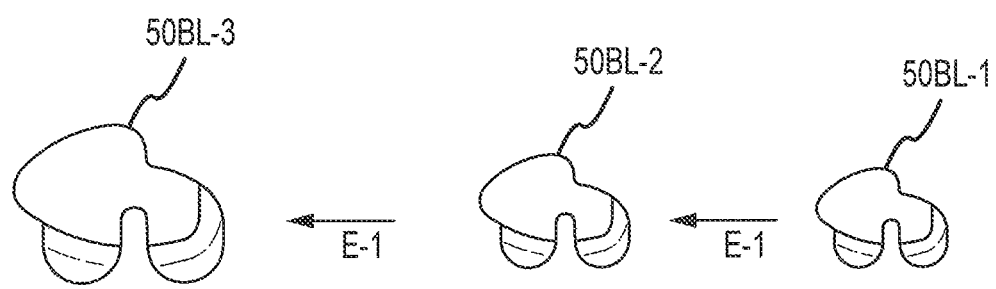
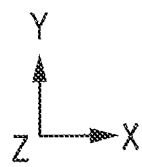
FIG.14B

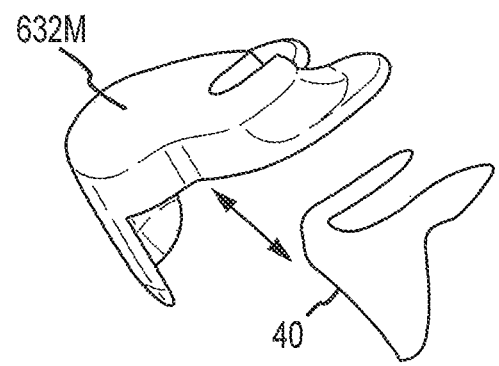
FIG.19A
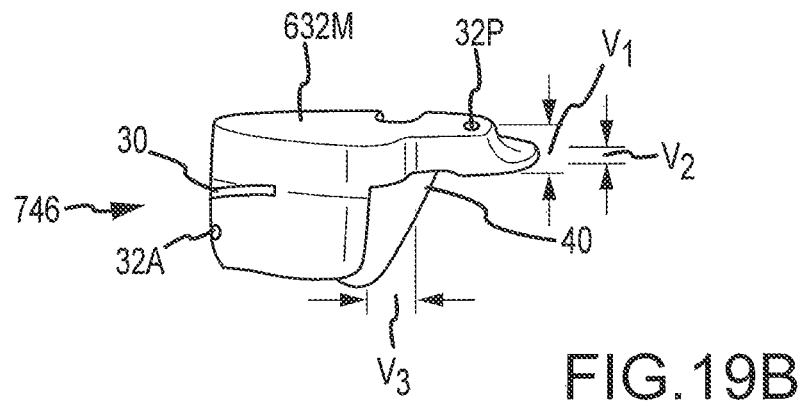
FIG.19B
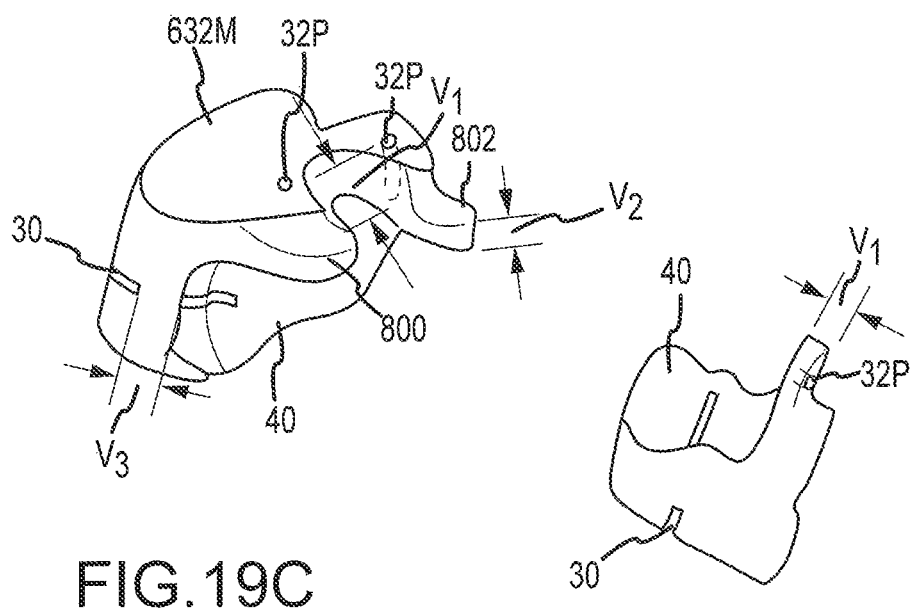
FIG.19C
FIG.19D

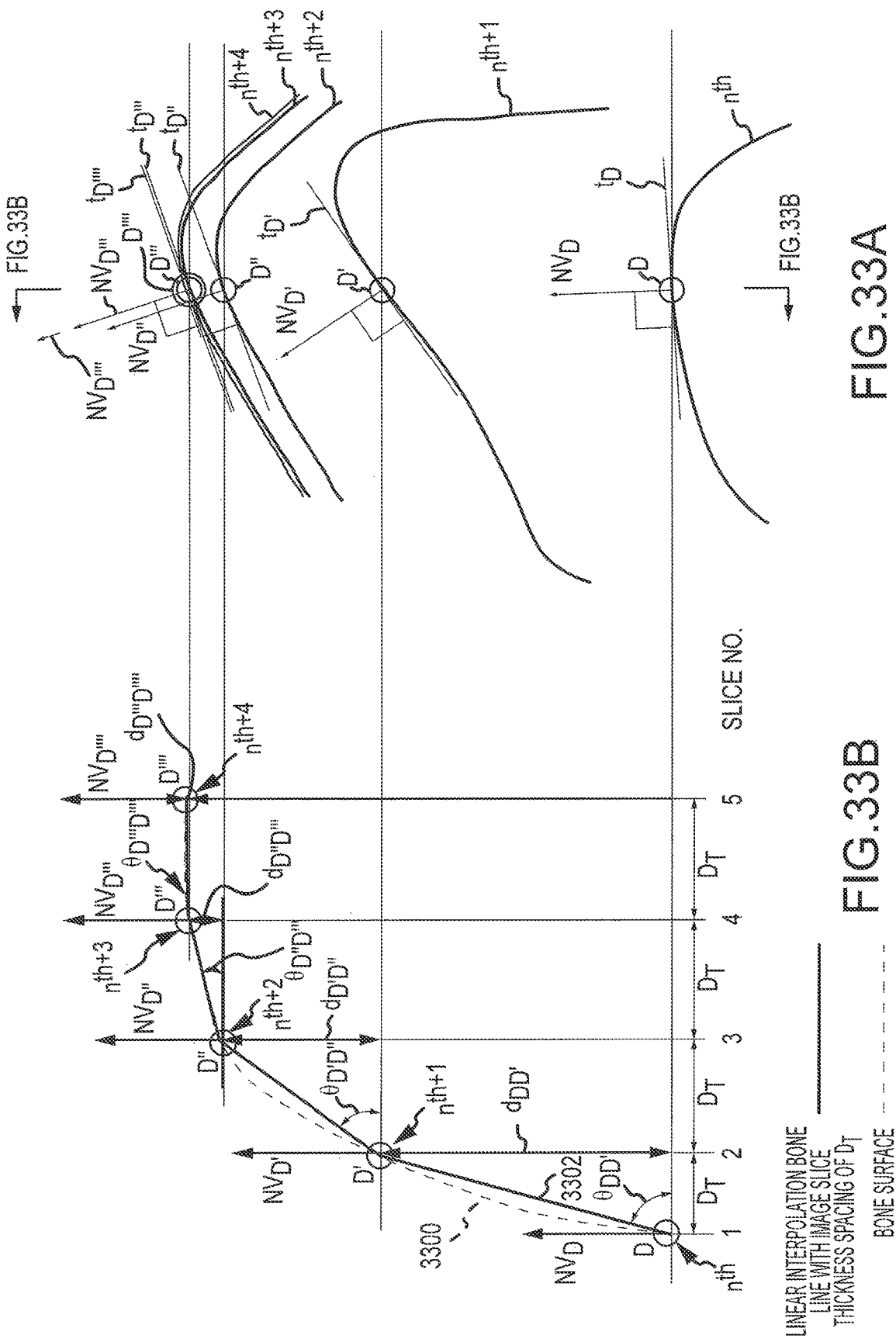

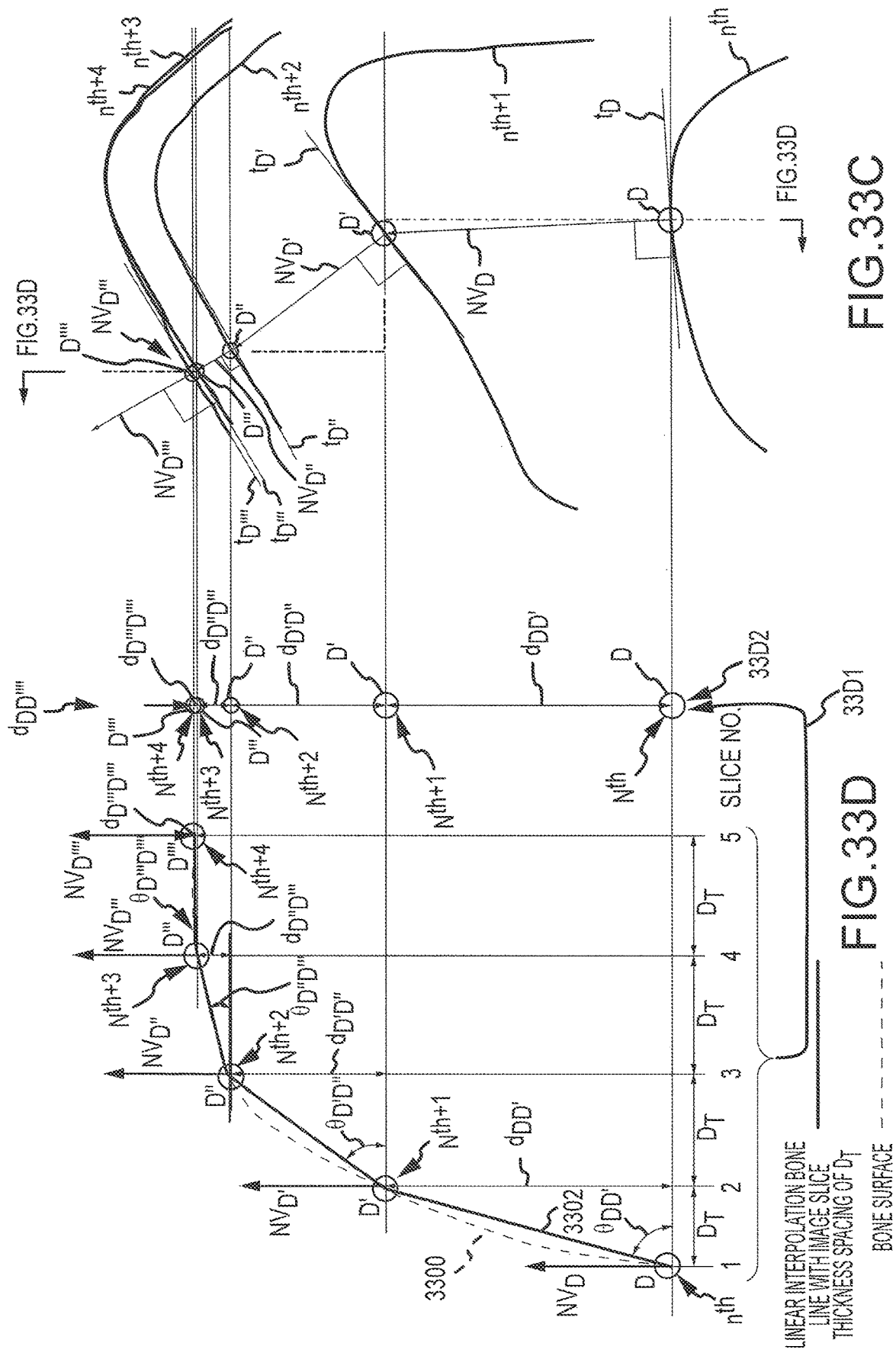

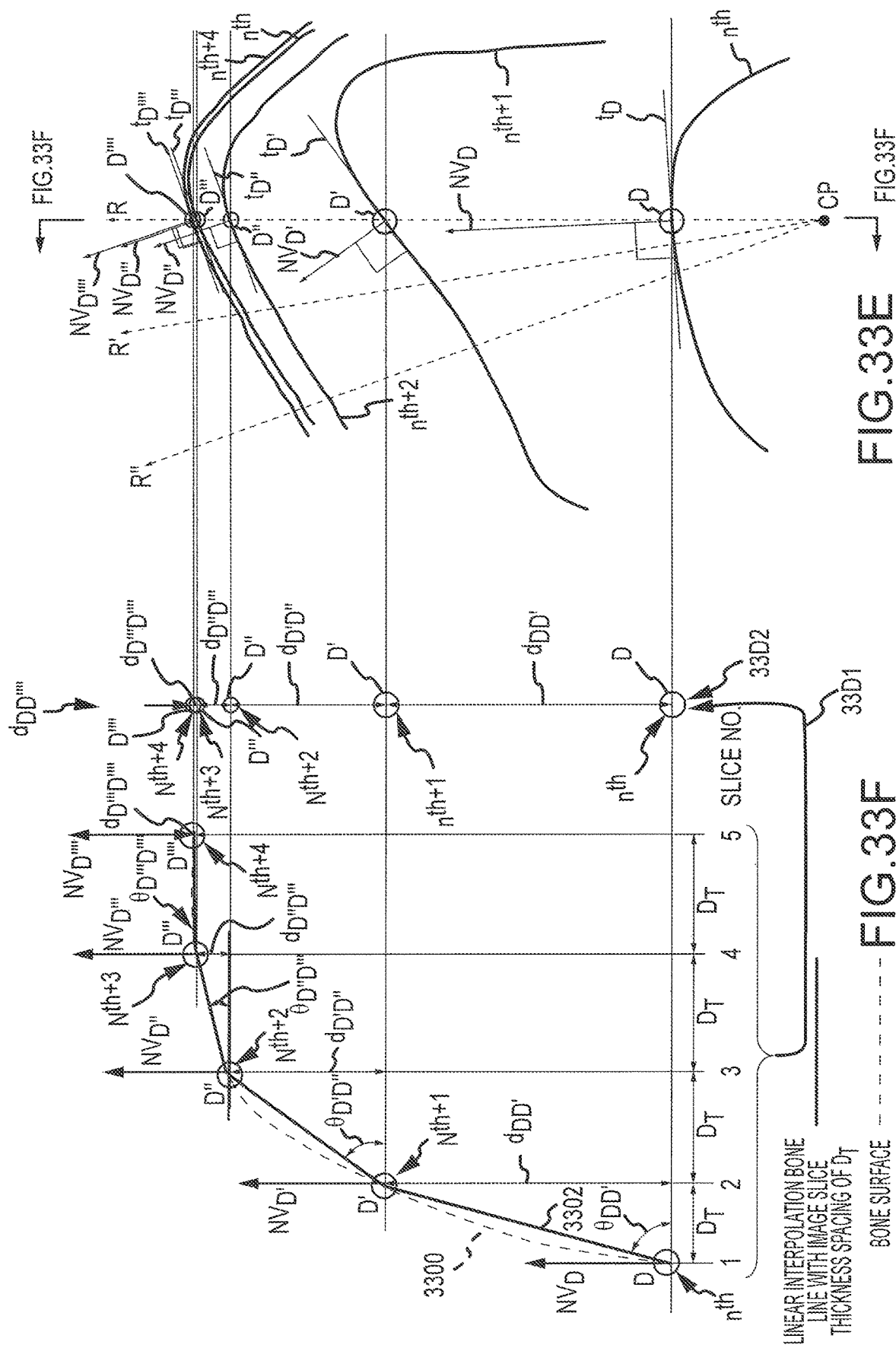

ARTHROPLASTY JIGS WITH MATING ACCURACY

CROSS-REFERENCE TO RELATED APPLICATIONS

The present application is a continuation application of U.S. application Ser. No. 16/017,320 filed Jun. 25, 2018, which application is a continuation application of U.S. application Ser. No. 15/802,137 filed Nov. 2, 2017, now U.S. Pat. No. 10,034,714, which application is a continuation application of U.S. application Ser. No. 15/469,171 filed Mar. 24, 2017, now U.S. Pat. No. 9,839,485, which application is a continuation application of U.S. application Ser. No. 15/242,312 filed Aug. 19, 2016, now U.S. Pat. No. 9,636,120, which application is a divisional application of U.S. application Ser. No. 14/476,500 filed Sep. 3, 2014, now U.S. Pat. No. 9,451,970, which application is a continuation application of U.S. application Ser. No. 13/731,850 filed Dec. 31, 2012, now U.S. Pat. No. 8,961,527, which application is a divisional application of U.S. application Ser. No. 12/505,056, filed Jul. 17, 2009, now U.S. Pat. No. 8,777,875, which application claims the benefit of priority under 35 USC § 119(e) to U.S. Patent Application No. 61/083,053 entitled "System and Method for Manufacturing Arthroplasty Jigs Having Improved Mating Accuracy," and filed Jul. 23, 2008. Each application referenced above is hereby incorporated by reference in its entirety as if fully set forth herein.

FIELD OF THE INVENTION

The present invention relates to systems and methods for manufacturing customized arthroplasty cutting jigs. More specifically, the present invention relates to automated systems and methods manufacturing such jigs.

BACKGROUND OF THE INVENTION

Over time and through repeated use, bones and joints can become damaged or worn. For example, repetitive strain on bones and joints (e.g., through athletic activity), traumatic events, and certain diseases (e.g., arthritis) can cause cartilage in joint areas, which normally provides a cushioning effect, to wear down. When the cartilage wears down, fluid can accumulate in the joint areas, resulting in pain, stiffness, and decreased mobility.

Arthroplasty procedures can be used to repair damaged joints. During a typical arthroplasty procedure, an arthritic or otherwise dysfunctional joint can be remodeled or realigned, or an implant can be implanted into the damaged region. Arthroplasty procedures may take place in any of a number of different regions of the body, such as a knee, a hip, a shoulder, or an elbow.

One type of arthroplasty procedure is a total knee arthroplasty ("TKA"), in which a damaged knee joint is replaced with prosthetic implants. The knee joint may have been damaged by, for example, arthritis (e.g., severe osteoarthritis or degenerative arthritis), trauma, or a rare destructive joint disease. During a TKA procedure, a damaged portion in the distal region of the femur may be removed and replaced with a metal shell, and a damaged portion in the proximal region of the tibia may be removed and replaced with a channeled piece of plastic having a metal stem. In some TKA procedures, a plastic button may also be added under the surface of the patella, depending on the condition of the patella.

Implants that are implanted into a damaged region may provide support and structure to the damaged region, and may help to restore the damaged region, thereby enhancing its functionality. Prior to implantation of an implant in a damaged region, the damaged region may be prepared to receive the implant. For example, in a knee arthroplasty procedure, one or more of the bones in the knee area, such as the femur and/or the tibia, may be treated (e.g., cut, drilled, reamed, and/or resurfaced) to provide one or more surfaces that can align with the implant and thereby accommodate the implant.

Accuracy in implant alignment is an important factor to the success of a TKA procedure. A one- to two-millimeter translational misalignment, or a one- to two-degree rotational misalignment, may result in imbalanced ligaments, and may thereby significantly affect the outcome of the TKA procedure. For example, implant misalignment may result in intolerable post-surgery pain, and also may prevent the patient from having full leg extension and stable leg flexion.

To achieve accurate implant alignment, prior to treating (e.g., cutting, drilling, reaming, and/or resurfacing) any regions of a bone, it is important to correctly determine the location at which the treatment will take place and how the treatment will be oriented. In some methods, an arthroplasty jig may be used to accurately position and orient a finishing instrument, such as a cutting, drilling, reaming, or resurfacing instrument on the regions of the bone. The arthroplasty jig may, for example, include one or more apertures and/or slots that are configured to accept such an instrument.

A system and method has been developed for producing customized arthroplasty jigs configured to allow a surgeon to accurately and quickly perform an arthroplasty procedure that restores the pre-deterioration alignment of the joint, thereby improving the success rate of such procedures. Specifically, the customized arthroplasty jigs are indexed such that they matingly receive the regions of the bone to be subjected to a treatment (e.g., cutting, drilling, reaming, and/or resurfacing). The customized arthroplasty jigs are also indexed to provide the proper location and orientation of the treatment relative to the regions of the bone. The indexing aspect of the customized arthroplasty jigs allows the treatment of the bone regions to be done quickly and with a high degree of accuracy that will allow the implants to restore the patient's joint to a generally pre-deteriorated state. However, the system and method for generating the customized jigs often relies on a human to "eyeball" bone models on a computer screen to determine configurations needed for the generation of the customized jigs. This is "eyeballing" or manual manipulation of the bone modes on the computer screen is inefficient and unnecessarily raises the time, manpower and costs associated with producing the customized arthroplasty jigs. Furthermore, a less manual approach may improve the accuracy of the resulting jigs.

There is a need in the art for a system and method for reducing the labor associated with generating customized arthroplasty jigs. There is also a need in the art for a system and method for increasing the accuracy of customized arthroplasty jigs.

SUMMARY

Disclosed herein is a method of manufacturing an arthroplasty jig. In one embodiment, the method includes: generating two-dimensional images of at least a portion of a bone forming a joint; generating a first three-dimensional computer model of the at least a portion of the bone from the two-dimensional images; generating a second three-dimensional computer model of the at least a portion of the bone from the two-dimensional images; causing the first and second three-dimensional computer models to have in common a reference position, wherein the reference position includes at least one of a location and an orientation relative to an origin; generating a first type of data with the first three-dimensional computer model; generating a second type of data with the second three-dimensional computer model; employing the reference position to integrate the first and second types of data into an integrated jig data; using the integrated jig data at a manufacturing device to manufacture the arthroplasty jig.

Disclosed herein is a method of manufacturing an arthroplasty jig. In one embodiment, the method includes: generating two-dimensional images of at least a portion of a bone forming a joint; extending an open-loop contour line along an arthroplasty target region in at least some of the two-dimensional images; generating a three-dimensional computer model of the arthroplasty target region from the open-loop contour lines; generating from the three-dimensional computer model surface contour data pertaining to the arthroplasty target area; and using the surface contour data at a manufacturing machine to manufacture the arthroplasty jig.

Disclosed herein is a method of manufacturing an arthroplasty jig. In one embodiment, the method includes: determining from an image at least one dimension associated with a portion of a bone; comparing the at least one dimension to dimensions of at least two candidate jig blank sizes; selecting the smallest of the jig blank sizes that is sufficiently large to accommodate the at least one dimension; providing a jig blank of the selected size to a manufacturing machine; and manufacturing the arthroplasty jig from the jig blank.

Disclosed herein are arthroplasty jigs manufactured according to any of the aforementioned methods of manufacture. In some embodiments, the arthroplasty jigs may be indexed to matingly receive arthroplasty target regions of a joint bone. The arthroplasty jigs may also be indexed to orient saw cut slots and drill hole guides such that when the arthroplasty target regions are matingly received by the arthroplasty jig, the saw cuts and drill holes administered to the arthroplasty target region via the saw cut slots and drill hole guides will facilitate arthroplasty implants generally restoring the joint to a pre-degenerated state (i.e., natural alignment state).

Disclosed herein is a method of computer generating a three-dimensional surface model of an arthroplasty target region of a bone forming a joint. In one embodiment, the method includes: generating two-dimensional images of at least a portion of the bone; generating an open-loop contour line along the arthroplasty target region in at least some of the two-dimensional images; and generating the three-dimensional model of the arthroplasty target region from the open-loop contour lines.

Disclosed herein is a method of generating a three-dimensional arthroplasty jig computer model. In one embodiment, the method includes: comparing a dimension of at least a portion of a bone of a joint to candidate jig blank sizes; and selecting from the candidate jig blank sizes a smallest jig blank size able to accommodate the dimensions of the at least a portion of the bone.

Disclosed herein is a method of generating a three-dimensional arthroplasty jig computer model. In one embodiment, the method includes: forming an interior three-dimensional surface model representing an arthroplasty target region of at least a portion of a bone; forming an exterior three-dimensional surface model representing an exterior surface of a jig blank; and combining the interior surface model and exterior surface model to respectively form the interior surface and exterior surface of the three-dimensional arthroplasty jig computer model.

Disclosed herein is a method of generating a production file associated with the manufacture of arthroplasty jigs. The method includes: generating first data associated a surface contour of an arthroplasty target region of a joint bone; generating second data associated with at least one of a saw cut and a drill hole to be administered to the arthroplasty target region during an arthroplasty procedure; and integrating first and second data, wherein a positional relationship of first data relative to an origin and a positional relationship of second data relative to the origin are coordinated with each other to be generally identical during the respective generations of first and second data.

Disclosed herein is a method of defining a mating surface in a first side of an arthroplasty jig. The mating surface is configured to matingly receive and contact a corresponding patient surface including at least one of a bone surface and a cartilage surface. The first side is oriented towards the patient surface when the mating surface matingly receives and contacts the patient surface. In one embodiment, the method includes: a) identifying a contour line associated with the patient surface as represented in a medical image; b) evaluating via an algorithm the adequacy of the contour line for defining a portion of the mating surface associated with the contour line; c) modifying the contour line if the contour line is deemed inadequate; and d) employing the modified contour line to define the portion of the mating surface associated with the contour line.

Disclosed herein is an arthroplasty jig for assisting in the performance of an arthroplasty procedure associated with a patient surface including at least one of a bone surface and a cartilage surface. In one embodiment, the jig may include a first side, a second side generally opposite the first side, and a mating surface in the first side and configured to matingly receive and contact at least a portion of the patient surface. The first side may be configured to be oriented towards the patient surface when the mating surface matingly receives and contacts the patient surface. The mating surface may be defined according to the following process steps: a) identifying a contour line associated with the patient surface as represented in a medical image; b) evaluating via an algorithm the adequacy of the contour line for defining a portion of the mating surface associated with the contour line; c) modifying the contour line if the contour line is deemed inadequate; and d) employing the modified contour line to define the portion of the mating surface associated with the contour line.

Disclosed herein is a femoral arthroplasty jig for assisting in the performance of a femoral arthroplasty procedure on a femoral arthroplasty target region. In one embodiment the jig includes a first side, a second side generally opposite the first side; and a mating surface in the first side and configured to matingly receive and contact certain surfaces of the femoral arthroplasty target region. The certain surfaces may bed limited to a medial articular condyle surface, a lateral articular condyle surface, and a generally planar area of an anterior side of a femoral shaft. The first side may be configured to be oriented towards the femoral arthroplasty target region surface when the mating surface matingly receives and contacts the certain surfaces.

Disclosed herein is a tibial arthroplasty jig for assisting in the performance of a tibial arthroplasty procedure on a tibial arthroplasty target region. In one embodiment, the jig includes a first side, a second side generally opposite the first side, and a mating surface. The mating surface may be in the first side and configured to matingly receive and contact certain surfaces of the tibial arthroplasty target region. The certain surfaces may be limited to a medial articular plateau surface, a lateral articular plateau surface, and a generally planar area of an anterior side of a tibial shaft. The first side may be configured to be oriented towards the tibial arthroplasty target region surface when the mating surface matingly receives and contacts the certain surfaces.

Disclosed herein is a tibial arthroplasty jig for assisting in the performance of a tibial arthroplasty procedure on a tibial arthroplasty target region. In one embodiment, the jig includes a first side, a second side generally opposite the first side. The second side may include a mating surface in the first side. The mating surface may be configured to matingly receive and contact a generally planar area of an anterior side of a tibial shaft distal of the tibial plateau edge and generally proximal of the tibial tuberosity. The first side may be configured to be oriented towards the tibial arthroplasty target region surface when the mating surface matingly receives and contacts the planar area.

Disclosed herein is a femoral arthroplasty jig for assisting in the performance of a femoral arthroplasty procedure on a femoral arthroplasty target region. In one embodiment, the jig includes a first side, a second side generally opposite the first side, and a mating surface in the first side. The mating surface may be configured to matingly receive and contact a generally planar area of an anterior side of a femoral shaft generally proximal of the patellar facet boarder and generally distal an articularis genu. The first side may be configured to be oriented towards the femoral arthroplasty target region surface when the mating surface matingly receives and contacts the planar area.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIG. 14A is a plurality of available sizes of right tibia jig blanks, each depicted in the same view as shown in FIG. 13C.

FIG. 14B is a plurality of available sizes of left tibia jig blanks, each depicted in the same view as shown in FIG. 13C.

FIG. 19A is a perspective view of the extracted jig blank exterior surface model being combined with the extracted tibia surface model.

FIGS. 19B-19D are perspective views of the extracted jig blank exterior surface model combined with the extracted tibia surface model.

FIG. 33A depicts portions of contour lines $n^{th}$, $n^{th+1}$, $n^{th+2}$, $n^{th+3}$ and $n^{th+4}$ in a sagittal view similar to that of FIG. 23.

FIG. 33B is a bone surface contour line and a linear interpolation bone surface contour line as viewed along a section line 33B-33B transverse to image slices containing the contour lines $n^{th}$, $n^{th+1}$, $n^{th+2}$, $n^{th+3}$ and $n^{th+4}$ of FIG. 33A.

FIG. 33C depicts portions of contour lines $n^{th}$, $n^{th+1}$, $n^{th+2}$, $n^{th+3}$ and $n^{th+4}$ in a sagittal view similar to that of FIG. 23.

FIG. 33D is a bone surface contour line and a linear interpolation bone surface contour line as viewed along a section line 33D-33D transverse to image slices containing the contour lines $n^{th}$, $n^{th+1}$, $n^{th+2}$, $n^{th+3}$ and $n^{th+4}$ of FIG. 33C.

FIG. 33E depicts portions of contour lines $n^{th}$, $n^{th+1}$, $n^{th+2}$, $n^{th+3}$ and $n^{th+4}$ in a sagittal view similar to that of FIG. 23.

FIG. 33F is a bone surface contour line and a linear interpolation bone surface contour line as viewed along a section line 33F-33F transverse to image slices containing the contour lines $n^{th}$, $n^{th+1}$, $n^{th+2}$, $n^{th+3}$ and $n^{th+4}$ of FIG. 33E.

DETAILED DESCRIPTION

Figure 1A:
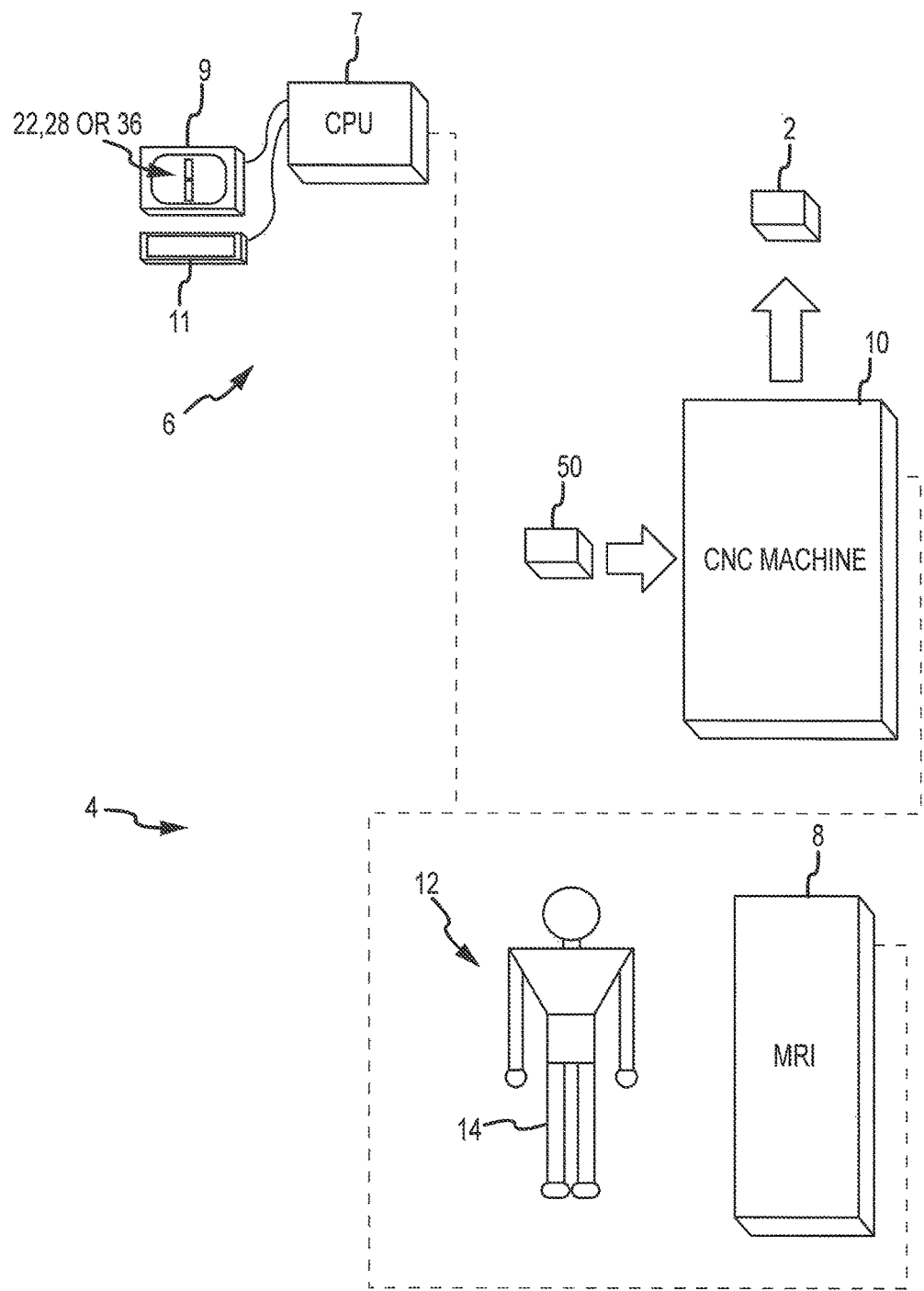
FIG. 1A is a schematic diagram of a system for employing the automated jig production method disclosed herein.

Disclosed herein are customized arthroplasty jigs 2 and systems 4 for, and methods of, producing such jigs 2. The jigs 2 are customized to fit specific bone surfaces of specific patients. Depending on the embodiment and to a greater or lesser extent, the jigs 2 are automatically planned and generated and may be similar to those disclosed in these three U.S. Patent Applications: U.S. patent application Ser. No. 11/656,323 to Park et al., titled "Arthroplasty Devices and Related Methods" and filed Jan. 19, 2007; U.S. patent application Ser. No. 10/146,862 to Park et al., titled "Improved Total Joint Arthroplasty System" and filed May 15, 2002; and U.S. patent. Ser. No. 11/642,385 to Park et al., titled "Arthroplasty Devices and Related Methods" and filed Dec. 19, 2006. The disclosures of these three U.S. Patent Applications are incorporated by reference in their entireties into this Detailed Description.

a. Overview of System and Method for Manufacturing Customized Arthroplasty Cutting Jigs For an overview discussion of the systems 4 for, and methods of, producing the customized arthroplasty jigs 2, reference is made to FIGS. 1A-1E. FIG. 1A is a schematic diagram of a system 4 for employing the automated jig production method disclosed herein. FIGS. 1B-1E are flow chart diagrams outlining the jig production method disclosed herein. The following overview discussion can be broken down into three sections.

The first section, which is discussed with respect to FIG. 1A and [blocks 100-125] of FIGS. 1B-1E, pertains to an example method of determining, in a three-dimensional ("3D") computer model environment, saw cut and drill hole locations 30, 32 relative to 3D computer models that are termed restored bone models 28. The resulting "saw cut and drill hole data" 44 is referenced to the restored bone models 28 to provide saw cuts and drill holes that will allow arthroplasty implants to restore the patient's joint to its pre-degenerated state or, in other words, its natural alignment state.

The second section, which is discussed with respect to FIG. 1A and [blocks 100-105 and 130-145] of FIGS. 1B-1E, pertains to an example method of importing into 3D computer generated jig models 38 3D computer generated surface models 40 of arthroplasty target areas 42 of 3D computer generated arthritic models 36 of the patient's joint bones. The resulting "jig data" 46 is used to produce a jig customized to matingly receive the arthroplasty target areas of the respective bones of the patient's joint.

Figure 1B:
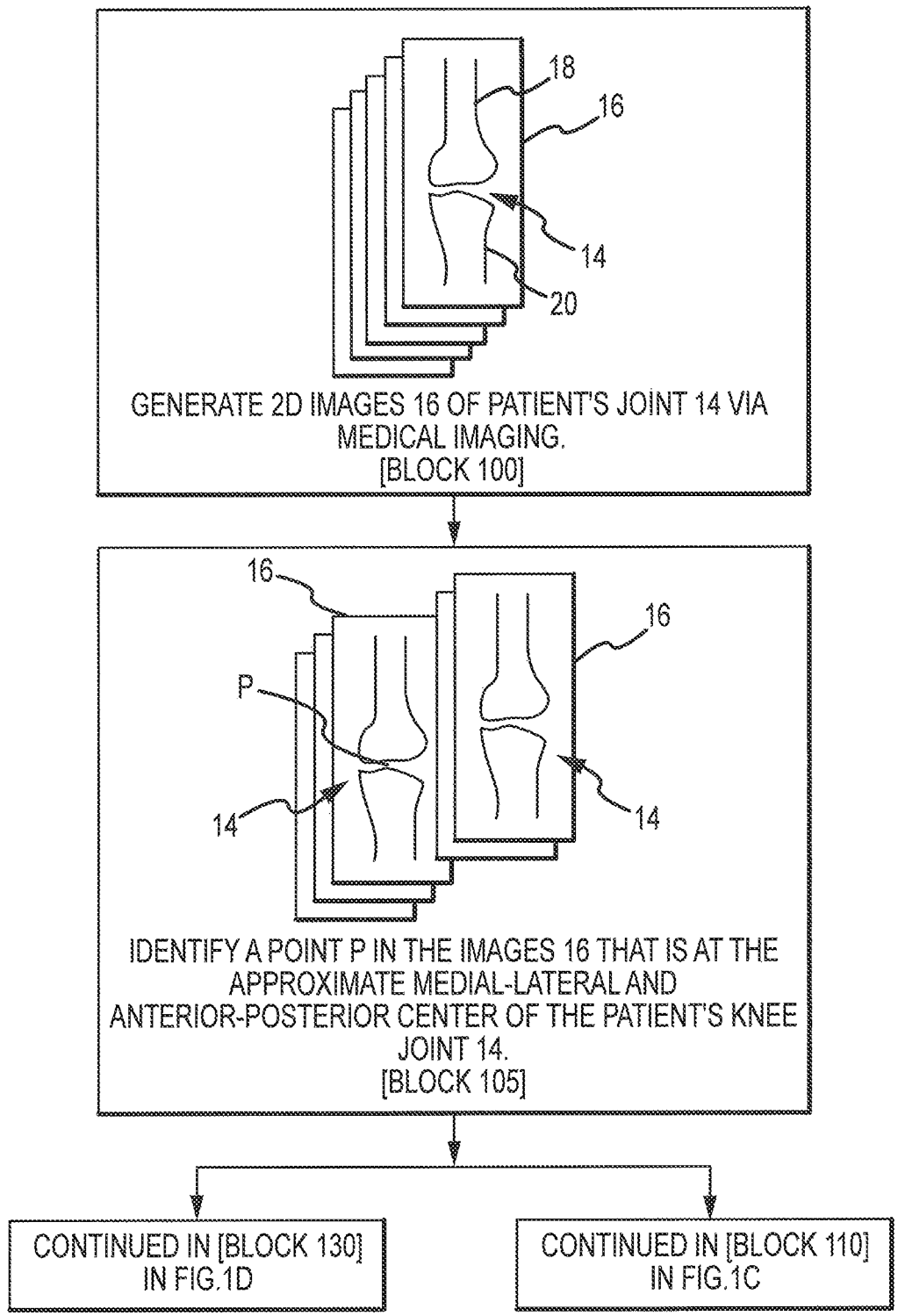
FIGS. 1B-1E are flow chart diagrams outlining the jig production method disclosed herein.
Figure 1C:
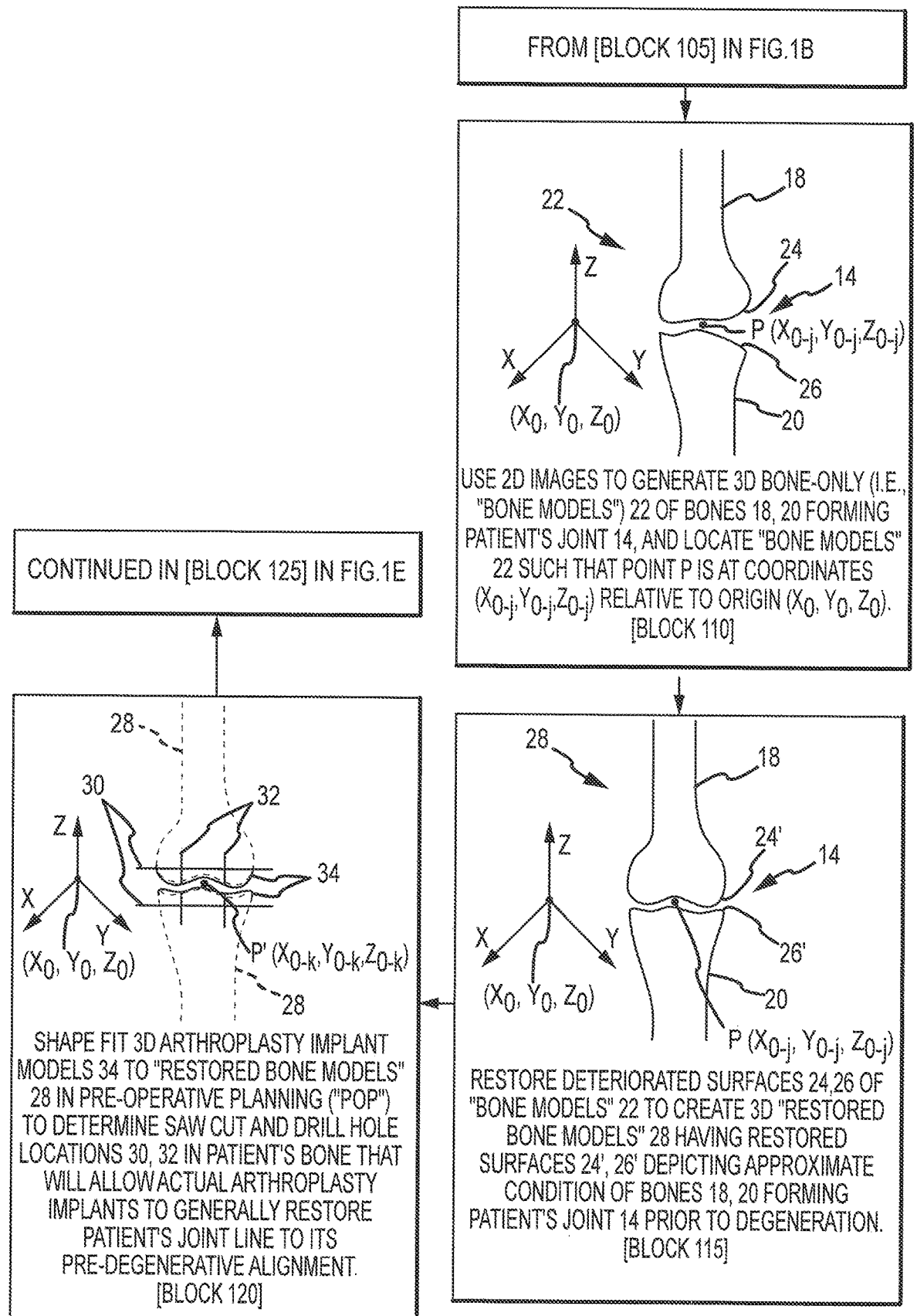
Figure 1D:
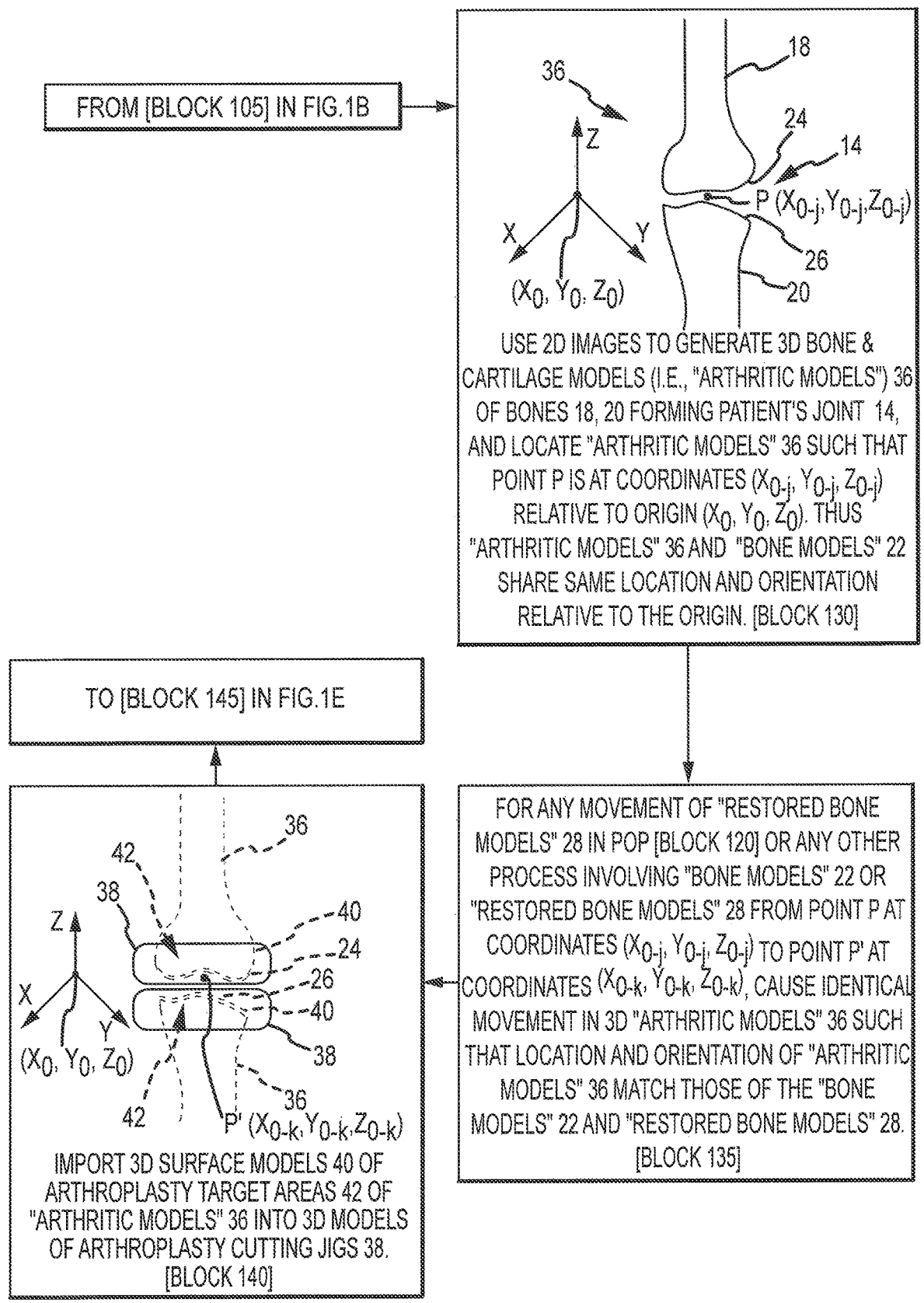
Figure 1E:
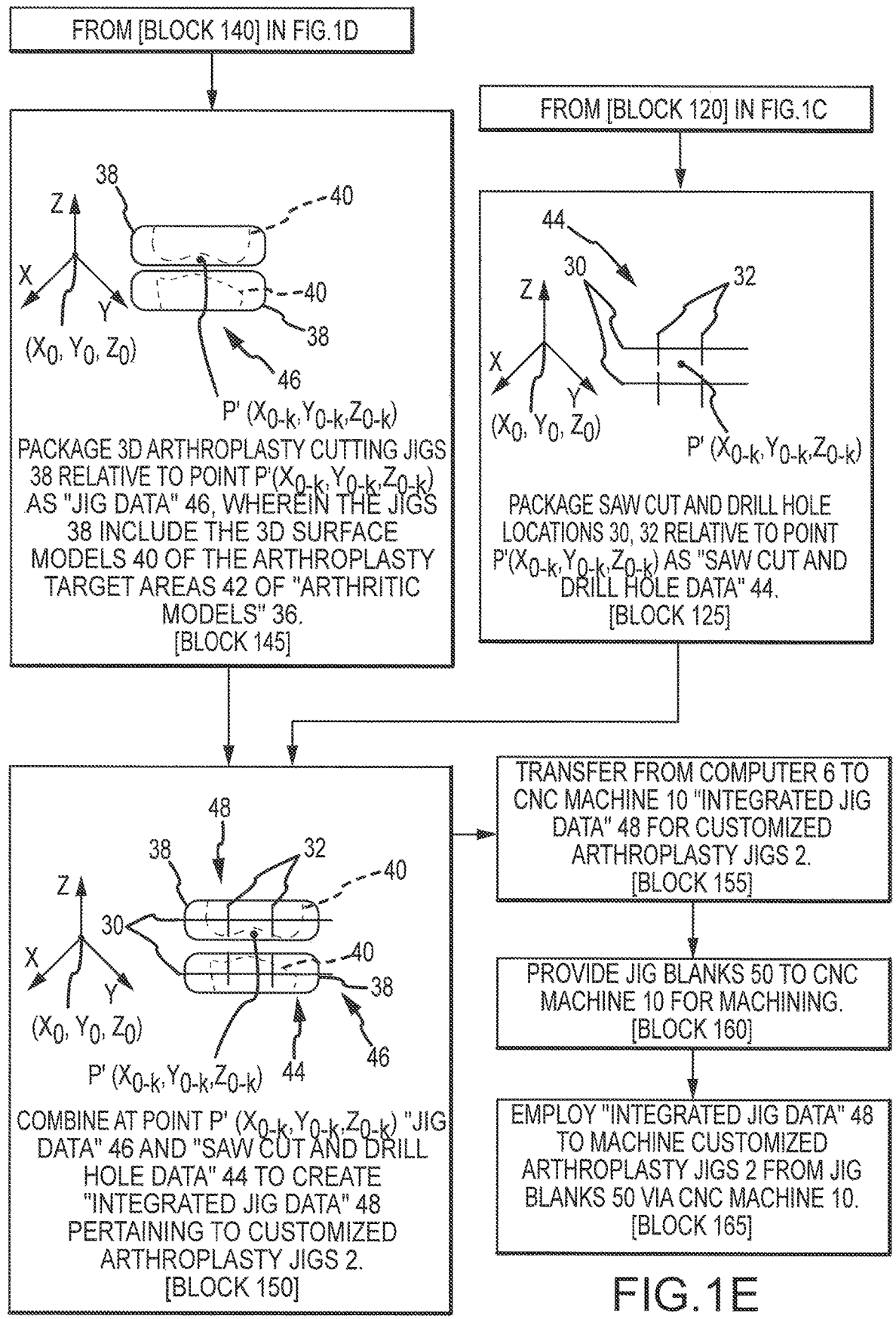

The third section, which is discussed with respect to FIG. 1A and [blocks 150-165] of FIG. 1E, pertains to a method of combining or integrating the "saw cut and drill hole data" 44 with the "jig data" 46 to result in "integrated jig data" 48. The "integrated jig data" 48 is provided to the CNC machine 10 for the production of customized arthroplasty jigs 2 from jig blanks 50 provided to the CNC machine 10. The resulting customized arthroplasty jigs 2 include saw cut slots and drill holes positioned in the jigs 2 such that when the jigs 2 matingly receive the arthroplasty target areas of the patient's bones, the cut slots and drill holes facilitate preparing the arthroplasty target areas in a manner that allows the arthroplasty joint implants to generally restore the patient's joint line to its pre-degenerated or natural alignment state.

As shown in FIG. 1A, the system 4 includes a computer 6 having a CPU 7, a monitor or screen 9 and an operator interface controls 11. The computer 6 is linked to a medical imaging system 8, such as a CT or MRI machine 8, and a computer controlled machining system 10, such as a CNC milling machine 10.

As indicated in FIG. 1A, a patient 12 has a joint 14 (e.g., a knee, elbow, ankle, wrist, hip, shoulder, skull/vertebrae or vertebrae/vertebrae interface, etc.) to be replaced. The patient 12 has the joint 14 scanned in the imaging machine 8. The imaging machine 8 makes a plurality of scans of the joint 14, wherein each scan pertains to a thin slice of the joint 14.

As can be understood from FIG. 1B, the plurality of scans is used to generate a plurality of two-dimensional ("2D") images 16 of the joint 14 [block 100]. Where, for example, the joint 14 is a knee 14, the 2D images will be of the femur 18 and tibia 20. The imaging may be performed via CT or MRI. In one embodiment employing MRI, the imaging process may be as disclosed in U.S. patent application Ser. No. 11/946,002 to Park, which is entitled "Generating MRI Images Usable For The Creation Of 3D Bone Models Employed To Make Customized Arthroplasty Jigs," was filed Nov. 27, 2007 and is incorporated by reference in its entirety into this Detailed Description.

As can be understood from FIG. 1A, the 2D images are sent to the computer 6 for creating computer generated 3D models. As indicated in FIG. 1B, in one embodiment, point P is identified in the 2D images 16 [block 105]. In one embodiment, as indicated in [block 105] of FIG. 1A, point P may be at the approximate medial-lateral and anterior-posterior center of the patient's joint 14. In other embodiments, point P may be at any other location in the 2D images 16, including anywhere on, near or away from the bones 18, 20 or the joint 14 formed by the bones 18, 20.

As described later in this overview, point P may be used to locate the computer generated 3D models 22, 28, 36 created from the 2D images 16 and to integrate information generated via the 3D models. Depending on the embodiment, point P, which serves as a position and/or orientation reference, may be a single point, two points, three points, a point plus a plane, a vector, etc., so long as the reference P can be used to position and/or orient the 3D models 22, 28, 36 generated via the 2D images 16.

As shown in FIG. 1C, the 2D images 16 are employed to create computer generated 3D bone-only (i.e., "bone models") 22 of the bones 18, 20 forming the patient's joint 14 [block 110]. The bone models 22 are located such that point P is at coordinates ($X_{0-j}$, $Y_{0-j}$, $Z_{0-j}$) relative to an origin ($X_0$, $Y_0$, $Z_0$) of an X-Y-Z axis [block 110]. The bone models 22 depict the bones 18, 20 in the present deteriorated condition with their respective degenerated joint surfaces 24, 26, which may be a result of osteoarthritis, injury, a combination thereof, etc.

Computer programs for creating the 3D computer generated bone models 22 from the 2D images 16 include: Analyze from AnalyzeDirect, Inc., Overland Park, Kans.; Insight Toolkit, an open-source software available from the National Library of Medicine Insight Segmentation and Registration Toolkit ("ITK"), www.itk.org; 3D Slicer, an open-source software available from www.slicer.org; Mimics from Materialise, Ann Arbor, Mich.; and Paraview available at www.paraview.org.

As indicated in FIG. 1C, the 3D computer generated bone models 22 are utilized to create 3D computer generated "restored bone models" or "planning bone models" 28 wherein the degenerated surfaces 24, 26 are modified or restored to approximately their respective conditions prior to degeneration [block 115]. Thus, the bones 18, 20 of the restored bone models 28 are reflected in approximately their condition prior to degeneration. The restored bone models 28 are located such that point P is at coordinates ($X_{0-j}$, $Y_{0-j}$, $Z_{0-j}$) relative to the origin ($X_0$, $Y_0$, $Z_0$). Thus, the restored bone models 28 share the same orientation and positioning relative to the origin ($X_0$, $Y_0$, $Z_0$) as the bone models 22.

In one embodiment, the restored bone models 28 are manually created from the bone models 22 by a person sitting in front of a computer 6 and visually observing the bone models 22 and their degenerated surfaces 24, 26 as 3D computer models on a computer screen 9. The person visually observes the degenerated surfaces 24, 26 to determine how and to what extent the degenerated surfaces 24, 26 surfaces on the 3D computer bone models 22 need to be modified to restore them to their pre-degenerated condition. By interacting with the computer controls 11, the person then manually manipulates the 3D degenerated surfaces 24, 26 via the 3D modeling computer program to restore the surfaces 24, 26 to a state the person believes to represent the pre-degenerated condition. The result of this manual restoration process is the computer generated 3D restored bone models 28, wherein the surfaces 24', 26' are indicated in a non-degenerated state.

In one embodiment, the above-described bone restoration process is generally or completely automated. In other words, a computer program may analyze the bone models 22 and their degenerated surfaces 24, 26 to determine how and to what extent the degenerated surfaces 24, 26 surfaces on the 3D computer bone models 22 need to be modified to restore them to their pre-degenerated condition. The computer program then manipulates the 3D degenerated surfaces 24, 26 to restore the surfaces 24, 26 to a state intended to represent the pre-degenerated condition. The result of this automated restoration process is the computer generated 3D restored bone models 28, wherein the surfaces 24', 26' are indicated in a non-degenerated state.

As depicted in FIG. 1C, the restored bone models 28 are employed in a pre-operative planning ("POP") procedure to determine saw cut locations 30 and drill hole locations 32 in the patient's bones that will allow the arthroplasty joint implants to generally restore the patient's joint line to it pre-degenerative alignment [block 120].

In one embodiment, the POP procedure is a manual process, wherein computer generated 3D implant models 34 (e.g., femur and tibia implants in the context of the joint being a knee) and restored bone models 28 are manually manipulated relative to each other by a person sitting in front of a computer 6 and visually observing the implant models 34 and restored bone models 28 on the computer screen 9 and manipulating the models 28, 34 via the computer controls 11. By superimposing the implant models 34 over the restored bone models 28, or vice versa, the joint surfaces of the implant models 34 can be aligned or caused to correspond with the joint surfaces of the restored bone models 28. By causing the joint surfaces of the models 28, 34 to so align, the implant models 34 are positioned relative to the restored bone models 28 such that the saw cut locations 30 and drill hole locations 32 can be determined relative to the restored bone models 28.

In one embodiment, the POP process is generally or completely automated. For example, a computer program may manipulate computer generated 3D implant models 34 (e.g., femur and tibia implants in the context of the joint being a knee) and restored bone models or planning bone models 28 relative to each other to determine the saw cut and drill hole locations 30, 32 relative to the restored bone models 28. The implant models 34 may be superimposed over the restored bone models 28, or vice versa. In one embodiment, the implant models 34 are located at point P' ($X_{0-k}$, $Y_{0-k}$, $Z_{0-k}$) relative to the origin ($X_0$, $Y_0$, $Z_0$), and the restored bone models 28 are located at point P ($X_{0-j}$, $Y_{0-j}$, $Z_{0-j}$). To cause the joint surfaces of the models 28, 34 to correspond, the computer program may move the restored bone models 28 from point P ($X_{0-j}$, $Y_{0-j}$, $Z_{0-j}$) to point P' ($X_{0-k}$, $Y_{0-k}$, $Z_{0-k}$), or vice versa. Once the joint surfaces of the models 28, 34 are in close proximity, the joint surfaces of the implant models 34 may be shape-matched to align or correspond with the joint surfaces of the restored bone models 28. By causing the joint surfaces of the models 28, 34 to so align, the implant models 34 are positioned relative to the restored bone models 28 such that the saw cut locations 30 and drill hole locations 32 can be determined relative to the restored bone models 28.

As indicated in FIG. 1E, in one embodiment, the data 44 regarding the saw cut and drill hole locations 30, 32 relative to point P' ($X_{0-k}$, $Y_{0-k}$, $Z_{0-k}$) is packaged or consolidated as the "saw cut and drill hole data" 44 [block 145]. The "saw cut and drill hole data" 44 is then used as discussed below with respect to [block 150] in FIG. 1E.

As can be understood from FIG. 1D, the 2D images 16 employed to generate the bone models 22 discussed above with respect to [block 110] of FIG. 1C are also used to create computer generated 3D bone and cartilage models (i.e., "arthritic models") 36 of the bones 18, 20 forming the patient's joint 14 [block 130]. Like the above-discussed bone models 22, the arthritic models 36 are located such that point P is at coordinates ($X_{0-j}$, $Y_{0-j}$, $Z_{0-j}$) relative to the origin ($X_0$, $Y_0$, $Z_0$) of the X-Y-Z axis [block 130]. Thus, the bone and arthritic models 22, 36 share the same location and orientation relative to the origin ($X_0$, $Y_0$, $Z_0$). This position/orientation relationship is generally maintained throughout the process discussed with respect to FIGS. 1B-1E. Accordingly, movements relative to the origin ($X_0$, $Y_0$, $Z_0$) of the bone models 22 and the various descendants thereof (i.e., the restored bone models 28, bone cut locations 30 and drill hole locations 32) are also applied to the arthritic models 36 and the various descendants thereof (i.e., the jig models 38). Maintaining the position/orientation relationship between the bone models 22 and arthritic models 36 and their respective descendants allows the "saw cut and drill hole data" 44 to be integrated into the "jig data" 46 to form the "integrated jig data" 48 employed by the CNC machine 10 to manufacture the customized arthroplasty jigs 2.

Computer programs for creating the 3D computer generated arthritic models 36 from the 2D images 16 include: Analyze from AnalyzeDirect, Inc., Overland Park, Kans.; Insight Toolkit, an open-source software available from the National Library of Medicine Insight Segmentation and Registration Toolkit ("ITK"), www.itk.org; 3D Slicer, an open-source software available from www.slicer.org; Mimics from Materialise, Ann Arbor, Mich.; and Paraview available at www.paraview.org.

Similar to the bone models 22, the arthritic models 36 depict the bones 18, 20 in the present deteriorated condition with their respective degenerated joint surfaces 24, 26, which may be a result of osteoarthritis, injury, a combination thereof, etc. However, unlike the bone models 22, the arthritic models 36 are not bone-only models, but include cartilage in addition to bone. Accordingly, the arthritic models 36 depict the arthroplasty target areas 42 generally as they will exist when the customized arthroplasty jigs 2 matingly receive the arthroplasty target areas 42 during the arthroplasty surgical procedure.

As indicated in FIG. 1D and already mentioned above, to coordinate the positions/orientations of the bone and arthritic models 36, 36 and their respective descendants, any movement of the restored bone models 28 from point P to point P' is tracked to cause a generally identical displacement for the "arthritic models" 36 [block 135].

As depicted in FIG. 1D, computer generated 3D surface models 40 of the arthroplasty target areas 42 of the arthritic models 36 are imported into computer generated 3D arthroplasty jig models 38 [block 140]. Thus, the jig models 38 are configured or indexed to matingly receive the arthroplasty target areas 42 of the arthritic models 36. Jigs 2 manufactured to match such jig models 38 will then matingly receive the arthroplasty target areas of the actual joint bones during the arthroplasty surgical procedure.

In some embodiments, the 3D surface models 40 may be modified to account for irregularities in the patient's bone anatomy or limitations in the imaging process. For example, the 3D surface models 40 may be subjected to, or the result of, an "overestimation" process. The "overestimated" 3D surface models 40 may result in bone mating surfaces of the actual jigs that matingly receive and contact certain portions of the arthroplasty target areas of the actual joint bones while other portions of the jigs are spaced apart from the bones, including, for example, some regions of the arthroplasty target areas of the actual joint bones. Thus, the bone mating surfaces of the actual jigs may matingly contact certain specific portions of the arthroplasty target areas of the actual joint bones while other areas of the arthroplasty target areas are not matingly contacted. In some embodiments, the specific portions of the arthroplasty target areas contacted by the jig's bone mating surfaces may be those areas that are most likely to be accurately 3D computer modeled and most likely to result in a reliably accurate mating contact between the jig's bone mating surface and the arthroplasty target areas, and the portions of the arthroplasty target areas not contacted by the jig's bone mating surfaces may be those areas that are the least likely to be accurately 3D computer modeled.

In other words, for some embodiments, overestimation may result in areas of mating contact for the bone mating surfaces of the actual jigs being based on the areas of the 3D surface models that are most reliably accurate with respect to the image scan data and most readily machined via the tooling of the CNC machine. Conversely, for some embodiments, overestimation may result in areas of non-contact for the bone mating or other surfaces of the actual jigs for those areas of the jig pertaining to those areas of the 3D surface models that result from image scan data that is less accurate or reliable and/or represent bone features that are too small to be readily machined via the tooling of the CNC machine. The result of the overestimation process described below is actual jigs with a bone mating surfaces that matingly contact certain reliable regions of the arthroplasty target areas of the actual joint bones while avoiding contact with certain less reliable regions of the arthroplasty target areas, resulting in jigs with bone mating surfaces that accurately and reliably matingly receive the arthroplasty target regions.

In one embodiment, the procedure for indexing the jig models 38 to the arthroplasty target areas 42 is a manual process. The 3D computer generated models 36, 38 are manually manipulated relative to each other by a person sitting in front of a computer 6 and visually observing the jig models 38 and arthritic models 36 on the computer screen 9 and manipulating the models 36, 38 by interacting with the computer controls 11. In one embodiment, by superimposing the jig models 38 (e.g., femur and tibia arthroplasty jigs in the context of the joint being a knee) over the arthroplasty target areas 42 of the arthritic models 36, or vice versa, the surface models 40 of the arthroplasty target areas 42 can be imported into the jig models 38, resulting in jig models 38 indexed to matingly receive the arthroplasty target areas 42 of the arthritic models 36. Point P' ($X_{0-k}$, $Y_{0-k}$, $Z_{0-k}$) can also be imported into the jig models 38, resulting in jig models 38 positioned and oriented relative to point P' ($X_{0-k}$, $Y_{0-k}$, $Z_{0-k}$) to allow their integration with the bone cut and drill hole data 44 of [block 125].

In one embodiment, the procedure for indexing the jig models 38 to the arthroplasty target areas 42 is generally or completely automated, as discussed in detail later in this Detailed Description. For example, a computer program may create 3D computer generated surface models 40 of the arthroplasty target areas 42 of the arthritic models 36. The computer program may then import the surface models 40 and point P' ($X_{0-k}$, $Y_{0-k}$, $Z_{0-k}$) into the jig models 38, resulting in the jig models 38 being indexed to matingly receive the arthroplasty target areas 42 of the arthritic models 36. In some embodiments, the surface models 40 may include accounting for irregularities in the patient's bone anatomy and/or limitations in the imaging technology by creating deliberate gaps between the jig's surface and the patient's bone. The resulting jig models 38 are also positioned and oriented relative to point P' ($X_{0-k}$, $Y_{0-k}$, $Z_{0-k}$) to allow their integration with the bone cut and drill hole data 44 of [block 125].

In one embodiment, the arthritic models 36 may be 3D volumetric models as generated from the closed-loop process discussed below with respect to FIGS. 2D-2F. In other embodiments, the arthritic models 36 may be 3D surface models as generated from the open-loop process discussed below with respect to FIGS. 2A-2C and 12A-12C.

As indicated in FIG. 1E, in one embodiment, the data regarding the jig models 38 and surface models 40 relative to point P' ($X_{0-k}$, $Y_{0-k}$, $Z_{0-k}$) is packaged or consolidated as the "jig data" 46 [block 145]. The "jig data" 46 is then used as discussed below with respect to [block 150] in FIG. 1E.

As can be understood from FIG. 1E, the "saw cut and drill hole data" 44 is integrated with the "jig data" 46 to result in the "integrated jig data" 48 [block 150]. As explained above, since the "saw cut and drill hole data" 44, "jig data" 46 and their various ancestors (e.g., models 22, 28, 36, 38) are matched to each other for position and orientation relative to point P and P', the "saw cut and drill hole data" 44 is properly positioned and oriented relative to the "jig data" 46 for proper integration into the "jig data" 46. The resulting "integrated jig data" 48, when provided to the CNC machine 10, results in jigs 2: (1) configured to matingly receive the arthroplasty target areas of the patient's bones; and (2) having cut slots and drill holes that facilitate preparing the arthroplasty target areas in a manner that allows the arthroplasty joint implants to generally restore the patient's joint line to its pre-degenerated or natural alignment state.

As can be understood from FIGS. 1A and 1E, the "integrated jig data" 48 is transferred from the computer 6 to the CNC machine 10 [block 155]. Jig blanks 50 are provided to the CNC machine 10 [block 160], and the CNC machine 10 employs the "integrated jig data" to machine the arthroplasty jigs 2 from the jig blanks 50.

Figure 1F:
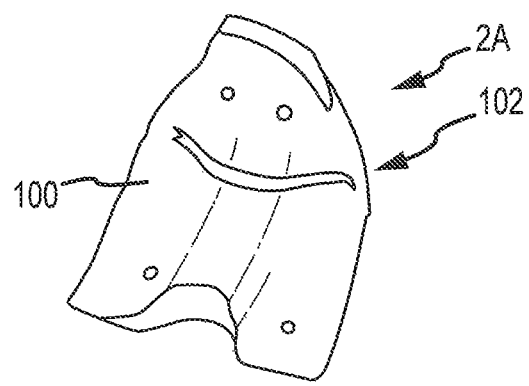
FIGS. 1F and 1G are, respectively, bottom and top perspective views of an example customized arthroplasty femur jig.
Figure 1G:
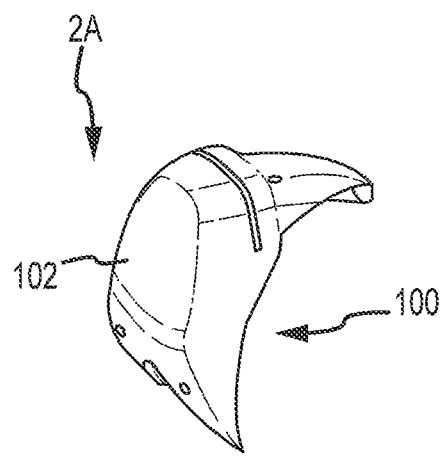
Figure 1H:
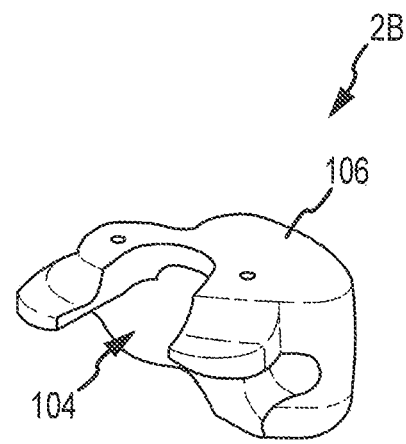
FIGS. 1H and 1I are, respectively, bottom and top perspective views of an example customized arthroplasty tibia jig.
Figure 1I:
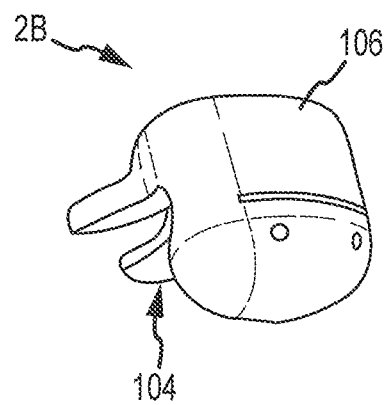

For a discussion of example customized arthroplasty cutting jigs 2 capable of being manufactured via the above-discussed process, reference is made to FIGS. 1F-1I. While, as pointed out above, the above-discussed process may be employed to manufacture jigs 2 configured for arthroplasty procedures involving knees, elbows, ankles, wrists, hips, shoulders, vertebra interfaces, etc., the jig examples depicted in FIGS. 1F-1I are for total knee replacement ("TKR") procedures. Thus, FIGS. 1F and 1G are, respectively, bottom and top perspective views of an example customized arthroplasty femur jig 2A, and FIGS. 1H and 1I are, respectively, bottom and top perspective views of an example customized arthroplasty tibia jig 2B.

As indicated in FIGS. 1F and 1G, a femur arthroplasty jig 2A may include an interior side or portion 100 and an exterior side or portion 102. When the femur cutting jig 2A is used in a TKR procedure, the interior side or portion 100 faces and matingly receives the arthroplasty target area 42 of the femur lower end, and the exterior side or portion 102 is on the opposite side of the femur cutting jig 2A from the interior portion 100.

The interior portion 100 of the femur jig 2A is configured to match the surface features of the damaged lower end (i.e., the arthroplasty target area 42) of the patient's femur 18. Thus, when the target area 42 is received in the interior portion 100 of the femur jig 2A during the TKR surgery, the surfaces of the target area 42 and the interior portion 100 match.

The surface of the interior portion 100 of the femur cutting jig 2A is machined or otherwise formed into a selected femur jig blank 50A and is based or defined off of a 3D surface model 40 of a target area 42 of the damaged lower end or target area 42 of the patient's femur 18. In some embodiments, the 3D surface model 40 may modified via the "overestimation" process described below to account for limitations in the medical imaging process and/or limitations in the machining process.

As indicated in FIGS. 1H and 1I, a tibia arthroplasty jig 2B may include an interior side or portion 104 and an exterior side or portion 106. When the tibia cutting jig 2B is used in a TKR procedure, the interior side or portion 104 faces and matingly receives the arthroplasty target area 42 of the tibia upper end, and the exterior side or portion 106 is on the opposite side of the tibia cutting jig 2B from the interior portion 104.

The interior portion 104 of the tibia jig 2B is configured to match the surface features of the damaged upper end (i.e., the arthroplasty target area 42) of the patient's tibia 20. Thus, when the target area 42 is received in the interior portion 104 of the tibia jig 2B during the TKR surgery, the surfaces of the target area 42 and the interior portion 104 match.

The surface of the interior portion 104 of the tibia cutting jig 2B is machined or otherwise formed into a selected tibia jig blank 50B and is based or defined off of a 3D surface model 40 of a target area 42 of the damaged upper end or target area 42 of the patient's tibia 20. In some embodiments, the 3D surface model 40 may modified via the "overestimation" process described below to account for limitations in the medical imaging process and/or limitations in the machining process.

b. Overview of Automated Process for Indexing 3D Arthroplasty Jig Models to Arthroplasty Target Areas As mentioned above with respect to [block 140] of FIG. 1D, the process for indexing the 3D arthroplasty jig models 38 to the arthroplasty target areas 42 can be automated. A discussion of an example of such an automated process will now concern the remainder of this Detailed Description, beginning with an overview of the automated indexing process.

As can be understood from FIG. 1A and [blocks 100-105] of FIG. 1B, a patient 12 has a joint 14 (e.g., a knee, elbow, ankle, wrist, shoulder, hip, vertebra interface, etc.) to be replaced. The patient 12 has the joint 14 scanned in an imaging machine 8 (e.g., a CT, MRI, etc. machine) to create a plurality of 2D scan images 16 of the bones (e.g., femur 18 and tibia 20) forming the patient's joint 14 (e.g., knee). Each scan image 16 is a thin slice image of the targeted bone(s) 18, 20. The scan images 16 are sent to the CPU 7, which employs an open-loop image analysis along targeted features 42 of the scan images 16 of the bones 18, 20 to generate a contour line for each scan image 16 along the profile of the targeted features 42.

As can be understood from FIG. 1A and [block 110] of FIG. 1C, the CPU 7 compiles the scan images 16 and, more specifically, the contour lines to generate 3D computer surface models ("arthritic models") 36 of the targeted features 42 of the patient's joint bones 18, 20. In the context of total knee replacement ("TKR") surgery, the targeted features 42 may be the lower or knee joint end of the patient's femur 18 and the upper or knee joint end of the patient's tibia 20. More specifically, the targeted features 42 may be the tibia contacting articulating surface of the patient's femur 18 and the femur contacting articulating surface of the patient's tibia 20.

In some embodiments, the "arthritic models" 36 may be surface models or volumetric solid models respectively formed via an open-loop or closed-loop process such that the contour lines are respectively open or closed loops. In one embodiment discussed in detail herein, the "arthritic models" 36 may be surface models formed via an open-loop process. By employing an open-loop and surface model approach, as opposed to a closed-loop and volumetric solid model approach, the computer modeling process requires less processing capability and time from the CPU 7 and, as a result, is more cost effective.

The system 4 measures the anterior-posterior extent and medial-lateral extent of the target areas 42 of the "arthritic models" 36. The anterior-posterior extent and medial-lateral extent may be used to determine an aspect ratio, size and/or configuration for the 3D "arthritic models" 36 of the respective bones 18, 20. In one embodiment of a jig blank grouping and selection method discussed below, the aspect ratio, size and/or configuration of the 3D "arthritic models" 36 of the respective bones 18, 20 may be used for comparison to the aspect ratio, size and/or configuration of 3D computer models of candidate jig blanks 50 in a jig blank grouping and selection method discussed below. In one embodiment of a jig blank grouping and selection method discussed below, the anterior-posterior and medial-lateral dimensions of the 3D "arthritic models" 36 of the respective bones 18, 20 may be used for comparison to the anterior-posterior and medial-lateral dimensions of 3D computer models of candidate jig blanks 50.

In the context of TKR, the jigs 2 will be femur and tibia arthroplasty cutting jigs 2A, 2B, which are machined or otherwise formed from femur and tibia jig blanks 50A, 50B. A plurality of candidate jig blank sizes exists, for example, in a jig blank library. While each candidate jig blank may have a unique combination of anterior-posterior and medial-lateral dimension sizes, in some embodiments, two or more of the candidate jig blanks may share a common aspect ratio or configuration. The candidate jig blanks of the library may be grouped along sloped lines of a plot according to their aspect ratios. The system 4 employs the jig blank grouping and selection method to select a jig blank 50 from a plurality of available jig blank sizes contained in the jig blank library. For example, the configurations, sizes and/or aspect ratios of the tibia and femur 3D arthritic models 36 are compared to the configurations, sizes and/or aspect ratios of the 3D models of the candidate jig blanks with or without a dimensional comparison between the arthritic models 36 and the models of the candidate jig blanks.

Alternatively, in one embodiment, the anterior-posterior and medial-lateral dimensions of the target areas of the arthritic models 36 of the patient's femur and tibia 18, 20 are increased via a mathematical formula. The resulting mathematically modified anterior-posterior and medial-lateral dimensions are then compared to the anterior-posterior and medial-lateral dimensions of the models of the candidate jig blanks 50A, 50B. In one embodiment, the jig blanks 50A, 50B selected are the jig blanks having anterior-posterior and medial-lateral dimensions that are the closest in size to the mathematically modified anterior-posterior and medial-lateral dimensions of the patient's bones 18, 20 without being exceeded by the mathematically modified dimensions of the patient's bones 18, 20. In one embodiment, the jig blank selection method results in the selection of a jig blank 50 that is as near as possible in size to the patient's knee features, thereby minimizing the machining involved in creating a jig 2 from a jig blank.

In one embodiment, as discussed with respect to FIGS. 1F-1I, each arthroplasty cutting jig 2 includes an interior portion and an exterior portion. The interior portion is dimensioned specific to the surface features of the patient's bone that are the focus of the arthroplasty. Thus, where the arthroplasty is for TKR surgery, the jigs will be a femur jig and/or a tibia jig. The femur jig will have an interior portion custom configured to match the damaged surface of the lower or joint end of the patient's femur. The tibia jig will have an interior portion custom configured to match the damaged surface of the upper or joint end of the patient's tibia.

In one embodiment, because of the jig blank grouping and selection method, the exterior portion of each arthroplasty cutting jig 2 is substantially similar in size to the patient's femur and tibia 3D arthritic models 36. However, to provide adequate structural integrity for the cutting jigs 2, the exterior portions of the jigs 2 may be mathematically modified to cause the exterior portions of the jigs 2 to exceed the 3D femur and tibia models in various directions, thereby providing the resulting cutting jigs 2 with sufficient jig material between the exterior and interior portions of the jigs 2 to provide adequate structural strength.

As can be understood from [block 140] of FIG. 1D, once the system 4 selects femur and tibia jig blanks 50 of sizes and configurations sufficiently similar to the sizes and configurations of the patient's femur and tibia computer arthritic models 36, the system 4 superimposes the 3D computer surface models 40 of the targeted features 42 of the femur 18 and tibia 20 onto the interior portion of the respective 3D computer models of the selected femur and tibia jigs 38, or more appropriately in one version of the present embodiment, the jig blanks 50. The result, as can be understood from [block 145] of FIG. 1E, is computer models of the femur and tibia jigs 2 in the form of "jig data" 46, wherein the femur and tibia jig computer models have: (1) respective exterior portions closely approximating the overall size and configuration of the patient's femur and tibia; and (2) respective interior portions having surfaces that match the targeted features 42 of the patient's femur 18 and tibia 20.

The system 4 employs the data from the jig computer models (i.e., "jig data" 46) to cause the CNC machine 10 to machine the actual jigs 2 from actual jig blanks. The result is the automated production of actual femur and tibia jigs 2 having: (1) exterior portions generally matching the patient's actual femur and tibia with respect to size and overall configuration; and (2) interior portions having patient-specific dimensions and configurations corresponding to the actual dimensions and configurations of the targeted features 42 of the patient's femur and tibia. The systems 4 and methods disclosed herein allow for the efficient manufacture of arthroplasty jigs 2 customized for the specific bone features of a patient.

The jigs 2 and systems 4 and methods of producing such jigs are illustrated herein in the context of knees and TKR surgery. However, those skilled in the art will readily understand the jigs 2 and system 4 and methods of producing such jigs can be readily adapted for use in the context of other joints and joint replacement surgeries, e.g., elbows, shoulders, hips, etc. Accordingly, the disclosure contained herein regarding the jigs 2 and systems 4 and methods of producing such jigs should not be considered as being limited to knees and TKR surgery, but should be considered as encompassing all types of joint surgeries.

c. Defining a 3D Surface Model of an Arthroplasty Target Area of a Femur Lower End for Use as a Surface of an Interior Portion of a Femur Arthroplasty Cutting Jig.

Figure 2A:
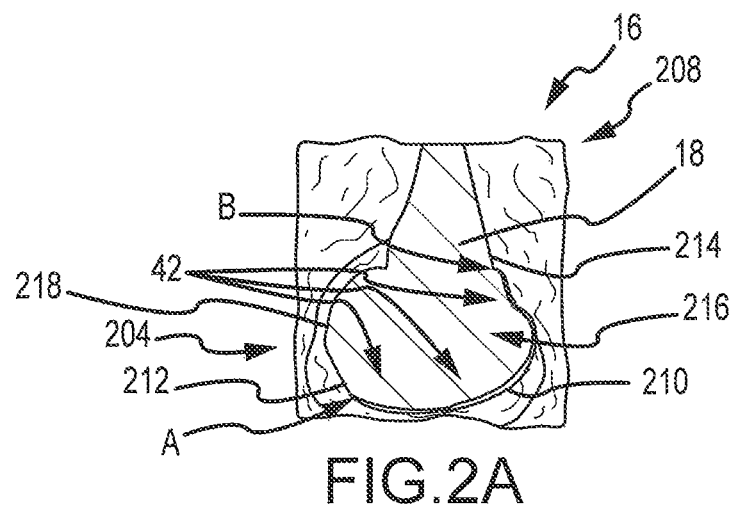
FIG. 2A is an anterior-posterior image slice of the damaged lower or knee joint end of the patient's femur, wherein the image slice includes an open-loop contour line segment corresponding to the targeted region of the damaged lower end.
Figure 2B:
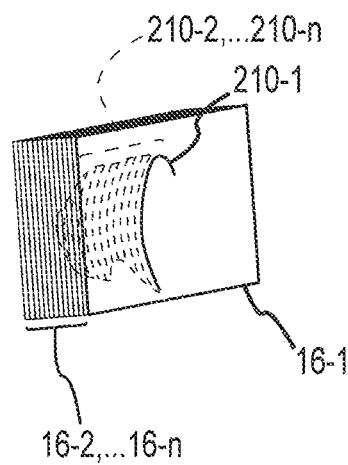
FIG. 2B is a plurality of image slices with their respective open-loop contour line segments, the open-loop contour line segments being accumulated to generate the 3D model of the targeted region.
Figure 2C:
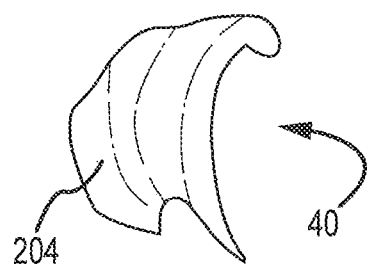
FIG. 2C is a 3D model of the targeted region of the damaged lower end as generated using the open-loop contour line segments depicted in FIG. 2B.
Figure 2D:
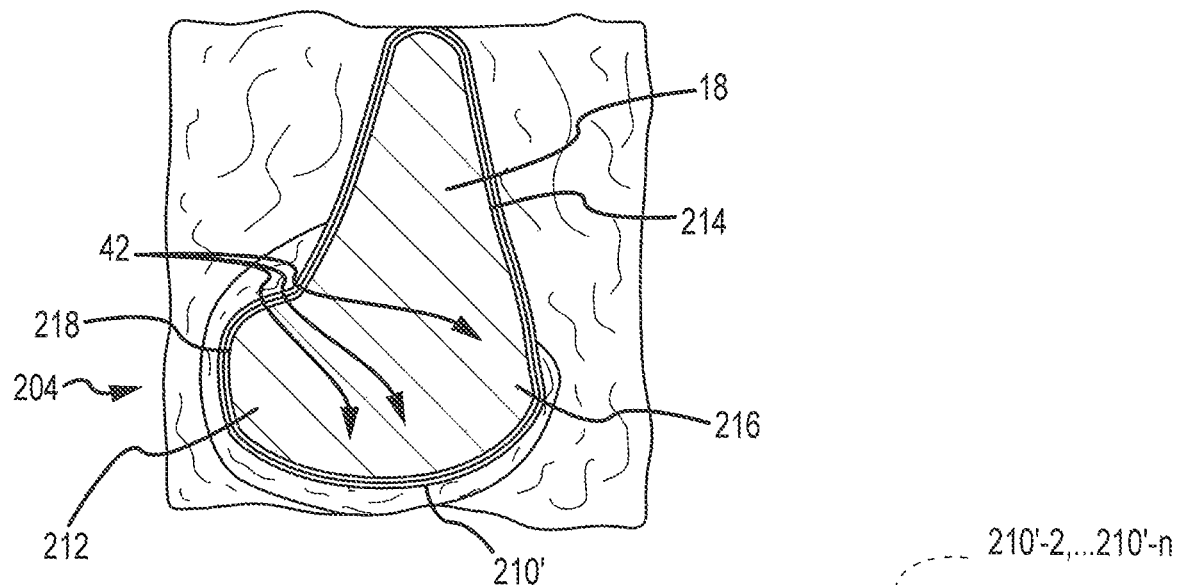
FIG. 2D is an anterior-posterior image slice of the damaged lower or knee joint end of the patient's femur, wherein the image slice includes a closed-loop contour line corresponding to the femur lower end, including the targeted region.
Figure 2E:
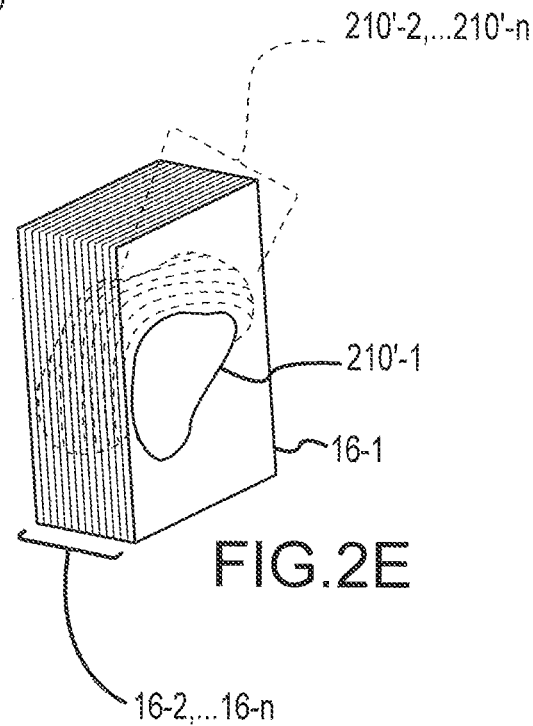
FIG. 2E is a plurality of image slices with their respective closed-loop contour line segments, the closed-loop contour lines being accumulated to generate the 3D model of the femur lower end, including the targeted region.
Figure 2F:
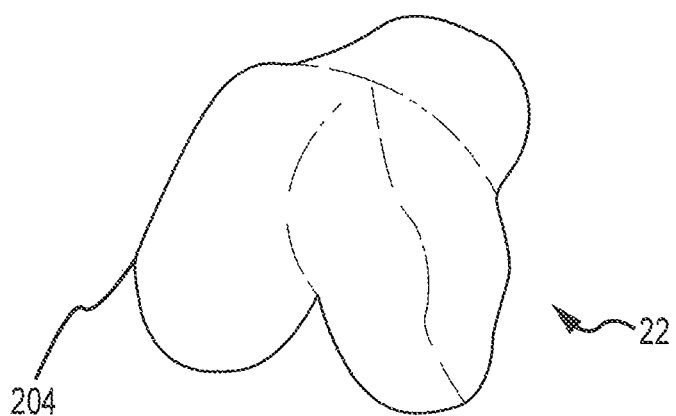
FIG. 2F is a 3D model of the femur lower end, including the targeted region, as generated using the closed-loop contour lines depicted in FIG. 2B.
Figure 2G:
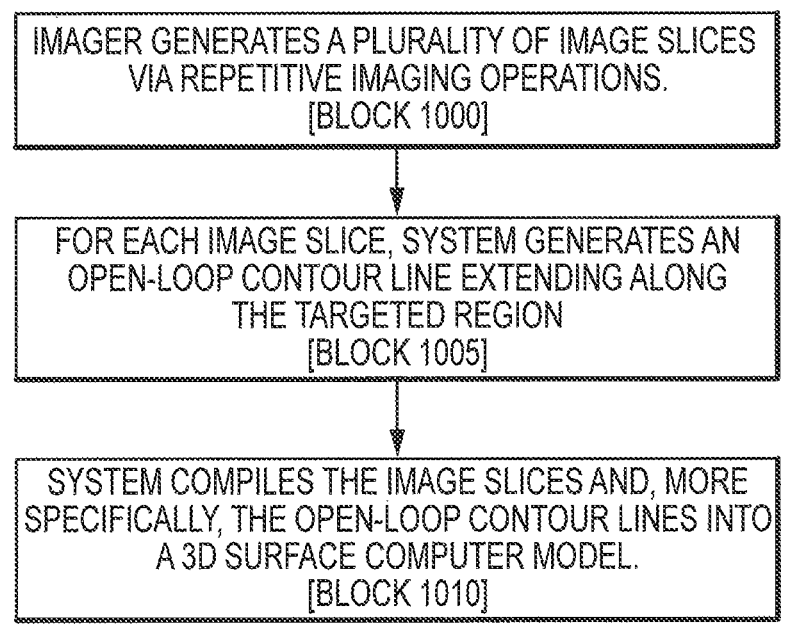
FIG. 2G is a flow chart illustrating an overview of the method of producing a femur jig.

For a discussion of a method of generating a 3D model 40 of a target area 42 of a damaged lower end 204 of a patient's femur 18, reference is made to FIGS. 2A-2G. FIG. 2A is an anterior-posterior ("AP") image slice 208 of the damaged lower or knee joint end 204 of the patient's femur 18, wherein the image slice 208 includes an open-loop contour line segment 210 corresponding to the target area 42 of the damaged lower end 204. FIG. 2B is a plurality of image slices (16-1, 16-1, 16-2, . . . 16-*n*) with their respective open-loop contour line segments (210-1, 210-2, . . . 210-*n*), the open-loop contour line segments 210 being accumulated to generate the 3D model 40 of the target area 42. FIG. 2C is a 3D model 40 of the target area 42 of the damaged lower end 204 as generated using the open-loop contour line segments (16-1, 16-2, . . . 16-*n*) depicted in FIG. 2B. FIGS. 2D-2F are respectively similar to FIGS. 2A-2C, except FIGS. 2D-2F pertain to a closed-loop contour line as opposed to an open-loop contour line. FIG. 2G is a flow chart illustrating an overview of the method of producing a femur jig 2A.

As can be understood from FIGS. 1A, 1B and 2A, the imager 8 is used to generate a 2D image slice 16 of the damaged lower or knee joint end 204 of the patient's femur 18. As depicted in FIG. 2A, the 2D image 16 may be an AP view of the femur 18. Depending on whether the imager 8 is a MRI or CT imager, the image slice 16 will be a MRI or CT slice. The damaged lower end 204 includes the posterior condyle 212, an anterior femur shaft surface 214, and an area of interest or targeted area 42 that extends from the posterior condyle 212 to the anterior femur shaft surface 214. The targeted area 42 of the femur lower end may be the articulating contact surfaces of the femur lower end that contact corresponding articulating contact surfaces of the tibia upper or knee joint end.

As shown in FIG. 2A, the image slice 16 may depict the cancellous bone 216, the cortical bone 218 surrounding the cancellous bone, and the articular cartilage lining portions of the cortical bone 218. The contour line 210 may extend along the targeted area 42 and immediately adjacent the cortical bone and cartilage to outline the contour of the targeted area 42 of the femur lower end 204. The contour line 210 extends along the targeted area 42 starting at point A on the posterior condyle 212 and ending at point B on the anterior femur shaft surface 214.

In one embodiment, as indicated in FIG. 2A, the contour line 210 extends along the targeted area 42, but not along the rest of the surface of the femur lower end 204. As a result, the contour line 210 forms an open-loop that, as will be discussed with respect to FIGS. 2B and 2C, can be used to form an open-loop region or 3D computer model 40, which is discussed with respect to [block 140] of FIG. 1D and closely matches the 3D surface of the targeted area 42 of the femur lower end. Thus, in one embodiment, the contour line is an open-loop and does not outline the entire cortical bone surface of the femur lower end 204. Also, in one embodiment, the open-loop process is used to form from the 3D images 16 a 3D surface model 36 that generally takes the place of the arthritic model 36 discussed with respect to [blocks 125-140] of FIG. 1D and which is used to create the surface model 40 used in the creation of the "jig data" 46 discussed with respect to [blocks 145-150] of FIG. 1E.

In one embodiment and in contrast to the open-loop contour line 210 depicted in FIGS. 2A and 2B, the contour line is a closed-loop contour line 210' that outlines the entire cortical bone surface of the femur lower end and results in a closed-loop area, as depicted in FIG. 2D. The closed-loop contour lines 210'-2, . . . 210'-*n* of each image slice 16-1, . . . 16-*n* are combined, as indicated in FIG. 2E. A closed-loop area may require the analysis of the entire surface region of the femur lower end 204 and result in the formation of a 3D model of the entire femur lower end 204 as illustrated in FIG. 2F. Thus, the 3D surface model resulting from the closed-loop process ends up having in common much, if not all, the surface of the 3D arthritic model 36. In one embodiment, the closed-loop process may result in a 3D volumetric anatomical joint solid model from the 2D images 16 via applying mathematical algorithms. U.S. Pat. No. 5,682,886, which was filed Dec. 26, 1995 and is incorporated by reference in its entirety herein, applies a snake algorithm forming a continuous boundary or closed-loop. After the femur has been outlined, a modeling process is used to create the 3D surface model, for example, through a Bézier patches method. Other 3D modeling processes, e.g., commercially-available 3D construction software as listed in other parts of this Detailed Description, are applicable to 3D surface model generation for closed-loop, volumetric solid modeling.

In one embodiment, the closed-loop process is used to form from the 3D images 16 a 3D volumetric solid model 36 that is essentially the same as the arthritic model 36 discussed with respect to [blocks 125-140] of FIG. 1D. The 3D volumetric solid model 36 is used to create the surface model 40 used in the creation of the "jig data" 46 discussed with respect to [blocks 145-150] of FIG. 1E.

The formation of a 3D volumetric solid model of the entire femur lower end employs a process that may be much more memory and time intensive than using an open-loop contour line to create a 3D model of the targeted area 42 of the femur lower end. Accordingly, although the closed-loop methodology may be utilized for the systems and methods disclosed herein, for at least some embodiments, the open-loop methodology may be preferred over the closed-loop methodology.

An example of a closed-loop methodology is disclosed in U.S. patent application Ser. No. 11/641,569 to Park, which is entitled "Improved Total Joint Arthroplasty System" and was filed Jan. 19, 2007. This application is incorporated by reference in its entirety into this Detailed Description.

As can be understood from FIGS. 2B and 2G, the imager 8 generates a plurality of image slices (16-1, 16-2 . . . 16-*n*) via repetitive imaging operations [block 1000]. Each image slice 16 has an open-loop contour line (210-1, 210-2 . . . 210-*n*) extending along the targeted region 42 in a manner as discussed with respect to FIG. 2A [block 1005]. In one embodiment, each image slice is a two-millimeter 2D image slice 16. The system 4 compiles the plurality of 2D image slices (16-1, 16-2 . . . 16-*n*) and, more specifically, the plurality of open-loop contour lines (210-1, 210-2, . . . 210-*n*) into the 3D femur surface computer model 40 depicted in FIG. 2C [block 1010]. This process regarding the generation of the surface model 40 is also discussed in the overview section with respect to [blocks 100-105] of FIG. 1B and [blocks 130-140] of FIG. 1D. A similar process may be employed with respect to the closed-loop contour lines depicted in FIGS. 2D-2F.

As can be understood from FIG. 2C, the 3D femur surface computer model 40 is a 3D computer representation of the targeted region 42 of the femur lower end. In one embodiment, the 3D representation of the targeted region 42 is a 3D representation of the articulated tibia contact surfaces of the femur distal end. As the open-loop generated 3D model 40 is a surface model of the relevant tibia contacting portions of the femur lower end, as opposed to a 3D model of the entire surface of the femur lower end as would be a result of a closed-loop contour line, the open-loop generated 3D model 40 is less time and memory intensive to generate.

In one embodiment, the open-loop generated 3D model 40 is a surface model of the tibia facing end face of the femur lower end, as opposed a 3D model of the entire surface of the femur lower end. The 3D model 40 can be used to identify the area of interest or targeted region 42, which, as previously stated, may be the relevant tibia contacting portions of the femur lower end. Again, the open-loop generated 3D model 40 is less time and memory intensive to generate as compared to a 3D model of the entire surface of the femur distal end, as would be generated by a closed-loop contour line. Thus, for at least some versions of the embodiments disclosed herein, the open-loop contour line methodology is preferred over the closed-loop contour line methodology. However, the system 4 and method disclosed herein may employ either the open-loop or closed-loop methodology and should not be limited to one or the other.

Regardless of whether the 3D model 40 is a surface model of the targeted region 42 (i.e., a 3D surface model generated from an open-loop process and acting as the arthritic model 22) or the entire tibia facing end face of the femur lower end (i.e., a 3D volumetric solid model generated from a closed-loop process and acting as the arthritic model 22), the data pertaining to the contour lines 210 can be converted into the 3D contour computer model 40 via the surface rendering techniques disclosed in any of the aforementioned U.S. patent applications to Park. For example, surface rending techniques employed include point-to-point mapping, surface normal vector mapping, local surface mapping, and global surface mapping techniques. Depending on the situation, one or a combination of mapping techniques can be employed.

In one embodiment, the generation of the 3D model 40 depicted in FIG. 2C may be formed by using the image slices 16 to determine location coordinate values of each of a sequence of spaced apart surface points in the open-loop region of FIG. 2B. A mathematical model may then be used to estimate or compute the 3D model 40 in FIG. 2C. Examples of other medical imaging computer programs that may be used include, but are not limited to: Analyze from AnalyzeDirect, Inc. of Overland Park, Kans.; open-source software such as Paraview of Kitware, Inc.; Insight Toolkit ("ITK") available at www.itk.org; 3D Slicer available at www.slicer.org; and Mimics from Materialise of Ann Arbor, Mich.

Alternatively or additionally to the aforementioned systems for generating the 3D model 40 depicted in FIG. 2C, other systems for generating the 3D model 40 of FIG. 2C include the surface rendering techniques of the Non-Uniform Rational B-spline ("NURB") program or the Bézier program. Each of these programs may be employed to generate the 3D contour model 40 from the plurality of contour lines 210.

In one embodiment, the NURB surface modeling technique is applied to the plurality of image slices 16 and, more specifically, the plurality of open-loop contour lines 210 of FIG. 2B. The NURB software generates a 3D model 40 as depicted in FIG. 2C, wherein the 3D model 40 has areas of interest or targeted regions 42 that contain both a mesh and its control points. For example, see Ervin et al., *Landscape Modeling*, McGraw-Hill, 2001, which is hereby incorporated by reference in its entirety into this detailed Description.

In one embodiment, the NURB surface modeling technique employs the following surface equation:

$$G(s, t) = \frac{\sum_{i=0}^{k1} \sum_{j=0}^{k2} W(i, j) P(i, j) b_i(s) b_j(t)}{\sum_{i=0}^{k1} \sum_{j=0}^{k2} W(i, j) b_i(s) b_j(t)},$$

wherein $P(i,j)$ represents a matrix of vertices with nrows=$(k1+1)$ and ncols=$(k2+1)$, $W(i,j)$ represents a matrix of vertex weights of one per vertex point, $b_i(s)$ represents a row-direction basis or blending of polynomial functions of degree M1, $b_j(t)$ represents a column-direction basis or blending polynomial functions of degree M2, s represents a parameter array of row-direction knots, and t represents a parameter array of column-direction knots.

In one embodiment, the Bézier surface modeling technique employs the Bézier equation (1972, by Pierre Bézier) to generate a 3D model 40 as depicted in FIG. 2C, wherein the model 40 has areas of interest or targeted regions 42. A given Bézier surface of order (n, m) is defined by a set of $(n+1)(m+1)$ control points $k_{i,j}$. It maps the unit square into a smooth-continuous surface embedded within a space of the same dimensionality as $(k_{i,j})$. For example, if k are all points in a four-dimensional space, then the surface will be within a four-dimensional space. This relationship holds true for a one-dimensional space, a two-dimensional space, a fifty-dimensional space, etc.

A two-dimensional Bézier surface can be defined as a parametric surface where the position of a point p as a function of the parametric coordinates u, v is given by:

$$p(u, v) = \sum_{i=0}^{n} \sum_{j=0}^{m} B_i^n(u) B_j^m(v) k_{i,j}$$

evaluated over the unit square, where $$B_i^n(u) = \binom{n}{i} u^i (1-u)^{n-i}$$

is a Bernstein polynomial and $$\binom{n}{i} = \frac{n!}{i! * (n-i)!}$$

is the binomial coefficient. See Grune et al, *On Numerical Algorithm and Interactive Visualization for Optimal Control Problems*, Journal of Computation and Visualization in Science, Vol. 1, No. 4, July 1999, which is hereby incorporated by reference in its entirety into this Detailed Description.

Various other surface rendering techniques are disclosed in other references. For example, see the surface rendering techniques disclosed in the following publications: Lorensen et al., *Marching Cubes: A high Resolution 3d Surface Construction Algorithm*, Computer Graphics, 21-3: 163-169, 1987; Farin et al., *NURB Curves & Surfaces: From Projective Geometry to Practical Use*, Wellesley, 1995; Kumar et al, *Robust Incremental Polygon Triangulation for*

*Surface Rendering*, WSCG, 2000; Fleischer et al., *Accurate Polygon Scan Conversion Using Half-Open Intervals*, Graphics Gems III, p. 362-365, code: p. 599-605, 1992; Foley et al., *Computer Graphics: Principles and Practice*, Addison Wesley, 1990; Glassner, *Principles of Digital Image Synthesis*, Morgan Kaufmann, 1995, all of which are hereby incorporated by reference in their entireties into this Detailed Description.

d. Selecting a Jig Blank Most Similar in Size and/or Configuration to the Size of the Patient's Femur Lower End.

As mentioned above, an arthroplasty jig 2, such as a femoral jig 2A includes an interior portion 100 and an exterior portion 102. The femoral jig 2A is formed from a femur jig blank 50A, which, in one embodiment, is selected from a finite number of femur jig blank sizes. The selection of the femur jig blank 50A is based on a comparison of the dimensions of the patient's femur lower end 204 to the dimensions and/or configurations of the various sizes of femur jig blanks 50A to select the femur jig blank 50A most closely resembling the patient's femur lower end 204 with respect to size and/or configuration. This selected femur jig blank 50A has an outer or exterior side or surface 232 that forms the exterior portion 232 of the femur jig 2A. The 3D surface computer model 40 discussed with respect to the immediately preceding section of this Detail Description is used to define a 3D surface 40 into the interior side 230 of computer model of a femur jig blank 50A. Furthermore, in some embodiments, the overestimation of the procedure described below may be used to adjust the 3D surface model 40.

By selecting a femur jig blank 50A with an exterior portion 232 close in size to the patient's lower femur end 204, the potential for an accurate fit between the interior portion 230 and the patient's femur is increased. Also, the amount of material that needs to be machined or otherwise removed from the jig blank 50A is reduced, thereby reducing material waste and manufacturing time.

Figure 3A:
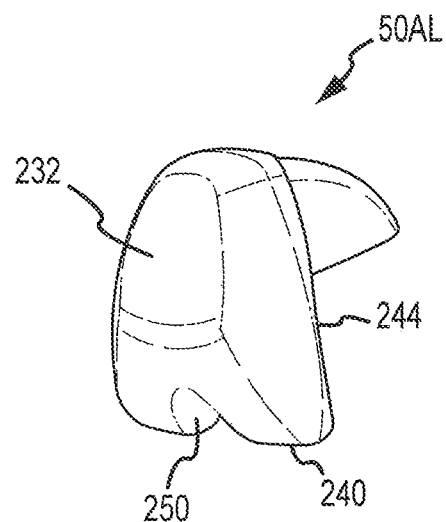
FIG. 3A is a top perspective view of a left femoral cutting jig blank having predetermined dimensions.
Figure 3B:
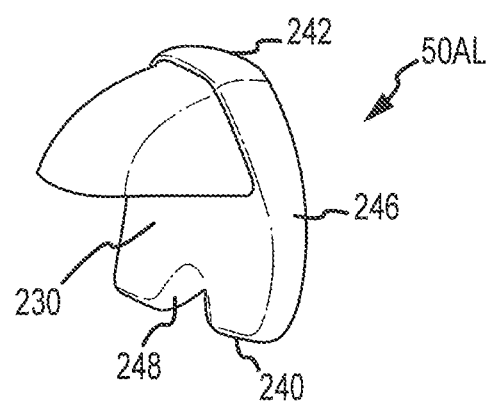
FIG. 3B is a bottom perspective view of the jig blank depicted in FIG. 3A.
Figure 3C:
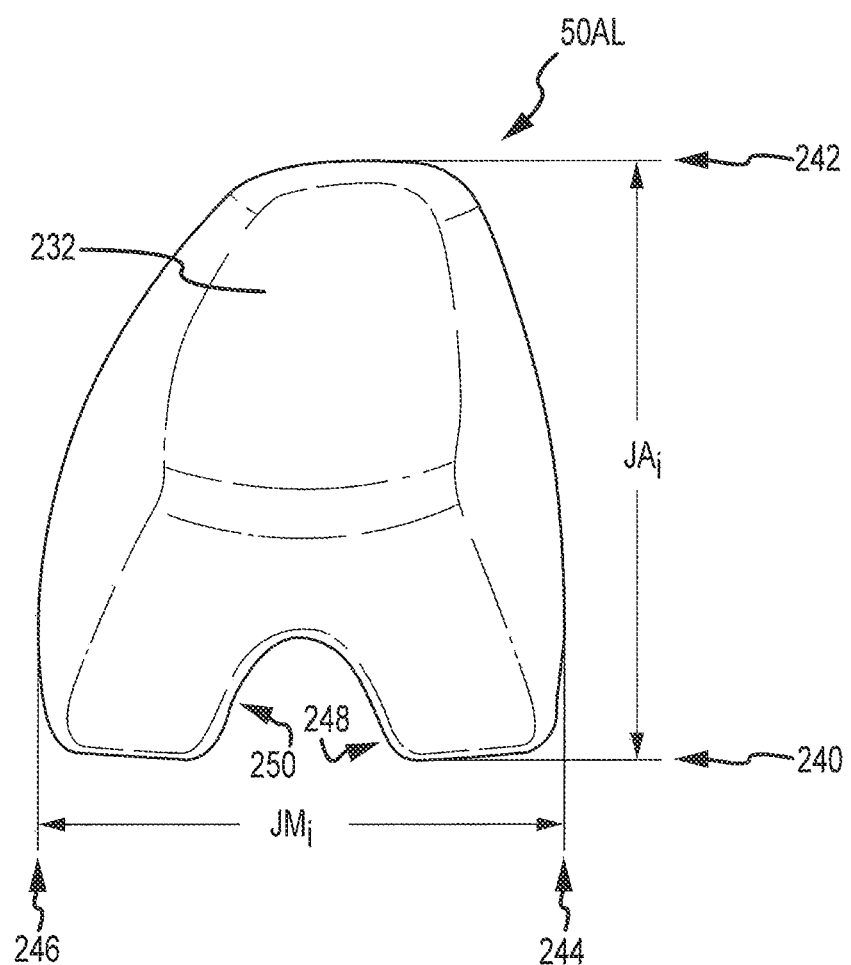
FIG. 3C is plan view of an exterior side or portion of the jig blank depicted in FIG. 3A.
Figure 4A:
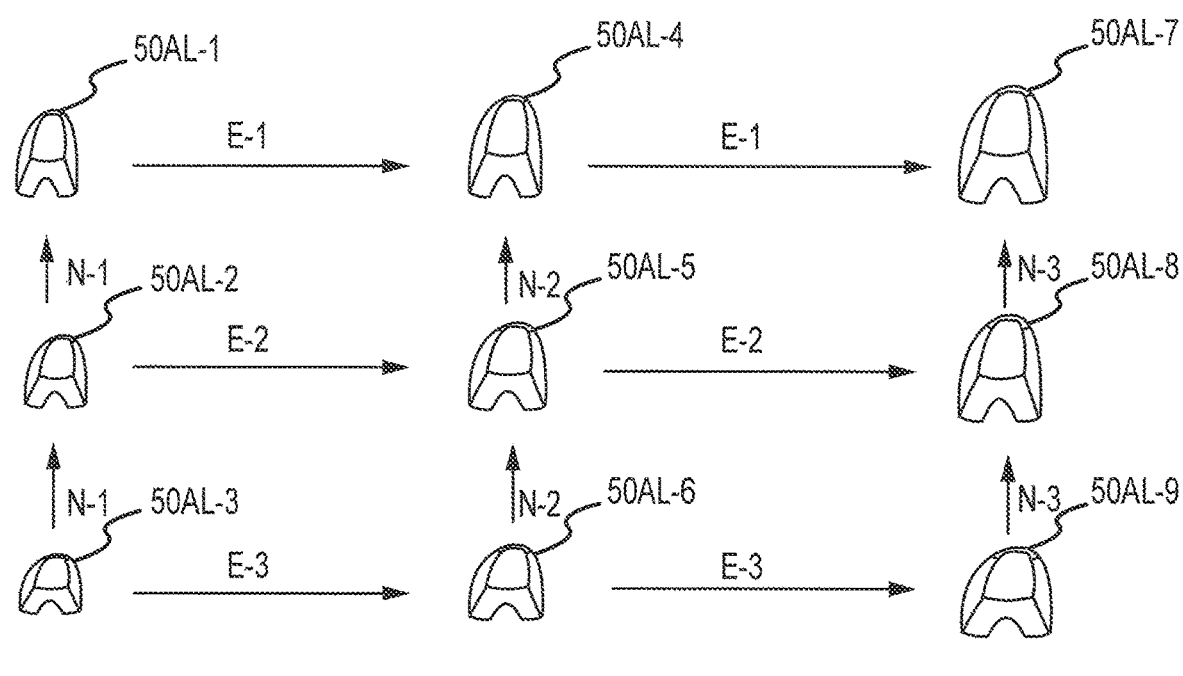
FIG. 4A is a plurality of available sizes of left femur jig blanks, each depicted in the same view as shown in FIG. 3C.
Figure 4B:
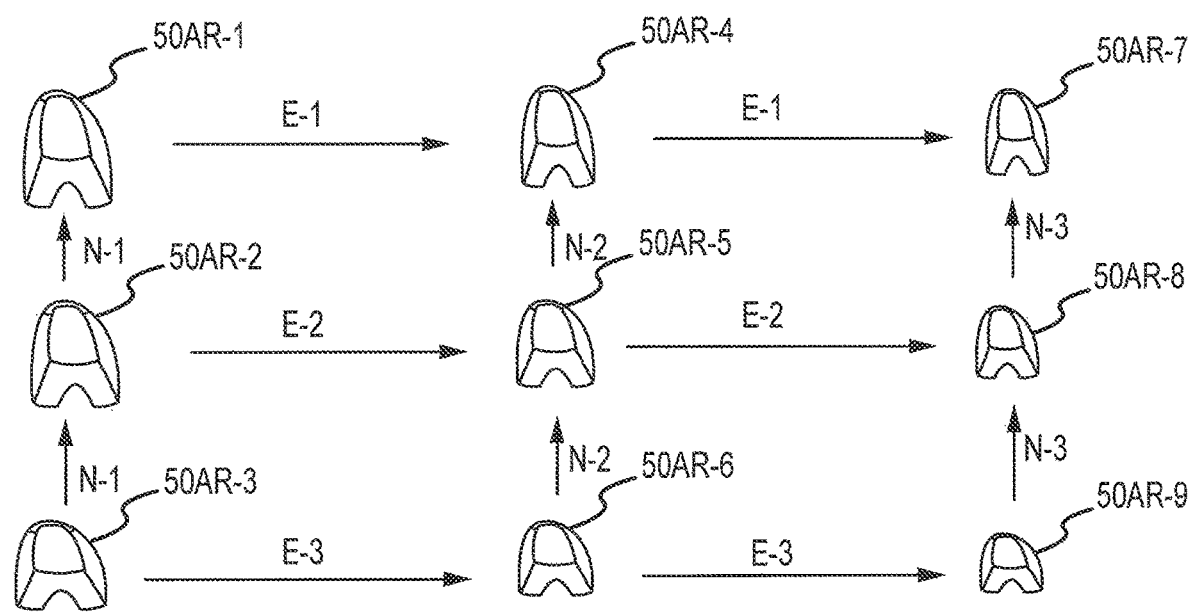
FIG. 4B is a plurality of available sizes of right femur jig blanks, each depicted in the same view as shown in FIG. 3C.

For a discussion of a method of selecting a jig blank 50 most closely corresponding to the size and/or configuration of the patient's lower femur end, reference is first made to FIGS. 3-4B. FIG. 3A is a top perspective view of a left femoral cutting jig blank 50AL having predetermined dimensions. FIG. 3B is a bottom perspective view of the jig blank 50AL depicted in FIG. 3A. FIG. 3C is plan view of an exterior side or portion 232 of the jig blank 50AL depicted in FIG. 3A. FIG. 4A is a plurality of available sizes of left femur jig blanks 50AL, each depicted in the same view as shown in FIG. 3C. FIG. 4B is a plurality of available sizes of right femur jig blanks 50AR, each depicted in the same view as shown in FIG. 3C.

A common jig blank 50, such as the left jig blank 50AL depicted in FIGS. 3A-3C and intended for creation of a left femur jig that can be used with a patient's left femur, may include a posterior edge 240, an anterior edge 242, a lateral edge 244, a medial edge 246, a lateral condyle portion 248, a medial condyle portion 250, the exterior side 232 and the interior side 230. The jig blank 50AL of FIGS. 3A-3C may be any one of a number of left femur jig blanks 50AL available in a limited number of standard sizes. For example, the jig blank 50AL of FIGS. 3A-3C may be an i-th left femur jig blank, where i=1, 2, 3, 4, . . . m and m represents the maximum number of left femur jig blank sizes.

As indicated in FIG. 3C, the anterior-posterior extent JAi of the jig blank 50AL is measured from the anterior edge 242 to the posterior edge 240 of the jig blank 50AL. The medial-lateral extent JMi of the jig blank 50AL is measured from the lateral edge 244 to the medial edge 246 of the jig blank 50AL.

As can be understood from FIG. 4A, a limited number of left femur jig blank sizes may be available for selection as the left femur jig blank size to be machined into the left femur cutting jig 2A. For example, in one embodiment, there are nine sizes (m=9) of left femur jig blanks 50AL available. As can be understood from FIG. 3C, each femur jig blank 50AL has an anterior-posterior/medial-lateral aspect ratio defined as JAi to JMi (e.g., "JAi/JMi" aspect ratio). Thus, as can be understood from FIG. 4A, jig blank 50AL-1 has an aspect ratio defined as "$JA_1/JM_1$", jig blank 50AL-2 has an aspect ratio defined as "$JA_2/JM_2$", jig blank 50AL-3 has an aspect ratio defined as "$JA_3/JM_3$", jig blank 50AL-4 has an aspect ratio defined as "$JA_4/JM_4$", jig blank 50AL-5 has an aspect ratio defined as "$JA_5/JM_5$", jig blank 50AL-6 has an aspect ratio defined as "$JA_6/JM_6$", jig blank 50AL-7 has an aspect ratio defined as "$JA_7/JM_7$", jig blank 50AL-8 has an aspect ratio defined as "$JA_8/JM_8$", and jig blank 50AL-9 has an aspect ratio defined as "$JA_9/JM_9$".

The jig blank aspect ratio is utilized to design left femur jigs 2A dimensioned specific to the patient's left femur features. In one embodiment, the jig blank aspect ratio can be the exterior dimensions of the left femur jig 2A. In another embodiment, the jig blank aspect ratio can apply to the left femur jig fabrication procedure for selecting the left jig blank 50AL having parameters close to the dimensions of the desired left femur jig 2A. This embodiment can improve the cost efficiency of the left femur jig fabrication process because it reduces the amount of machining required to create the desired jig 2 from the selected jig blank 50.

In FIG. 4A, the N-1 direction represents increasing jig aspect ratios moving from jig 50AL-3 to jig 50AL-2 to jig 50AL-1, where "$JA_3/JM_3$"<"$JA_2/JM_2$"<"$JA_1/JM_1$". The increasing ratios of the jigs 50AL represent the corresponding increment of JAi values, where the jigs' JMi values remain the same. In other words, since $JA_3<JA_2<JA_1$, and $JM_3=JM_2=JM_1$, then "$JA_3/JM_3$"<"$JA_2/JM_2$"<"$JA_1/JM_1$". One example of the increment level can be an increase from 5% to 20%.

The same rationale applies to the N-2 direction and the N-3 direction. For example, the N-2 direction represents increasing jig aspect ratios from jig 50AL-6 to jig 50AL-5 to jig 50AL-4, where "$JA_4/JM_4$"<"$JA_5/JM_5$"<"$JA_6/JM_6$". The increasing ratios of the jigs 50AL represent the corresponding increment of JAi values, where the JMi values remain the same. The N-3 direction represents increasing jig aspect ratios from jig 50AL-9 to jig 50AL-8 to jig 50AL-7, where "$JA_7/JM_7$"<"$JA_8/JM_8$"<"$JA_9/JM_9$". The increasing ratios of the jigs 50AL represent the corresponding increment of JAi values, where the JMi values remain the same.

As can be understood from the plot 300 depicted in FIG. 7 and discussed later in this Detailed Discussion, the E-1 direction corresponds to the sloped line joining Group 1, Group 4 and Group 7. Similarly, the E-2 direction corresponds to the sloped line joining Group 2, Group 5 and Group 8. Also, the E-3 direction corresponds to the sloped line joining Group 3, Group 6 and Group 9.

As indicated in FIG. 4A, along direction E-2, the jig aspect ratios remain the same among jigs 50AL-2, 50AL-5 and jig 50AL-8, where "$JA_2/JM_2$"="$JA_5/JM_5$"="$JA_8/JM_8$". However, comparing to jig 50AL-2, jig 50AL-5 is dimensioned larger and longer than jig 50AL-2. This is because the $JA_5$ value for jig 50AL-5 increases proportionally with the increment of its $JM_5$ value in certain degrees in all X, Y, and Z-axis directions. In a similar fashion, jig 50AL-8 is dimensioned larger and longer than jig 50AL-5 because the $JA_8$ increases proportionally with the increment of its $JM_8$ value in certain degrees in all X, Y, and Z-axis directions. One example of the increment can be an increase from 5% to 20%.

The same rationale applies to directions E-1 and E-3. For example, in E-3 direction the jig ratios remain the same among the jigs 50AL-3, 50AL-6 and jig 50AL-9. Compared to jig 50AL-3, jig 50AL-6 is dimensioned bigger and longer because both $JM_6$ and $JA_6$ values of jig 50AL-6 increase proportionally in all X, Y, and Z-axis directions. Compared to jig 50AL-6, jig 50AL-9 is dimensioned bigger and longer because both $JM_9$ and $JA_9$ values of jig 50AL-9 increase proportionally in all X, Y, and Z-axis.

As can be understood from FIG. 4B, a limited number of right femur jig blank sizes may be available for selection as the right femur jig blank size to be machined into the right femur cutting jig 2A. For example, in one embodiment, there are nine sizes (m=9) of right femur jig blanks 50AR available. As can be understood from FIG. 3, each femur jig blank 50AR has an anterior-posterior/medial-lateral aspect ratio defined as JAi to JMi (e.g., "JAi/JMi" aspect ratio). Thus, as can be understood from FIG. 4B, jig blank 50AR-1 has an aspect ratio defined as "$JA_1/JM_1$", jig blank 50AR-2 has an aspect ratio defined as "$JA_2/JM_2$", jig blank 50AR-3 has an aspect ratio defined as "$JA_3/JM_3$", jig blank 50AR-4 has an aspect ratio defined as "$JA_4/JM_4$", jig blank 50AR-5 has an aspect ratio defined as "$JA_5/JM_5$", jig blank 50AR-6 has an aspect ratio defined as "$JA_6/JM_6$", jig blank 50AR-7 has an aspect ratio defined as "$JA_7/JM_7$", jig blank 50AR-8 has an aspect ratio defined as "$JA_8/JM_8$", and jig blank 50AR-9 has an aspect ratio defined as "$JA_9/JM_9$".

The jig blank aspect ratio may be utilized to design right femur jigs 2A dimensioned specific to the patient's right femur features. In one embodiment, the jig blank aspect ratio can be the exterior dimensions of the right femur jig 2A. In another embodiment, the jig blank aspect ratio can apply to the right femur jig fabrication procedure for selecting the right jig blank 50AR having parameters close to the dimensions of the desired right femur jig 2A. This embodiment can improve the cost efficiency of the right femur jig fabrication process because it reduces the amount of machining required to create the desired jig 2 from the selected jig blank 50.

In FIG. 4B, the N-1 direction represents increasing jig aspect ratios moving from jig 50AR-3 to jig 50AR-2 to jig 50AR-1, where "$JA_3/JM_3$"<"$JA_2/JM_2$"<"$JA_1/JM_1$". The increasing ratios of the jigs 50AR represent the corresponding increment of JAi values, where the jigs' JMi values remain the same. In other words, since $JA_3<JA_2<JA_1$, and $JM_3=JM_2=JM_1$, then "$JA_3/JM_3$"<"$JA_2/JM_2$"<"$JA_1/JM_1$". One example of the increment level can be an increase from 5% to 20%.

The same rationale applies to the N-2 direction and the N-3 direction. For example, the N-2 direction represents increasing jig aspect ratios from jig 5OAR-6 to jig 5OAR-5 to jig 5OAR-4, where "$JA_4/JM_4$"<"$JA_5/JM_5$"<"$JA_6/JM_6$". The increasing ratios of the jigs 5OAR represent the corresponding increment of JAi values, where the JMi values remain the same. The N-3 direction represents increasing jig aspect ratios from jig 5OAR-9 to jig 50AR-8 to jig 50AR-7, where "$JA_7/JM_7$"<"$JA_8/JM_8$"<"$JA_9/JM_9$". The increasing ratios of the jigs SOAR represent the corresponding increment of JAi values, where the JMi values remain the same.

As indicated in FIG. 4B, along direction E-2, the jig aspect ratios remain the same among jigs 50AR-2, 50AR-5 and jig 50AR-8, where "$JA_2/JM_2$"="$JA_5/JM_5$"="$JA_8/JM_8$". However, comparing to jig 50AR-2, jig 50AR-5 is dimensioned larger and longer than jig 50AR-2. This is because the $JA_5$ value for jig 50AR-5 increases proportionally with the increment of its $JM_5$ value in certain degrees in all X, Y, and Z-axis directions. In a similar fashion, jig 50AR-8 is dimensioned larger and longer than jig 50AR-5 because the $JA_8$ increases proportionally with the increment of its $JM_8$ value in certain degrees in all X, Y, and Z-axis directions. One example of the increment can be an increase from 5% to 20%.

The same rationale applies to directions E-1 and E-3. For example, in E-3 direction the jig ratios remain the same among the jigs 50AR-3, 50AR-6 and jig 50AR-9. Compared to jig 50AR-3, jig 50AR-6 is dimensioned bigger and longer because both $JM_6$ and $JA_6$ values of jig 50AR-6 increase proportionally in all X, Y, and Z-axis directions. Compared to jig 50AR-6, jig 50AR-9 is dimensioned bigger and longer because both $JM_9$ and $JA_9$ values of jig 50AR-9 increase proportionally in all X, Y, and Z-axis.

Figure 5:
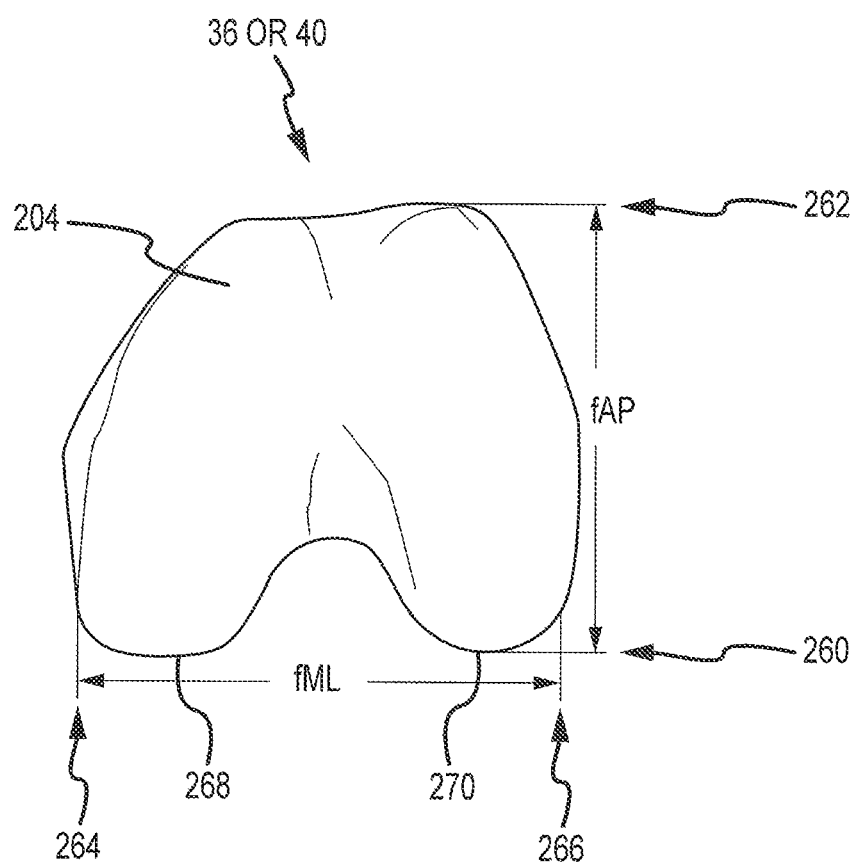
FIG. 5 is an axial view of the 3D surface model or arthritic model of the patient's left femur as viewed in a direction extending distal to proximal.

The dimensions of the lower or knee joint forming end 204 of the patient's femur 18 can be determined by analyzing the 3D surface model 40 or 3D arthritic model 36 in a manner similar to those discussed with respect to the jig blanks 50. For example, as depicted in FIG. 5, which is an axial view of the 3D surface model 40 or arthritic model 36 of the patient's left femur 18 as viewed in a direction extending distal to proximal, the lower end 204 of the surface model 40 or arthritic model 36 may include an anterior edge 262, a posterior edge 260, a medial edge 264, a lateral edge 266, a medial condyle 268, and a lateral condyle 270. The femur dimensions may be determined for the bottom end face or tibia articulating surface 204 of the patient's femur 18 via analyzing the 3D surface model 40 of the 3D arthritic model 36. These femur dimensions can then be utilized to configure femur jig dimensions and select an appropriate femur jig.

As shown in FIG. 5, the anterior-posterior extent fAP of the lower end 204 of the patient's femur 18 (i.e., the lower end 204 of the surface model 40 of the arthritic model 36, whether formed via open or closed-loop analysis) is the length measured from the anterior edge 262 of the femoral lateral groove to the posterior edge 260 of the femoral lateral condyle 270. The medial-lateral extent fML of the lower end 204 of the patient's femur 18 is the length measured from the medial edge 264 of the medial condyle 268 to the lateral edge 266 of the lateral condyle 270.

In one embodiment, the anterior-posterior extent fAP and medial-lateral extent fML of the femur lower end 204 can be used for an aspect ratio fAP/fML of the femur lower end. The aspect ratios fAP/fML of a large number (e.g., hundreds, thousands, tens of thousands, etc.) of patient knees can be compiled and statistically analyzed to determine the most common aspect ratios for jig blanks that would accommodate the greatest number of patient knees. This information may then be used to determine which one, two, three, etc. aspect ratios would be most likely to accommodate the greatest number of patient knees.

The system 4 analyzes the lower ends 204 of the patient's femur 18 as provided via the surface model 40 of the arthritic model 36 (whether the arthritic model 36 is an 3D surface model generated via an open-loop or a 3D volumetric solid model generated via a closed-loop process) to obtain data regarding anterior-posterior extent fAP and medial-lateral extent fML of the femur lower ends 204. As can be understood from FIG. 6, which depicts the selected model jig blank 50AL of FIG. 3C superimposed on the model femur lower end 204 of FIG. 5, the femur dimensional extents fAP, fML are compared to the jig blank dimensional extents jAP, jML to determine which jig blank model to select as the starting point for the machining process and the exterior surface model for the jig model.

Figure 6:
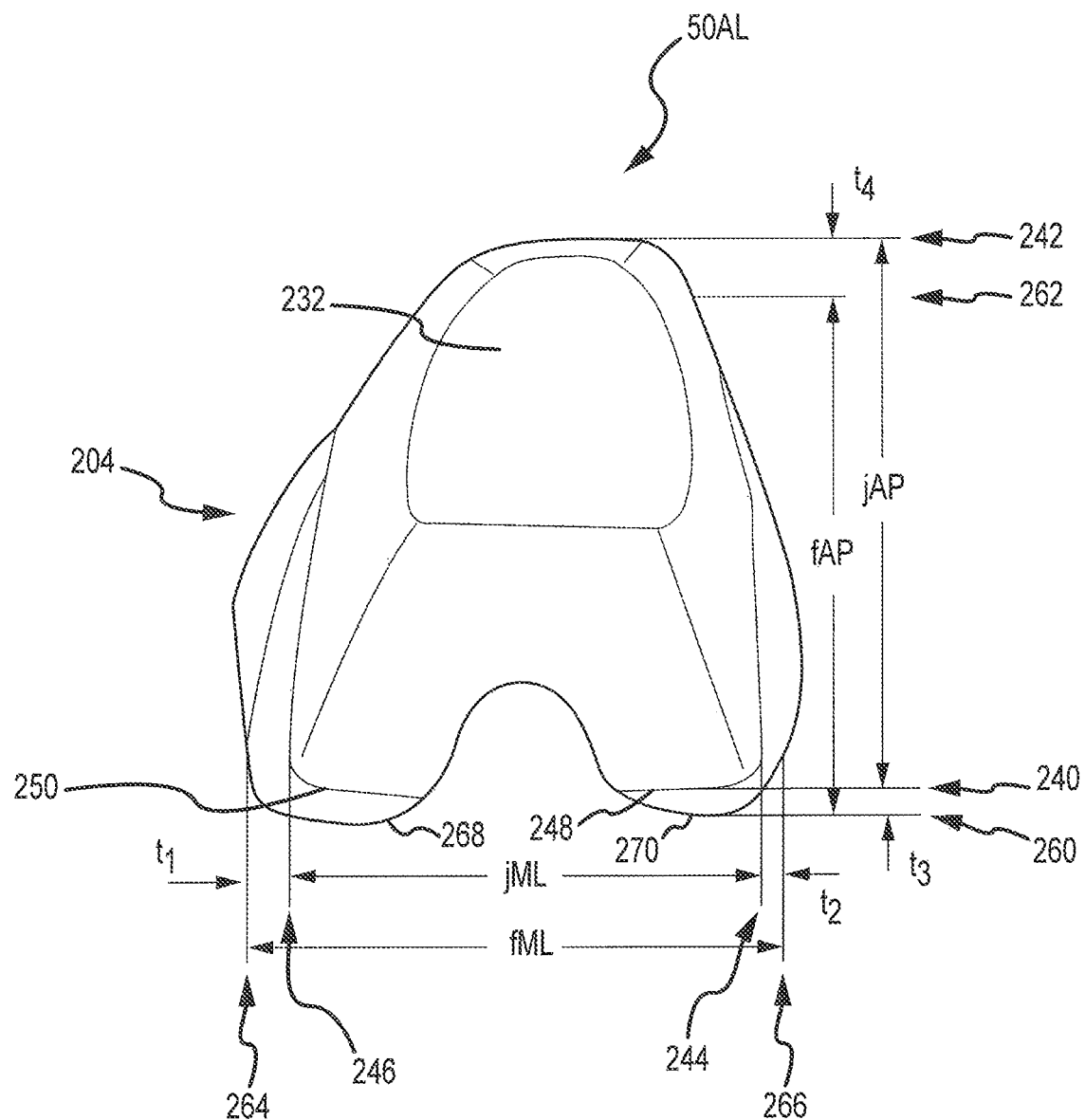
FIG. 6 depicts the selected model jig blank of FIG. 3C superimposed on the model femur lower end of FIG. 5.

As shown in FIG. 6, a prospective left femoral jig blank 50AL is superimposed to mate with the left femur lower end 204 of the patient's anatomical model as represented by the surface model 40 or arthritic model 36. The jig blank 50AL covers most of medial condyle 268 and the lateral condyle 270, leaving small exposed condyle regions including t1, t2, t3. The medial medial-lateral condyle region t1 represents the region between the medial edge 264 of the medial condyle 268 and the medial edge 246 of the jig blank 50AL. The lateral medial-lateral condyle region t2 represents the region between the lateral edge 266 of the lateral condyle 270 and the lateral edge 244 of the jig blank 50AL. The posterior anterior-posterior region t3 represents the condyle region between the posterior edge 260 of the lateral condyle 270 and the posterior edge 240 of the jig blank 50AL.

The anterior edge 242 of the jig blank 50AL extends past the anterior edge 262 of the left femur lower end 204 as indicated by anterior anterior-posterior overhang t4. Specifically, the anterior anterior-posterior overhang t4 represents the region between the anterior edge 262 of the lateral groove of femur lower end 204 and the anterior edge 242 of the jig blank 50AL. By obtaining and employing the femur anterior-posterior fAP data and the femur medial-lateral fML data, the system 4 can size the femoral jig blank 50AL according to the following formulas: as jFML=fML−t1−t2 and jFAP=fAP−t3+t4, wherein jFML is the medial-lateral extent of the femur jig blank 50AL and jFAP is the anterior-posterior extent of the femur jig blank 50AL. In one embodiment, t1, t2, t3 and t4 will have the following ranges: 2 mm≤t1≤6 mm; 2 mm≤t2≤6 mm; 2 mm≤t3≤12 mm; and 15 mm≤t4≤25 mm. In another embodiment, t1, t2, t3 and t4 will have the following values: t1=3 mm; t2=3 mm; t3=6 mm; and t4=20 mm.

Figure 7A:
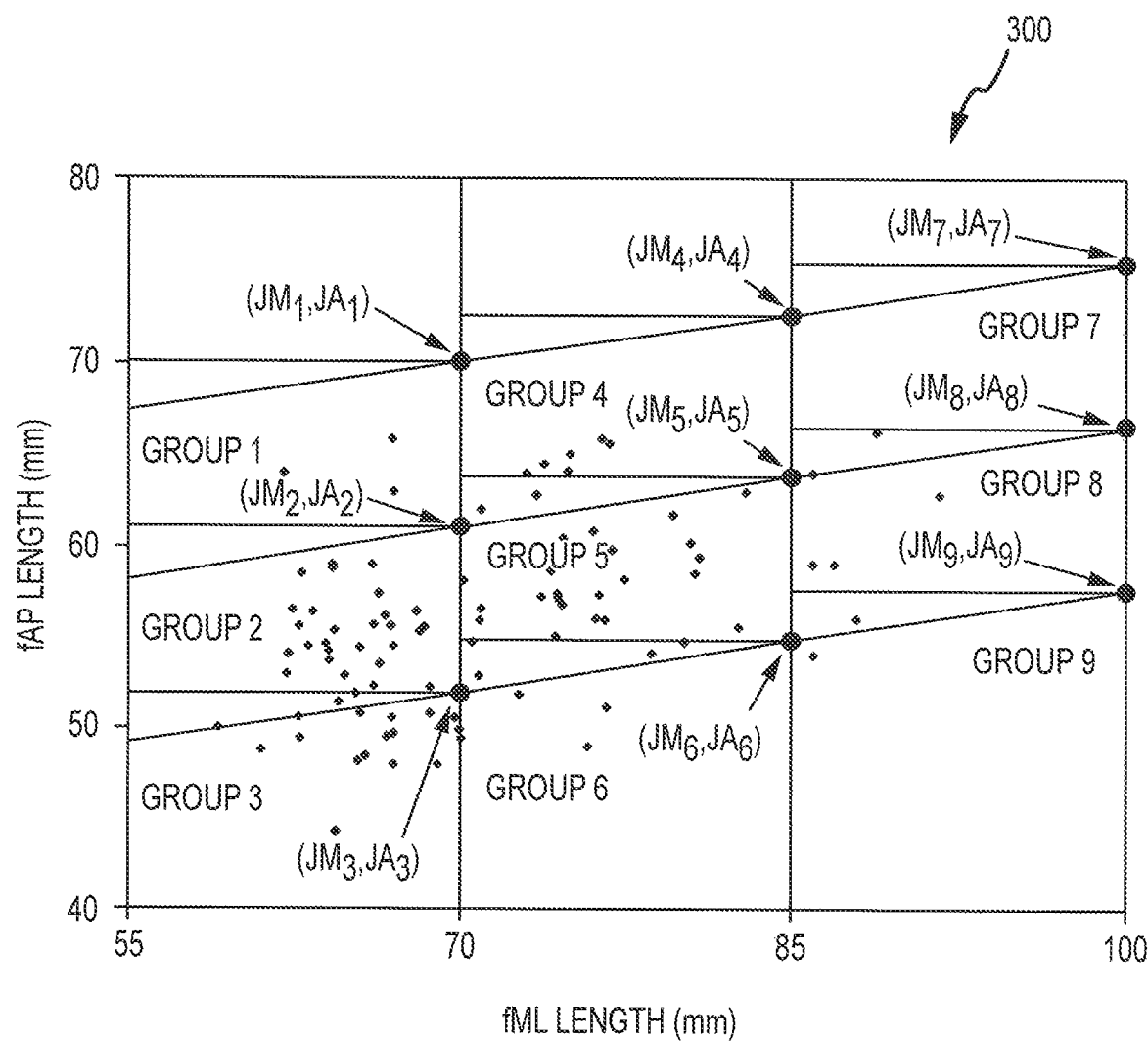
FIG. 7A is an example scatter plot for selecting from a plurality of candidate jig blanks sizes a jig blank size appropriate for the lower end of the patient's femur.

FIG. 7A is an example scatter plot 300 for selecting from a plurality of candidate jig blanks sizes a jig blank size appropriate for the lower end 204 of the patient's femur 18. In one embodiment, the X-axis represents the patient's femoral medial-lateral length fML in millimeters, and the Y-axis represents the patient's femoral anterior-posterior length fAP in millimeters. In one embodiment, the plot is divided into a number of jig blank size groups, where each group encompasses a region of the plot 300 and is associated with specific parameters $JM_r$, $JA_r$ of a specific candidate jig blank size.

In one embodiment, the example scatter plot 300 depicted in FIG. 7A has nine jig blank size groups, each group pertaining to a single candidate jig blank size. However, depending on the embodiment, a scatter plot 300 may have a greater or lesser number of jig blank size groups. The higher the number of jig blank size groups, the higher the number of the candidate jig blank sizes and the more dimension specific a selected candidate jig blank size will be to the patient's knee features and the resulting jig 2. The more dimension specific the selected candidate jig blank size, the lower the amount of machining required to produce the desired jig 2 from the selected jig blank 50.

Conversely, the lower the number of jig blank size groups, the lower the number of candidate jig blank sizes and the less dimension specific a selected candidate jig blank size will be to the patient's knee features and the resulting jig 2. The less dimension specific the selected candidate jig blank size, the higher the amount of machining required to produce the desired jig 2 from the selected jig blank 50, adding extra roughing during the jig fabrication procedure.

As can be understood from FIG. 7A, in one embodiment, the nine jig blank size groups of the plot 300 have the parameters $JM_r$, $JA_r$, as follows. Group 1 has parameters $JM_1$, $JA_1$. $JM_1$ represents the medial-lateral extent of the first femoral jig blank size, wherein $JM_1$=70 mm. $JA_1$ represents the anterior-posterior extent of the first femoral jig blank size, wherein $JA_1$=70.5 mm. Group 1 covers the patient's femur fML and fAP data wherein 55 mm<fML<70 mm and 61 mm<fAP<70.5 mm.

Group 2 has parameters $JM_2$, $JA_2$. $JM_2$ represents the medial-lateral extent of the second femoral jig blank size, wherein $JM_2$=70 mm. $JA_2$ represents the anterior-posterior extent of the second femoral jig blank size, wherein $JA_2$=61.5 mm. Group 2 covers the patient's femur fML and fAP data wherein 55 mm<fML<70 mm and 52 mm<fAP<61.5 mm.

Group 3 has parameters $JM_3$, $JA_3$. $JM_3$ represents the medial-lateral extent of the third femoral jig blank size, wherein $JM_3$=70 mm. $JA_3$ represents the anterior-posterior extent of the third femoral jig blank size, wherein $JA_3$=52 mm. Group 3 covers the patient's femur fML and fAP data wherein 55 mm<fML<70 mm and 40 mm<fAP<52 mm.

Group 4 has parameters $JM_4$, $JA_4$. $JM_4$ represents the medial-lateral extent of the fourth femoral jig blank size, wherein $JM_4$=85 mm. $JA_4$ represents the anterior-posterior extent of the fourth femoral jig blank size, wherein $JA_4$=72.5 mm. Group 4 covers the patient's femur fML and fAP data wherein 70 mm<fML<85 mm and 63.5 mm <fAP<72.5 mm.

Group 5 has parameters $JM_5$, $JA_5$. $JM_5$ represents the medial-lateral extent of the fifth femoral jig blank size, wherein $JM_5$=85 mm. $JA_5$ represents the anterior-posterior extent of the fifth femoral jig blank size, wherein $JA_5$=63.5 mm. Group 5 covers the patient's femur fML and fAP data wherein 70 mm<fML<85 mm and 55 mm<fAP<63.5 mm.

Group 6 has parameters $JM_6$, $JA_6$. $JM_6$ represents the medial-lateral extent of the sixth femoral jig blank size, wherein $JM_6$=85 mm. $JA_6$ represents the anterior-posterior extent of the sixth femoral jig blank size, wherein $JA_6$=55 mm. Group 6 covers the patient's femur fML and fAP data wherein 70 mm<fML<85 mm and 40 mm<fAP<55 mm.

Group 7 has parameters $JM_7$, $JA_7$. $JM_7$ represents the medial-lateral extent of the seventh femoral jig blank size, wherein $JM_7$=100 mm. $JA_7$ represents the anterior-posterior extent of the seventh femoral jig blank size, wherein $JA_7$=75 mm. Group 7 covers the patient's femur fML and fAP data wherein 85 mm<fML<100 mm and 65 mm<fAP<75 mm.

Group 8 has parameters $JM_8$, $JA_8$. $JM_8$ represents the medial-lateral extent of the eighth femoral jig blank size, wherein $JM_8$=100 mm. $JA_8$ represents the anterior-posterior extent of the eighth femoral jig blank size, wherein $JA_8$=65 mm. Group 8 covers the patient's femur fML and fAP data wherein 85 mm<fML<100 mm and 57.5 mm<fAP<65 mm.

Group 9 has parameters $JM_9$, $JA_9$. $JM_9$ represents the medial-lateral extent of the ninth femoral jig blank size, wherein $JM_9$=100 mm. $JA_9$ represents the anterior-posterior extent of the ninth femoral jig blank size, wherein $JA_9$=57.5 mm. Group 9 covers the patient's femur fML and fAP data wherein 85 mm<fML<100 mm and 40 mm<fAP<57.5 mm.

Figure 7B:
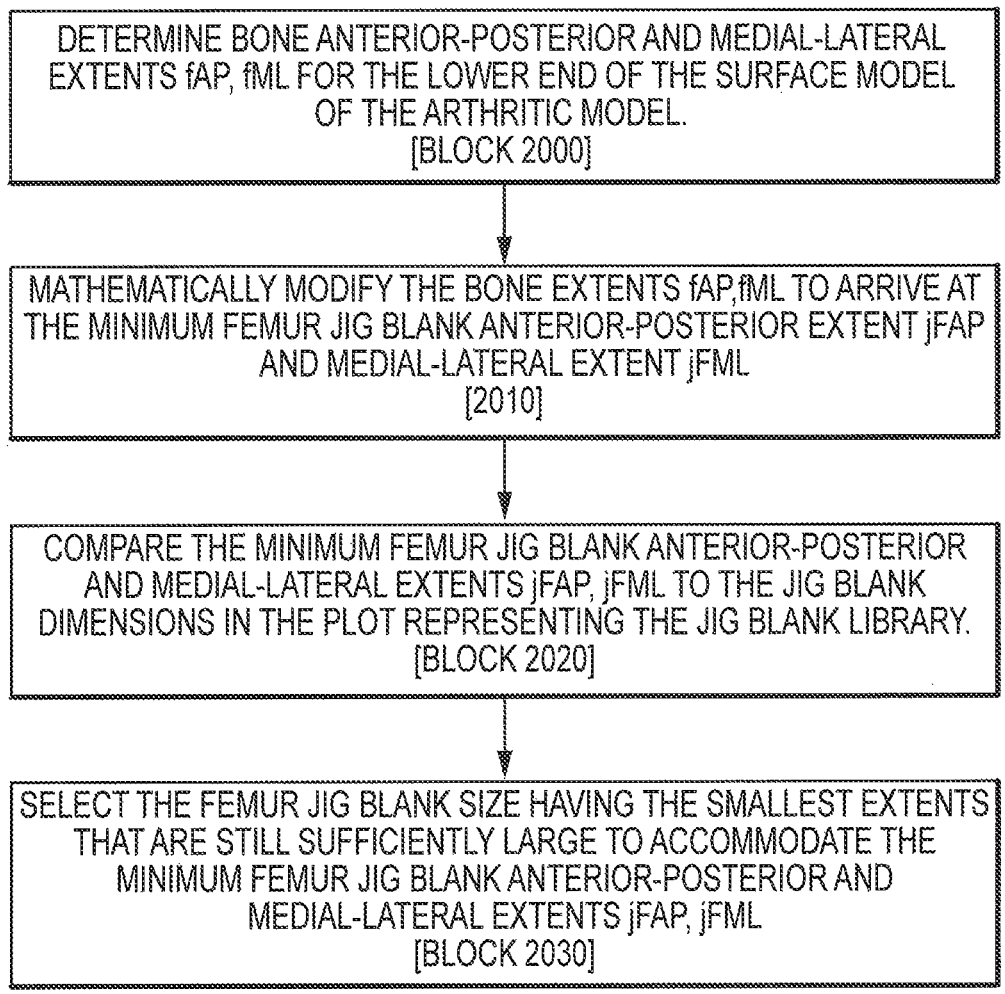
FIG. 7B is a flow diagram illustrating an embodiment of a process of selecting an appropriately sized jig blank.

As can be understood from FIG. 7B, which is a flow diagram illustrating an embodiment of a process of selecting an appropriately sized jig blank, bone anterior-posterior and medial-lateral extents fAP, fML are determined for the lower end 204 of the surface model 40 of the arthritic model 36 [block 2000]. The bone extents fAP, fML of the lower end 204 are mathematically modified according to the above discussed jFML and jFAP formulas to arrive at the minimum femur jig blank anterior-posterior extent jFAP and medial-lateral extent jFML [block 2010]. The mathematically modified bone extents fAP, fML or, more specifically, the minimum femur jig blank anterior-posterior and medial-lateral extents jFAP, jFML are referenced against the jig blank dimensions in the plot 300 of FIG. 7A [block 2020]. The plot 300 may graphically represent the extents of candidate femur jig blanks forming a jig blank library. The femur jig blank 50A is selected to be the jig blank size having the smallest extents that are still sufficiently large to accommodate the minimum femur jig blank anterior-posterior and medial-lateral extents JFAP, jFML [block 2030].

In one embodiment, the exterior of the selected jig blank size is used for the exterior surface model of the jig model, as discussed below. In one embodiment, the selected jig blank size corresponds to an actual jig blank that is placed in the CNC machine and milled down to the minimum femur jig blank anterior-posterior and medial-lateral extents jFAP, jFML to machine or otherwise form the exterior surface of the femur jig 2A.

The method outlined in FIG. 7B and in reference to the plot 300 of FIG. 7A can be further understood from the following example. As measured in FIG. 6 with respect to the lower end 204 of the patient's femur 18, the extents of the patient's femur are as follows: fML=79.2 mm and fAP=54.5 mm [block 2000]. As previously mentioned, the lower end 204 may be part of the surface model 40 of the arthritic model 36. Once the fML and fAP measurements are determined from the lower end 204, the corresponding jig jFML data and jig jFAP data can be determined via the above-described jFML and jFAP formulas: jFML=fML−t1−t2, wherein t1=3 mm and t2=3 mm; and jFAP=fAP−t3+t4, wherein t3=6 mm and t4=20 mm [block 2010]. The result of the jFML and jFAP formulas is jFML=73.2 mm and jFAP=68.5 mm.

As can be understood from the plot 300 of FIG. 7, the determined jig data (i.e., jFML=73.2 mm and jFAP=68.5 mm) falls in Group 4 of the plot 300. Group 4 has the predetermined femur jig blank parameters ($JM_4$, $JA_4$) of $JM_4$=85 mm and $JA_4$=72.5 mm. These predetermined femur jig blank parameters are the smallest of the various groups that are still sufficiently large to meet the minimum femur blank extents jFAP, jFML [block 2020]. These predetermined femur jig blank parameters ($JM_4$=85 mm and $JA_4$=72.5 mm) may be selected as the appropriate femur jig blank size [block 2030].

In one embodiment, the predetermined femur jig blank parameters (85 mm, 72.5 mm) can apply to the femur exterior jig dimensions as shown in FIG. 3C. In other words, the jig blank exterior is used for the jig model exterior as discussed with respect to FIGS. 8A-9C. Thus, the exterior of the femur jig blank 50A undergoes no machining, and the unmodified exterior of the jig blank 50A with its predetermined jig blank parameters (85 mm, 72.5 mm) serves as the exterior of the finished femur jig 2A.

In another embodiment, the femur jig blank parameters (85 mm, 72.5 mm) can be selected for jig fabrication in the machining process. Thus, a femur jig blank 50A having predetermined parameters (85 mm, 72.5 mm) is provided to the machining process such that the exterior of the femur jig blank 50A will be machined from its predetermined parameters (85 mm, 72.5 mm) down to the desired femur jig parameters (73.2, 68.5 mm) to create the finished exterior of the femur jig 2A. As the predetermined parameters (85 mm, 72.5 mm) are selected to be relatively close to the desired femur jig parameters (73.2, 68.5 mm), machining time and material waste are reduced.

While it may be advantageous to employ the above-described jig blank selection method to minimize material waste and machining time, in some embodiments, a jig blank will simply be provided that is sufficiently large to be applicable to all patient bone extents fAP, fML. Such a jig blank is then machined down to the desired jig blank extents jFAP, jFML, which serve as the exterior surface of the finished jig 2A.

In one embodiment, the number of candidate jig blank size groups represented in the plot 300 is a function of the number of jig blank sizes offered by a jig blank manufacturer. For example, a first plot 300 may pertain only to jig blanks manufactured by company A, which offers nine jig blank sizes. Accordingly, the plot 300 has nine jig blank size groups. A second plot 300 may pertain only to jig blanks manufactured by company B, which offers twelve jig blank size groups. Accordingly, the second plot 300 has twelve jig blank size groups.

A plurality of candidate jig blank sizes exist, for example, in a jig blank library as represented by the plot 300 of FIG. 7B. While each candidate jig blank may have a unique combination of anterior-posterior and medial-lateral dimension sizes, in some embodiments, two or more of the candidate jig blanks may share a common aspect ratio jAP/jML or configuration. The candidate jig blanks of the library may be grouped along sloped lines of the plot 300 according to their aspect ratios jAP/jML.

In one embodiment, the jig blank aspect ratio jAP/jML may be used to take a workable jig blank configuration and size it up or down to fit larger or smaller individuals.

As can be understood from FIG. 7A, a series of 98 OA patients having knee disorders were entered into the plot 300 as part of a femur jig design study. Each patient's femur fAP and fML data was measured and modified via the above-described jFML and jFAP formulas to arrive at the patient's jig blank data (jFML, jFAP). The patient's jig blank data was then entered into the plot 300 as a point. As can be understood from FIG. 7A, no patient point lies outside the parameters of an available group. Such a process can be used to establish group parameters and the number of needed groups.

In one embodiment, the selected jig blank parameters can be the femoral jig exterior dimensions that are specific to patient's knee features. In another embodiment, the selected jig blank parameters can be chosen during fabrication process.

e. Formation of 3D Femoral Jig Model.

Figure 8A:
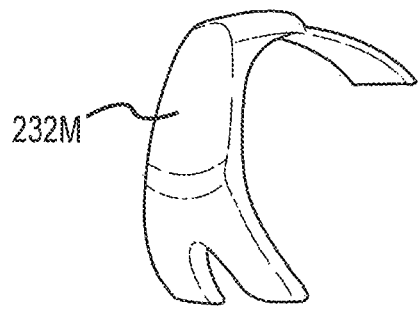
FIG. 8A is an exterior perspective view of a femur jig blank exterior surface model.
Figure 8B:
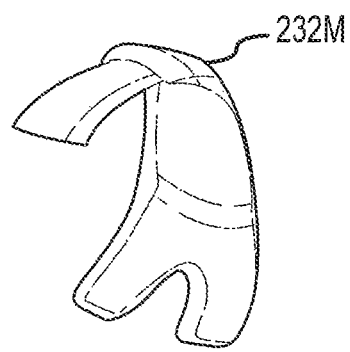
FIG. 8B is an interior perspective view of the femur jig blank exterior surface model of FIG. 8A.
Figure 9A:
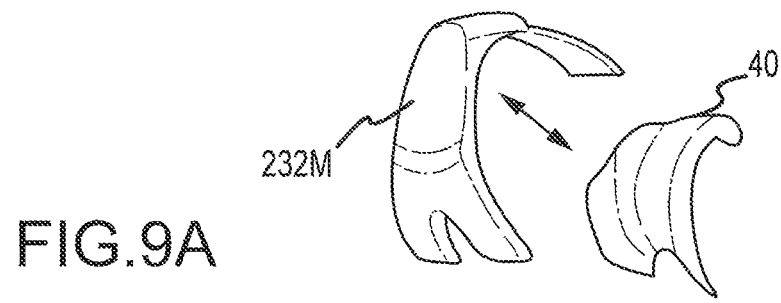
FIG. 9A is a perspective view of the extracted jig blank exterior surface model being combined with the extracted femur surface model.
Figure 9B:
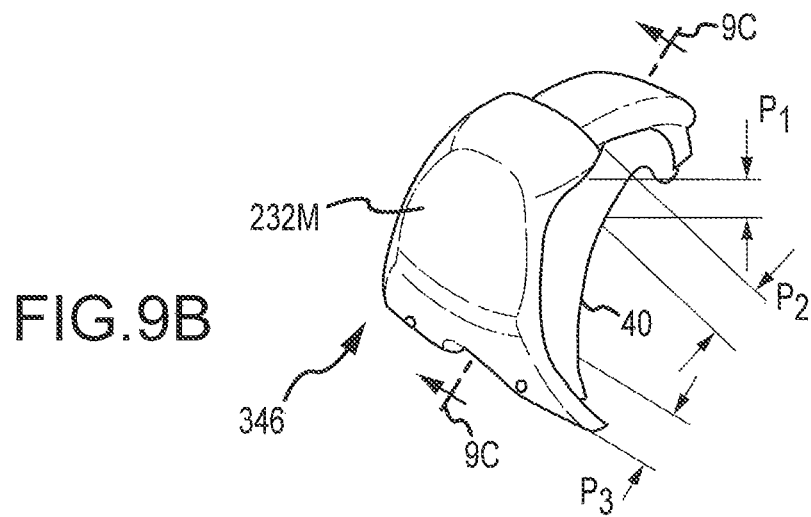
FIG. 9B is a perspective view of the extracted jig blank exterior surface model combined with the extracted femur surface model.
Figure 9C:
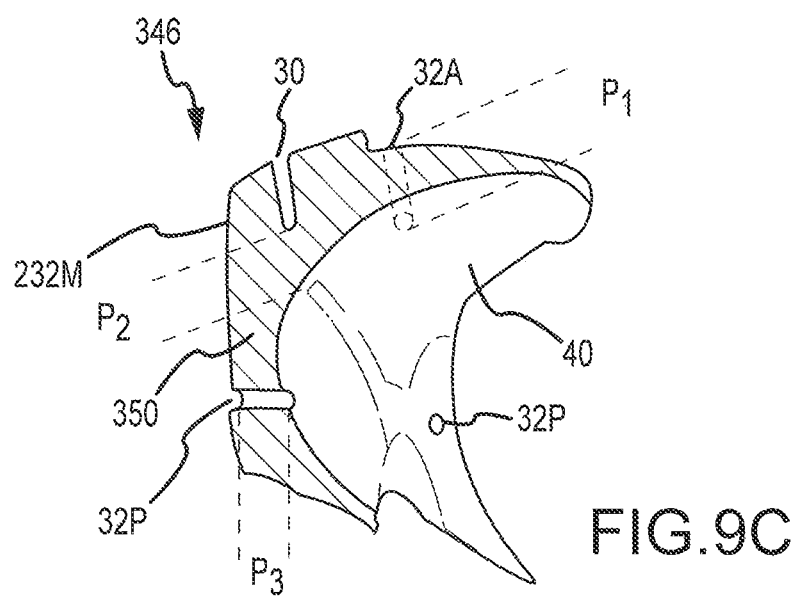
FIG. 9C is a cross section of the combined jig blank exterior surface model and the femur surface model as taken along section line 9C-9C in FIG. 9B.
Figure 10A:
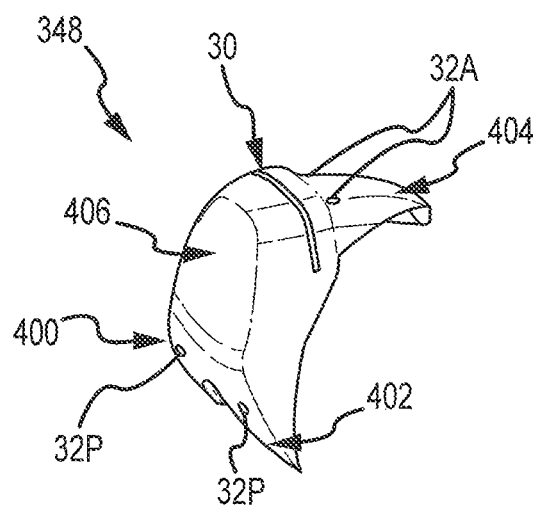
FIG. 10A is an exterior perspective view of the resulting femur jig model.
Figure 10B:
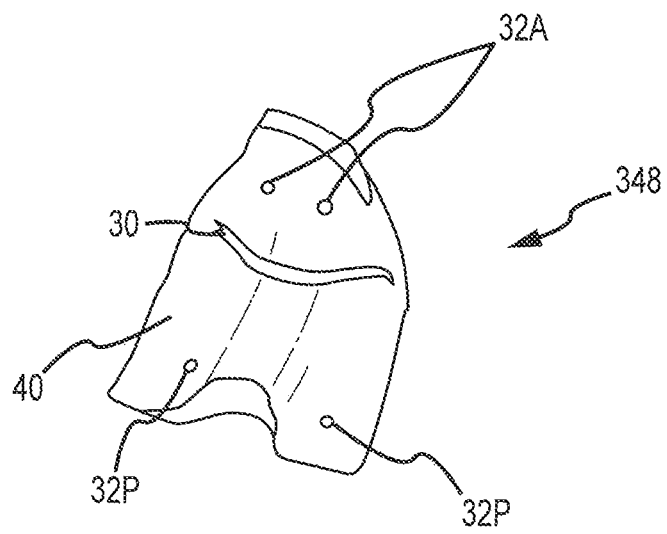
FIG. 10B is an interior perspective view of the femur jig model of FIG. 10A.

For a discussion of an embodiment of a method of generating a 3D femur jig model 346 generally corresponding to the "integrated jig data" 48 discussed with respect to [block 150] of FIG. 1E, reference is made to FIGS. 3A-3C, FIGS. 8A-8B, FIGS. 9A-9C and FIG. 10A-10B. FIGS. 3A-3C are various views of a femur jig blank 50A. FIGS. 8A-8B are, respectively, exterior and interior perspective views of a femur jig blank exterior surface model 232M. FIGS. 9A and 9B are exterior perspective views of the jig blank exterior model 232M and bone surface model 40 being combined, and FIG. 9C is a cross section through the combined models 232M, 40 as taken along section line 9C-9C in FIG. 9B. FIGS. 10A and 10B are, respectively, exterior and interior perspective views of the resulting femur jig model 346 after having "saw cut and drill hole data" 44 integrated into the jig model 346 to become an integrated or complete jig model 348 generally corresponding to the "integrated jig data" 48 discussed with respect to [block 150] of FIG. 1E.

As can be understood from FIGS. 3A-3C, the jig blank 50A, which has selected predetermined dimensions as discussed with respect to FIG. 7, includes an interior surface 230 and an exterior surface 232. The exterior surface model 232M depicted in FIGS. 8A and 8B is extracted or otherwise created from the exterior surface 232 of the jig blank model 50A. Thus, the exterior surface model 232M is based on the jig blank aspect ratio of the femur jig blank 50A selected as discussed with respect to FIG. 7 and is dimensioned specific to the patient's knee features. The femoral jig surface model 232M can be extracted or otherwise generated from the jig blank model 50A of FIGS. 3A-3C by employing any of the computer surface rendering techniques described above.

As can be understood from FIGS. 9A-9C, the exterior surface model 232M is combined with the femur surface model 40 to respectively form the exterior and interior surfaces of the femur jig model 346. The femur surface model 40 represents the interior or mating surface of the femur jig 2A and corresponds to the femur arthroplasty target area 42. Thus, the model 40 allows the resulting femur jig 2A to be indexed to the arthroplasty target area 42 of the patient's femur 18 such that the resulting femur jig 2A will matingly receive the arthroplasty target area 42 during the arthroplasty procedure. The two surface models 232M, 40 combine to provide a patient-specific jig model 346 for manufacturing the femur jig 2A. In some embodiments, this patient-specific jig model 346 may include one or more areas of overestimation (as described below) to accommodate for irregularities in the patient's bone surface and/or limitations in jig manufacturing capabilities.

As can be understood from FIGS. 9B and 9C, once the models 232M, 40 are properly aligned, a gap will exist between the two models 232M, 40. An image sewing method or image sewing tool is applied to the aligned models 232M, 40 to join the two surface models together to form the 3D computer generated jig model 346 of FIG. 9B into a single-piece, joined-together, and filled-in jig model 346 similar in appearance to the integrated jig model 348 depicted in FIGS. 10A and 10B. In one embodiment, the jig model 346 may generally correspond to the description of the "jig data" 46 discussed with respect [block 145] of FIG. 1E.

As can be understood from FIGS. 9B and 9C, the geometric gaps between the two models 232M, 40, some of which are discussed below with respect to thicknesses $P_1$, $P_2$ and $P_3$, may provide certain space between the two surface models 232M, 40 for slot width and length and drill bit length for receiving and guiding cutting tools during TKA surgery. Because the resulting femur jig model 348 depicted in FIGS. 10A and 10B may be a 3D volumetric model generated from 3D surface models 232M, 40, a space or gap should be established between the 3D surface models 232M, 40. This allows the resulting 3D volumetric jig model 348 to be used to generate an actual physical 3D volumetric femur jig 2.

In some embodiments, the image processing procedure may include a model repair procedure for repairing the jig model 346 after alignment of the two models 232M, 40. For example, various methods of the model repairing include, but are not limit to, user-guided repair, crack identification and filling, and creating manifold connectivity, as described in: Nooruddin et al., *Simplification and Repair of Polygonal Models Using Volumetric Techniques* (IEEE Transactions on Visualization and Computer Graphics, Vol. 9, No. 2, April-June 2003); C. Erikson, *Error Correction of a Large Architectural Model: The Henderson County Courthouse* (Technical Report TR95-013, Dept. of Computer Science, Univ. of North Carolina at Chapel Hill, 1995); D. Khorramabdi, *A Walk through the Planned CS Building* (Technical Report UCB/CSD 91/652, Computer Science Dept., Univ. of California at Berkeley, 1991); Morvan et al., *IVECS: An Interactive Virtual Environment for the Correction of .STL files* (Proc. Conf. Virtual Design, August 1996); Bohn et al., *A Topology-Based Approach for Shell-Closure*, Geometric Modeling for Product Realization, (P. R. Wilson et al., pp. 297-319, North-Holland, 1993); Barequet et al., *Filling Gaps in the Boundary of a Polyhedron*, Computer Aided Geometric Design (vol. 12, no. 2, pp. 207-229, 1995); Barequet et al., *Repairing CAD Models* (Proc. *IEEE Visualization '97*, pp. 363-370, October 1997); and Gueziec et al., *Converting Sets of Polygons to Manifold Surfaces by Cutting and Stitching*, (Proc. *IEEE Visualization* 1998, pp. 383-390, October 1998). Each of these references is incorporated into this Detailed Description in their entireties.

As can be understood from FIGS. 10A and 10B, the integrated jig model 348 may include several features based on the surgeon's needs. For example, the jig model 348 may include a slot feature 30 for receiving and guiding a bone saw and drill holes 32 for receiving and guiding bone drill bits. As can be understood from FIGS. 9B and 9C, to provide sufficient structural integrity to allow the resulting femur jig 2A to not buckle or deform during the arthroplasty procedure and to adequately support and guide the bone saw and drill bits, the gap 350 between the models 232M, 40 may have the following offsets $P_1$, $P_2$, and $P_3$.

As can be understood from FIGS. 9B-10B, in one embodiment, thickness $P_1$ extends along the length of the anterior drill holes 32A between the models 232M, 40 and is for supporting and guiding a bone drill received therein during the arthroplasty procedure. Thickness $P_1$ may be at least approximately four millimeters or at least approximately five millimeters thick. The diameter of the anterior drill holes 32A may be configured to receive a cutting tool of at least one-third inches.

Thickness $P_2$ extends along the length of a saw slot 30 between the models 232M, 40 and is for supporting and guiding a bone saw received therein during the arthroplasty procedure. Thickness $P_2$ may be at least approximately 10 mm or at least 15 mm thick.

Thickness $P_3$ extends along the length of the posterior drill holes 32P between the models 232M, 40 and is for supporting and guiding a bone drill received therein during the arthroplasty procedure. Thickness $P_3$ may be at least approximately five millimeters or at least eight millimeters thick. The diameter of the drill holes 32 may be configured to receive a cutting tool of at least one-third inches.

In addition to providing sufficiently long surfaces for guiding drill bits or saws received therein, the various thicknesses $P_1$, $P_2$, $P_3$ are structurally designed to enable the femur jig 2A to bear vigorous femur cutting, drilling and reaming procedures during the TKR surgery.

As indicated in FIGS. 10A and 10B, the integrated jig model 348 may include: feature 400 that matches the patient's distal portion of the medial condyle cartilage; feature 402 that matches the patient's distal portion of the lateral condyle cartilage; projection 404 that can be configured as a contact or a hook and may securely engage the resulting jig 2A onto the patient's anterior femoral joint surface during the TKR surgery; and the flat surface 406 that provides a blanked labeling area for listing information regarding the patient, surgeon or/and the surgical procedure. Also, as discussed above, the integrated jig model 348 may include the saw cut slot 30 and the drill holes 32. The inner portion or side 100 of the jig model 348 (and the resulting femur jig 2A) is the femur surface model 40, which will matingly receive the arthroplasty target area 42 of the patient's femur 18 during the arthroplasty procedure. In some embodiments, the overestimation of the procedure described below may be used to adjust the 3D surface model 40.

As can be understood by referring to [block 105] of FIG. 1B and FIGS. 2A-2F, in one embodiment when cumulating the image scans 16 to generate the one or the other of the models 40, 22, the models 40, 22 are referenced to point P, which may be a single point or a series of points, etc. to reference and orient the models 40, 22 relative to the models 22, 28 discussed with respect to FIG. 1C and utilized for POP. Any changes reflected in the models 22, 28 with respect to point P (e.g., point P becoming point P') on account of the POP is reflected in the point P associated with the models 40, 22 (see [block 135] of FIG. 1D). Thus, as can be understood from [block 140] of FIG. 1D and FIGS. 9A-9C, when the jig blank exterior surface model 232M is combined with the surface model 40 (or a surface model developed from the arthritic model 22) to create the jig model 346, the jig model 346 is referenced and oriented relative to point P' and is generally equivalent to the "jig data" 46 discussed with respect to [block 145] of FIG. 1E.

Because the jig model 346 is properly referenced and oriented relative to point P', the "saw cut and drill hole data" 44 discussed with respect to [block 125] of FIG. 1E can be properly integrated into the jig model 346 to arrive at the integrated jig model 348 depicted in FIGS. 10A-10B. The integrated jig model 348 includes the saw cuts 30, drill holes 32 and the surface model 40. Thus, the integrated jig model 348 is generally equivalent to the "integrated jig data" 48 discussed with respect to [block 150] of FIG. 1E.

Figure 11:
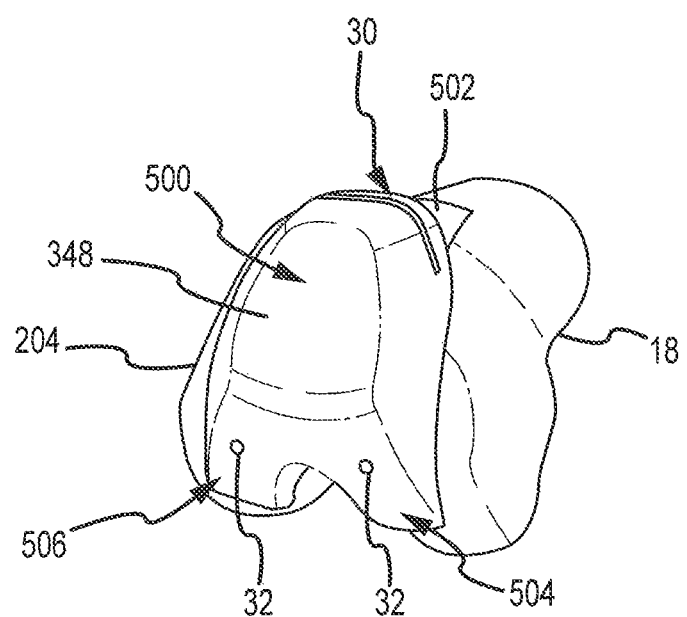
FIG. 11 illustrates a perspective view of the integrated jig model mating with the "arthritic model".

As can be understood from FIG. 11, which illustrates a perspective view of the integrated jig model 348 mating with the "arthritic model" 22, the interior surface 40 of the jig model 348 matingly receives the arthroplasty target area 42 of the femur lower end 204 such that the jig model 348 is indexed to mate with the area 42. (In some embodiments, the interior surface 40 includes areas of overestimation, described below, to accommodate for irregularities in the patient's bone surface.) Because of the referencing and orientation of the various models relative to the points P, P' throughout the procedure, the saw cut slot 30 and drill holes 32 are properly oriented to result in saw cuts and drill holes that allow a resulting femur jig 2A to restore a patient's joint to a pre-degenerated or natural alignment condition.

As indicated in FIG. 11, the integrated jig model 348 may include a jig body 500, a projection 502 on one side, and two projections 504, 506 the other side of jig body 500. The projections 504, 506 match the medial and lateral condyle cartilage. The projections 502, 504, 506 extend integrally from the two opposite ends of the jig body 500.

As can be understood from [blocks 155-165] of FIG. 1E, the integrated jig 348 or, more specifically, the integrated jig data 48 can be sent to the CNC machine 10 to machine the femur jig 2A from the selected jig blank 50A. For example, the integrated jig data 48 may be used to produce a production file that provides automated jig fabrication instructions to a rapid production machine 10, as described in the various Park patent applications referenced above. The rapid production machine 10 then fabricates the patient-specific arthroplasty femur jig 2A from the femur jig blank 50A according to the instructions.

The resulting femur jig 2A may have the features of the integrated jig model 348. Thus, as can be understood from FIG. 11, the resulting femur jig 2A may have the slot 30 and the drilling holes 32 formed on the projections 502, 504, 506, depending on the needs of the surgeon. The drilling holes 32 are configured to prevent the possible IR/ER (internal/external) rotational axis misalignment between the femoral cutting jig 2A and the patient's damaged joint surface during the distal femur cut portion of the TKR procedure. The slot 30 is configured to accept a cutting instrument, such as a reciprocating slaw blade for transversely cutting during the distal femur cut portion of the TKR.

f. Defining a 3D Surface Model of an Arthroplasty Target Area of a Tibia Upper End for Use as a Surface of an Interior Portion of a Tibia Arthroplasty Cutting Jig.

Figure 12A:
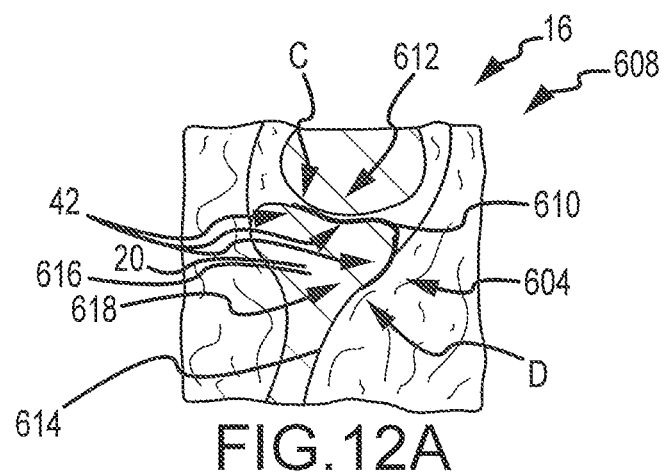
FIG. 12A is an anterior-posterior image slice of the damaged upper or knee joint end of the patient's tibia, wherein the image slice includes an open-loop contour line segment corresponding to the target area of the damaged upper end.
Figure 12B:
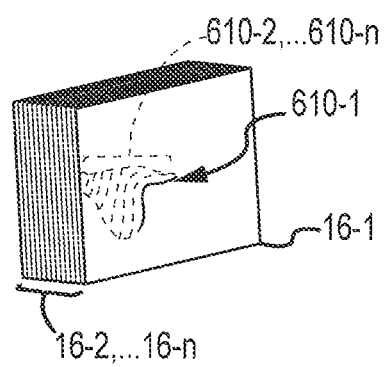
FIG. 12B is a plurality of image slices with their respective open-loop contour line segments, the open-loop contour line segments being accumulated to generate the 3D model of the target area.
Figure 12C:
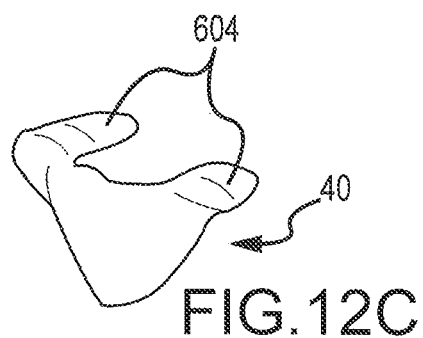
FIG. 12C is a 3D model of the target area of the damaged upper end as generated using the open-loop contour line segments depicted in FIG. 12B.

For a discussion of a method of generating a 3D model 40 of a target area 42 of a damaged upper end 604 of a patient's tibia 20, reference is made to FIGS. 12A-12C. FIG. 12A is an anterior-posterior ("AP") image slice 608 of the damaged upper or knee joint end 604 of the patient's tibia 20, wherein the image slice 608 includes an open-loop contour line segment 610 corresponding to the target area 42 of the damaged upper end 604. FIG. 12B is a plurality of image slices (16-1, 16-1, 16-2, . . . 16-n) with their respective open-loop contour line segments (610-1, 610-2, . . . 610-n), the open-loop contour line segments 610 being accumulated to generate the 3D model 40 of the target area 42. FIG. 12C is a 3D model 40 of the target area 42 of the damaged upper end 604 as generated using the open-loop contour line segments (16-1, 16-2, . . . 16-n) depicted in FIG. 12B.

As can be understood from FIGS. 1A, 1B and 12A, the imager 8 is used to generate a 2D image slice 16 of the damaged upper or knee joint end 604 of the patient's tibia 20. As depicted in FIG. 12A, the 2D image 16 may be an AP view of the tibia 20. Depending on whether the imager 8 is a MRI or CT imager, the image slice 16 will be a MRI or CT slice. The damaged upper end 604 includes the tibia plateau 612, an anterior tibia shaft surface 614, and an area of interest or targeted area 42 that extends along the tibia meniscus starting from a portion of the lateral tibia plateau surface to the anterior tibia surface 614. The targeted area 42 of the tibia upper end may be the articulating contact surfaces of the tibia upper end that contact corresponding articulating contact surfaces of the femur lower or knee joint end.

As shown in FIG. 12A, the image slice 16 may depict the cancellous bone 616, the cortical bone 618 surrounding the cancellous bone, and the articular cartilage lining portions of the cortical bone 618. The contour line 610 may extend along the targeted area 42 and immediately adjacent the cortical bone and cartilage to outline the contour of the targeted area 42 of the tibia upper end 604. The contour line 610 extends along the targeted area 42 starting at point C on the lateral or medial tibia plateau 612 (depending on whether the slice 16 extends through the lateral or medial portion of the tibia) and ends at point D on the anterior tibia shaft surface 614.

In one embodiment, as indicated in FIG. 12A, the contour line 610 extends along the targeted area 42, but not along the rest of the surface of the tibia upper end 604. As a result, the contour line 610 forms an open-loop that, as will be discussed with respect to FIGS. 12B and 12C, can be used to form an open-loop region or 3D computer model 40, which is discussed with respect to [block 140] of FIG. 1D and closely matches the 3D surface of the targeted area 42 of the tibia upper end. (In some embodiments, the 3D model 40 may be deliberately configured to be larger than the bone surface, in one or more areas, to accommodate for irregularities. See description below in the context of overestimating the tibial mating surface.) Thus, in one embodiment, the contour line is an open-loop and does not outline the entire cortical bone surface of the tibia upper end 604. Also, in one embodiment, the open-loop process is used to form from the 2D images 16 a 3D surface model 36 that generally takes the place of the arthritic model 36 discussed with respect to [blocks 125-140] of FIG. 1D and which is used to create the surface model 40 used in the creation of the "jig data" 46 discussed with respect to [blocks 145-150] of FIG. 1E.

In one embodiment and in contrast to the open-loop contour line 610 depicted in FIGS. 12A and 12B, the contour line is a closed-loop contour line generally the same as the closed-loop contour line 210' discussed with respect to FIGS. 2D-2E, except the closed-loop contour line pertains to a tibia instead of a femur. Like the femur closed-loop contour line discussed with respect to FIG. 2D, a tibia closed-loop contour line may outline the entire cortical bone surface of the tibia upper end and results in a closed-loop area. The tibia closed-loop contour lines are combined in a manner similar that discussed with respect to the femur contour lines in FIG. 2E. As a result, the tibia closed-loop area may require the analysis of the entire surface region of the tibia upper end and result in the formation of a 3D model of the entire tibia upper end 604 in a manner similar to the femur lower end 204 illustrated in FIG. 2F. Thus, the 3D surface model resulting from the tibia closed-loop process ends up having in common much, if not all, the surface of the 3D tibia arthritic model 36. In one embodiment, the tibia closed-loop process may result in a 3D volumetric anatomical joint solid model from the 2D images 16 via applying mathematical algorithms. U.S. Pat. No. 5,682,886, which was filed Dec. 26, 1995 and is incorporated by reference in its entirety herein, applies a snake algorithm forming a continuous boundary or closed-loop. After the tibia has been outlined, a modeling process is used to create the 3D surface model, for example, through a Bézier patches method. Other 3D modeling processes, e.g., commercially-available 3D construction software as listed in other parts of this Detailed Description, are applicable to 3D surface model generation for closed-loop, volumetric solid modeling.

In one embodiment, the closed-loop process is used to form from the 2D images 16 a 3D volumetric solid model 36 that is essentially the same as the arthritic model 36 discussed with respect to [blocks 125-140] of FIG. 1D. The 3D volumetric solid model 36 is used to create the surface model 40 used in the creation of the "jig data" 46 discussed with respect to [blocks 145-150] of FIG. 1E.

The formation of a 3D volumetric solid model of the entire tibia upper end employs a process that may be much more memory and time intensive than using an open-loop contour line to create a 3D model of the targeted area 42 of the tibia upper end. Accordingly, although the closed-loop methodology may be utilized for the systems and methods disclosed herein, for at least some embodiments, the open-loop methodology may be preferred over the closed-loop methodology.

An example of a closed-loop methodology is disclosed in U.S. patent application Ser. No. 11/641,569 to Park, which is entitled "Improved Total Joint Arthroplasty System" and was filed Jan. 19, 2007. This application is incorporated by reference in its entirety into this Detailed Description.

As can be understood from FIGS. 12B and 2G, the imager 8 generates a plurality of image slices (16-1, 16-2 . . . 16-n) via repetitive imaging operations [block 1000]. Each image slice 16 has an open-loop contour line (610-1, 610-2 . . . 610-n) extending along the targeted region 42 in a manner as discussed with respect to FIG. 12A [block 1005]. In one embodiment, each image slice is a two-millimeter 2D image slice 16. The system 4 compiles the plurality of 2D image slices (16-1, 16-2 . . . 16-n) and, more specifically, the plurality of open-loop contour lines (610-1, 610-2, . . . 610-n) into the 3D femur surface computer model 40 depicted in FIG. 12C [block 1010]. This process regarding the generation of the surface model 40 is also discussed in the overview section with respect to [blocks 100-105] of FIG. 1B and [blocks 130-140] of FIG. 1D. A similar process may be employed with respect to tibia closed-loop contour lines As can be understood from FIG. 12C, the 3D tibia surface computer model 40 is a 3D computer representation of the targeted region 42 of the tibia upper end. In one embodiment, the 3D representation of the targeted region 42 is a 3D representation of the articulated femur contact surfaces of the tibia proximal end. As the open-loop generated 3D model 40 is a surface model of the relevant femur contacting portions of the tibia upper end, as opposed to a 3D model of the entire surface of the tibia upper end as would be a result of a closed-loop contour line, the open-loop generated 3D model 40 is less time and memory intensive to generate.

In one embodiment, the open-loop generated 3D model 40 is a surface model of the femur facing end face of the tibia upper end, as opposed a 3D model of the entire surface of the tibia upper end. The 3D model 40 can be used to identify the area of interest or targeted region 42, which, as previously stated, may be the relevant femur contacting portions of the tibia upper end. Again, the open-loop generated 3D model 40 is less time and memory intensive to generate as compared to a 3D model of the entire surface of the tibia proximal end, as would be generated by a closed-loop contour line. Thus, for at least some versions of the embodiments disclosed herein, the open-loop contour line methodology is preferred over the closed-loop contour line methodology. However, the system 4 and method disclosed herein may employ either the open-loop or closed-loop methodology and should not be limited to one or the other.

Regardless of whether the 3D model 40 is a surface model of the targeted region 42 (i.e., a 3D surface model generated from an open-loop process and acting as the arthritic model 22) or the entire femur facing end face of the tibia upper end (i.e., a 3D volumetric solid model generated from a closed-loop process and acting as the arthritic model 22), the data pertaining to the contour lines 610 can be converted into the 3D contour computer model 40 via the surface rendering techniques disclosed in any of the aforementioned U.S. patent applications to Park. For example, surface rending techniques employed include point-to-point mapping, surface normal vector mapping, local surface mapping, and global surface mapping techniques. Depending on the situation, one or a combination of mapping techniques can be employed.

In one embodiment, the generation of the 3D model 40 depicted in FIG. 12C may be formed by using the image slices 16 to determine location coordinate values of each of a sequence of spaced apart surface points in the open-loop region of FIG. 12B. A mathematical model may then be used to estimate or compute the 3D model 40 in FIG. 12C. Examples of other medical imaging computer programs that may be used include, but are not limited to: Analyze from AnalyzeDirect, Inc. of Overland Park, Kans.; open-source software such as Paraview of Kitware, Inc.; Insight Toolkit ("ITK") available at www.itk.org; 3D Slicer available at www.slicer.org; and Mimics from Materialise of Ann Arbor, Mich.

Alternatively or additionally to the aforementioned systems for generating the 3D model 40 depicted in FIG. 12C, other systems for generating the 3D model 40 of FIG. 12C include the surface rendering techniques of the Non-Uniform Rational B-spline ("NURB") program or the Bézier program. Each of these programs may be employed to generate the 3D contour model 40 from the plurality of contour lines 610.

In one embodiment, the NURB surface modeling technique is applied to the plurality of image slices 16 and, more specifically, the plurality of open-loop contour lines 610 of FIG. 2B. The NURB software generates a 3D model 40 as depicted in FIG. 12C, wherein the 3D model 40 has areas of interest or targeted regions 42 that contain both a mesh and its control points. For example, see Ervin et al., Landscape Modeling, McGraw-Hill, 2001, which is hereby incorporated by reference in its entirety into this Detailed Description.

In one embodiment, the NURB surface modeling technique employs the following surface equation:

$$G(s, t) = \frac{\sum_{i=0}^{k1} \sum_{j=0}^{k2} W(i, j) P(i, j) b_i(s) b_j(t)}{\sum_{i=0}^{k1} \sum_{j=0}^{k2} W(i, j) b_i(s) b_j(t)},$$

wherein P(i,j) represents a matrix of vertices with nrows=(k1+1) and ncols=(k2+1), W(i,j) represents a matrix of vertex weights of one per vertex point, $b_i(s)$ represents a row-direction basis or blending of polynomial functions of degree M1, $b_j(t)$ represents a column-direction basis or blending polynomial functions of degree M2, s represents a parameter array of row-direction knots, and t represents a parameter array of column-direction knots.

In one embodiment, the Bézier surface modeling technique employs the Bézier equation (1972, by Pierre Bézier) to generate a 3D model 40 as depicted in FIG. 12C, wherein the model 40 has areas of interest or targeted regions 42. A given Bézier surface of order (n, m) is defined by a set of (n+1)(m+1) control points $k_{i,j}$. It maps the unit square into a smooth-continuous surface embedded within a space of the same dimensionality as ($k_{i,j}$). For example, if k are all points in a four-dimensional space, then the surface will be within a four-dimensional space. This relationship holds true for a one-dimensional space, a two-dimensional space, a fifty-dimensional space, etc.

A two-dimensional Bézier surface can be defined as a parametric surface where the position of a point p as a function of the parametric coordinates u, v is given by:

$$p(u, v) = \sum_{i=0}^{n} \sum_{j=0}^{m} B_i^n(u) B_j^m(v) k_{i,j}$$

evaluated over the unit square, where $$B_i^n(u) = \binom{n}{i} u^i (1-u)^{n-i}$$

is a Bernstein polynomial and $$\binom{n}{i} = \frac{n!}{i! * (n-i)!}$$

is the binomial coefficient. See Grune et al, *On Numerical Algorithm and Interactive Visualization for Optimal Control Problems*, Journal of Computation and Visualization in Science, Vol. 1, No. 4, July 1999, which is hereby incorporated by reference in its entirety into this Detailed Description.

Various other surface rendering techniques are disclosed in other references. For example, see the surface rendering techniques disclosed in the following publications: Lorensen et al., *Marching Cubes: A high Resolution 3d Surface Construction Algorithm*, Computer Graphics, 21-3: 163-169, 1987; Farin et al., *NURB Curves & Surfaces: From Projective Geometry to Practical Use*, Wellesley, 1995; Kumar et al, *Robust Incremental Polygon Triangulation for Surface Rendering*, WSCG, 2000; Fleischer et al., *Accurate Polygon Scan Conversion Using Half-Open Intervals*, Graphics Gems III, p. 362-365, code: p. 599-605, 1992; Foley et al., *Computer Graphics: Principles and Practice*, Addison Wesley, 1990; Glassner, *Principles of Digital Image Synthesis*, Morgan Kaufmann, 1995, all of which are hereby incorporated by reference in their entireties into this Detailed Description.

g. Selecting a Jig Blank Most Similar in Size and/or Configuration to the Size of the Patient's Tibia Upper End.

As mentioned above, an arthroplasty jig 2, such as a tibia jig 2B includes an interior portion 104 and an exterior portion 106. The tibia jig 2B is formed from a tibia jig blank 50B, which, in one embodiment, is selected from a finite number of femur jig blank sizes. The selection of the tibia jig blank 50B is based on a comparison of the dimensions of the patient's tibia upper end 604 to the dimensions and/or configurations of the various sizes of tibia jig blanks 50B to select the tibia jig blank 50B most closely resembling the patient's tibia upper end 604 with respect to size and/or configuration. This selected tibia jig blank 50B has an outer or exterior side or surface 632 that forms the exterior portion 632 of the tibia jig 2B. The 3D surface computer model 40 discussed with respect to the immediately preceding section of this Detail Description is used to define a 3D surface 40 into the interior side 630 of the computer model of a tibia jig blank 50B. Furthermore, in some embodiments, the overestimation of the procedure described below may be used to adjust the 3D surface model 40.

By selecting a tibia jig blank 50B with an exterior portion 632 close in size to the patient's upper tibia end 604, the potential for an accurate fit between the interior portion 630 and the patient's tibia is increased. Also, the amount of material that needs to be machined or otherwise removed from the jig blank 50B is reduced, thereby reducing material waste and manufacturing time.

Figure 13A:
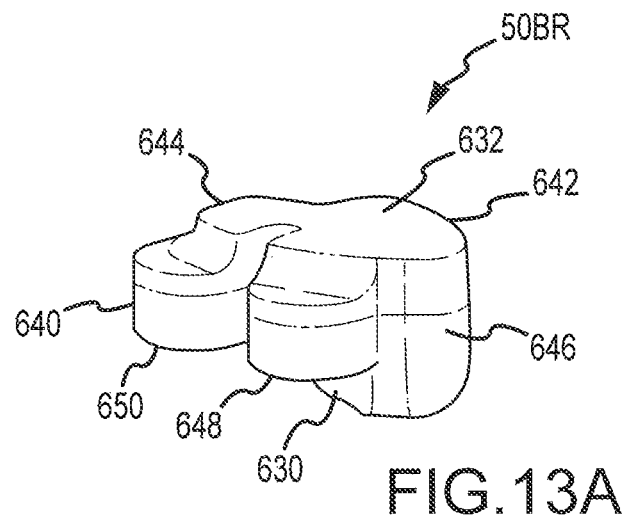
FIG. 13A is a top perspective view of a right tibia cutting jig blank having predetermined dimensions.

For a discussion of a method of selecting a jig blank 50 most closely corresponding to the size and/or configuration of the patient's upper tibia end, reference is first made to FIGS. 13A-14B. FIG. 13A is a top perspective view of a right tibia cutting jig blank 50BR having predetermined dimensions. FIG. 13B is a bottom perspective view of the jig blank 50BR depicted in FIG. 13A. FIG. 13C is plan view of an exterior side or portion 232 of the jig blank 50BR depicted in FIG. 13A. FIG. 14A is a plurality of available sizes of right tibia jig blanks 50BR, each depicted in the same view as shown in FIG. 13C. FIG. 14B is a plurality of available sizes of left tibia jig blanks, each depicted in the same view as shown in FIG. 13C.

Figure 13B:
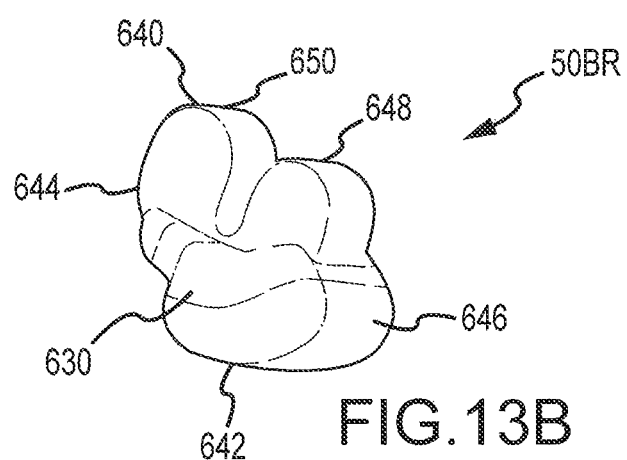
FIG. 13B is a bottom perspective view of the jig blank depicted in FIG. 13A.
Figure 13C:
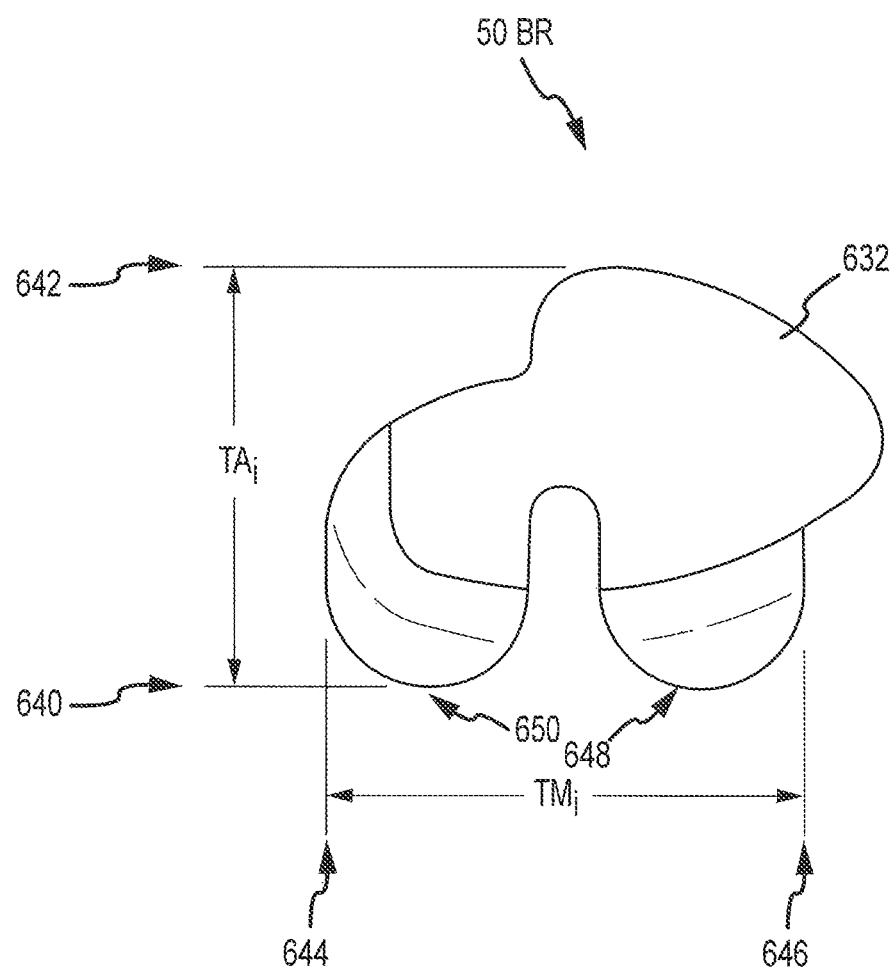
FIG. 13C is plan view of an exterior side or portion of the jig blank depicted in FIG. 13A.

A common jig blank 50, such as the right jig blank 50BR depicted in FIGS. 13A-13C and intended for creation of a right tibia jig that can be used with a patient's right tibia, may include a medial tibia foot projection 648 for mating with the medial tibia plateau, a lateral tibia foot projection 650 for mating with the lateral tibia plateau, a posterior edge 640, an anterior edge 642, a lateral edge 644, a medial edge 646, the exterior side 632 and the interior side 630. The jig blank 50BR of FIGS. 13A-13C may be any one of a number of right tibia jig blanks 50BR available in a limited number of standard sizes. For example, the jig blank 50BR of FIGS. 13A-13C may be an i-th right tibia jig blank, where i=1, 2, 3, 4, . . . m and m represents the maximum number of right tibia jig blank sizes.

As indicated in FIG. 13C, the anterior-posterior extent TAi of the jig blank 50BR is measured from the anterior edge 642 to the posterior edge 640 of the jig blank 50BR. The medial-lateral extent TMi of the jig blank 50BR is measured from the lateral edge 644 to the medial edge 646 of the jig blank 50BR.

As can be understood from FIG. 14A, a limited number of right tibia jig blank sizes may be available for selection as the right tibia jig blank size to be machined into the right tibia cutting jig 2B. For example, in one embodiment, there are three sizes (m=3) of right tibia jig blanks 50BR available. As can be understood from FIG. 13C, each tibia jig blank 50BR has an anterior-posterior/medial-lateral aspect ratio defined as TAi to TMi (e.g., "TAi/TMi" aspect ratio). Thus, as can be understood from FIG. 14A, jig blank 50BR-1 has an aspect ratio defined as "$TA_1/TM_1$", jig blank 50BR-2 has an aspect ratio defined as "$TA_2/TM_2$", and jig blank 50BR-3 has an aspect ratio defined as "$TA_3/TM_3$".

The jig blank aspect ratio is utilized to design right tibia jigs 2B dimensioned specific to the patient's right tibia features. In one embodiment, the jig blank aspect ratio can be the exterior dimensions of the right tibia jig 2B. In another embodiment, the jig blank aspect ratio can apply to the right tibia jig fabrication procedure for selecting the right jig blank 50BR having parameters close to the dimensions of the desired right tibia jig 2B. This embodiment can improve the cost efficiency of the right tibia jig fabrication process because it reduces the amount of machining required to create the desired jig 2 from the selected jig blank 50.

In FIG. 14A there is a single jig blank aspect ratio depicted for the candidate tibia jig blank sizes. In embodiments having a greater number of jig blank aspect ratios for the candidate tibia jig blank sizes, FIG. 14A would be similar to FIG. 4A and would have an N-1 direction, and potentially N-2 and N-3 directions, representing increasing jig blank aspect ratios. The relationships between the various tibia jig blank aspect ratios would be similar to those discussed with respect to FIG. 4A for the femur jig blank aspect ratios.

As can be understood from the plot 900 depicted in FIG. 17 and discussed later in this Detailed Discussion, the E-1 direction corresponds to the sloped line joining Group 1, Group 2 and Group 3 in the plot 900.

As indicated in FIG. 14A, along direction E-1, the jig blank aspect ratios remain the same among jigs blanks 50BR-1, 50BR-2 and 50BR-3, where "$TA_1/TM_1$"="$TA_2/TM_2$"="$TA_3/TM_3$". However, comparing to jig blank 50BR-1, jig blank 50BR-2 is dimensioned larger and longer than jig blank 50BR-1. This is because the $TA_2$ value for jig blank 50BR-2 increases proportionally with the increment of its $TM_2$ value in certain degrees in all X, Y, and Z-axis directions. In a similar fashion, jig blank 50BR-3 is dimensioned larger and longer than jig blank 50BR-2 because the $TA_3$ increases proportionally with the increment of its $TM_3$ value in certain degrees in all X, Y, and Z-axis directions. One example of the increment can be an increase from 5% to 20%. In embodiments where there are additional aspect ratios available for the tibia jig blank sizes, as was illustrated in FIG. 4A with respect to the femur jig blank sizes, the relationship between tibia jig blank sizes may be similar to that discussed with respect to FIGS. 4A and 14A.

As can be understood from FIG. 14B, a limited number of left tibia jig blank sizes may be available for selection as the left tibia jig blank size to be machined into the left tibia cutting jig 2B. For example, in one embodiment, there are three sizes (m=3) of left tibia jig blanks 50BL available. As can be understood from FIG. 13C, each tibia jig blank 50BL has an anterior-posterior/medial-lateral aspect ratio defined as TAi to TMi (e.g., "TAi/TMi" aspect ratio). Thus, as can be understood from FIG. 14B, jig blank 50BL-1 has an aspect ratio defined as "$TA_1/TM_1$", jig blank 50BL-2 has an aspect ratio defined as "$TA_2/TM_2$", and jig blank 50BL-3 has an aspect ratio defined as "$TA_3/TM_3$".

The jig blank aspect ratio is utilized to design left tibia jigs 2B dimensioned specific to the patient's left tibia features. In one embodiment, the jig blank aspect ratio can be the exterior dimensions of the left tibia jig 2B. In another embodiment, the jig blank aspect ratio can apply to the left tibia jig fabrication procedure for selecting the left jig blank 50BL having parameters close to the dimensions of the desired left tibia jig 2B. This embodiment can improve the cost efficiency of the left tibia jig fabrication process because it reduces the amount of machining required to create the desired jig 2 from the selected jig blank 50.

In FIG. 14B there is a single jig blank aspect ratio depicted for the candidate tibia jig blank sizes. In embodiments having a greater number of jig blank aspect ratios for the candidate tibia jig blank sizes, FIG. 14B would be similar to FIG. 4B and would have an N-1 direction, and potentially N-2 and N-3 directions, representing increasing jig blank aspect ratios. The relationships between the various tibia jig blank aspect ratios would be similar to those discussed with respect to FIG. 4B for the femur jig blank aspect ratios.

As indicated in FIG. 14B, along direction E-1, the jig blank aspect ratios remain the same among jigs blanks 50BL-1, 50BL-2 and 50BL-3, where "$TA_1/TM_1$"="$TA_2/TM_2$"="$TA_3/TM_3$". However, comparing to jig blank 50BL-1, jig blank 50BL-2 is dimensioned larger and longer than jig blank 50BL-1. This is because the $TA_2$ value for jig blank 50BL-2 increases proportionally with the increment of its $TM_2$ value in certain degrees in all X, Y, and Z-axis directions. In a similar fashion, jig blank 50BL-3 is dimensioned larger and longer than jig blank 50BL-2 because the $TA_3$ increases proportionally with the increment of its $TM_3$ value in certain degrees in all X, Y, and Z-axis directions. One example of the increment can be an increase from 5% to 20%. In embodiments where there are additional aspect ratios available for the tibia jig blank sizes, as was illustrated in FIG. 4B with respect to the femur jig blank sizes, the relationship between tibia jig blank sizes may be similar to that discussed with respect to FIGS. 4B and 14B.

Figure 15:
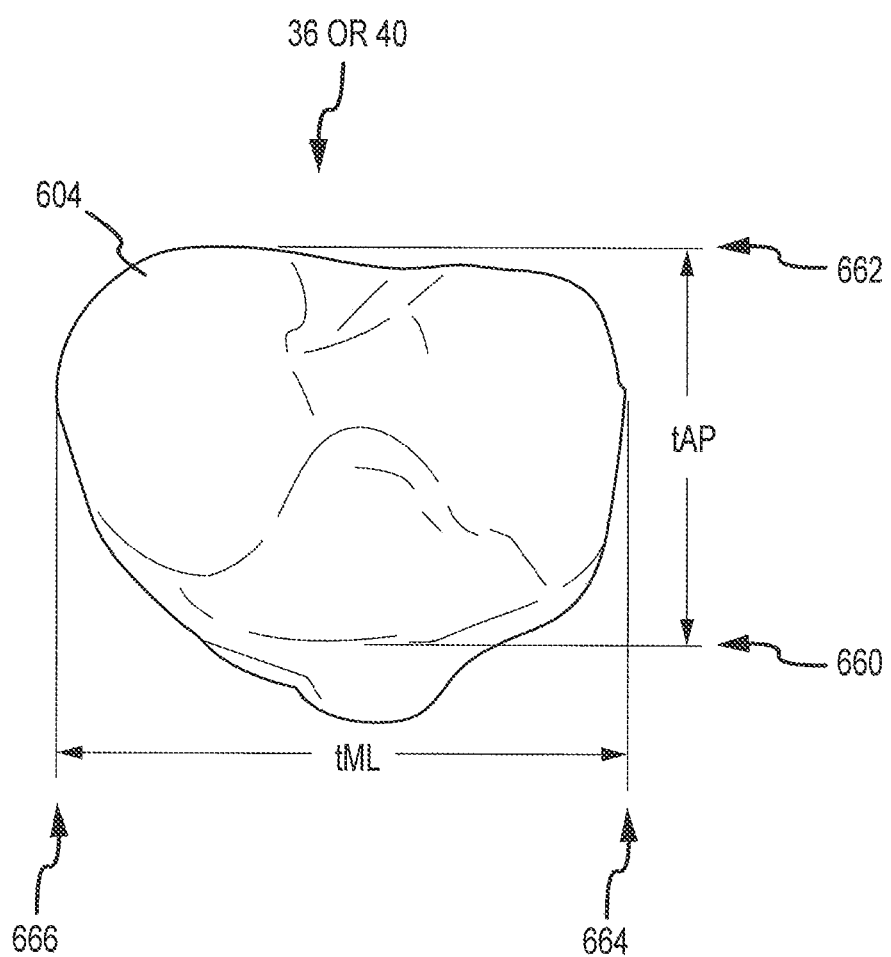
FIG. 15 is an axial view of the 3D surface model or arthritic model of the patient's right tibia as viewed in a direction extending proximal to distal.

The dimensions of the upper or knee joint forming end 604 of the patient's tibia 20 can be determined by analyzing the 3D surface model 40 or 3D arthritic model 36 in a manner similar to those discussed with respect to the jig blanks 50. For example, as depicted in FIG. 15, which is an axial view of the 3D surface model 40 or arthritic model 36 of the patient's right tibia 20 as viewed in a direction extending proximal to distal, the upper end 604 of the surface model 40 or arthritic model 36 may include an anterior edge 660, a posterior edge 662, a medial edge 664 and a lateral edge 666. The tibia dimensions may be determined for the top end face or femur articulating surface 604 of the patient's tibia 20 via analyzing the 3D surface model 40 of the 3D arthritic model 36. These tibia dimensions can then be utilized to configure tibia jig dimensions and select an appropriate tibia jig.

As shown in FIG. 15, the anterior-posterior extent tAP of the upper end 604 of the patient's tibia 20 (i.e., the upper end 604 of the surface model 40 of the arthritic model 36, whether formed via open or closed-loop analysis) is the length measured from the anterior edge 660 of the tibia plateau to the posterior edge 662 of the tibia plateau. The medial-lateral extent tML of the upper end 604 of the patient's tibia 20 is the length measured from the medial edge 664 of the medial tibia plateau to the lateral edge 666 of the lateral tibia plateau.

In one embodiment, the anterior-posterior extent tAP and medial-lateral extent tML of the tibia upper end 604 can be used for an aspect ratio tAP/tML of the tibia upper end. The aspect ratios tAP/tML of a large number (e.g., hundreds, thousands, tens of thousands, etc.) of patient knees can be compiled and statistically analyzed to determine the most common aspect ratios for jig blanks that would accommodate the greatest number of patient knees. This information may then be used to determine which one, two, three, etc. aspect ratios would be most likely to accommodate the greatest number of patient knees.

The system 4 analyzes the upper ends 604 of the patient's tibia 20 as provided via the surface model 40 of the arthritic model 36 (whether the arthritic model 36 is an 3D surface model generated via an open-loop or a 3D volumetric solid model generated via a closed-loop process), to obtain data regarding anterior-posterior extent tAP and medial-lateral extent tML of the tibia upper ends 604. As can be understood from FIG. 16, which depicts the selected model jig blank 50BR of FIG. 13C superimposed on the model tibia upper end 604 of FIG. 15, the tibia dimensional extents tAP, tML are compared to the jig blank dimensional extents TAi, TMi to determine which jig blank model to select as the starting point for the machining process and the exterior surface model for the jig model.

Figure 16:
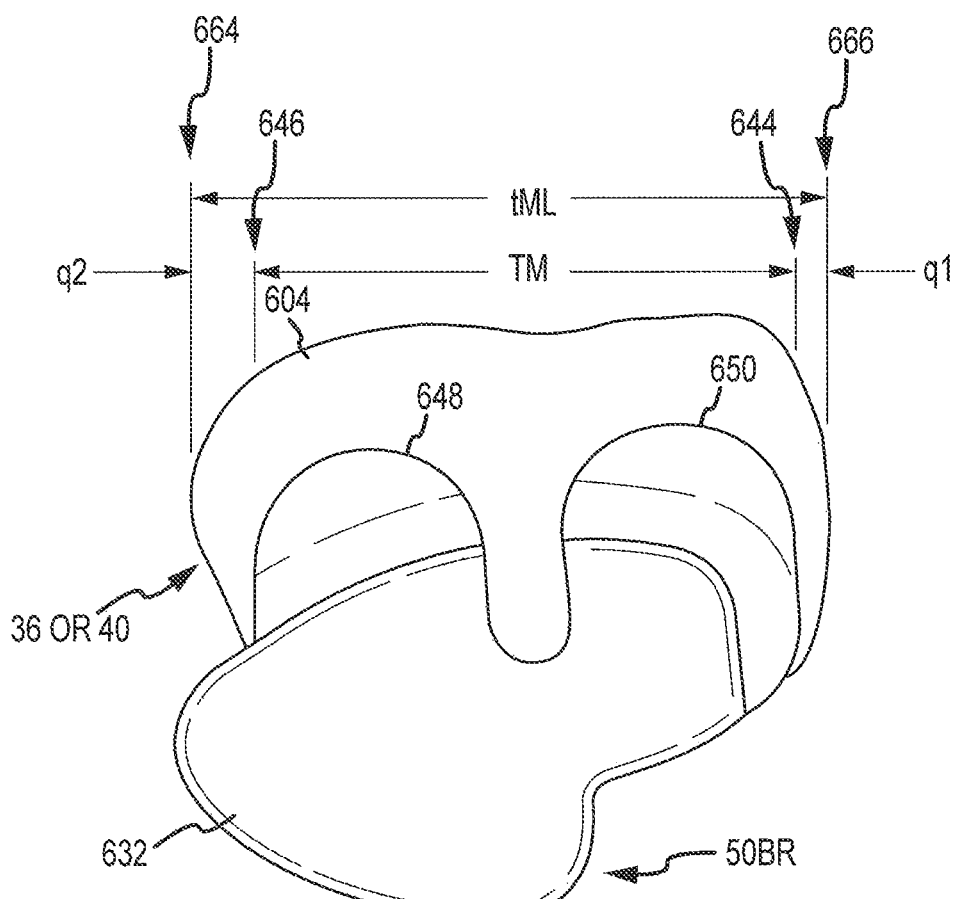
FIG. 16 depicts the selected model jig blank of FIG. 13C superimposed on the model tibia upper end of FIG. 15.

As shown in FIG. 16, a prospective right tibia jig blank 50BR is superimposed to mate with the right tibia upper end 604 of the patient's anatomical model as represented by the surface model 40 or arthritic model 36. In one embodiment, the jig blank 50BR may cover the anterior approximately two thirds of the tibia plateau, leaving the posterior approximately one third of the tibia exposed. Included in the exposed portion of the tibia plateau are lateral and medial exposed regions of the tibia plateau, as respectively represented by regions q1 and q2 in FIG. 16. Specifically, exposed region q1 is the region of the exposed tibia plateau between the tibia and jig blank lateral edges 666, 644, and exposed region q2 is the region of the exposed tibia plateau between the tibia and jig blank medial edges 664, 646.

By obtaining and employing the tibia anterior-posterior tAP data and the tibia medial-lateral tML data, the system 4 can size the tibia jig blank 50BR according to the following formula: jTML=tML−q1−q2, wherein jTML is the medial-lateral extent of the tibia jig blank 50BR. In one embodiment, q1 and q2 will have the following ranges: 2 mm≤q1≤4 mm; and 2 mm≤q2≤4 mm. In another embodiment, q1 will be approximately 3 mm and q2 will approximately 3 mm.

Figure 17A:
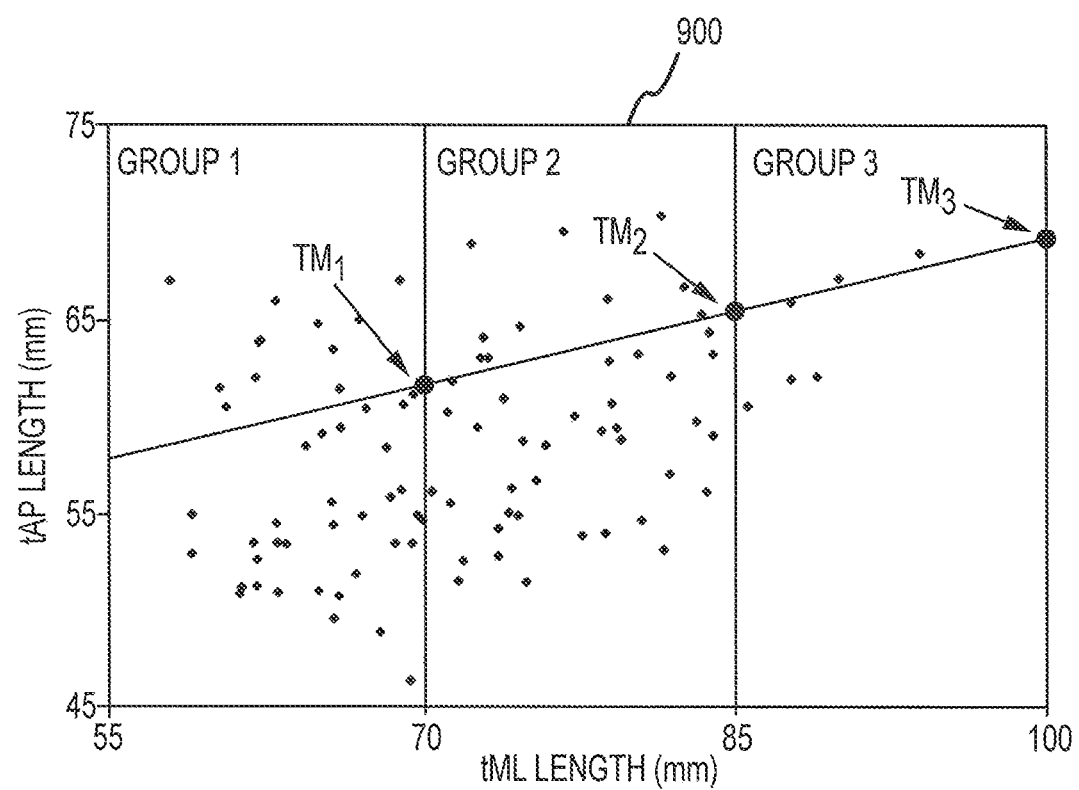
FIG. 17A is an example scatter plot for selecting from a plurality of candidate jig blanks sizes a jig blank size appropriate for the upper end of the patient's tibia.

FIG. 17A is an example scatter plot 900 for selecting from a plurality of candidate jig blanks sizes a jig blank size appropriate for the upper end 604 of the patient's tibia 20. In one embodiment, the X-axis represents the patient's tibia medial-lateral length tML in millimeters, and the Y-axis represents the patient's tibia anterior-posterior length tAP in millimeters. In one embodiment, the plot 900 is divided into a number of jig blank size groups, where each group encompasses a region of the plot 900 and is associated with a specific parameter $TM_r$ of a specific candidate jig blank size.

In one embodiment, the example scatter plot 900 depicted in FIG. 17A has three jig blank size groups, each group pertaining to a single candidate jig blank size. However, depending on the embodiment, a scatter plot 900 may have a greater or lesser number of jig blank size groups. The higher the number of jig blank size groups, the higher the number of the candidate jig blank sizes and the more dimension specific a selected candidate jig blank size will be to the patient's knee features and the resulting jig 2. The more dimension specific the selected candidate jig blank size, the lower the amount of machining required to produce the desired jig 2 from the selected jig blank 50.

Conversely, the lower the number of jig blank size groups, the lower the number of candidate jig blank sizes and the less dimension specific a selected candidate jig blank size will be to the patient's knee features and the resulting jig 2. The less dimension specific the selected candidate jig blank size, the higher the amount of machining required to produce the desired jig 2 from the selected jig blank 50, adding extra roughing during the jig fabrication procedure.

The tibia anterior-posterior length tAP may be relevant because it may serve as a value for determining the aspect ratio $TA_i/TM_i$. for tibia jig blanks 50B such as those discussed with respect to FIGS. 13C-14B and 17A. Despite this, in some embodiments, tibia anterior-posterior length $TA_i$ of the candidate jig blanks may not be reflected in the plot 900 depicted in FIG. 17A or the relationship depicted in FIG. 16 because in a practical setting for some embodiments, tibia jig anterior-posterior length may be less significant than tibia jig medial-lateral length. For example, although a patient's tibia anterior-posterior distance varies according to their knee features, the length of the foot projection 800, 802 (see FIG. 20A) of a tibia jig 2B is simply increased without the need to create a jig blank or jig that is customized to correspond to the tibia anterior-posterior length TAi. In other words, in some embodiments, the only difference in anterior-posterior length between various tibia jigs is the difference in the anterior-posterior length of their respective foot projections 800, 802.

Figure 21:
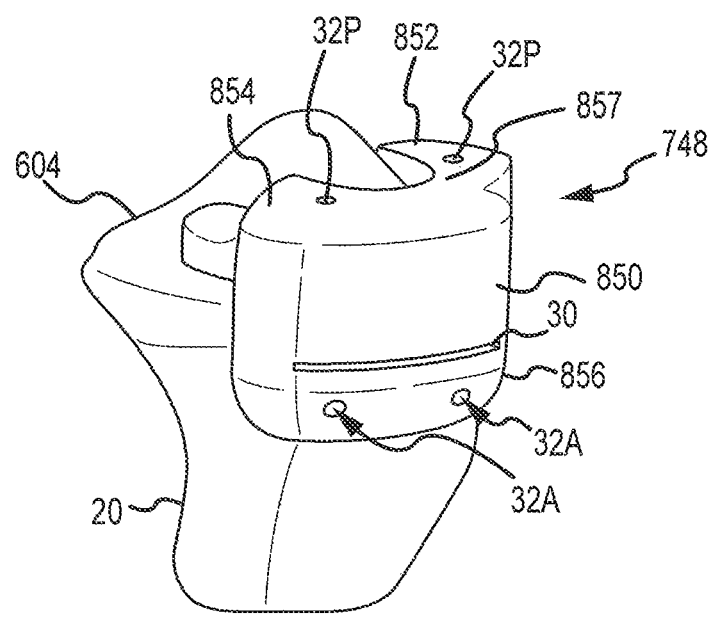
FIG. 21 illustrates a perspective view of the integrated jig model mating with the "arthritic model".

In some embodiments, as can be understood from FIGS. 16 and 21, the anterior-posterior length of a tibia jig 2B, with its foot projection 800, 802, covers approximately half of the tibia plateau. Due in part to this "half" distance coverage, which varies from patient-to-patient by only millimeters to a few centimeter, in one embodiment, the anterior-posterior length of the jig may not be of a significant concern. However, because the jig may cover a substantial portion of the medial-lateral length of the tibia plateau, the medial-lateral length of the jig may be of substantial significance as compared to the anterior-posterior length.

While in some embodiments the anterior-posterior length of a tibia jig 2B may not be of substantial significance as compared to the medial-lateral length, in some embodiments the anterior-posterior length of the tibia jig is of significance.

In such an embodiment, jig sizes may be indicated in FIG. 17A by their aspect ratios $TA_i/TM_i$ as opposed to just $TM_i$. In other words, the jig sizes may be depicted in FIG. 17A in a manner similar to that depicted in FIG. 7A. Furthermore, in such embodiments, FIGS. 14A and 14B may have additional jig blank ratios similar to that depicted in FIGS. 4A and 4B. As a result, the plot 900 of 17A may have additional diagonal lines joining the jig blank sizes belonging to each jig blank ratio in a manner similar to that depicted in plot 300 of FIG. 7A. Also, in FIG. 17A and in a manner similar to that shown in FIG. 7A, there may be additional horizontal lines dividing plot 900 according to anterior-posterior length to represent the boundaries of the various jig blank sizes.

As can be understood from FIG. 17A, in one embodiment, the three jig blank size groups of the plot 900 have parameters $TM_r$, $TA_r$, as follows. Group 1 has parameters $TM_1$, TA1. $TM_1$ represents the medial-lateral extent of the first tibia jig blank size, wherein $TM_1$=70 mm. $TA_1$ represents the anterior-posterior extent of the first femoral jig blank size, wherein $TA_1$=62 mm. Group 1 covers the patient's tibia tML and tAP data wherein 55 mm<tML<70 mm and 45 mm<tAP<75 mm.

Group 2 has parameters $TM_2$, TA2. $TM_2$ represents the medial-lateral extent of the second tibia jig blank size, wherein $TM_2$=85 mm. $TA_2$ represents the anterior-posterior extent of the second femoral jig blank size, wherein $TA_2$=65 mm. Group 2 covers the patient's tibia tML and tAP data wherein 70 mm<tML<85 mm and 45 mm<tAP<75 mm.

Group 3 has parameters $TM_3$, TA3. $TM_3$ represents the medial-lateral extent of the third tibia jig blank size, wherein $TM_3$=100 mm. $TA_3$ represents the anterior-posterior extent of the second femoral jig blank size, wherein $TA_3$=68.5 mm. Group 3 covers the patient's tibia tML and tAP data wherein 85 mm<tML<100 mm and 45 mm<tAP<75 mm.

In some embodiments and in contrast to the selection process for the femur jig blanks discussed with respect to FIGS. 3A-7B, the tibia jig blank selection process discussed with respect to FIGS. 13A-17B may only consider or employ the medial-lateral tibia jig value jTML and related medial-lateral values TMi, tML. Accordingly, in such embodiments, the anterior-posterior tibia jig value JTAP and related anterior-posterior values TAi, tAP for the tibia jig and tibia plateau are not considered.

Figure 17B:
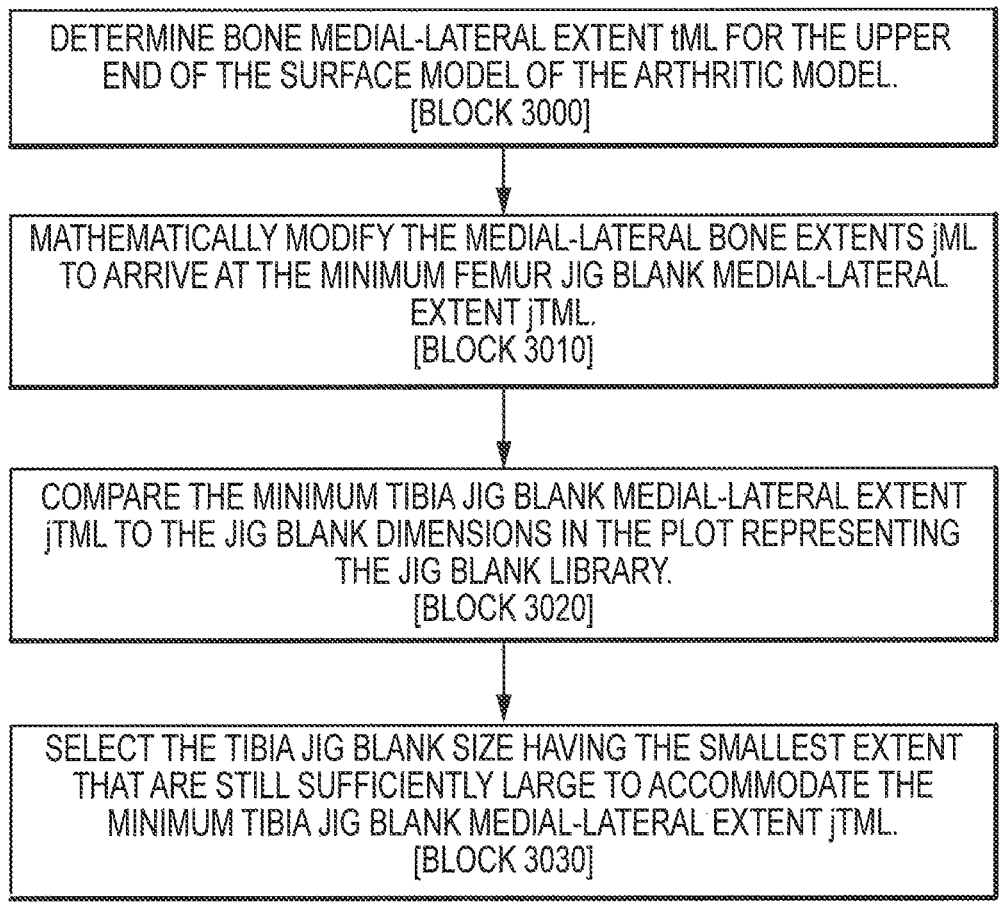
FIG. 17B is a flow diagram illustrating an embodiment of a process of selecting an appropriately sized jig blank.

As can be understood from FIG. 17B, which is a flow diagram illustrating an embodiment of a process of selecting an appropriately sized jig blank, the bone medial-lateral extent tML is determined for the upper end 604 of the surface model 40 of the arthritic model 36 [block 3000]. The medial-lateral bone extent tML of the upper end 604 is mathematically modified according to the above discussed jTML formula to arrive at the minimum tibia jig blank medial-lateral extent jTML [block 3010]. The mathematically modified bone medial-lateral extent tML or, more specifically, the minimum tibia jig blank medial-lateral extent jTML is referenced against the jig blank dimensions in the plot 900 of FIG. 17A [block 3020]. The plot 900 may graphically represent the extents of candidate tibia jig blanks forming a jig blank library. The tibia jig blank 50B is selected to be the jig blank size having the smallest extents that are still sufficiently large to accommodate the minimum tibia jig blank medial-lateral extent jTML [block 3030].

In one embodiment, the exterior of the selected jig blank size is used for the exterior surface model of the jig model, as discussed below. In one embodiment, the selected jig blank size corresponds to an actual jig blank that is placed in the CNC machine and milled down to the minimum tibia jig blank anterior-posterior and medial-lateral extents jTAP, jTML to machine or otherwise form the exterior surface of the tibia jig 2B The method outlined in FIG. 17B and in reference to the plot 900 of FIG. 17A can be further understood from the following example. As measured in FIG. 16 with respect to the upper end 604 of the patient's tibia 20, the extents of the patient's tibia are as follows: tML=85.2 mm [block 3000]. As previously mentioned, the upper end 604 may be part of the surface model 40 of the arthritic model 36. Once the tML measurement is determined from the upper end 604, the corresponding jig jTML data can be determined via the above-described jTML formula: jTML=tML−q1−q2, wherein q1=3 mm and q2=3 mm [block 3010]. The result of the jTML formula is jTML=79.2 mm.

As can be understood from the plot 900 of FIG. 17A, the determined jig data (i.e., jTML=79.2 mm) falls in Group 2 of the plot 900. Group 2 has the predetermined tibia jig blank parameters ($TM_2$) of $TM_2$=85 mm. This predetermined tibia jig blank parameter is the smallest of the various groups that are still sufficiently large to meet the minimum tibia blank extents jTML [block 3020]. This predetermined tibia jig blank parameters ($TM_2$=85 mm) may be selected as the appropriate tibia jig blank size [block 3030].

In one embodiment, the predetermined tibia jig blank parameter (85 mm) can apply to the tibia exterior jig dimensions as shown in FIG. 13C. In other words, the jig blank exterior is used for the jig model exterior as discussed with respect to FIGS. 18A-19C. Thus, the exterior of the tibia jig blank 50B undergoes no machining, and the unmodified exterior of the jig blank 50B with its predetermined jig blank parameter (85 mm) serves as the exterior of the finished tibia jig 2B.

In another embodiment, the tibia jig blank parameter (85 mm) can be selected for jig fabrication in the machining process. Thus, a tibia jig blank 50B having a predetermined parameter (85 mm) is provided to the machining process such that the exterior of the tibia jig blank 50B will be machined from its predetermined parameter (85 mm) down to the desired tibia jig parameter (79.2 mm) to create the finished exterior of the tibia jig 2B. As the predetermined parameter (85 mm) is selected to be relatively close to the desired femur jig parameter (79.2 mm), machining time and material waste are reduced.

While it may be advantageous to employ the above-described jig blank selection method to minimize material waste and machining time, in some embodiments, a jig blank will simply be provided that is sufficiently large to be applicable to all patient bone extents tML. Such a jig blank is then machined down to the desired jig blank extent jTML, which serve as the exterior surface of the finished jig 2B.

In one embodiment, the number of candidate jig blank size groups represented in the plot 900 is a function of the number of jig blank sizes offered by a jig blank manufacturer. For example, a first plot 900 may pertain only to jig blanks manufactured by company A, which offers three jig blank sizes. Accordingly, the plot 900 has three jig blank size groups. A second plot 900 may pertain only to jig blanks manufactured by company B, which offers six jig blank size groups. Accordingly, the second plot 900 has six jig blank size groups.

A plurality of candidate jig blank sizes exist, for example, in a jig blank library as represented by the plot 900 of FIG. 17B. While each candidate jig blank may have a unique combination of anterior-posterior and medial-lateral dimension sizes, in some embodiments, two or more of the candidate jig blanks may share a common aspect ratio tAP/tML or configuration. The candidate jig blanks of the library may be grouped along sloped lines of the plot 900 according to their aspect ratios tAP/tML.

In one embodiment, the jig blank aspect ratio tAP/tML may be used to take a workable jig blank configuration and size it up or down to fit larger or smaller individuals.

As can be understood from FIG. 17A, a series of 98 OA patients having knee disorders were entered into the plot 900 as part of a tibia jig design study. Each patient's tibia tAP and tML data was measured. Each patient tibia tML data was modified via the above-described jTML formula to arrive at the patient's jig blank data (jFML). The patient's jig blank data was then entered into the plot 900 as a point. As can be understood from FIG. 17A, no patient point lies outside the parameters of an available group. Such a process can be used to establish group parameters and the number of needed groups.

In one embodiment, the selected jig blank parameters can be the tibia jig exterior dimensions that are specific to patient's knee features. In another embodiment, the selected jig blank parameters can be chosen during fabrication process.

h. Formation of 3D Tibia Jig Model.

Figure 18A:
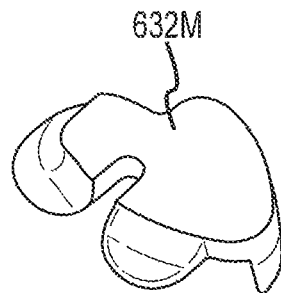
FIG. 18A is an exterior perspective view of a tibia jig blank exterior surface model.
Figure 18B:
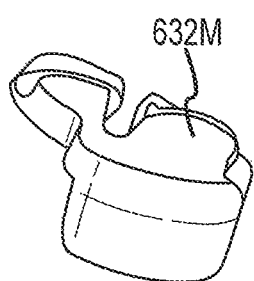
FIG. 18B is an interior perspective view of the tibia jig blank exterior surface model of FIG. 18A.
Figure 20A:
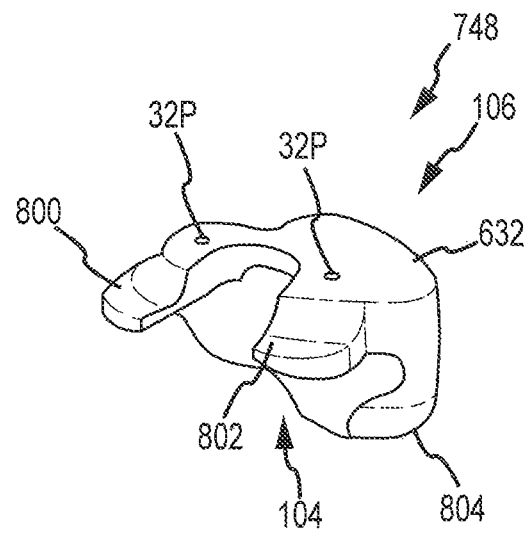
FIG. 20A is an exterior perspective view of the resulting tibia jig model.
Figure 20B:
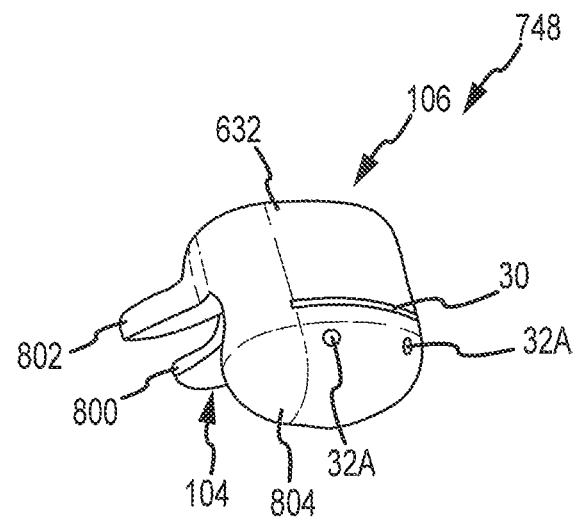
FIG. 20B is an interior perspective view of the tibia jig model of FIG. 20A.

For a discussion of an embodiment of a method of generating a 3D tibia jig model 746 generally corresponding to the "integrated jig data" 48 discussed with respect to [block 150] of FIG. 1E, reference is made to FIGS. 13A-13C, FIGS. 18A-18B, FIGS. 19A-19D and FIG. 20A-20B. FIGS. 13A-13C are various views of a tibia jig blank 50B. FIGS. 18A-18B are, respectively, exterior and interior perspective views of a tibia jig blank exterior surface model 632M. FIGS. 19A-19D are exterior perspective views of the tibia jig blank exterior model 632M and bone surface model 40 being combined. FIGS. 20A and 20B are, respectively, exterior and interior perspective views of the resulting tibia jig model 746 after having "saw cut and drill hole data" 44 integrated into the jig model 746 to become an integrated or complete jig model 748 generally corresponding to the "integrated jig data" 48 discussed with respect to [block 150] of FIG. 1E.

As can be understood from FIGS. 13A-13C, the jig blank 50B, which has selected predetermined dimensions as discussed with respect to FIGS. 17A and 17B, includes an interior surface 630 and an exterior surface 632. The exterior surface model 632M depicted in FIGS. 18A and 18B is extracted or otherwise created from the exterior surface 632 of the jig blank model 50B. Thus, the exterior surface model 632M is based on the jig blank aspect ratio of the tibia jig blank 50B selected as discussed with respect to FIGS. 17A and 17B and is dimensioned specific to the patient's knee features. The tibia jig surface model 632M can be extracted or otherwise generated from the jig blank model 50B of FIGS. 13A-13C by employing any of the computer surface rendering techniques described above.

As can be understood from FIGS. 19A-19C, the exterior surface model 632M is combined with the tibia surface model 40 to respectively form the exterior and interior surfaces of the tibia jig model 746. The tibia surface model 40 represents the interior or mating surface of the tibia jig 2B and corresponds to the tibia arthroplasty target area 42. Thus, the model 40 allows the resulting tibia jig 2B to be indexed to the arthroplasty target area 42 of the patient's tibia 20 such that the resulting tibia jig 2B will matingly receive the arthroplasty target area 42 during the arthroplasty procedure. The two surface models 632M, 40 combine to provide a patient-specific jig model 746 for manufacturing the tibia jig 2B.

As can be understood from FIGS. 19B and 19C, once the models 632M, 40 are properly aligned, a gap will exist between the two models 632M, 40. An image sewing method or image sewing tool is applied to the aligned models 632M, 40 to join the two surface models together to form the 3D computer generated jig model 746 of FIG. 19B into a single-piece, joined-together, and filled-in jig model 746 similar in appearance to the integrated jig model 748 depicted in FIGS. 20A and 20B. In one embodiment, the jig model 746 may generally correspond to the description of the "jig data" 46 discussed with respect [block 145] of FIG. 1E.

As can be understood from FIGS. 19B-19D, 20A and 20B, the geometric gaps between the two models 632M, 40, some of which are discussed below with respect to thicknesses $V_1$, $V_2$ and $V_3$, may provide certain space between the two surface models 632M, 40 for slot width and length and drill bit length for receiving and guiding cutting tools during TKA surgery. Because the resulting tibia jig model 748 depicted in FIGS. 20A and 20B may be a 3D volumetric model generated from 3D surface models 632M, 40, a space or gap should be established between the 3D surface models 632M, 40. This allows the resulting 3D volumetric jig model 748 to be used to generate an actual physical 3D volumetric tibia jig 2B.

In some embodiments, the image processing procedure may include a model repair procedure for repairing the jig model 746 after alignment of the two models 632M, 40. For example, various methods of the model repairing include, but are not limit to, user-guided repair, crack identification and filling, and creating manifold connectivity, as described in: Nooruddin et al., *Simplification and Repair of Polygonal Models Using Volumetric Techniques* (IEEE Transactions on Visualization and Computer Graphics, Vol. 9, No. 2, April-June 2003); C. Erikson, *Error Correction of a Large Architectural Model: The Henderson County Courthouse* (Technical Report TR95-013, Dept. of Computer Science, Univ. of North Carolina at Chapel Hill, 1995); D. Khorramabdi, *A Walk through the Planned CS Building* (Technical Report UCB/CSD 91/652, Computer Science Dept., Univ. of California at Berkeley, 1991); Morvan et al., *IVECS: An Interactive Virtual Environment for the Correction of .STL files* (Proc. Conf. Virtual Design, August 1996); Bohn et al., *A Topology-Based Approach for Shell-Closure*, Geometric Modeling for Product Realization, (P. R. Wilson et al., pp. 297-319, North-Holland, 1993); Barequet et al., *Filling Gaps in the Boundary of a Polyhedron*, Computer Aided Geometric Design (vol. 12, no. 2, pp. 207-229, 1995); Barequet et al., *Repairing CAD Models* (Proc. IEEE Visualization '97, pp. 363-370, October 1997); and Gueziec et al., *Converting Sets of Polygons to Manifold Surfaces by Cutting and Stitching*, (Proc. IEEE Visualization 1998, pp. 383-390, October 1998). Each of these references is incorporated into this Detailed Description in their entireties.

As can be understood from FIGS. 20A and 20B, the integrated jig model 748 may include several features based on the surgeon's needs. For example, the jig model 748 may include a slot feature 30 for receiving and guiding a bone saw and drill holes 32 for receiving and guiding bone drill bits. As can be understood from FIGS. 19B and 19C, to provide sufficient structural integrity to allow the resulting tibia jig 2B to not buckle or deform during the arthroplasty procedure and to adequately support and guide the bone saw and drill bits, the gap between the models 232M, 40 may have the following offsets $V_1$, $V_2$, and $V_3$.

As can be understood from FIGS. 19B-20B, in one embodiment, thickness $V_1$ extends along the length of the posterior drill holes 32P between the models 632M, 40 and is for supporting and guiding a bone drill received therein during the arthroplasty procedure. Thickness $V_1$ may be at least approximately four millimeters or at least approximately five millimeters thick. The diameter of the posterior drill holes 32P may be configured to receive a cutting tool of at least one-third inches.

Thickness $V_2$ extends is the thickness of the jig foots 800, 802 between the inner and exterior surfaces 40, 632M. The thickness provides adequate structural strength for jig foots 800, 802, to resist buckling and deforming of the jig to manufacture and use. Thickness $V_2$ may be at least approximately five millimeters or at least eight millimeters thick.

Thickness $V_3$ extends along the length of a saw slot 30 between the models 632M, 40 and is for supporting and guiding a bone saw received therein during the arthroplasty procedure. Thickness $V_3$ may be at least approximately 10 mm or at least 15 mm thick.

In addition to providing sufficiently long surfaces for guiding drill bits or saws received therein, the various thicknesses $V_1$, $V_2$, $V_3$ are structurally designed to enable the tibia jig 2B to bear vigorous tibia cutting, drilling and reaming procedures during the TKR surgery.

As indicated in FIGS. 20A and 20B, the exterior portion or side 106 of the integrated jig model 748 may include: feature or jig foot 800 that extends over and matches the patient's medial portion of the tibia plateau; feature or jig foot 802 that extends over and matches the patient's lateral portion of the tibia plateau; projection 804 that extends downward from the upper exterior surface 632 of the tibia jig 2B; and a flat portion of the exterior surface 632 that provides a blanked labeling area for listing information regarding the patient, surgeon or/and the surgical procedure. Also, as discussed above, the integrated jig model 748 may include the saw cut slot 30 and the drill holes 32. The inner portion or side 104 of the jig model 748 (and the resulting tibia jig 2B) is the tibia surface model 40, which will matingly receive the arthroplasty target area 42 of the patient's tibia 20 during the arthroplasty procedure.

As can be understood by referring to [block 105] of FIG. 1B and FIGS. 12A-12C, in one embodiment when cumulating the image scans 16 to generate the one or the other of the models 40, 22, the models 40, 22 are referenced to point P, which may be a single point or a series of points, etc. to reference and orient the models 40, 22 relative to the models 22, 28 discussed with respect to FIG. 1C and utilized for POP. Any changes reflected in the models 22, 28 with respect to point P (e.g., point P becoming point P') on account of the POP is reflected in the point P associated with the models 40, 22 (see [block 135] of FIG. 1D). Thus, as can be understood from [block 140] of FIG. 1D and FIGS. 19A-19C, when the jig blank exterior surface model 632M is combined with the surface model 40 (or a surface model developed from the arthritic model 22) to create the jig model 746, the jig model 746 is referenced and oriented relative to point P' and is generally equivalent to the "jig data" 46 discussed with respect to [block 145] of FIG. 1E.

Because the jig model 746 is properly referenced and oriented relative to point P', the "saw cut and drill hole data" 44 discussed with respect to [block 125] of FIG. 1E can be properly integrated into the jig model 746 to arrive at the integrated jig model 748 depicted in FIGS. 20A-20B. The integrated jig model 748 includes the saw cuts 30, drill holes 32 and the surface model 40. Thus, the integrated jig model 748 is generally equivalent to the "integrated jig data" 48 discussed with respect to [block 150] of FIG. 1E.

As can be understood from FIG. 21, which illustrates a perspective view of the integrated jig model 748 mating with the "arthritic model" 22, the interior surface 40 of the jig model 748 matingly receives the arthroplasty target area 42 of the tibia upper end 604 such that the jig model 748 is indexed to mate with the area 42. Because of the referencing and orientation of the various models relative to the points P, P' throughout the procedure, the saw cut slot 30 and drill holes 32 are properly oriented to result in saw cuts and drill holes that allow a resulting tibia jig 2B to restore a patient's joint to a pre-degenerated condition.

As indicated in FIG. 21, the integrated jig model 748 may include a jig body 850, a medial tibia plateau covering projection 852, a lateral tibia plateau covering projection 854, a lower portion 856 extending form the body 850, posterior drill holes 32P, anterior drill holes 32A, a saw slot 30 and an upper flat portion 857 for receiving thereon patient, surgery and physician data. The projections 852, 854 extend over their respective medial and lateral tibia plateau portions. The projections 852, 854, 856, 857 extend integrally from the jig body 850.

As can be understood from [blocks 155-165] of FIG. 1E, the integrated jig 748 or, more specifically, the integrated jig data 48 can be sent to the CNC machine 10 to machine the tibia jig 2B from the selected jig blank 50B. For example, the integrated jig data 48 may be used to produce a production file that provides automated jig fabrication instructions to a rapid production machine 10, as described in the various Park patent applications referenced above. The rapid production machine 10 then fabricates the patient-specific arthroplasty tibia jig 2B from the tibia jig blank 50B according to the instructions.

The resulting tibia jig 2B may have the features of the integrated jig model 748. Thus, as can be understood from FIG. 21, the resulting tibia jig 2B may have the slot 30 and the drilling holes 32 formed on the projections 852, 854, 856, 857, depending on the needs of the surgeon. The drilling holes 32 are configured to prevent the possible IR/ER (internal/external) rotational axis misalignment between the tibia cutting jig 2B and the patient's damaged joint surface during the proximal tibia cut portion of the TKR procedure. The slot 30 is configured to accept a cutting instrument, such as a reciprocating slaw blade for transversely cutting during the proximal tibia cut portion of the TKR.

i. Overestimation Process

As mentioned above in Subsection a of this Detailed Description, certain regions of the 3D surface models 40 may be a more accurate representation of the actual patient bone surface than other regions and/or may be more readily machined. For example, because of limitations in the medical imaging process (e.g., having to rely on a finite number of image slices 16 as opposed to an infinite number of image slices, volume averaging issues, and issues presented by irregular contours due to the presence of osteophytes, fat tissue, broken cartilage, etc.), the 3D surface models 40 in certain regions may not be an accurate representation of the corresponding actual bone surfaces of the arthroplasty target areas. As a result, a bone mating surface of an actual jig 2 based upon such less accurate data may end up having an interfering fit as opposed to a mating fit with the arthroplasty target area of the actual bone surfaces.

With respect to machining, the size of the tooling used to machine the bone mating surface of the actual jig may exceed the size of certain features in the 3D surface models 40. As a result, the CNC machine may not be able to accurately machine the bone mating surface of the actual jig to match the 3D surface models.

To address these issues presented by the imaging and machining limitations, the 3D surface models 40, or more specifically, the contour lines 210, 210' used to generate the 3D surface models, may be subjected to the overestimation process described below. The result of the overestimation process is an actual jig with: (1) bone mating surfaces that matingly receive and contact certain regions of the actual bone surface of the arthroplasty target region, wherein the certain regions correspond to regions of the actual bone surface that can be accurately and reliably 3D computer modeled and actually machined; and (2) bone-facing surfaces of the jig (i.e., those surfaces of the jig that face the bone when the bone mating surfaces of the jig matingly receive and contact the bone surfaces of the arthroplasty target region) that avoid contact with certain other regions of the actual bone surface of the arthroplasty target region, wherein the certain other regions correspond to regions of the actual bone surface that are less likely to be accurately and reliably 3D computer modeled and/or less likely to be actually machined.

In creating bone-facing surfaces of the jig that correspond to bone surface regions that are less likely to be accurately 3D modeled and/or actually machined, the overestimation process overestimates or moves the contour lines 210 away or outward from the bone area of the image slice 16 such that the CNC machine will be caused to over-machine along the overestimated contour line. This outward displacement of the contour line 210 results in the jig's bone-facing surface corresponding to the overestimated contour line being spaced apart from the corresponding actual bone surface of the arthroplasty target region when the jig's bone mating surface matingly receives and contacts the arthroplasty target region.

Due to the overestimation process, in one embodiment, the contact between the jig's bone mating surface and the bone surface of the arthroplasty target region is limited to those regions of the arthroplasty target region that can be accurately and reliably 3D computer modeled and actually machined. All other bone-facing surfaces of the jig may be the result of the overestimation process such that these other bone-facing surfaces are spaced apart from, and do not contact, their corresponding regions of the bone surface of the arthroplasty target region, as these bone regions correspond to regions that are less likely to be accurately 3D computer modeled and/or less likely to be actually machined. The result of the overestimated bone-facing surfaces of the jig 2 is a jig that is more likely to accurately and reliably matingly receive the arthroplasty target region during an arthroplasty procedure.

Example overestimation processes are provided below in the context of generating bone-facing surfaces for a femur jig and a tibia jig, wherein some of the bone-facing surfaces are bone mating surfaces and other bone-facing surfaces are the result of overestimation. While the following examples are provided in the context of jigs for knee arthroplasty, the overestimation process should not be considered as being limited to the knee context. Instead, the overestimation concepts disclosed herein should be considered to be applicable to all types of orthopedic surgeries by those skilled in the art, including those surgeries for other types of bone-to-bone interfaces such as ankle, hip, wrist, elbow, shoulder, toe, finger and other types of joints, vertebrae-to-vertebrae interfaces, vertebrae-to-hip structure interfaces, vertebrae-to-skull interfaces, etc.

1. Overestimating the 3D Femur Surface Models

As described above with regard to block 140 of FIG. 1D, the "jig data" 46 is used to produce a jigs having bone mating surfaces customized to matingly receive the target areas 42 of the respective bones of the patent's joint. Data for the target areas 42 may be based, at least in part, on the 3D computer generated surface models 40 of the patient's joint bones. Furthermore, as described above with regard to FIG. 1A and [blocks 100-105] of FIG. 1B, these 3D computer generated surface models 40 may be based on the plurality of 2D scan image slices 16 taken from the imaging machine 8 and, more precisely, from the contour lines derived from those 2D scan image slices via image segmentation processes known in the art or, alternatively, as disclosed in U.S. Provisional Patent Application 61/126,102, which was filed Apr. 30, 2008 and is incorporated by reference herein in its entirety.

Figure 22A:
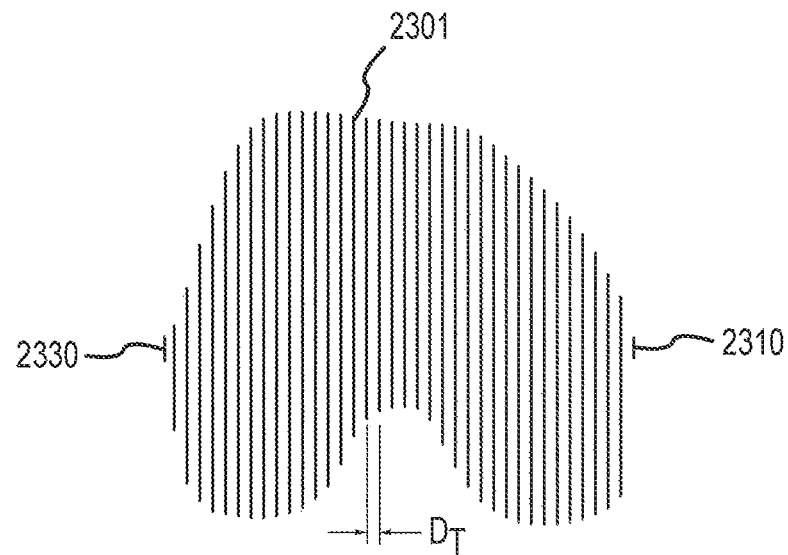
FIG. 22A illustrates the distal axial view of the 3D model of the patient's femur shown in FIG. 5 with the contour lines of the image slices shown and spaced apart by the thickness $D_T$ of the slices.
Figure 22B:
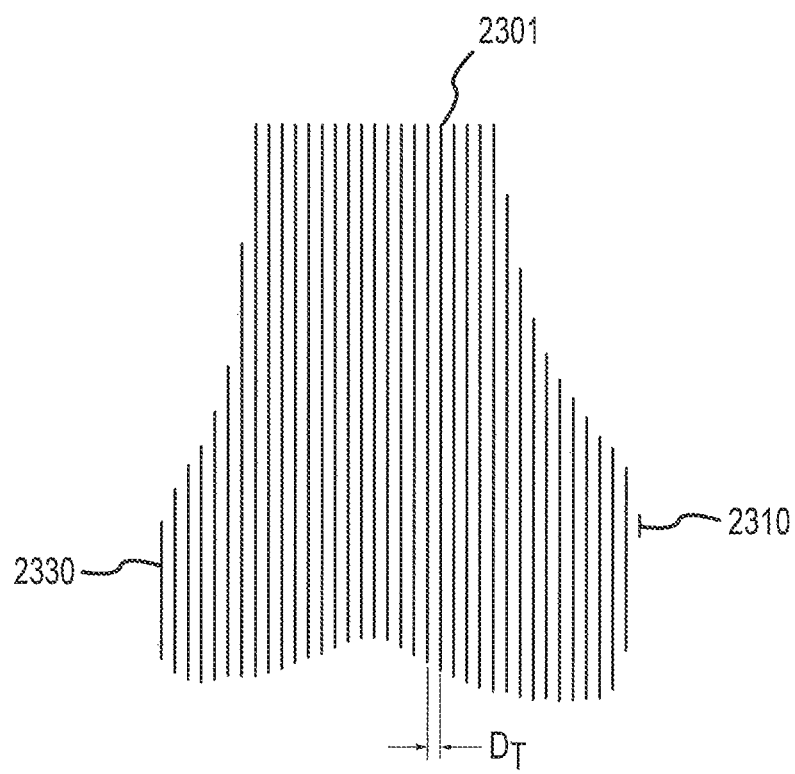
FIG. 22B represents a coronal view of a 3D model of the patient's femur with the contour lines of the image slices shown and spaced apart by the thickness $D_T$ of the slices.

Each scan image slice 16 represents a thin slice of the desired bones. FIG. 22A illustrates the distal axial view of the 3D model of the patient's femur shown in FIG. 5 with the contour lines 2301 of the image slices shown and spaced apart by the thickness $D_T$ of the slices. FIG. 22B represents a coronal view of a 3D model of the patient's femur with the contour lines 2301 of the image slices shown and spaced apart by the thickness $D_T$ of the slices.

The slices shown in FIGS. 22A-B have contour lines 2301 similar to the open and closed loop contour line segments 210, 210' depicted in FIGS. 2B and 2E. The contour lines 2301 of each respective image slice 16 are compiled together to form the 3D model of the patient's femur. The overall resolution or preciseness of the 3D models 40 (shown in FIGS. 2C and 2F) resulting from compiling together the contour lines of each of these slices (shown in [block 1010]) may be impacted by the thickness $D_T$ of the slices shown in FIGS. 22A-B. Specifically, the greater the thickness $D_T$ of the slices, the lower the resolution/preciseness of the resulting 3D models, and the smaller the thickness $D_T$ of the slices, the higher the resolution/preciseness of the resulting 3D models.

As the resolution/preciseness of the 3D models increases, more accurate customized arthroplasty jigs 2 may be generated. Thus, the general impetus is to have thinner slices rather than thicker slices. However, depending upon the imaging technology used, the feasible thickness $D_T$ of the image slices may vary and may be limited due a variety of reasons. For example, an imaging thickness $D_T$ that is sufficiently precise to provide the desired imaging resolution may also need to be balanced with an imaging duration that is sufficiently brief to allow a patient to remain still for the entire imaging duration.

In embodiments utilizing MRI technology, the range of slice thickness $D_T$ may be from approximately 0.8 mm to approximately 5 mm. MRI slice thicknesses $D_T$ below this range may be unfeasible because they have associated imaging durations that are too long for most patients to remain still. Also, MRI slice thicknesses $D_T$ below this range may be unfeasible because they may result in higher levels of noise with regard to actual signals present, residuals left between slices, and volume averaging limitations of the MRI machine. MRI slice thicknesses above this range may not provide sufficient image resolution/preciseness. In one embodiment, the MRI slice thicknesses $D_T$ is approximately 2 mm.

While embodiments utilizing CT technology may have a range of slice thicknesses $D_T$ from approximately 0.3 mm to approximately 5 mm, CT imaging may not capture the cartilage present in the patient's joints to generate the arthritic models mentioned above.

Regardless of the imaging technology used and the resulting resolution/preciseness of the 3D models, the CNC machine 10 may be incapable of producing the customized arthroplasty jigs 2 due to mechanical limitations, especially where irregularities in the bone surface are present. This, for example, may result where a milling tool bit has dimensions that exceed those of the feature to be milled.

Figure 23:
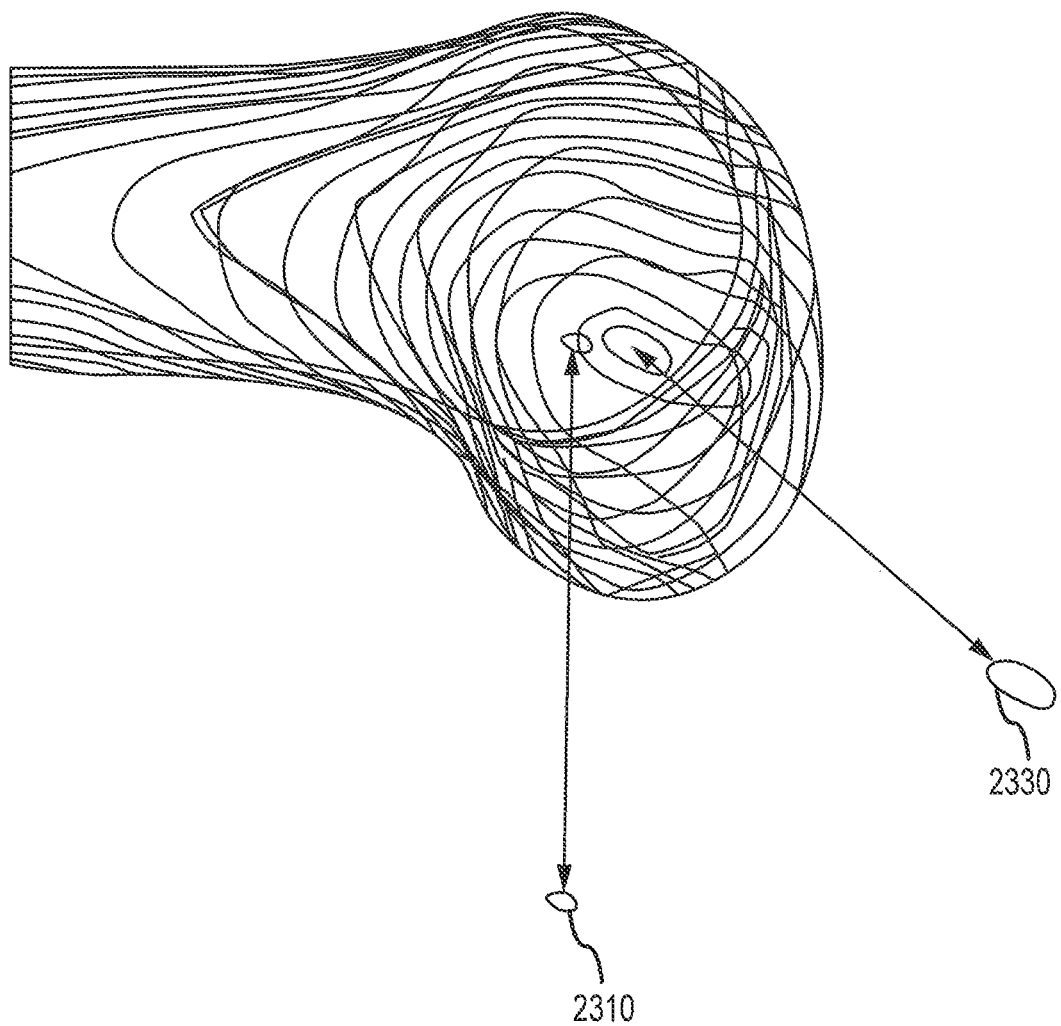
FIG. 23 illustrates an example sagittal view of compiled contour lines of successive sagittal 2D MRI images based on the slices shown in FIGS. 22A-B with a slice thickness $D_T$ of 2 mm.

FIG. 23 illustrates an example sagittal view of compiled contour lines of successive sagittal 2D MRI images based on the slices shown in FIGS. 22A-B with a slice thickness $D_T$ of 2 mm. As can be understood from FIGS. 22A-23, the contour lines shown begin on the medial side of the knee at the image slice corresponding to contour line 2310 and conclude on the lateral side of the knee at the image slice corresponding to contour line 2330. Thus, in one embodiment, contour lines 2310 and 2330 represent the contour lines of the first and last images slices taken of the femur, with the other contour lines between contour lines 2310, 2330 representing the contour lines of the intermediate image slices taken of the femur. Each of the contour lines is unique is size and shape, may be either open-loop or closed-loop, and corresponds to a unique image slice 16.

Figure 24:
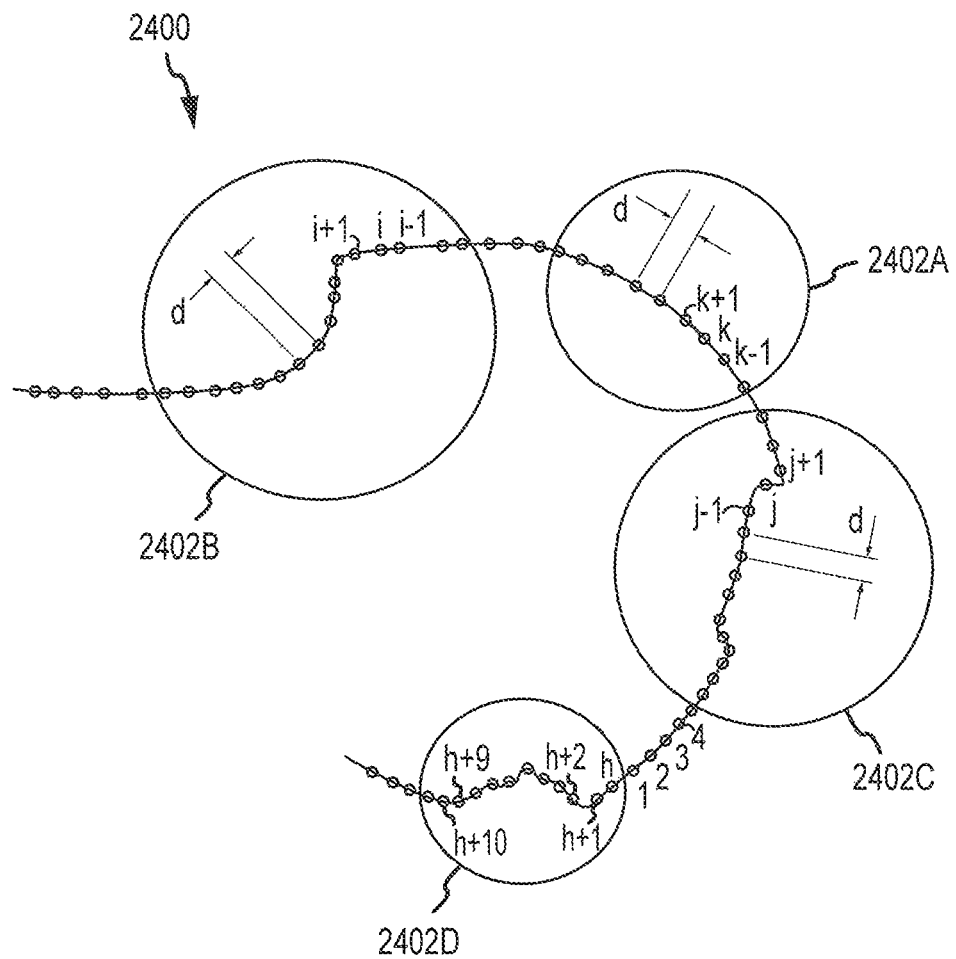
FIG. 24 illustrates an example contour line of one of the contour lines depicted in FIGS. 22A-23, wherein the contour line is depicted in a sagittal view and is associated with an image slice of the femoral condyle.

FIG. 24 illustrates an example contour line 2400 of one of the contour lines depicted in FIGS. 22A-23, wherein the contour line 2400 is depicted in a sagittal view and is associated with an image slice 16 of the femoral condyle. As shown, the contour line 2400 includes a plurality of surface coordinate points (e.g., h-n, . . . , h-3, h-2, h-1, h, h+1, h+2, h+3, . . . , h+n; j-n, . . . , j-3, j-2, j-1, j, j+1, j+2, j+3, . . . , j+n; k-n, . . . , k-3, k-2, k-1, k, k+1, k+2, k+3, . . . , k+n; and i-n, . . . , i-3, i-2, i-1, i, i+1, i+2, i+3, . . . , i+n). The contour line and associated points may be generated by imaging technology, for example, via an image segmentation process that may employ, for example, a shape recognition process and/or a pixel intensity recognition process. In one embodiment, the contour line 2400 may represent the boundary line along the cortical-cancellous bone edge. In one embodiment, the boundary line may represent the outer boundary line of the cartilage surface.

Each of the surface contour points in the plurality may be separated by a distance "d". In one embodiment, distance "d" may be a function of the minimum imaging resolution. In some embodiments, distance "d" may be function of, or associated with, the size of the milling tool used to manufacture the jig. For example, the distance "d" may be set to be approximately 10 times smaller than the diameter of the milling tool. In other words, the distance "d" may be set to be approximately $\frac{1}{10}^{th}$ or less of the diameter of the milling tool. In other embodiments, the distance "d" may be in the range of between approximately one half of the diameter of the milling tool to approximately $\frac{1}{100}^{th}$ or less of the diameter of the milling tool.

Depending on the embodiment, the separation distance d may be either uniform along the contour line 2400, or may be non-uniform. For example, in some embodiments, areas of bone irregularities may have points that are closer together than areas where no irregularities are present. In one embodiment, the points shown along the example contour line 2400 may have a separation distance d of approximately 2 mm. In other embodiments, distance d may be in the range of approximately 0.8 mm to approximately 5 mm.

The bone surface of the example contour line 2400 includes a regular region 2402A on the distal-posterior portion of the contour line 2400 as well as an irregular region 2402B of the same. The contour line 2400 also includes irregular regions 2402C-D on the distal and distal-anterior portions, respectively. The irregular regions 2402B-D may be due to a variety of patient specific factors. For example, irregular region 2402B illustrates a type of bone irregularity, referred to as an "osteophyte", where a bony outgrowth has occurred in the femoral condyle. Osteophytes may be present in patients that have undergone trauma to the bone or who have experienced degenerative joint disease.

The irregular regions 2402C-D illustrate areas of the femoral condyle that have experienced cartilage damage and appear as notches in the contour line 2400. Regardless of the cause of the irregularity, the presence of irregularities in the contour line 2400 may adversely impact the ability to generate a mating surface in the actual arthroplasty jig that accurately and reliably mates with the corresponding bone surface of the patient during the arthroplasty procedure. This may be the result of the imaging impreciseness in the vicinity of the contour irregular regions 2402B-D or because the contour irregular regions 2402B-D represent surface contours that are too small for the tooling of the CNC machine 10 to generate. To account for contour line regions associated with imaging impreciseness and/or features too small to be milled via the tooling of the CNC machine, in some embodiments, such contour line regions may be identified and corrected or adjusted via the overestimation process prior to being compiled to form the 3D models 40.

Figure 25:
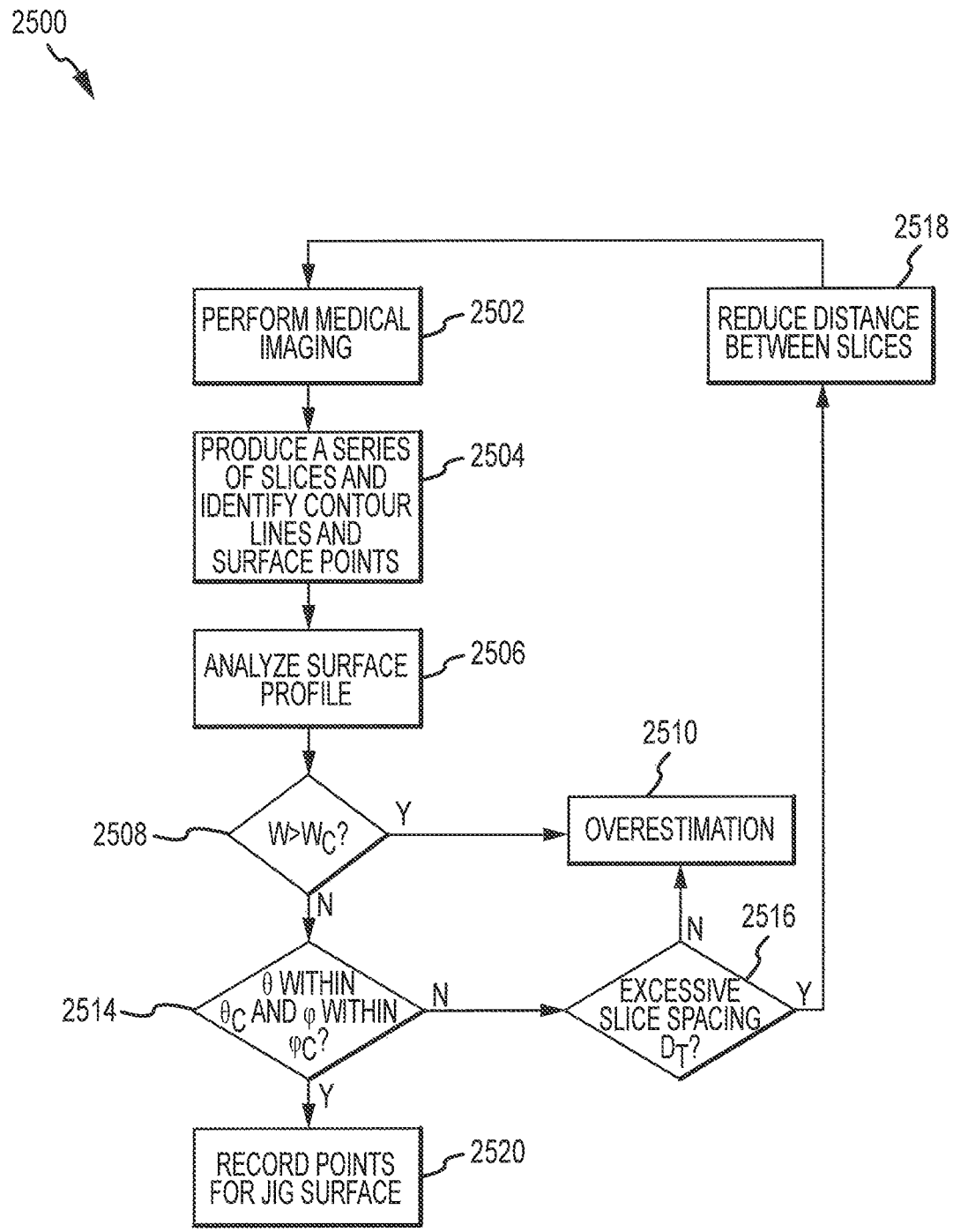
FIG. 25 represents an example overestimation algorithm that may be used to identify and adjust for irregular contour line regions when forming the 3D model.

FIG. 25 represents an example overestimation algorithm 2500 that may be used to identify and adjust for irregular regions 2402B-D when forming the 3D models 40. In block 2502, medical imaging may be performed on the damaged bone at desired slice thicknesses $D_T$, which in some embodiments may be equal to those slice thicknesses $D_T$ mentioned above with regard to FIGS. 22A-22B. For example, MRI and/or CT scans may be performed at predetermined thicknesses $D_T$ as shown in FIGS. 22A-B. In some embodiments, the desired thickness $D_T$ used in block 2502 is set at 2 mm or any other thickness $D_T$ within the range of thicknesses $D_T$ mentioned above.

From this medical imaging, a series of slices 16 may be produced and image segmentation processes can be used to generate the contour lines 210, 210', 2301, 2310, 2330, 2400 discussed with respect to FIGS. 2, 22A-B, and 24 (see block 2504). Also in block 2504, a plurality of surface coordinate points along each contour line segment 2402A-D may be identified as shown in FIG. 24 with respect to contour line 2400. For example, the points in the irregular region corresponding to contour line segment 2402B may be identified and indexed as i-n, i-1, i, i+1, i+2, i+3, i+n.

With the surface coordinate points along the contour 2400 defined, an analysis may be performed on two or more of the points (e.g., i and i+1) to determine if an irregularity exists in the contour line segment per block 2506.

Figure 26:
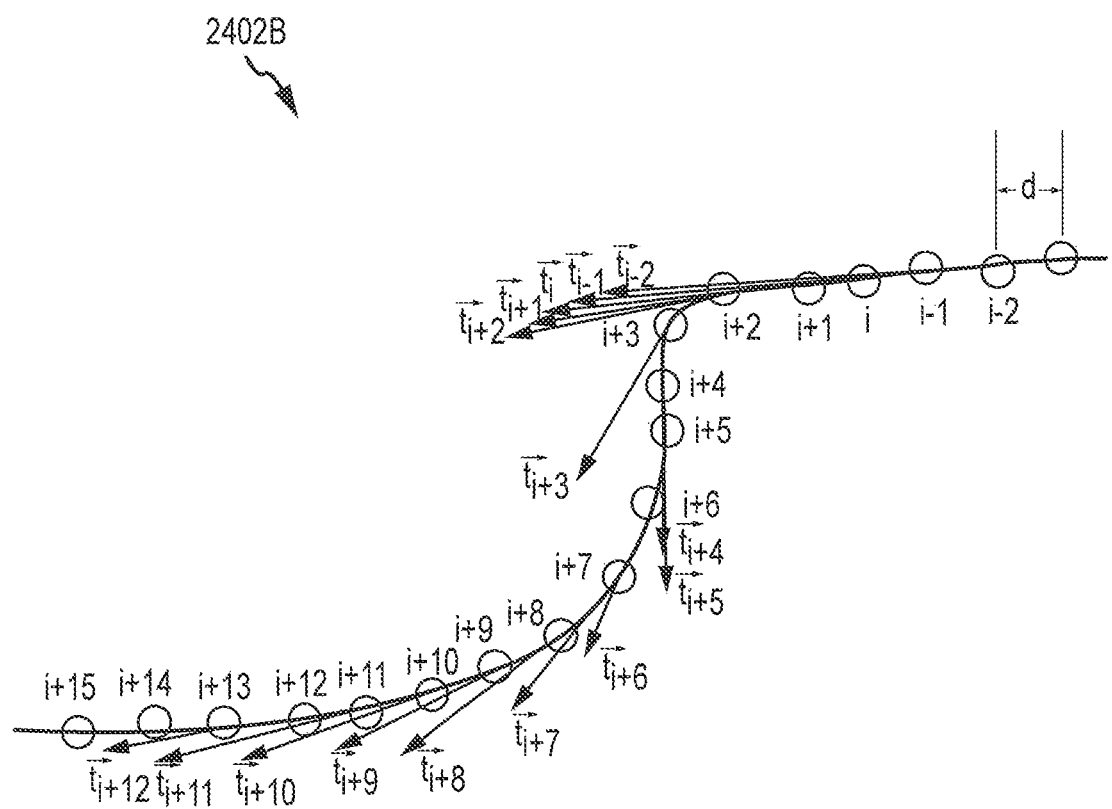
FIG. 26 depicts implementing an example analysis scheme (according to block 2506) on the irregular contour line region 2402B of FIG. 24.

FIG. 26 depicts implementing an example analysis scheme (according to block 2506) on the irregular contour line region 2402B of FIG. 24. As shown, the analysis may include constructing one or more tangent lines (labeled as $t_{i-i}$, $t_i$, $t_{i+1}$, $t_{i+2}$, $t_{i+3}$, $t_{i+4}$, etc.), corresponding to the points in the irregular region 2402B. The analysis of block 2506 may further include calculating differences between the angles formed by one or more of the tangent lines. For example, the difference between the angles formed by the tangent lines $t_i$ and $t_{i+1}$ may be defined as $w_i$, where $$w_i = \cos^{-1}\left(\frac{t_{i+1} \cdot t_i}{|t_{i+1}||t_i|}\right).$$

In some embodiments, the operations of block 2506 may be performed repetitively on each point within the contour segment.

The operations of block 2506 may be calculated on subsequent points (e.g., between $t_i$ and $t_{i+1}$) in some embodiments, and on non-subsequent points in other embodiments (e.g., $t_{i+2}$ and $t_{i+4}$).

The angular difference $w_i$ may indicate whether portions of the contour line segment are too eccentric for use in constructing the 3D models 40. In block 2508, the angular difference $w_i$ may be compared to a predetermined angular criterion $w_c$. The angular criterion $w_c$ may be determined based on several factors, including the physical dimensions and characteristics of the CNC machine 10. In some embodiments, the predetermined angular criterion $w_c$ is set at approximately 5 degrees. In other embodiments, the predetermined angular criterion $w_c$ is set at between approximately 5 degrees and approximately 20 degrees.

For the sake of discussing the example irregular region 2402B shown in FIG. 26, the angular criterion $w_c$ is set to 5 degrees in one embodiment. The angular differences between tangent lines associated with adjacent points i−2, i−1, i, i+1, i+2 are within the predetermined angular criterion $w_c$ of 5 degrees, but the differences between tangent lines associated with adjacent points i+2 and i+3 and adjacent points i+3 and i+4 exceeds the predetermined angular criterion $w_c$ of 5 degrees and therefore indicates an irregular region of the contour line. The difference between tangent lines associated with adjacent points, such as i+5 and i+6, may indicate similar irregular regions. As mentioned above, these irregularities may result from conditions of the patient's bone such as arthritis or osteoarthritis and generally result in a contour line segment being unsuitable for using when forming the 3D models 40. Accordingly, if the comparison from block 2508 indicates that the angular difference $w_i$ is greater than the predetermined criterion $w_c$, then the data associated with the irregular contour line segment may be modified by overestimating (e.g., adjusting the irregular contour line segment outward or away from the bone portion of the image slice 16) as discussed in greater detail below with respect to FIG. 27 (see block 2510).

Figure 27:
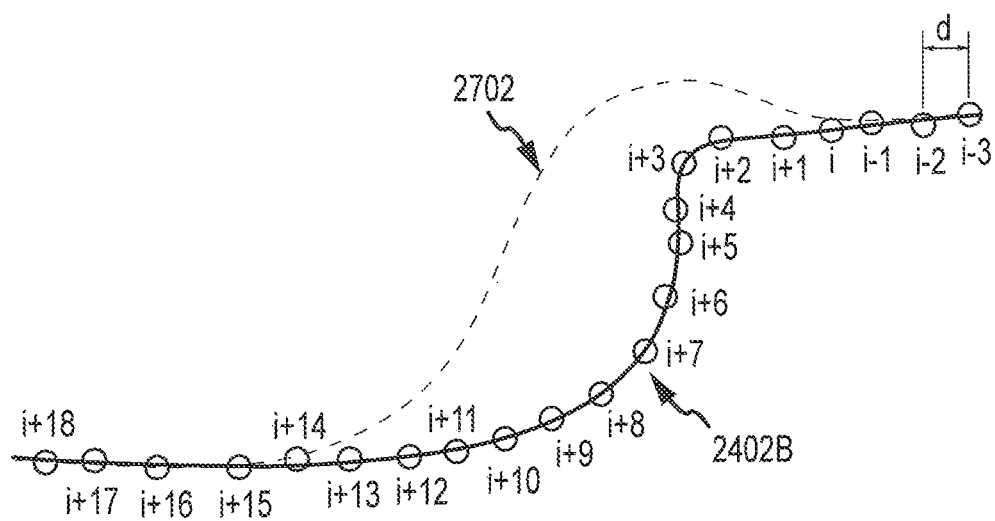
FIG. 27 depicts the irregular region 2402B from FIG. 26 including a proposed area of overestimation, wherein an overestimation procedure creates an adjusted contour line and positionally deviates the adjusted contour line from the original surface profile contour line.

FIG. 27 depicts the irregular region 2402B from FIG. 26 including a proposed area of overestimation, wherein an overestimation procedure creates an adjusted contour line 2702 and positionally deviates the adjusted contour line 2702 from the original surface profile contour line 2402B. In the event that the comparison performed in block 2508 indicates that the angular differences between any of the points i through i+14 exceed the predetermined angular criterion $w_c$, then the contour line segment may be overestimated between these points as shown by the dashed line 2702. As can be understood from a comparison of contour line 2402B to the overestimated or adjusted line 2702, the adjusted line 2702 is adjusted or moved outward or away from the location of the contour line 2402B by an offset distance. Depending on the embodiment, the offset distance between the contour line 2402B and the adjusted line 2702 may range between a few millimeters to a few centimeters. This overestimation may be built into the data used to construct 3D surface models 40 and result in a gap between the respective region of the bone mating surface of the jig 2 and the corresponding portion of the patient's bone surface, thereby avoiding contact between these respective areas of the jig and bone surface. The other areas, such as i−1, i−2, i−3, i+15, i+16, i+17, and i+18, need not be overestimated, per block 2510, because the differences between their tangent lines fall within the angular difference criterion $w_c$.

These areas may be designated as potential target areas that may later be used as the 3D surface models 40 if other angular criteria (described below) are satisfied.

By building overestimation data into the 3D surface models 40, deliberate spaces may be created in regions of the custom arthroplasty jig 2 corresponding to irregularities in the patient's bone, where it is often difficult to predict the size and shape of these irregularities from 2D MRI or where it is difficult to accurately machine the contour line into the jig's bone mating surface because of the largeness of the milling tool relative to the changes in contour. Thus, the jig 2 may include one or more deliberate spaces to accommodate these irregularities or inability to machine. Without these deliberate spaces, the jig 2 may be potentially misaligned during the TKR surgery and may reduce the chances of the surgery's success.

Figure 28:
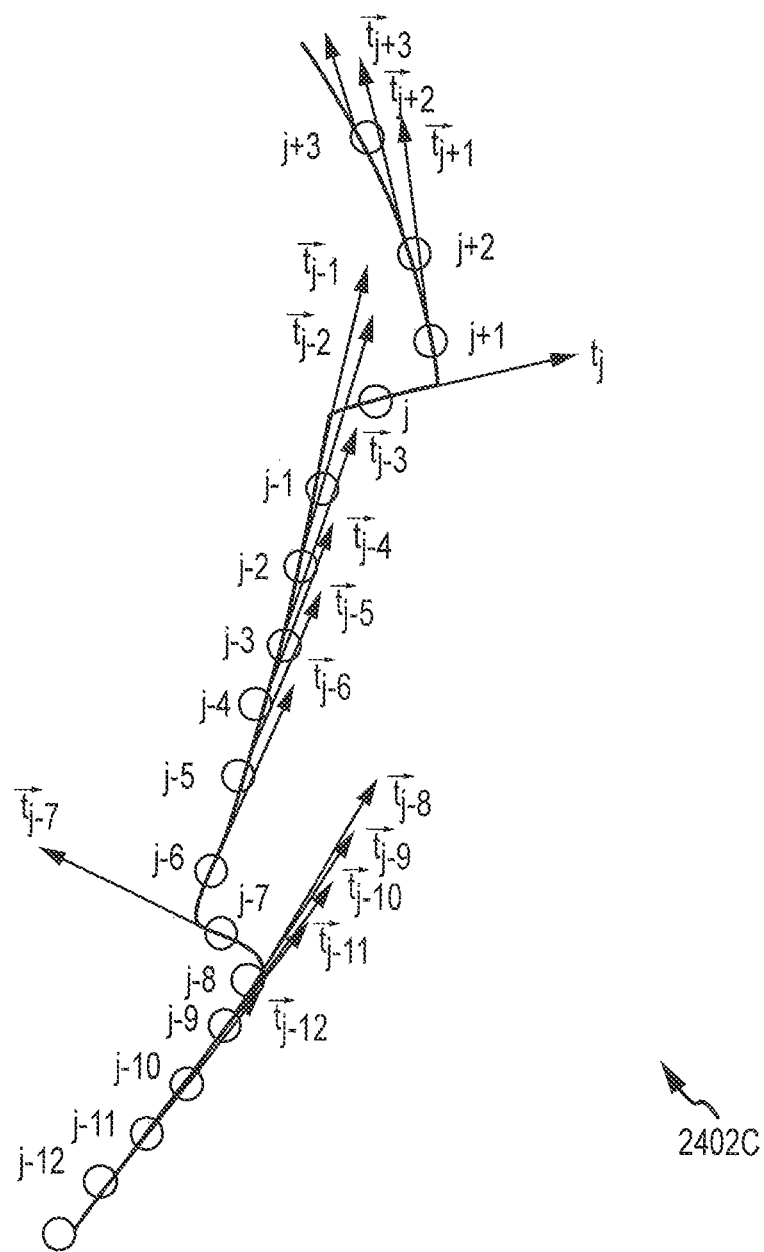
FIG. 28 illustrates the example analysis scheme according to the algorithm of FIG. 25 implemented on the irregular region 2402C from FIG. 24 where an irregular surface of the condylar contour is observed.

The image generation, analysis and overestimation of blocks 2506, 2508 and 2510 may be performed on the other irregularities shown in FIG. 24. FIG. 28 illustrates the example analysis scheme according to algorithm 2500 implemented on the irregular region 2402C where an irregular surface of the condylar contour is observed. Akin to the analysis of irregular region 2402B, the analysis may include constructing one or more tangent lines (labeled as $t_{j-1}$, $t_j$, $t_{j+1}$, $t_{j+2}$, $t_{j+3}$, etc.), corresponding to the points in the irregular region 2402C. The analysis of block 2506 may further include calculating differences between the angles formed by one or more of the tangent lines, defined as $w_1$, where $$w_j = \cos^{-1}\left(\frac{t_{j+1} \cdot t_j}{|t_{j+1}||t_j|}\right)$$

between subsequent points $t_j$ and $t_{j+1}$. Other embodiments include analysis between non-subsequent points (e.g., $t_{j+2}$ and $t_{j+4}$).

Akin to the analysis of irregular region 2402B, the angular difference $w_j$ may indicate whether portions of the contour line segment in the irregular region 2402C are too eccentric for use in constructing the 3D models 40. In block 2508, the angular difference $w_j$ may be compared to a predetermined angular criterion $w_c$. If the angular criterion $w_c$ is set to 5 degrees, the angular differences between adjacent tangent lines associated with j−6, j−5, j−4, j−3, j−2 and j−1 are within the predetermined angular criterion $w_c$. The difference between j−1, j, and j+1, however, may exceed the predetermined angular criterion $w_c$ of 5 degrees and therefore may indicate an irregular region of the contour line 2400. In a similar fashion, the angular criterion $w_c$ for angular differences between tangent lines associated with subsequent points j−6, j−7, and j−8 may indicate similar irregular regions.

As mentioned above, these irregularities may result from conditions in the patient's bone such as arthritis or osteoarthritis and generally result in a contour line segment being unsuitable for using when forming the 3D models 40. Accordingly, if the comparison from block 2508 indicates that the angular difference $w_j$ is greater than the predetermined criterion $w_c$, such as the case at points j−1, j, and j+1 as well as j−6, j−7, and j−8, then the data used in forming 3D models 40 may be adjusted by the overestimating process prior to being used in forming the 3D models 40.

Figure 29A:
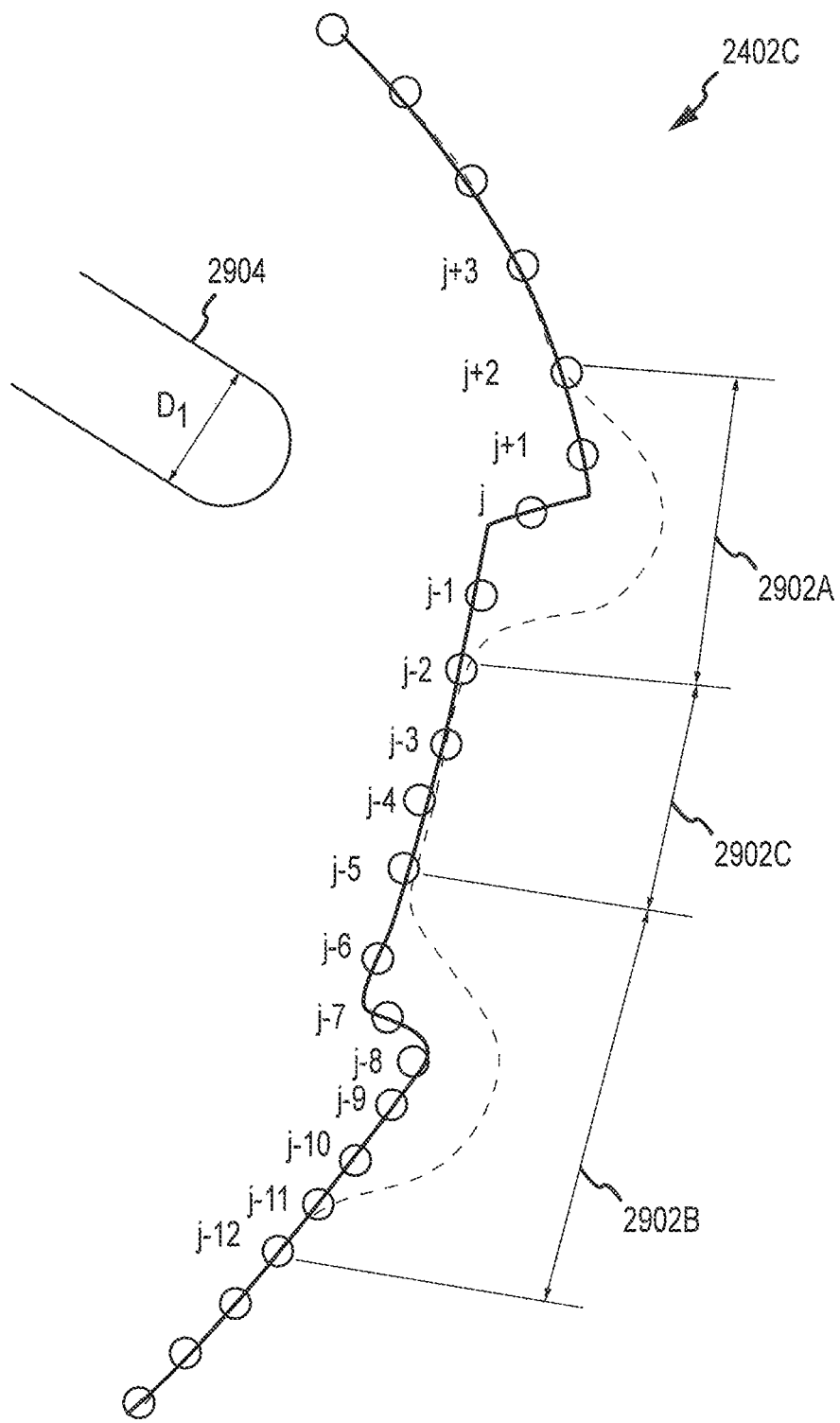
FIG. 29A depicts the irregular region 2402C from FIG. 28 including a proposed area of overestimation indicated by the dashed line areas 2902A-B.

FIG. 29A depicts the irregular region 2402C from FIG. 28 including a proposed area of overestimation indicated by the dashed line areas 2902A-B, wherein the dashed line areas 2902A-B are deviated from the original cortical-cancellous boundary or contour line 2402C. Since the comparison performed in block 2508 indicates that the angular difference $w_j$ is greater than the predetermined criterion $w_c$ at points j−1, j, and j+1 as well as at points j−6, j−7, and j−8, overestimation is performed at these points (labeled as regions 2902A-B respectively). In some embodiments to allow for an adequate transition from the non-overestimate regions to the overestimated regions in view of the diameter of the tool to be used, the overestimation may include additional points to either side of the points falling outside of the predetermined criterion $w_c$ (i.e., points j−1, j, and j+1 as well as at points j−6, j−7, and j−8). Thus, the overestimation in region 2902A may extend from j−2 through j+2, and the overestimation in region 2902B may extend from j−10 through j−5. Furthermore, since the comparison performed in block 2508 indicates that the angular difference $w_j$ is less than the predetermined criterion $w_c$ at points j−6, j−5, j−4, j−3, and j−2, (labeled as region 2902C) these points j−5, j−4, and j−3 (adjusting for the addition of points j−6 and j−2 to the regions 2902A-B) may be used in constructing the 3D models 40 as long as other criteria (described below in the context of blocks 2514-2520) are met.

A tool 2904 may be used to form the surface of the jig's bone mating surface from the 3D models 40 formed from the compiled contour lines, some of which may have been modified via the overestimation process. The tool 2904 may be part of the CNC machine 10 or any other type of machining or manufacturing device having any type of tool or device for forming a surface in a jig blank. Regardless of the type of the device used to mill or form the jigs 2, the tool 2904 may have certain attributes associated with jig machining process that are taken into account when performing the overestimating per block 2510. The associated attributes may include the accessible space for the machining tools to reach and machine the jig's bone mating surface. Examples of such attributes may include the collar diameter of the drilling cutter device, the allowable angle the drilling device can make with the surface to be drilled (e.g., 45 degrees±10%), and/or the overall length of the drilling cutter head.

For example, if the minimum diameter of the overestimated regions 2902A-B is larger than the diameter $D_1$ of the tool 2904, then overestimation of block 2510 may not need to account for the dimensions of the tool 2904, except to provide adequate transitions leading to the overestimated regions as illustrated above by the addition of a single or few points (e.g., points j−2, j+2, j−5, and j−10) to either side of the points outside predetermined criterion $w_c$.

Figure 29B:
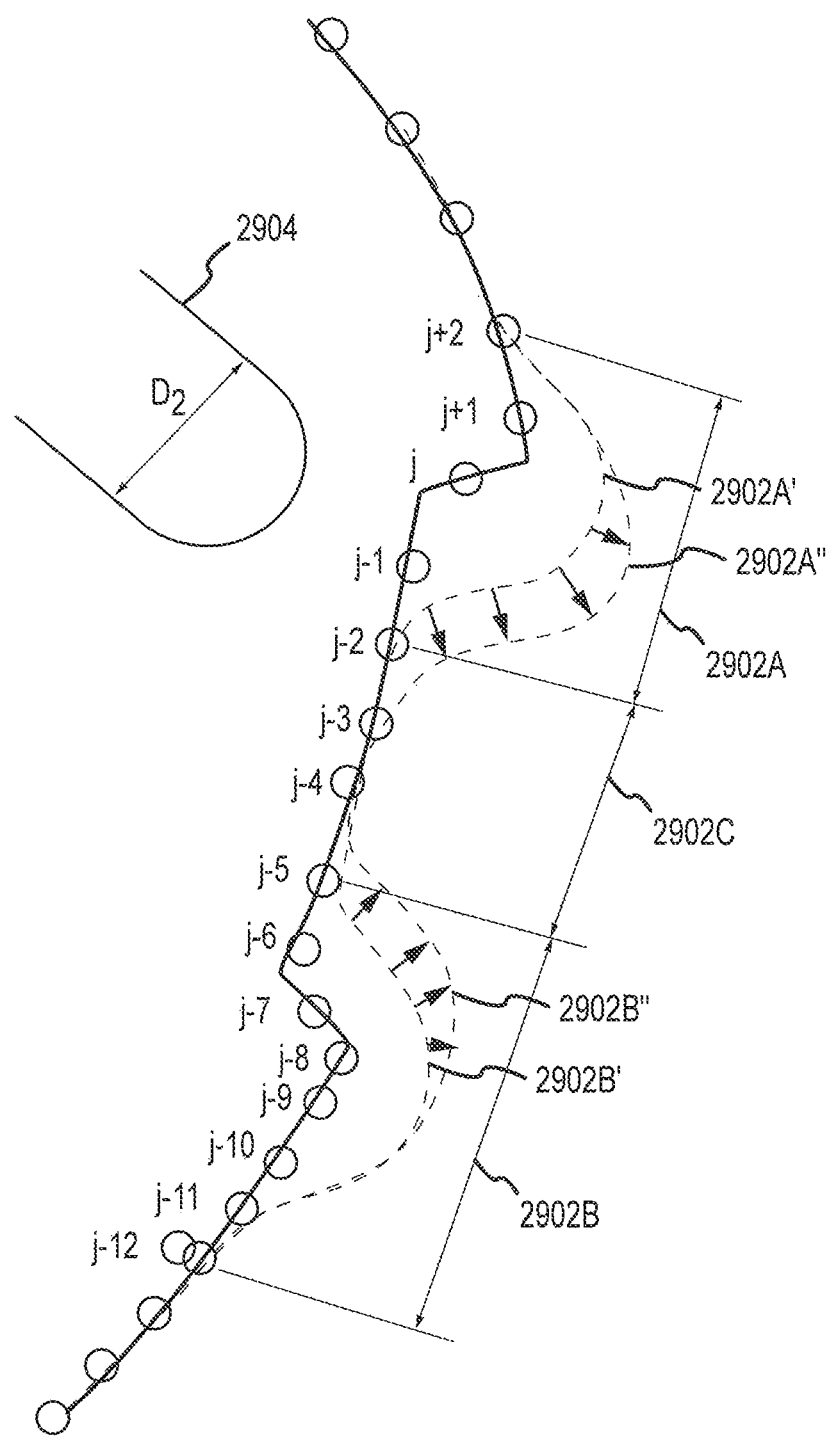
FIG. 29B is similar to FIG. 29A, except depicting a tool with a larger diameter.

If, on the other hand, the tool 2904 has a larger diameter $D_2$ as shown in the example implementation of FIG. 29B, then the overestimation performed in block 2510 may include accounting for this larger tool size in its overestimation. To determine if the overestimation needs to be adjusted to accommodate the larger diameter $D_2$, a first measurement of the minimum diameter of curvatures 2902A' and 2902B' for regions 2902A-B may be made. In addition, a second measurement of half of the distance associated with region 2902C plus the minimum diameter of curvatures 2902A' and 2902B' for regions 2902A-B may be made. If both the first and second measurements are less than the diameter $D_2$, then the amount of overestimation implemented in block 2510 may be set such that the minimum curvatures of regions 2902A-B, respectively, are greater than or equal to $D_2$ and are increased to 2902A" and 2902B", respectively. Logically, this example curvature requirement may be expressed as: if $\text{diameter}_{MIN}$(2902A OR 2902B)<$D_2$ AND ($\text{diameter}_{MIN}$(2902A OR 2902B)+ (2902C)/2)<$D_2$, then overestimate so that $\text{diameter}_{MIN}$(2902A and/or 2902B)≥$D_2$. Also, in the event that the overestimation needs to account for the tool diameter $D_2$, one or more additional points, over what would normally be required absent the need to account for tool diameter, may be included such that the regions 2902A-B respectively extend through points j−4 through j+2 and j−12 through j−4. The curvatures 2902A' and 2902B' for the respective regions 2902A-B may be further adjusted outward (as indicated by the arrows in FIG. 29B) to the respective diameter-accounted curvatures 2902A" and 2902B" to define the potential jig mating surface for the 3D models 40. Thus, regions 2902A-B may increase in size to accommodate the diameter $D_2$ of the tool 2904 by sacrificing the area of region 2902C. It should be noted that, if adding a one or more points on either side of an overestimation region 2902A, 2902B in the course of accounting for tool diameter does not result in a smooth transition into the resulting curvature 2902A", 2902B", then still further points can be added to the overestimation region until a smooth transition is achieved.

Figure 29C:
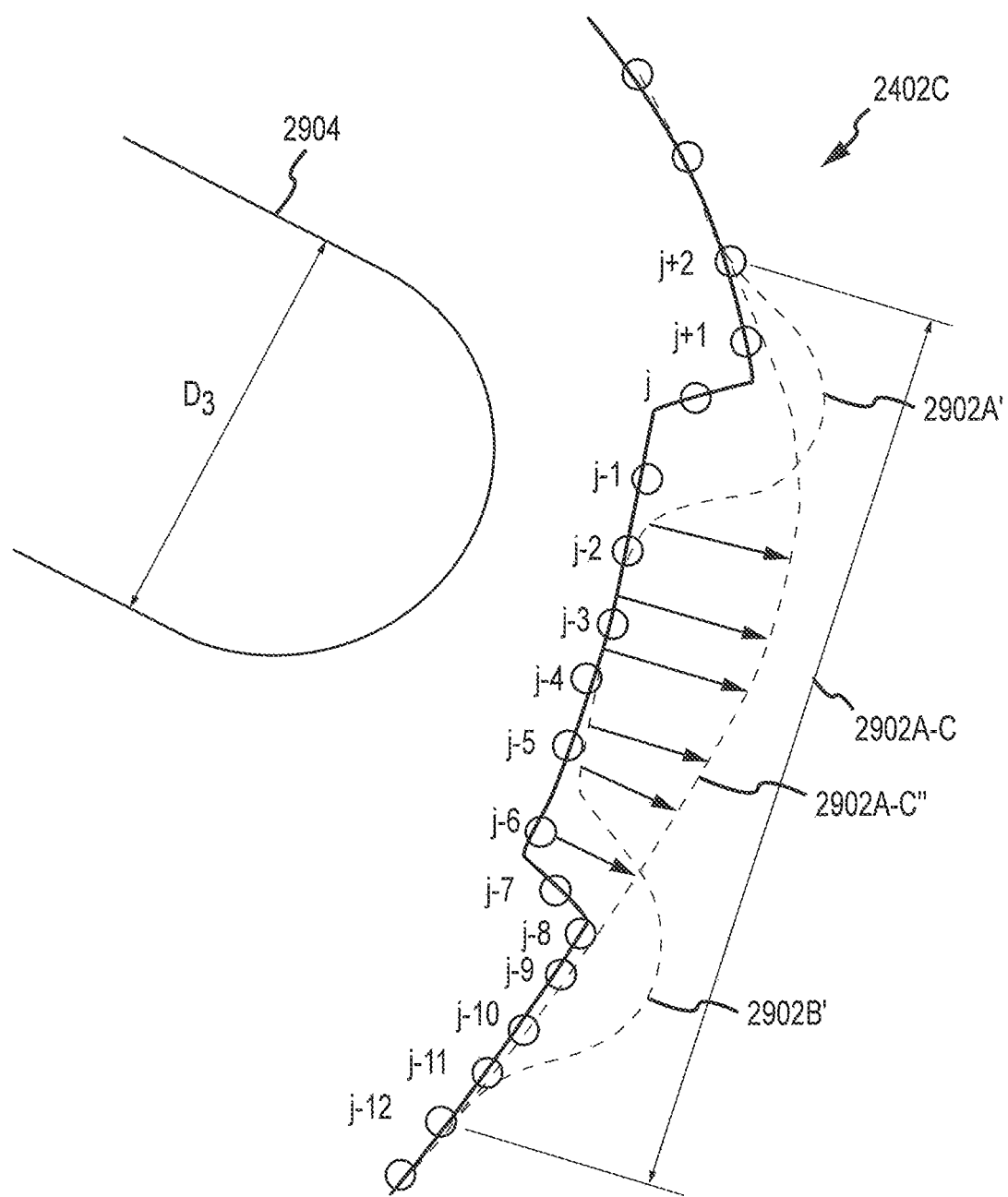
FIG. 29C is similar to FIG. 29B, except depicting a tool with a larger diameter.

FIG. 29C shows an example implementation of the tool 2904 having an even larger diameter $D_3$ than what is shown in FIGS. 29A-B. In this scenario, if $\text{diameter}_{MIN}$(2902A OR 2902B)<$D_3$ AND ($\text{diameter}_{MIN}$(2902A OR 2902B)+ (2902C)/2)<$D_3$, then overestimate so that $\text{diameter}_{MIN}$ (2902A-C)<$D_3$. As illustrated by the arrows, all three regions 2902A-C may need to be overestimated if the size of tool diameter is large enough, sacrificing the entirety of region 2902C to the overestimation associated with regions 2902A-B. Thus, the initial overestimation curvatures 2902A' and 2902B' end up being a single curvature 2902A-C" encompassing all of regions 2902A-C. Of course, additional points can be added as needed to either side of overestimation region 2902A-C to provide a smooth transition into the resulting curvature 2902A-C".

With the curves overestimated to account for factors related to the tool 2904, the resulting overestimated surface profile or contour may be saved for generating the 3D model 40 as long as other criteria (described below in the context of block 2514-2520) are met.

Figure 30:
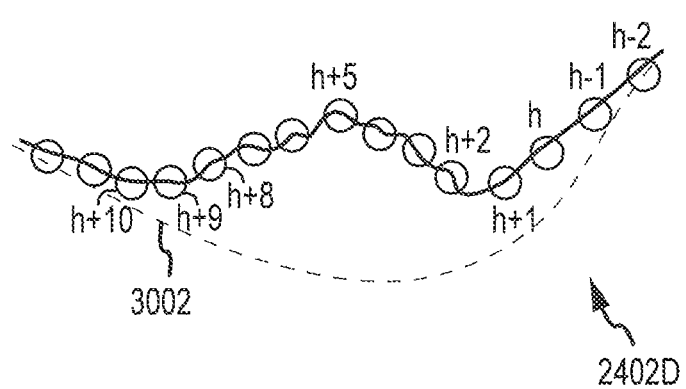
FIG. 30 depicts the irregular region 2402D from FIG. 24 including a proposed area of overestimation indicated by the dashed line.

Referring briefly back to FIG. 24, the analysis and overestimation of algorithm 2500 may be performed on the irregular region 2402D, where the boundary between the cortical and cancellous bone in the femoral condyle is irregular and may not be clearly identified by the imaging slices. FIG. 30 illustrates the example overestimation scheme on the irregular region 2402D according to block 2510. As shown in FIG. 30, the irregular region 2402D extends between points h+1 to h+10. The tangent lines (not shown in FIG. 30) of every two adjacent coordinate points shown have an angular difference greater than $w_c$, and therefore, overestimation may be performed as shown by the dashed line 3002 between points h−2 to h+13.

Figure 31:
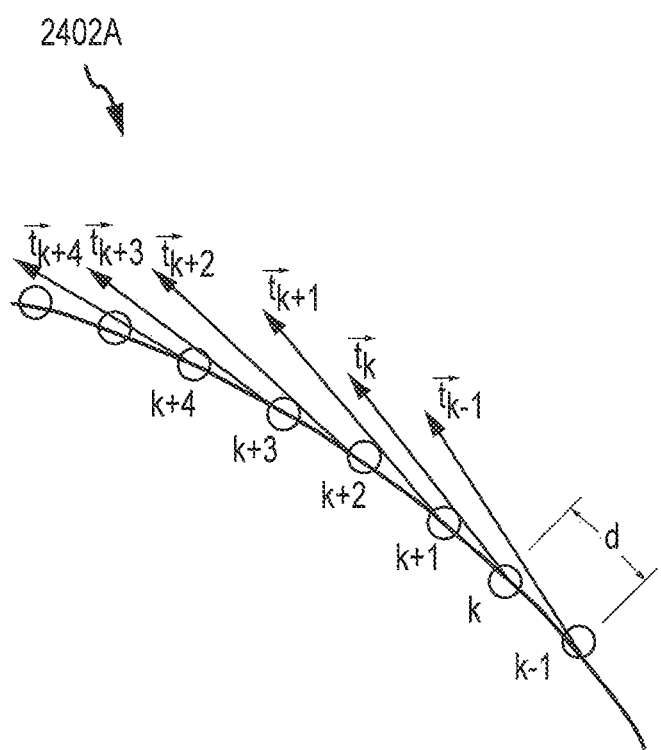
FIG. 31 shows an analysis of the regular region 2402A from FIG. 24.

FIG. 31 shows a similar analysis of the regular region 2402A (from FIG. 24). As was the case with the irregular regions 2402B-D, points along the contour line k−1 through k+4 may be identified and then tangent lines (labeled as $t_{k-1}$, $t_k$, $t_{k+1}$, $t_{k+2}$, $t_{k+3}$, etc.) may be constructed per block 2506. Per block 2508, comparing the angular differences $w_k$ between these tangent lines using the formula $$w_k = \cos^{-1}\left(\frac{t_{k+1} \cdot t_k}{|t_{k+1}||t_k|}\right)$$

shows that they are within the angular criterion $w_c$, which in this example is 5 degrees. Thus, the points shown in FIG. 31 may be saved and used as a potential surface profile for the mating surface of the femoral jig if the surface variations between these points and points on contour lines of adjacent slices are not too extreme. That is, if the angular differences associated with a contour line of a particular slice fall within the angular criterion $w_c$, and the points are used as a potential jig surface, then surface variation between contour lines of adjacent slices may be checked in block 2514. This approach may help to identify certain areas where no cartilage damage or osteophyte is observed in the imaging, yet there is a need to overestimate because the surface variation, between the adjacent slices shown in FIGS. 22A-B, may be too great to be used as an accurate representation of the actual bone surface to be a potential femoral jig surface. Example areas falling within this category for the femoral condyle include, the area of anterior condylar portion close to the trochlear groove and the area of distal condylar portion close to the intercondylar notch to name a few examples.

Figure 32A:
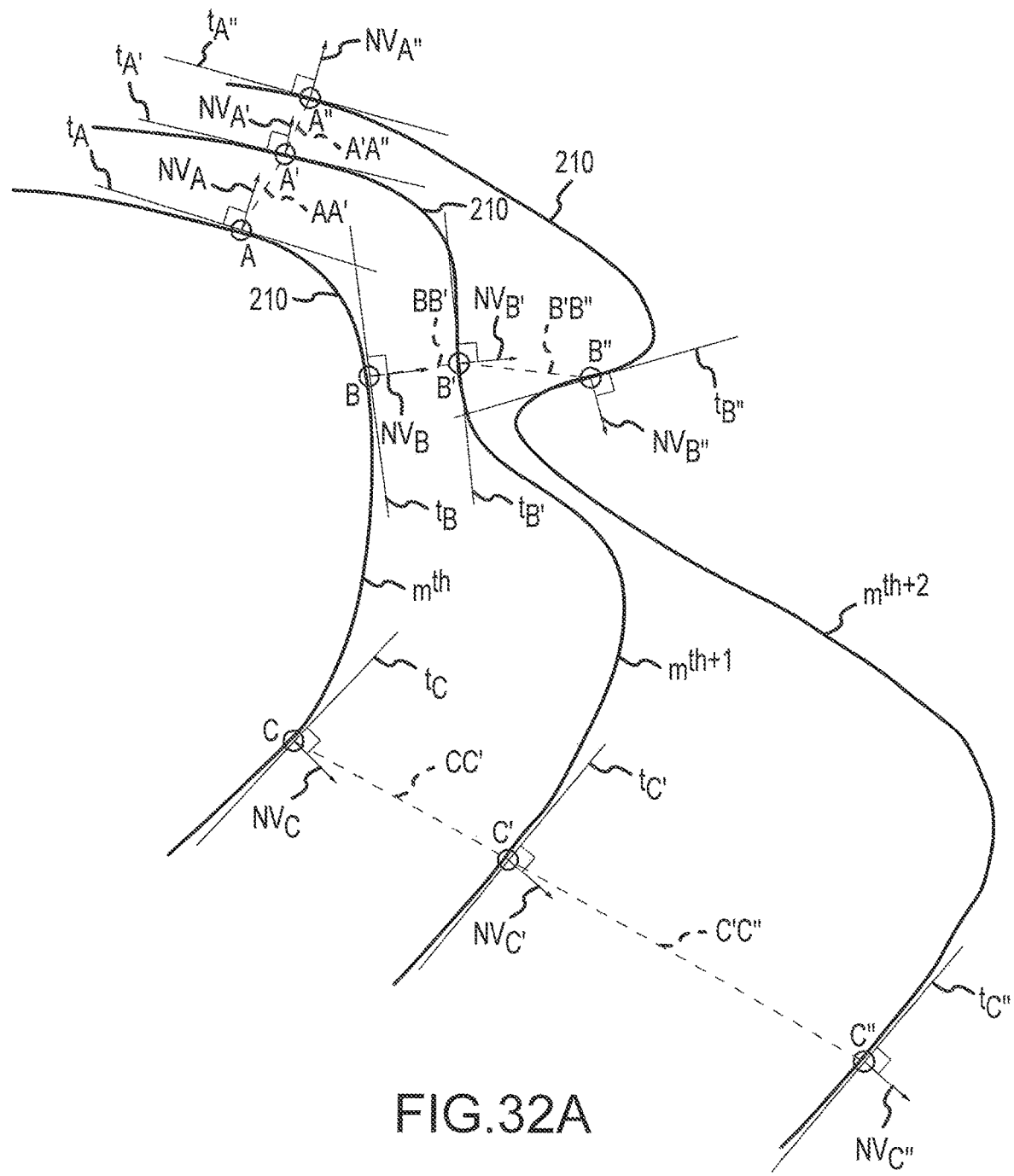
FIG. 32A is a diagrammatic sagittal-coronal-distal isometric view of three contour lines of three adjacent image slices depicting angular relationships that may be used to determine whether portions of the one or more contour lines may be employed to generate 3D computer models.

FIG. 32A is a diagrammatic sagittal-coronal-distal isometric view of three contour lines 210 of three adjacent image slices 16 depicting angular relationships that may be used to determine whether portions of the one or more contour lines may be employed to generate 3D computer models 40. As mentioned above, despite contour line segments and their associated coordinate points meeting the angular criterion $w_c$ so as to not require overestimation as discussed with respect to blocks 2508 and 2510, such contour line segments and associated coordinate points may still require overestimation if the surface variations between surface contour lines 210 of adjacent imaging slices 16 is excessive. Excessive surface variation may result in volume averaging error in the regions of the 3D computer generated models corresponding to the excessive surface variation. Jig mating surfaces based on regions of the 3D computer generated models that are the result of volume averaging error are may have difficulty accurately matingly receiving the associated bone surfaces of the arthroplasty target region.

Such excessiveness is typically the result of variations in the patient's knee features. For example, in the majority of cases, the area of the anterior condylar portion close to the trochlear groove is observed as a smooth depression. However, in other patients, a sharp edge is present in place of the smooth depression. Because of the variation in anatomy between various patients for these varying surface areas and/or other varying surface areas (e.g., the area of distal condylar portion close to the intercondylar notch), these varying surface areas may be generally excluded from being a potential contour line for generating a 3D model 40. In other words, such varying surface areas may be subjected to an overestimation process as described below.

The three contour line segments are respectively labeled in FIG. 32A as the $m^{th}$, $m^{th+1}$, $M^{th+2}$ contour line segments corresponding to three consecutive image slices 16 spaced apart from each other by slice thickness $D_T$. Each contour line includes surface contour points A-C, A'-C' and A"-C" that are saved for use in the potential jig surface profile because, for example, the points fall within the angular criteria discussed with respect to blocks 2506 and 2508. The points A-C, A'-C' and A"-C" now may be used to determine if the slice-to-slice surface variation exceeds a predetermined threshold. For example, on the $m^{th}$ contour line in FIG. 32A, points A, B, and C may have been identified in blocks 2506 and 2508 as defining potential jig mating surfaces. Similarly, in the $m^{th+1}$ contour line in FIG. 32A, points A', B', and C' may have been identified in blocks 2506 and 2508 as defining potential jig mating surfaces. Likewise, in the $M^{th+2}$ contour line in FIG. 32A, points A", B", and C" may have been identified in blocks 2506 and 2508 as defining potential jig mating surfaces.

Because each patient's bone anatomy may be unique, changes in surface contour between corresponding points on contour lines of adjacent slices (i.e., from A-A', A'-A", B-B', B'-B", C-C', or C'-C") may be too significant for use as potential jig surfaces, resulting in volume averaging errors that may lead to surface inaccuracies for the 3D computer models. As will be described in detail below with respect to the example bone contour lines depicted in FIG. 32A, the bone surface defined by points A-A'-A" may provide a potential jig mating surface, the bone surface defined by points B-B'-B" may have too much associated normal vector angular deviation to be used as potential jig mating surface, and the bone surface defined by points C-C'-C" may have too much associate angular deviation between corresponding points of contour lines of adjacent image slices to be used as a potential jig mating surface.

As discussed above with respect to FIG. 24, a contour line 2400 may have a plurality of coordinate points. According to the operation of block 2508 of FIG. 25, the coordinate points may fall into one of two classifications, namely, those coordinate points within a potential jig mating area 2402A and those coordinate points within a non-jig mating area 2402B, 2402C and 2402D. Via the criteria of block 2514 of FIG. 25, the surface coordinate points of one contour line 2400 in potential jig mating area 2402A may be further investigated by a multi-slice (e.g., three-slice) check. For example, coordinate point k+1 located within area 2402A may be coordinate point A in FIG. 32A. Similarly, coordinate points k and k−1 within area 2402A may be coordinate points B and C, respectively. Coordinate points A, A' and A" may correspond to each other, coordinate points B, B' and B" may correspond to each other, and coordinate points C, C' and C" may correspond to each other. Corresponding points A', A", B', B", C', C" for respective points A, B, C may be identified via a variety of methods, including the three methods discussed below with respect to FIGS. 33A-33F.

Block 2514 in FIG. 25 illustrates example comparisons and/or determinations that may be made between corresponding points on contour lines of adjacent image slices to determine if surface variation is too great for the points and contour line segments to be used in generating jig mating surfaces. The comparisons and/or determinations may involve two facets, which are: (1) determining the angular deviation θ between corresponding coordinate points of contour lines of adjacent image slices; and (2) comparing the angular differences φ of normal vectors associated with corresponding coordinate points of contour lines of adjacent image slices. These two facets of the determination are explained in turn below, followed by an application of these two facets of the determination to the contours depicted in FIG. 32A.

As can be understood from FIG. 32A, in one embodiment, the comparisons of the contour lines with respect to angular deviation θ and angular differences φ may take place relative to the contour lines of three adjacent image slices. In other embodiments, the comparisons of the contour lines with respect to angular deviation θ and angular differences φ may take place relative to the contour lines of two, four or more adjacent image slices. In other words, depending on the embodiment, the comparison of the contour lines may be accomplished in groups of two, three, four or more contour lines. In one embodiment, the groups of contour lines evaluated together may be made up of adjacent contour lines. In other embodiments, one or more of the contour lines of a group of contour lines may not be an adjacent contour line (e.g. a contour line falling within a group may be skipped).

Where the image slices 16 are sagittal slices such as those slices 2301, 2310 and 2330 depicted in FIGS. 22A-23, in one embodiment as provided below with respect to FIG. 32A and then again with respect to FIGS. 33A-33B, corresponding coordinate points on contour lines 210 of adjacent image slices 16 may be those coordinate points that all exist in a single plane that is generally perpendicular to the sagittal image slices. Thus, as can be understood from FIG. 32A, points A, A' and A" may all exist in a single plane that is perpendicular to the respective image slices. Line segment AA' extends between points A and A', and line segment A'A" extends between points A' and A". Although the line segments AA' and A'A" may all exist in the same single plane that is perpendicular to the respective image slices, the line segments AA' and A'A" may be angularly deviated from each other such that they do not extend along a common line. This angular deviation may be the result of each point A, A' and A" being located on its respective contour line $m^{th}$, $m^{th+1}$, and $m^{th+2}$ and each contour line having a different elevation at its respective point relative to the corresponding points on the adjacent contour lines. This elevation difference between the points A, A' and A" may be because the bone contour geometric shape changes from contour line $m^{th}$, $m^{th+1}$, $m^{th+2}$ to contour line. The order of the contour lines $m^{th}$, $m^{th+1}$, $m^{th+2}$ may correspond to the order of the respective image slices, the image slice order corresponding to the movement of the MRI scan along the knee. Similar relationships exist for points B, B' and B" and for points C, C' and C", resulting in similar line segments BB', B'B" and CC', C'C", respectively.

Once corresponding coordinate points are identified via the method already discussed above and below with respect to FIGS. 32A and 33A-33B or via any of the methods discussed below with respect to FIGS. 33C-33F, the surface variation between adjacent contour lines may be analyzed by: (1) determining the angular deviation θ between corresponding coordinate points of contour lines of adjacent image slices; and (2) comparing the angular differences φ of normal vectors associated with corresponding coordinate points of contour lines of adjacent image slices.

As can be understood from FIG. 32A and already mentioned above, in one embodiment, the comparisons of the contour lines with respect to angular deviation θ and angular differences φ may take place relative to the contour lines of three adjacent image slices. In other embodiments, the comparisons of the contour lines with respect to angular deviation θ and angular differences φ may take place relative to the contour lines of two, four or more adjacent image slices. In other words, depending on the embodiment, the comparison of the contour lines may be accomplished in groups of two, three, four or more contour lines. In one embodiment, the groups of contour lines evaluated together may be made up of adjacent contour lines. In other embodiments, one or more of the contour lines of a group of contour lines may not be an adjacent contour line (e.g. a contour line falling within a group may be skipped).

As can be understood from FIG. 32A, in one embodiment, the contour lines $m^{th}$, $m^{th+1}$, $M^{th+2}$ may be evaluated as a group of three contour lines, wherein contour line $m^{th}$ is compared to contour lines $M^{th+1}$ and $M^{th+2}$. Contour line $M^{th+1}$ may then be compared to contour lines $m^{th+2}$ and $m^{th+3}$, and contour line $m^{th+2}$ may then be compared to contour line $m^{th+3}$ and contour line $m^{th+4}$. Alternatively, once contour line $m^{th}$ is compared to contour lines $M^{th+1}$ and $M^{th+2}$, the comparison may begin again with a comparison of contour line $m^{th+2}$ to contour line $m^{th+3}$ and contour line $m^{th+4}$. Alternatively, once contour line $m^{th}$ is compared to contour lines $M^{th+1}$ and $M^{th+2}$, the comparison may begin again with a comparison of contour line $m^{th+4}$ to contour line $m^{th+5}$ and contour line $M^{th+6}$. Similar orders for comparing the contour lines may be used regardless of whether the contour lines are compared in groups of two, four or more.

Figure 32B:
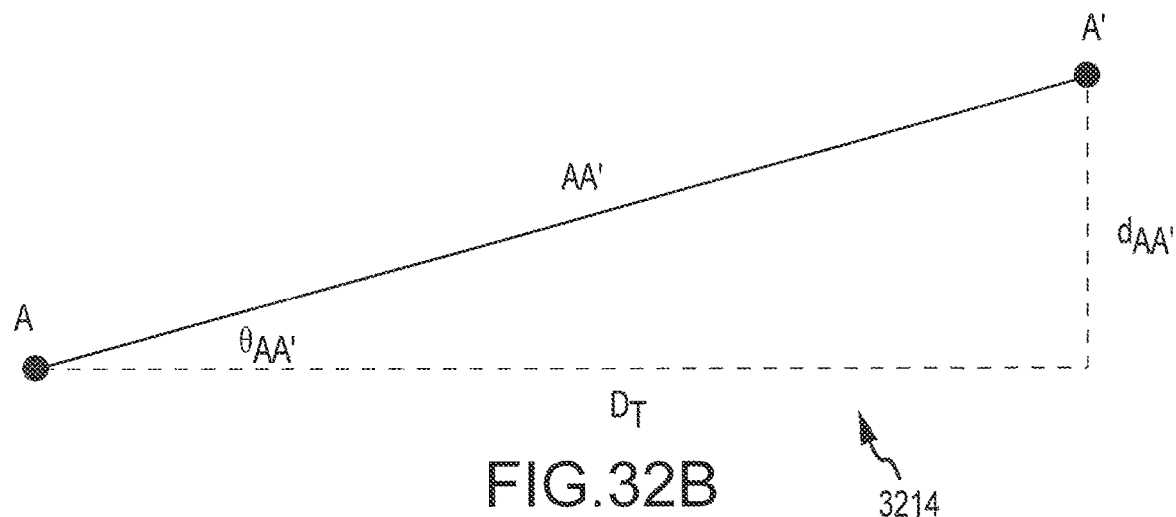
FIGS. 32B-G are example right triangles that may be used for determining the angular deviation θ between corresponding coordinate points of contour lines of adjacent image slices per block 2514 of FIG. 25.

A discussion will now be given regarding the first facet of the surface variation analysis, namely, the determination of the angular deviation θ between corresponding coordinate points of contour lines of adjacent image slices per block 2514. FIG. 32B is an example right triangle 3214 that may be used for determining the angular deviation θ between corresponding coordinate points of contour lines of adjacent image slices per block 2514. The right triangle 3214 illustrates points A and A' with the line segment AA' extending between these two points. The points A and A' lie on respective contour lines $m^{th}$ and $M^{th+1}$. The image slices containing the two contour lines $m^{th}$ and $M^{th+1}$ are separated by the slice thickness $D_T$, which is the perpendicular distance between the two image slices. Thus, the slice thickness $D_T$ can be represented in the right triangle 3214 as the long leg of the right triangle 3214, wherein the line segment AA' is the hypotenuse of the right triangle 3214. The rise or fall distance $d_{AA'}$ between the two points A and A' is a distance perpendicular to the slice thickness $D_T$ and is represented on the right triangle 3214 by the short leg of the right triangle 3214. The small angle $\theta_{AA'}$ of the right triangle 3214 represents the angular deviation $\theta_{AA'}$ between the corresponding coordinate points A and A' of contour lines $m^{th}$ and $m^{th+1}$ of adjacent image slices per block 2514. Thus, as can be understood from the triangle 3214, the angular deviation $\theta_{AA'}$ between the corresponding coordinate points A and A' of contour lines $m^{th}$ and $m^{th+1}$ of adjacent image slices may be calculated by any of the following three formulas:

$$\theta_{AA'} = \tan^{-1}\left(\frac{d_{AA'}}{D_T}\right); \theta_{AA'} = \cos^{-1}\left(\frac{D_T}{AA'}\right); \text{ or } \theta_{AA'} = \sin^{-1}\left(\frac{d_{AA'}}{AA'}\right).$$

Ideally if there were no surface variation between points A and A', then the length of line segment AA' would be equal to the slice thickness $D_T$ and the angular deviation $\theta_{AA'}$ between the corresponding coordinate points A and A' of contour lines $M^{th}$ and $m^{th+1}$ would be zero.

Determining the angular deviation $\theta_{AA'}$ between the corresponding coordinate points A and A' in this manner may indicate if the surface between points A and A' is too steep or varied to be used as a potential jig mating surface. For example, the angular deviation θ between the coordinate points may be compared to an angular criterion $\theta_c$, and the surface corresponding to the coordinate points may be considered unsuitable for the creation of the jig's bone mating surfaces where the angular deviation θ between the coordinate points is greater than the angular criterion $\theta_c$. Stated in the reverse and in the context of coordinate points A and A', the surface corresponding to coordinate points A and A' may be a potential candidate for creation of the jig's bone mating surfaces if the angular deviation $\theta_{AA'}$ is less than the angular criterion $\theta_c$ (i.e., $[\theta_{AA'}<\theta_c]$=surface corresponding to coordinate points A and A' being a potential candidate for the creation of the jig's bone mating surfaces).

In one embodiment, the angular criterion $\theta_c$ may be approximately one degree. However, in some embodiments, the angular criterion $\theta_c$ may be in the range of approximately one to approximately five degrees. In other embodiments, the angular criterion $\theta_c$ may be less than or greater than these recited values for the angular criterion $\theta_c$.

Figure 32C:
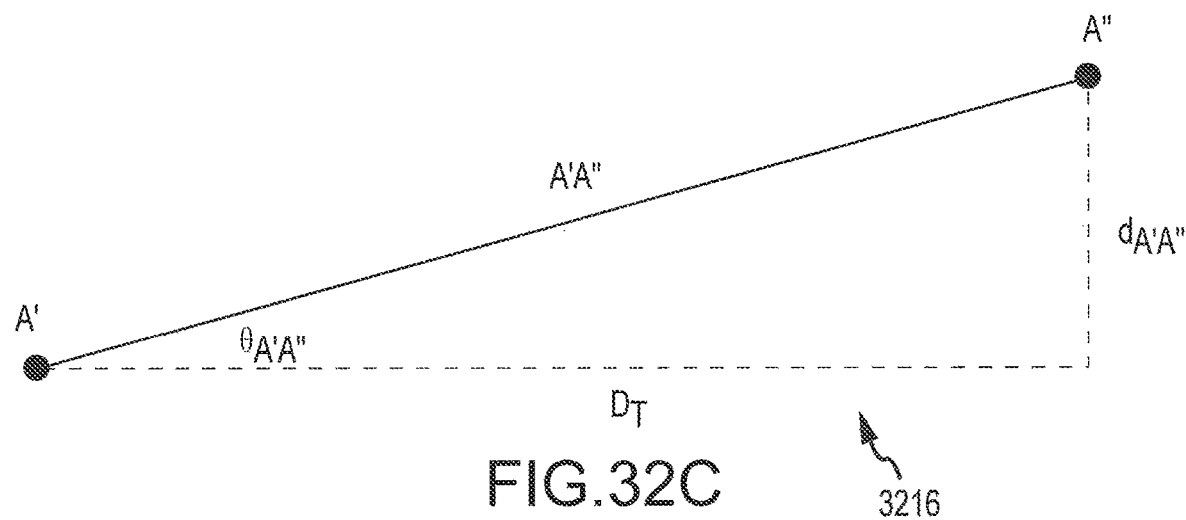

As can be understood from FIG. 32C, the example right triangle 3214 of FIG. 32B can be modified to become another example right triangle 3216 and used in determining the angular deviation $\theta_{A'A''}$ between corresponding coordinate points A' and A" of contour lines $m^{th+1}$ and $m^{th+2}$ of adjacent image slices per block 2514. The preceding three $\tan^{-1}$, $\sin^{-1}$ and $\cos^{-1}$ functions may be modified to match the circumstances of the example right triangle 3216 of FIG. 32C to calculate the respective angular deviation $\theta_{A'A''}$. Thus, as can be understood from FIG. 32C, the angular deviation $\theta_{A'A''}$ between the corresponding coordinate points A' and A" of contour lines $m^{th+1}$ and $m^{th+2}$ of adjacent image slices may be calculated by any of the following three formulas:

$$\theta_{A'A''} = \tan^{-1}\left(\frac{d_{A'A''}}{D_T}\right); \theta_{A'A''} = \cos^{-1}\left(\frac{D_T}{A'A''}\right); \text{ or } \theta_{A'A''} = \sin^{-1}\left(\frac{d_{A'A''}}{A'A''}\right).$$

As can be understood from FIGS. 32D-32G, the right triangle 3214 of FIG. 32B can be similarly modified into the respective example right triangles 3218, 3220, 3222 and 3224 of FIGS. 32D-32G, which respectively will facilitate the determination of the angular deviations $\theta_{BB'}$, $\theta_{B'B''}$, $\theta_{CC'}$, and $\theta_{C'C''}$ between corresponding coordinate points B and B', B' and B", C and C', and C' and C", respectively. The preceding three $\tan^{-1}$, $\sin^{-1}$ and $\cos^{-1}$ functions may be modified to match the circumstances of the respective example right triangles 3218, 3220, 3222 and 3224 of FIGS. 32D-32G to calculate the respective angular deviations $\theta_{BB'}$, $\theta_{B'B''}$, $\theta_{CC'}$, and $\theta_{C'C''}$.

In a manner like that discussed with respect to the angular deviation $\theta_{AA'}$ between the corresponding coordinate points A and A', the angular deviation $\theta$ between any of the other pairs of corresponding coordinate points (i.e., A' and A", B and B', B' and B", C and C', and C' and C") may be compared to an angular criterion $\theta_c$. Thus, where the angular deviation $\theta$ between corresponding coordinate points exceeds the angular criterion $\theta_c$, the surface associated with the coordinate points may be considered unsuitable for use in the creation of the jig's bone mating surfaces. Stated in the reverse, the surface corresponding to the coordinate points may be a potential candidate for creation of the jig's bone mating surfaces if the angular deviation $\theta$ is less than the angular criterion $\theta_c$ (i.e., $[\theta<\theta_c]$=surface corresponding to the coordinate points being a potential candidate for the creation of the jig's bone mating surfaces).

In one embodiment, the angular criterion $\theta_c$ may be approximately one degree. However, in some embodiments, the angular criterion $\theta_c$ may be in the range of approximately one to approximately four degrees. In other embodiments, the angular criterion $\theta_c$ may be less than or greater than these recited values for the angular criterion $\theta_c$.

A discussion will now be given regarding the second facet of the surface variation analysis, namely, comparing the angular differences $\varphi$ of normal vectors associated with corresponding coordinate points of contour lines of adjacent image slices. As indicated in FIG. 32A, each contour line surface coordinate point A, A', A", B, B', B", C, C' and C" includes a respective tangent line $t_A$, $t_{A'}$, $t_{A''}$, $t_B$, $t_{B'}$, $t_{B''}$, $t_C$, $t_{C'}$, and $t_{C''}$ that is parallel to the plane in which the associated contour line $m^{th}$, $m^{th+1}$ and $m^{th+2}$ resides and tangent to the curvature of the associated contour line $m^{th}$, $m^{th+1}$ and $m^{th+2}$ at the respective coordinate point A, A', A", B, B', B", C, C' and C". A normal vector line $NV_A$, $NV_{A'}$, $NV_{A''}$, $NV_B$, $NV_{B'}$, $NV_{B''}$, $NV_C$, $NV_{C'}$, and $NV_{C''}$ extends from each respective coordinate point A, A', A", B, B', B", C, C' and C" and is perpendicular to each respective tangent line $t_A$, $t_{A'}$, $t_B$, $t_{B'}$, $t_{B''}$, $t_{B'''}$, $t_C$, $t_{C'}$, and $t_{C''}$. The angular differences $\varphi_{A-A'}$ of normal vectors $NV_A$ and $NV_{A'}$ associated with respective corresponding coordinate points A and A' of respective contour lines $M^{th}$ and $m^{th+1}$ may be determined with the following formula:

$$\varphi_{A-A'} = \cos^{-1}\left(\frac{NV_A \bullet NV_{A'}}{|NV_A||NV_{A'}|}\right).$$

Similarly, the angular differences $\varphi_{A'-A''}$ of normal vectors $NV_{A'}$ and $NV_{A''}$ associated with respective corresponding coordinate points A' and A" of respective contour lines $m^{th+1}$ and $m^{th+2}$ may be determined with the following formula:

$$\varphi_{A'-A''} = \cos^{-1}\left(\frac{NV_{A'} \bullet NV_{A''}}{|NV_A||NV_{A''}|}\right).$$

The angular differences $\varphi_{B-B'}$ of normal vectors $NV_B$ and $NV_{B'}$ associated with respective corresponding coordinate points B and B' of respective contour lines $M^{th}$ and $m^{th+1}$ may be determined with the following formula:

$$\varphi_{B-B'} = \cos^{-1}\left(\frac{NV_B \bullet NV_{B'}}{|NV_B||NV_{B'}|}\right).$$

Similarly, the angular differences $\varphi_{B'-B''}$ of normal vectors $NV_{B'}$ and $NV_{B''}$ associated with respective corresponding coordinate points B' and B" of respective contour lines $m^{th+1}$ and $m^{th+2}$ may be determined with the following formula:

$$\varphi_{B'-B''} = \cos^{-1}\left(\frac{NV_{B'} \bullet NV_{B''}}{|NV_{B'}||NV_{B''}|}\right).$$

The angular differences $\varphi_{C-C'}$ of normal vectors $NV_C$ and $NV_{C'}$ associated with respective corresponding coordinate points C and C' of respective contour lines $M^{th}$ and $m^{th+1}$ may be determined with the following formula:

$$\varphi_{C-C'} = \cos^{-1}\left(\frac{NV_C \bullet NV_{C'}}{|NV_C||NV_{C'}|}\right).$$

Similarly, the angular differences $\varphi_{C'-C''}$ of normal vectors $NV_{C'}$ and $NV_{C''}$ associated with respective corresponding coordinate points C' and C" of respective contour lines $m^{th+1}$ and $m^{th+2}$ may be determined with the following formula:

$$\varphi_{C'-C''} = \cos^{-1}\left(\frac{NV_{C'} \bullet NV_{C''}}{|NV_{C'}||NV_{C''}|}\right).$$

Determining in this manner the angular differences φ of normal vectors associated with respective corresponding coordinate points of respective contour lines may indicate if the surface between the corresponding points is too varied to be used as a potential jig mating surface. For example, the angular differences φ of normal vectors associated with respective corresponding coordinate points may be compared to an angular criterion $\varphi_c$, and the surface associated with the corresponding points may be considered unsuitable for use in the creation of the jig's bone contacting surfaces where values for the angular differences φ are greater than the angular criterion $\varphi_c$. Stated in the reverse, where the angular differences φ of normal vectors associated with respective corresponding coordinate points is less than an angular criterion $\varphi_c$, the surface corresponding to the coordinate points may be a potential candidate for the creation of the jig's bone mating surfaces (i.e., $\varphi < \varphi_c$=surface corresponding to the coordinate points being a potential candidate for the creation of the jig's bone mating surfaces). In one embodiment, the angular criterion $\varphi_c$ may be approximately two degrees. In some embodiments, the angular criterion $\varphi_c$ may be in the range of approximately two to approximately six degrees. In other embodiments, the angular criterion $\varphi_c$ may be greater or less than these recited values for the angular criterion $\varphi_c$.

Thus, although one or more coordinate points of a contour line may satisfy the tangent angle criterion $w_c$ of block 2508 as discussed above with respect to FIGS. 24 and 26-31, the coordinate points may still be inadequate for use in generating the jig's bone contacting surfaces. This inadequateness may result from the failure of the coordinate points to meet the criterion of block 2514, namely, the failure of the angular deviation θ between any of the corresponding coordinate points to meet the angular deviation criterion $\theta_c$ and/or the failure of the angular differences φ of normal vectors associated with respective corresponding coordinate points to meet the angular differences criterion $\varphi_c$. In some embodiments, when one or more coordinate points fail to meet both the criterion $\theta_c$ and $\varphi_c$ of block 2508, the contour lines in the locations of those failed coordinate points may be modified via an overestimation process similar to that discussed above with respect block 2510 and FIGS. 29A-30.

In other embodiments as reflected in block 2516, when one or more coordinate points fail to meet both the criterion $\theta_c$ and $\varphi_c$ of block 2508, a determination may be made regarding whether or not the slice thickness $D_T$ may be adjusted to a thinner slice thickness $D_T$. Reducing the slice thickness $D_T$ per block 2518 may reduce the variations between adjacent contour lines, making it more likely that the criterion $\theta_c$ and $\varphi_c$ will be satisfied for the coordinate points were the entire process started over at block 2502 with a new slice thickness $D_T$. If it is determined that modifying the slice thickness $D_T$ would not be beneficial (e.g., due to slice thickness $D_T$ already being at a minimum because further reduction in slice thickness $D_T$ may generate significant high interferences, residuals, signal-to-noise ratios and unreliable volume-averaging in the pixels), then the contour lines may be subjected to overestimation per block 2510.

If the one or more coordinate points of a contour line satisfy the tangent angle criterion $w_c$ of block 2508 and both of the angular criterion $\theta_c$ and $\varphi_c$ of block 2514, then such one or more coordinate points may be recorded for the generation of the jig's bone mating surface, as indicated in block 2520 of FIG. 25. In other words, if the one or more coordinate points of a contour line satisfy the tangent angle criterion $w_c$ of block 2508 and both of the angular criterion $\theta_c$ and $\varphi_c$ of block 2514, then the surfaces associated with such one or more coordinate points may be employed in the generation of corresponding bone mating surfaces of the jig, as indicated in block 2520.

An example application of the functions of block 2514 with respect to the contour lines $m^{th}$, $m^{th+1}$ and $m^{th+2}$ depicted in FIG. 32A will now be provided. In this example, it is assumed the coordinate points A, A', A", B, B', B", C, C' and C'" and their respective contour lines portions have already satisfied the tangent angle criterion $w_c$ of block 2508.

As can be understood from FIGS. 32A-C, points A, A' and A" are in close proximity to each other due to the close proximity of their respective contour line segments. The close proximity of the respective contour lines is a result of the rise or fall distances $d_{AA'}$ and $d_{A'A''}$ being small at points A, A' and A", as the contour lines $m^{th}$, $m^{th+1}$ and $m^{th+2}$ at all points A, A', A", B, B', B", C, C' and C" are evenly spaced medially-laterally due to having equal slice thicknesses $D_T$. Due to the close proximity of points A, A' and A", line segments AA' and A'A" are relatively short, resulting in angular deviations $\theta_{AA'}$ and $\theta_{A'A''}$ that are less than the angular criterion $\theta_c$, which in one embodiment, may be in the range of approximately one to approximately four degrees. As the angular deviations $\theta_{AA'}$ and $\theta_{A'A''}$ are less than the angular criterion $\theta_c$, the angular criterion $\theta_c$ is satisfied for points A, A' and A", and these points are potential candidates for the generation of the jig's bone mating surfaces.

As indicated in FIG. 32A, the angular differences $\varphi_{A-A'}$ and $\varphi_{A'-A''}$ between the normal vectors $NV_A$, $NV_{A'}$ and $NV_{A''}$ is small, resulting in angular differences $\varphi_{A-A'}$ and $\varphi_{A'-A''}$ that are less than the angular criterion $\varphi_c$, which in one embodiment, may be in the range of approximately two to approximately five degrees. As the angular differences $\varphi_{A-A'}$ and $\varphi_{A'-A''}$ are less than the angular criterion $\varphi_c$, the angular criterion $\varphi_c$ is satisfied. Because the points A, A' and A" have satisfied both of the angular criterion $\theta_c$ and $\varphi_c$ of block 2514, the surface represented by the points A, A' and A" may be employed to generate the jig's surfaces that matingly contact the patient's arthroplasty target surfaces per block 2520.

Figure 32D:
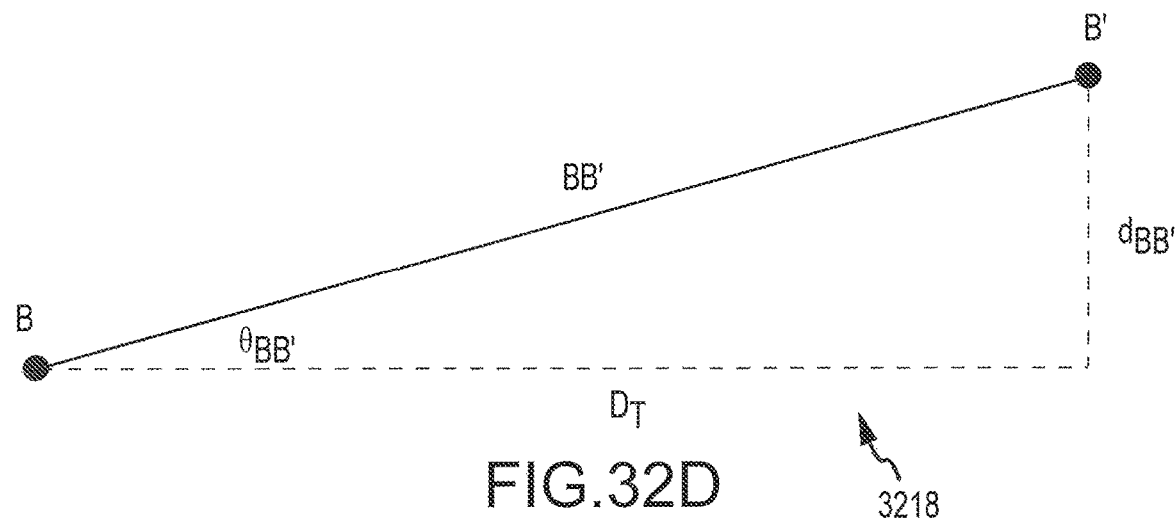
Figure 32E:
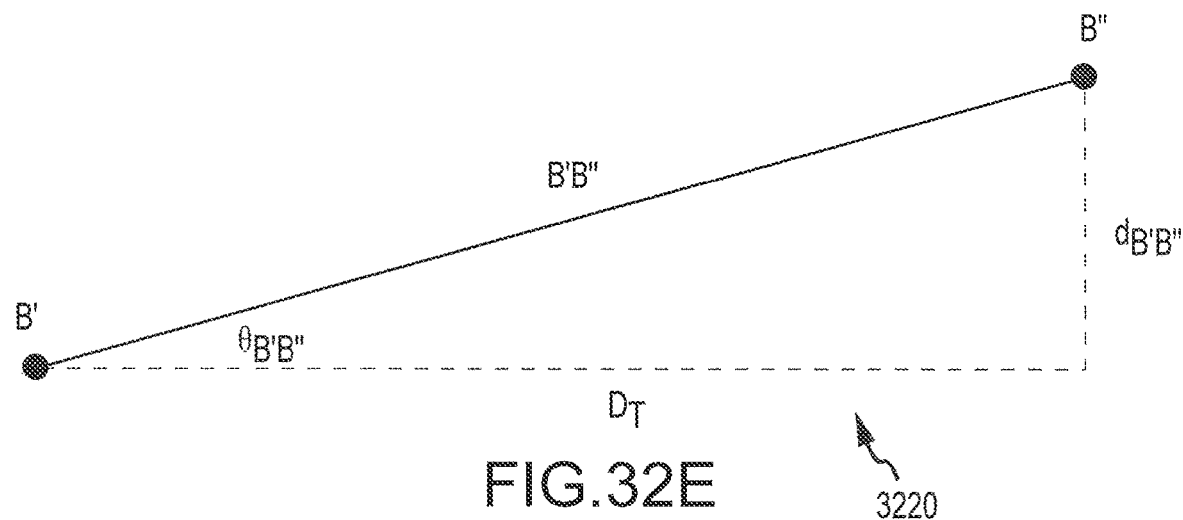

As can be understood from FIGS. 32A and 32D-E and for reasons similar to those discussed with respect to points A, A' and A", points B, B' and B" are in close proximity to each other due to the close proximity of their respective contour line segments. Consequently, line segments BB' and B'B" are relatively short, resulting in angular deviations $\theta_{BB'}$ and $\theta_{B'B''}$ that are less than the angular criterion $\theta_c$. As the angular deviations $\theta_{BB'}$ and $\theta_{B'B''}$ are less than the angular criterion $\theta_c$, the angular criterion $\theta_c$ is satisfied for points B, B' and B", and these points are potential candidates for the generation of the jig's bone mating surfaces.

As indicated in FIG. 32A, the angular difference $\varphi_{B-B'}$ between the normal vectors $NV_B$ and $NV_{B'}$ is small such that it is less than the angular criterion $\varphi_c$ and, therefore, satisfies the angular criterion $\varphi_c$. However, the angular difference $\varphi_{B'-B''}$ between the normal vectors $NV_{B'}$ and $NV_{B''}$ is large such that it is greater than the angular criterion $\varphi_c$ and, therefore, does not satisfy the angular criterion $\varphi_c$. As the points B and B' have satisfied both of the angular criterion $\theta_c$ and $\varphi_c$ of block 2514, the surface represented by the points B and B' may be employed to generate the jig's surfaces for matingly contacting the patient's arthroplasty target surfaces per block 2520. However, as the points B' and B" have failed to satisfy both of the angular criterion $\theta_c$ and $\varphi_c$ of block 2514, the surface represented by the points B' and B" may not be employed to generate the jig's surfaces for matingly contacting the patient's arthroplasty target surfaces. Instead, the slice spacing $D_T$ may be evaluated per block 2516 and reset per block 2518, with the process then started over at block 2502. Alternatively, the points may be subjected to overestimation per block 2510.

Figure 32F:
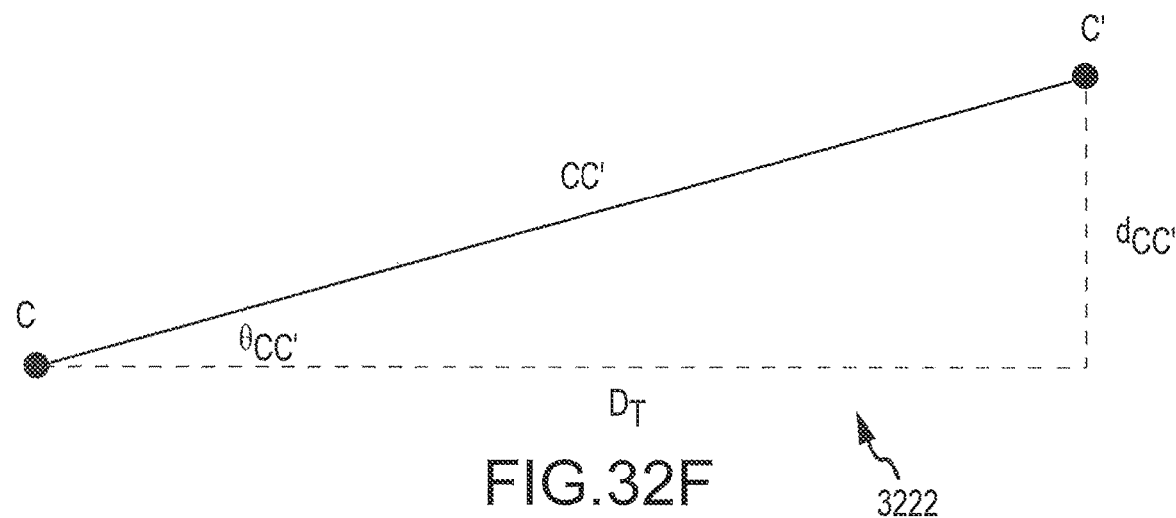
Figure 32G:
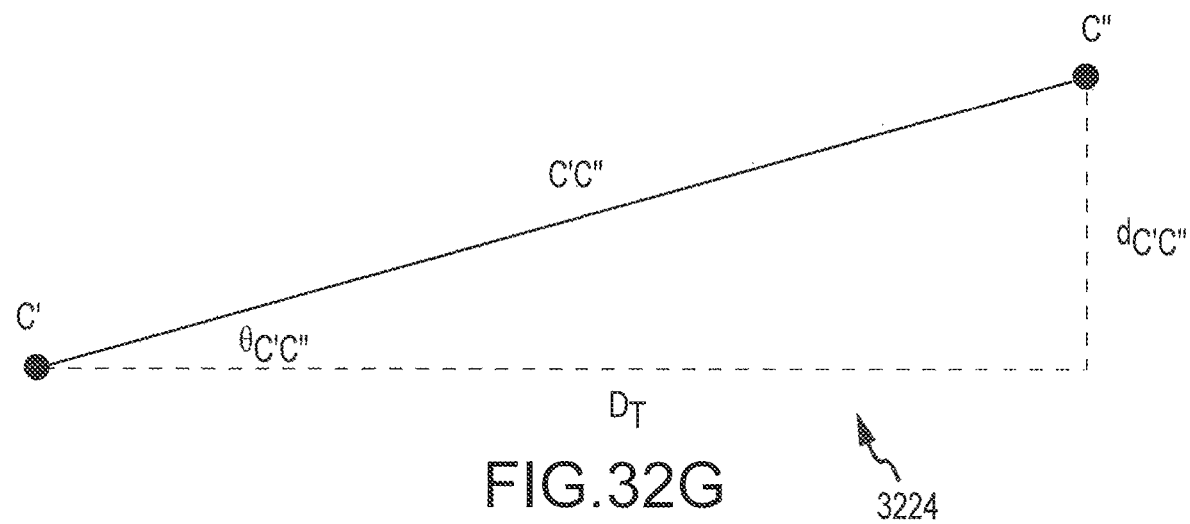

As can be understood from FIGS. 32A and 32F-G and because of significant rise and fall distances $d_{cc'}$ and $d_{c'c''}$ between the contour lines at points C, C' and C", points C, C' and C" are not in close proximity to each other due to the significant distance between their respective contour line segments. Consequently, line segments CC' and C'C" are relatively long, resulting in angular deviations $\theta_{CC'}$ and $\theta_{C'C''}$ that exceed the angular criterion $\theta_c$ and, therefore, do not satisfy the angular criterion $\theta_c$.

As indicated in FIG. 32A, the angular differences $\varphi_{C-C'}$ and $\varphi_{C-C''}$ between the normal vectors $NV_C$, $NV_{C'}$, and $NV_{C''}$ are small such that they are less than the angular criterion $\varphi_c$ and, therefore, satisfy the angular criterion $\varphi_c$. However, as the points C, C' and C" do not satisfied both of the angular criterion $\theta_c$ and $\varphi_c$, the surfaces represented by the points C, C' and C" may not be employed to generate the jig's surfaces for matingly contacting the patient's arthroplasty target surfaces. Instead, the slice spacing $D_T$ may be evaluated per block 2516 and reset per block 2518, with the process then started over at block 2502. Alternatively, the points may be subjected to overestimation per block 2510.

As can be understood from the preceding discussion, in one embodiment, the analysis of the contour lines may be performed slice-by-slice across the series of contour lines. In other words, a first contour line $m^{th+1}$ is compared at its respective coordinate points to the corresponding coordinate points of the immediate neighbor contour lines (e.g., contour lines $M^{th}$ and $m^{th+2}$) medial and lateral of the first contour line.

While the preceding example process discussed with respect to FIGS. 32A-32G is given in the context of three contour lines $m^{th}$, $M^{th+1}$ and $m^{th+2}$ and nine coordinate points A-C", of course the process can be readily applied to a greater or less number or contour lines and coordinate points. Therefore, the process should not be interpreted as being limited to any number of contour lines or coordinate points.

For another example application of the functions of block 2514, reference is made to FIGS. 33A-33F. FIGS. 33A, 33C and 33E each depict portions of contour lines $n^{th}$, $n^{th+1}$, $n^{th+2}$, $n^{th+3}$ and $n^{th+4}$ in sagittal views similar to that of FIG. 23. FIGS. 33B, 33D and 33F each represent a bone surface contour line 3300 and a linear interpolation bone surface contour line 3302 as viewed along section lines 33B-33B, 33D-33D and 33F-33F transverse to image slices containing the contour lines $n^{th}$, $n^{th+1}$, $n^{th+2}$, $n^{th+3}$ and $n^{th+4}$ of respective FIGS. 33A, 33C and 33E.

As indicated in FIGS. 33A-F, contour lines $n^{th}$, $n^{th+1}$, $n^{th+2}$, $n^{th+3}$ and $n^{th+4}$ each include a respective coordinate point D, D', D", D''' and D''''. In one embodiment, corresponding coordinate points may be identified via the method discussed above with respect to FIG. 32A. Specifically, as can be understood from FIGS. 33A-B, corresponding coordinate points D, D', D", D''' and D'''' may be those coordinate points D, D', D", D''' and D'''' that each exist in the same medial-lateral plane that is generally perpendicular to the sagittal image slices containing the contour lines and coordinate points. Other groups of corresponding coordinate points may be identified via a similar perpendicular plane methodology.

As can be understood from FIGS. 33C-D, corresponding coordinate points D, D', D", D''' and D'''' may be identified via a second method. Specifically, the contour lines $n^{th}$, $n^{th+1}$, $n^{th+2}$, $n^{th+3}$ and $n^{th+4}$ may be superimposed into the same image slice layer as indicated in FIG. 33D by arrow 33D1, resulting in a composite plane 33D2 having a total rise or fall distance $d_{DD''''}$ between coordinate points D and D''''. The total rise or fall distance $d_{D'''D''''}$ may be the sum of the respective rise or fall distances $d_{DD'}$, $d_{D'D''}$, $d_{D''D'''}$, $d_{D'''D''''}$ discussed below with respect to FIGS. 33B, 33C and 33F.

As indicated in FIG. 33C, the normal vector lines $NV_D$, $NV_{D'}$, $NV_{D''}$, $NV_{D'''}$ and $NV_{D''''}$, the determination of which is discussed below with respect to FIGS. 33A, 33C and 33E, are utilized to identify the corresponding coordinate points D, D', D", D''' and D''''. For example, the normal vector line $NV_D$ of coordinate point D is extended to contour line $n^{th+1}$, and the intersection between normal vector line $NV_D$ and contour line $n^{th+1}$ identifies the coordinate point corresponding to coordinate point D, namely, coordinate point D'. The normal vector line $NV_{D'}$ of coordinate point D' is extended to contour line $n^{th+2}$, and the intersection between normal vector line $NV_{D'}$ and contour line $n^{th+2}$ identifies the coordinate point corresponding to coordinate point D', namely, coordinate point D". The normal vector line $NV_{D''}$ of coordinate point D" is extended to contour line $n^{th+3}$, and the intersection between normal vector line $NV_{D''}$ and contour line $n^{th+3}$ identifies the coordinate point corresponding to coordinate point D", namely, coordinate point D'''. The normal vector line $NV_{D'''}$ of coordinate point D''' is extended to contour line $n^{th+4}$, and the intersection between normal vector line $NV_{D'''}$ and contour line $n^{th+4}$ identifies the coordinate point corresponding to coordinate point D''', namely, coordinate point D''''. Other groups of corresponding coordinate points may be identified via a normal vector line methodology.

As can be understood from FIGS. 33F-E, corresponding coordinate points D, D', D", D''' and D'''' may be identified via a third method. Specifically, the contour lines $n^{th}$, $n^{th+1}$, $n^{th+2}$, $n^{th+3}$ and $n^{th+4}$ may be superimposed into the same image slice layer as indicated in FIG. 33F by arrow 33D1, resulting in a composite plane 33D2 having a total rise or fall distance $d_{DD''''}$ between coordinate points D and D''''. The total rise or fall distance $d_{DD''''}$ may be the sum of the respective rise or fall distances $d_{DD'}$, $d_{D'D''}$, $d_{D''D'''}$, $d_{D'''D''''}$ discussed below with respect to FIGS. 33B, 33C and 33F.

As indicated in FIG. 33E, a center point CP is identified. The center point CP may generally correspond to an axis extending generally perpendicular to the sagittal image slices. The center point CP may be considered to be a center point generally common to the curvature of all of the contour lines $n^{th}$, $n^{th+1}$, $n^{th+2}$, $n^{th+3}$ and $n^{th+4}$ and about which all of the contour lines $n^{th}$, $n^{th+1}$, $n^{th+2}$, $n^{th+3}$ and $n^{th+4}$ arcuately extend.

As shown in FIG. 33E, radius lines R, R', R", etc. may radially extend in a straight line from the center point CP across the contour lines $n^{th}$, $n^{th+1}$, $n^{th+2}$, $n^{th+3}$ and $n^{th+4}$. As can be understood from radius line R, the corresponding coordinate lines D, D', D", D''' and D'''' are identified where radius line R intersects each respective contour lines $n^{th}$, $n^{th+1}$, $n^{th+2}$, $n^{th+3}$ and $n^{th+4}$. Other groups of corresponding coordinate points may be identified with radius lines R', R" and etc.

Once the corresponding coordinate points D, D', D", D''' and D'''' are identified via any of the three methods, the extent of the surface variation between the corresponding coordinate points D, D', D", D'" and D"" may be analyzed as follows.

As can be understood from FIGS. 33A-F, each coordinate point D, D', D", D'" and D"" includes a respective tangent line $t_D$, $t_{D'}$, $t_{D''}$, $t_{D'''}$, and $t_{D''''}$ that is tangent to the corresponding contour line $n^{th}$, $n^{th+1}$, $n^{th+2}$, $n^{th+3}$ and $n^{th+4}$ at the coordinate point D, D', D", D'" and D"", each tangent line $t_D$, $t_{D'}$, $t_{D''}$, $t_{D'''}$ and $t_{D''''}$ being parallel to and contained within the image slice of its contour line. A vector line $NV_D$, $NV_{D'}$ and $NV_{D''}$, $NV_{D'''}$ and $NV_{D''''}$ extends normally from each respective tangent line $t_D$, $t_{D'}$, $t_{D''}$, $t_{D'''}$ and $t_{D''''}$ at each respective coordinate point D, D', D", D'" and D"". Line segments DD', D'D", D"D'" and D'"D"" extend between their associated coordinate points to create a linear interpolation 3302 of the bone contour line 3300.

In this example, it is assumed the coordinate points D, D', D", D'" and D"" and their respective contour lines portions have already satisfied the tangent angle criterion $w_c$ of block 2508. For example, point D may be point k of potential mating region 2402A of contour line 2400 in FIG. 24, and coordinate points D'-D"" may be points on contour lines of adjacent image slices, wherein coordinate points D'-D"" are identified as coordinate points corresponding to coordinate point D. Each of the coordinate points D, D', D", D'" and D"" is then evaluated to determine if the criterion of $\theta_c$ and $\varphi_c$ of block 2514 are satisfied too.

As can be understood from FIGS. 33B, 33D and 33F, points D", D'" and D"" are in close proximity to each other due to the close proximity of their respective contour line segments. The close proximity of the respective contour lines is a result of the rise or fall distances $d_{D''D'''}$ and $d_{D'''D''''}$ being small at points D", D'" and D"", as the contour lines $n^{th}$, $n^{th+1}$, $n^{th+2}$, $n^{th+3}$ at all points D, D', D", D'" and D"" are evenly spaced medially-laterally due to having equal slice thicknesses $D_T$, which, for example, may be a slice thickness $D_T$ of 2 mm. Due to the close proximity of points D", D'" and D"", line segments D"D'" and D'"D"" range in size from relatively short to nearly zero, resulting in angular deviations $\theta_{D''D'''}$ and $\theta_{D'''D''''}$ that are less than the angular criterion $\theta_c$, which in one embodiment, may be in the range of approximately one to approximately four degrees. As the angular deviations $\theta_{D''D'''}$ and $\theta_{D'''D''''}$ are less than the angular criterion $\theta_c$, the angular criterion $\theta_c$ is satisfied for points D", D'" and D"", and these points are potential candidates for the generation of the jig's bone mating surfaces. As can be understood from FIGS. 33B, 33D and 33F, the angular deviations $\theta_{D''D'''}$ and $\theta_{D'''D''''}$ being less than the angular criterion $\theta_c$ results in the corresponding line segments D"D'" and D'"D"" closely approximating the contour of the bone surface 3300.

As indicated in FIGS. 33A, 33C and 33E, the angular differences $\varphi_{D''-D'''}$ and $\varphi_{D'''-D''''}$ between the normal vectors $NV_{D''}$, $NV_{D'''}$ and $NV_{D''''}$ is small, resulting in angular differences $\varphi_{D''-D'''}$ and $\varphi_{D'''-D''''}$ that are less than the angular criterion $\varphi_c$, which in one embodiment, may be in the range of approximately two to approximately five degrees. As the angular differences $\varphi_{D''-D'''}$ and $\varphi_{D'''-D''''}$ are less than the angular criterion $\varphi_c$, the angular criterion $\varphi_c$ is satisfied. As can be understood from the tangent lines $t_{D''}$, $t_{D'''}$ and $t_{D''''}$ depicted in FIGS. 33A, 33C and 33E, the contour line slopes at the respective coordinate points D", D'" and D"" are nearly identical, indicating that there is little surface variation between the coordinate points and the coordinate points would be a close approximation of the actual bone surface.

Because the points D", D'" and D"" have satisfied both of the angular criterion $\theta_c$ and $\varphi_c$ of block 2514, the surface represented by the points D", D'" and D"" may be employed to generate the jig's surfaces that matingly contact the patient's arthroplasty target surfaces per block 2520.

As can be understood from FIGS. 33B, 33D and 33F and because of significant rise and fall distances $d_{DD'}$ and $d_{D'D''}$ between the contour lines at points D, D' and D", points D, D' and D" are not in close proximity to each other due to the significant distance between their respective contour line segments. Consequently, line segments DD' and D'D" are relatively long, resulting in angular deviations $\theta_{DD'}$ and $\theta_{D'D''}$ that exceed the angular criterion $\theta_c$ and, therefore, do not satisfy the angular criterion $\theta_c$. As the angular deviations $\theta_{D''D'''}$ and $\theta_{D'''D''''}$ are greater than the angular criterion $\theta_c$, the angular criterion $\theta_c$ is not satisfied for points D, D' and D", and these points are not potential candidates for the generation of the jig's bone mating surfaces. As can be understood from FIGS. 33B, 33D and 33F, the angular deviations $\theta_{DD'}$ and $\theta_{D'D''}$ being greater than the angular criterion $\theta_c$ results in the corresponding line segments DD' and D'D" not closely approximating the contour of the bone surface 3300.

As indicated in FIGS. 33A, 33C and 33E, the angular differences $\varphi_{D-D'}$ and $\varphi_{D'-D''}$ between the normal vectors $NV_D$ and $NV_{D'}$ and $NV_{D'}$ and $NV_{D''}$ are large such that they are greater than the angular criterion $\varphi_c$ and, therefore, do not satisfy the angular criterion $\varphi_c$. Thus, as the points D, D' and D" do not satisfied both of the angular criterion $\theta_c$ and $\varphi_c$, the surfaces represented by the points D, D' and D" may not be employed to generate the jig's surfaces for matingly contacting the patient's arthroplasty target surfaces. Instead, the slice spacing $D_T$ may be evaluated per block 2516 and reset per block 2518, with the process then started over at block 2502. Alternatively, the points may be subjected to overestimation per block 2510.

Figure 34:
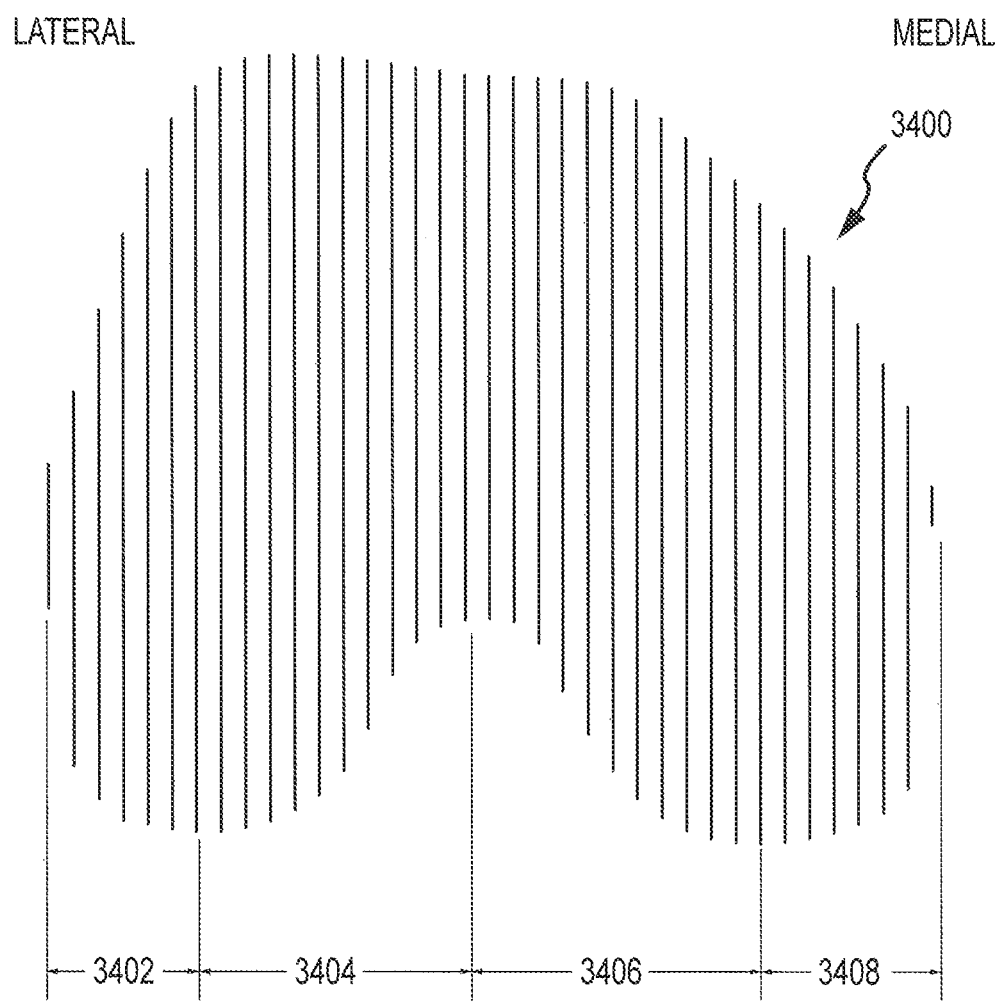
FIG. 34 is a distal view similar to that of FIG. 5 depicting contour lines produced by imaging the right femur at an image spacing $D_T$ of, for example, 2 mm.

FIG. 34 is a distal view similar to that of FIGS. 5 and 22A depicting contour lines 3400 produced by imaging the right femur at an image spacing $D_T$ of, for example, 2 mm. As shown, the contour lines 3400 may be grouped into multiple regions in the lateral-medial direction 3402-3408 for the sake of discussion. The region 3402 includes the contour lines 3400 of the most lateral half of the femoral lateral condyle and extends medially from the most lateral side of the femoral lateral condyle to the medial-lateral middle of the femoral lateral condyle. The region 3404 includes the contour lines 3400 of the most medial half of the femoral lateral condyle and extends medially from the middle of the femoral lateral condyle to the medial-lateral center of intercondylar notch. The region 3406 includes the contour lines 3400 of the most lateral half of the femoral medial condyle and extends medially from the medial-lateral center of the intercondylar notch to the medial-lateral middle of the femoral medial condyle. The region 3408 includes the contour lines 3400 of the most medial half of the femoral medial condyle and extends medially from the medial-lateral middle of the femoral medial condyle to the most medial side of the femoral medial condyle.

Figure 35:
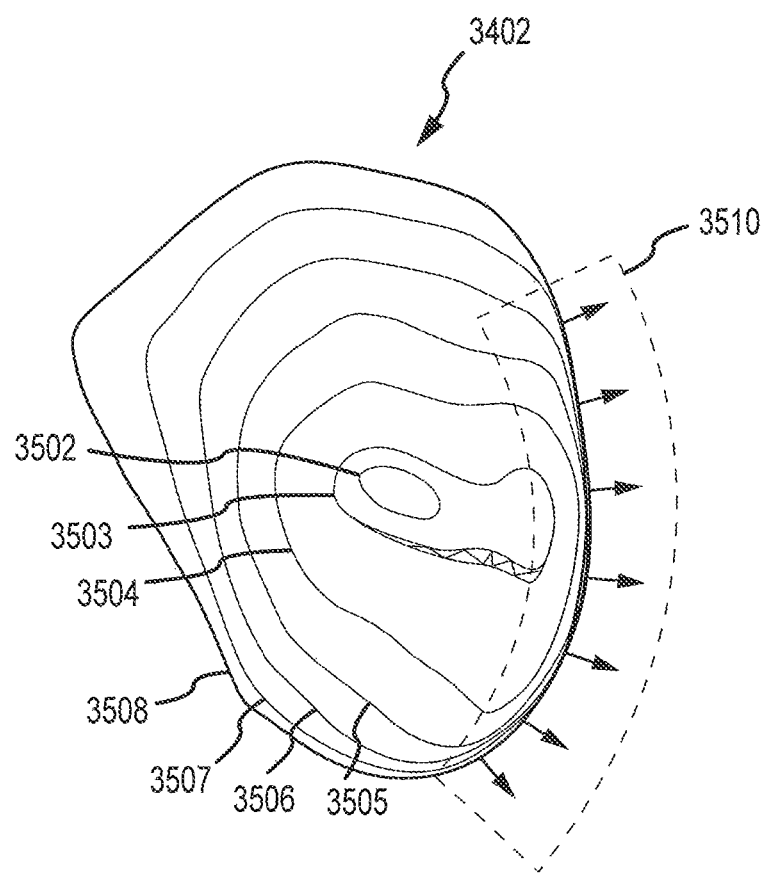
FIGS. 35-38 are sagittal views of the contour lines of respective regions of FIG. 34.

FIG. 35 is a sagittal view of the contour lines 3400 of region 3402 of FIG. 34. The contour lines 3400 of region 3402 include contour lines 3502, 3503, 3504, 3505, 3506, 3507 and 3508, with the most lateral portion of the femoral lateral condyle being indicated by contour line 3502. The size of each successive contour line 3400 of region 3402 increases moving medially from the most lateral contour line 3502 of region 3402 to the most medial contour line 3508 of region 3402, which is near the medial-lateral middle of the lateral condyle.

As can be understood from FIG. 35, the contour lines 3502-3504 are spaced apart from their respective adjacent contour lines a substantial amount around their entire boarders. Such wide spacing corresponds to a substantial amount of rise or fall distances between adjacent contour lines, as discussed above with respect to FIG. 33B. Thus, such contour lines would likely fail to meet the angular criterion $\theta_c$ and be subject to the overestimation process such that jig surfaces corresponding to the contour lines 3502-3504 would not contact the corresponding surfaces of the arthroplasty target areas.

As can be understood from FIG. 35, in the distal portion of the femoral condyle, the contour lines 3505-3508 in the region 3510 converge such that there is little, if any, amount of rise or fall distance between adjacent contour lines. Thus, such contour lines 3505-3508 in the region 3510 would likely meet the first angular criterion $\theta_c$.

As can be understood from the arrows in region 3510, the angular differences between normal vectors for the contour line portions within the region 3510 would be minimal, likely meeting the second angular criterion $\varphi_c$. Thus, as the portions of the contour lines 3505-3508 within region 3510 likely meet both angular criterion $\theta_c$ and $\varphi_c$, the portions of the contour lines 3505-3508 within the region 3510 represent an optimal contact area 3510 for mating contact with the jig's bone mating surface 40. In one embodiment, as can be understood from FIG. 39A discussed below, the optimal contact area 3510 may be the lateral half of the surface of the lateral condyle that displaces against the recess of the lateral tibia plateau.

In one embodiment, the optimal contact area 3510 matingly corresponds to the jig's bone mating surface 40 such that the portions of the contour lines 3402 indicated by region 3510 may be used to generate the jig's bone mating surface 40, per the algorithm 2500 of FIG. 25. Conversely, per the algorithm 2500, the portions of the contour lines 3402 outside region 3510 may be subjected to the overestimation process discussed above such that the jig's surfaces created from the overestimated contour line portions results in jig surfaces that do not contact the corresponding portions of the patient's arthroplasty target regions.

Figure 36:
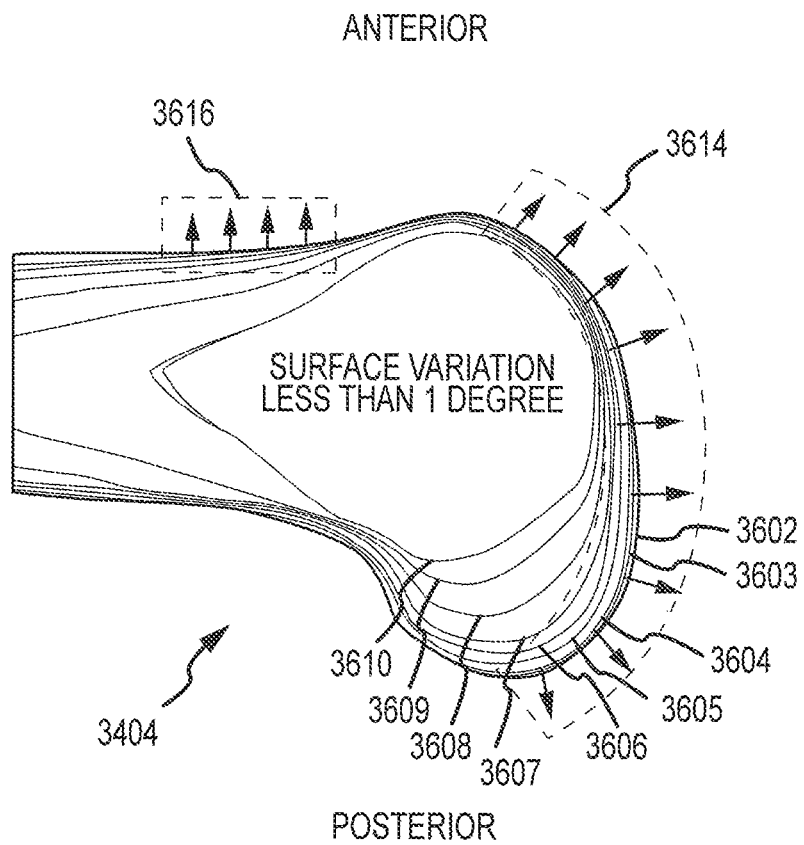

FIG. 36 is a sagittal view of the contour lines 3400 of region 3404 of FIG. 34. The contour lines 3400 of region 3404 include contour lines 3602, 3603, 3604, 3605, 3606, 3607, 3608, 3609 and 3610 with the most lateral portion of region 3404 being indicated by contour line 3602, which is near the medial-lateral middle of the lateral condyle, and the most medial portion of region 3404 being indicated by contour line 3610, which is near the medial-lateral center of intercondylar notch. The size of each successive contour line 3400 of region 3404 decreases moving medially from the most lateral contour line 3602 to the most medial contour line 3610.

As can be understood from FIG. 36, the contour lines 3607-3610 are spaced apart from their respective adjacent contour lines a substantial amount in their posterior portions and to a lesser extent in their distal portions, these distal portions corresponding to the intercondylar notch and trochlear groove. Such wide spacing corresponds to a substantial amount of rise or fall distances between adjacent contour lines, as discussed above with respect to FIG. 33B. Thus, such contour lines would likely fail to meet the angular criterion $\theta_c$ and be subject to the overestimation process such that jig surfaces corresponding to the contour lines 3607-3610 would not contact the corresponding surfaces of the arthroplasty target areas.

As can be understood from FIG. 36, in the distal portion of the femoral condyle, the contour lines 3602-3606 in the region 3614 converge such that there is little, if any, amount of rise or fall distance between adjacent contour lines. Similarly, in the anterior condylar portion of the distal femur, the contour lines 3602-3606 in the region 3616 converge such that there is little, if any, amount of rise or fall distance between adjacent contour lines. Thus, such contour lines 3602-3606 in the regions 3614 and 3616 would likely meet the first angular criterion $\theta_c$.

As can be understood from the arrows in regions 3614 and 3616, the angular differences between normal vectors for the contour line portions within the regions 3614 and 3616 would be minimal, likely meeting the second angular criterion $\varphi_c$. Thus, as the portions of the contour lines 3602-3606 within regions 3614 and 3616 likely meet both angular criterion $\theta_c$ and $\varphi_c$, the portions of the contour lines 3602-3606 within the regions 3614 and 3616 represent optimal contact areas 3614 and 3616 for mating contact with the jig's bone mating surface 40.

In one embodiment, the optimal contact areas 3614 and 3616 matingly correspond to the jig's bone mating surface 40 such that the portions of the contour lines 3404 indicated by regions 3614 and 3616 may be used to generate the jig's bone mating surface 40, per the algorithm 2500 of FIG. 25. Conversely, per the algorithm 2500, the portions of the contour lines 3404 outside regions 3614 and 3616 may be subjected to the overestimation process discussed above such that the jig's surfaces created from the overestimated contour line portions results in jig surfaces that do not contact the corresponding portions of the patient's arthroplasty target regions.

In one embodiment, as can be understood from FIG. 39A discussed below, the optimal contact area 3614 may be the medial half of the surface of the lateral condyle that displaces against the recess of the lateral tibia plateau. In one embodiment, as can be understood from FIG. 39A discussed below, the optimal contact area 3616 may be the lateral half of a generally flat surface of the anterior condyle, wherein the flat surface is located in an area proximal the concave trochlear groove of the patellar face and extends to a point near the anterior portion of the femoral shaft.

Figure 37:
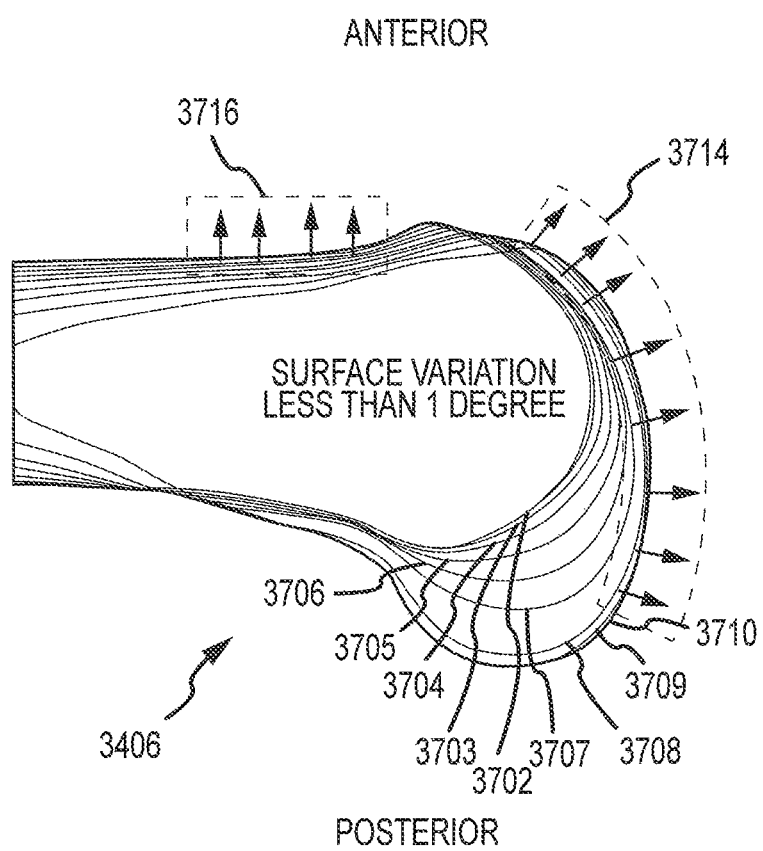

FIG. 37 is a sagittal view of the contour lines 3400 of region 3406 of FIG. 34. The contour lines 3400 of region 3406 include contour lines 3702, 3703, 3704, 3705, 3706, 3707, 3708, 3709 and 3710 with the most lateral portion of region 3404 being indicated by contour line 3702, which is near the medial-lateral center of intercondylar notch, and the most medial portion of region 3406 being indicated by contour line 3710, which is near the medial-lateral middle of the medial condyle. The size of each successive contour line 3400 of region 3406 increases moving medially from the most lateral contour line 3702 to the most medial contour line 3710.

As can be understood from FIG. 37, the contour lines 3702-3706 are spaced apart from their respective adjacent contour lines a substantial amount in their posterior portions and to a lesser extent in their distal portions, these distal portions corresponding to the intercondylar notch and trochlear groove. Such wide spacing corresponds to a substantial amount of rise or fall distances between adjacent contour lines, as discussed above with respect to FIG. 33B. Thus, such contour lines would likely fail to meet the angular criterion $\theta_c$ and be subject to the overestimation process such that jig surfaces corresponding to the contour lines 3607-3610 would not contact the corresponding surfaces of the arthroplasty target areas.

As can be understood from FIG. 37, in the distal portion of the femoral condyle, the contour lines 3707-3710 in the region 3714 converge such that there is little, if any, amount of rise or fall distance between adjacent contour lines. Similarly, in the anterior condylar portion of the distal femur, the contour lines 3707-3710 in the region 3716 converge such that there is little, if any, amount of rise or fall distance between adjacent contour lines. Thus, such contour lines 3707-3710 in the regions 3714 and 3716 would likely meet the first angular criterion $\theta_c$.

As can be understood from the arrows in regions 3714 and 3716, the angular differences between normal vectors for the contour line portions within the regions 3714 and 3716 would be minimal, likely meeting the second angular criterion $\varphi_c$. Thus, as the portions of the contour lines 3707-3710 within regions 3714 and 3716 likely meet both angular criterion $\theta_c$ and $\varphi_c$, the portions of the contour lines 3707-3710 within the regions 3714 and 3716 represent optimal contact areas 3714 and 3716 for mating contact with the jig's bone mating surface 40.

In one embodiment, the optimal contact areas 3714 and 3716 matingly correspond to the jig's bone mating surface 40 such that the portions of the contour lines 3406 indicated by regions 3714 and 3716 may be used to generate the jig's bone mating surface 40, per the algorithm 2500 of FIG. 25. Conversely, per the algorithm 2500, the portions of the contour lines 3406 outside regions 3714 and 3716 may be subjected to the overestimation process discussed above such that the jig's surfaces created from the overestimated contour line portions results in jig surfaces that do not contact the corresponding portions of the patient's arthroplasty target regions.

In one embodiment, as can be understood from FIG. 39A discussed below, the optimal contact area 3714 may be the lateral half of the surface of the medial condyle that displaces against the recess of the medial tibia plateau. In one embodiment, as can be understood from FIG. 39A discussed below, the optimal contact area 3716 may be the medial half of a generally flat surface of the anterior condyle, wherein the flat surface is located in an area proximal the concave trochlear groove of the patellar face and extends to a point near the anterior portion of the femoral shaft.

Figure 38:
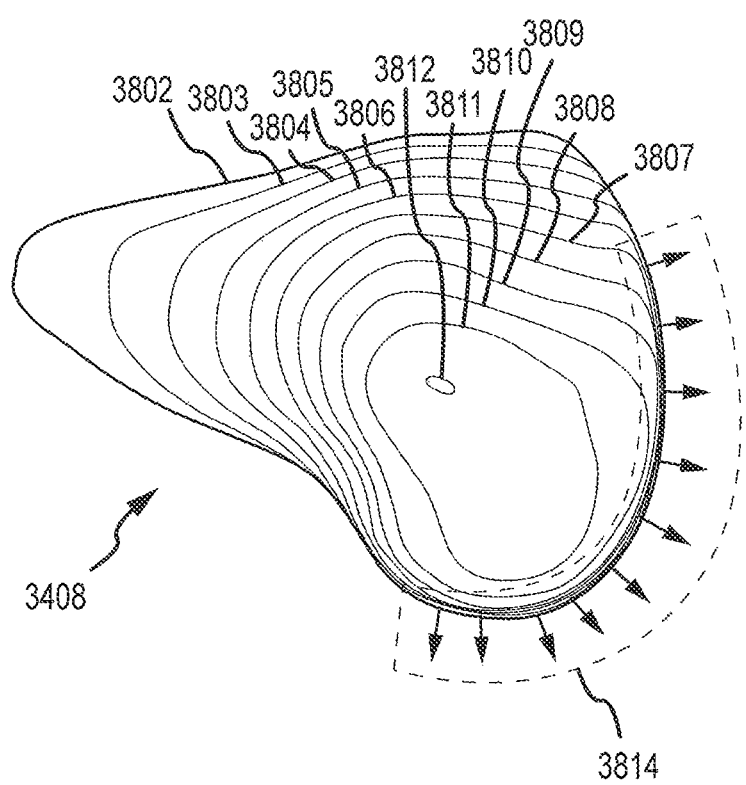

FIG. 38 is a sagittal view of the contour lines 3400 of region 3408 of FIG. 34. The contour lines 3400 of region 3408 include contour lines 3802, 3803, 3804, 3805, 3806, 3807, 3808, 3809, 3810, 3811 and 3812, with the most medial portion of the femoral lateral condyle being indicated by contour line 3812. The size of each successive contour line 3400 of region 3408 decreases moving medially from the most lateral contour line 3802 of region 3408, which is near the medial-lateral middle of the medial condyle, to the most medial contour line 3812 of region 3408.

As can be understood from FIG. 38, the contour lines 3810-3812 are spaced apart from their respective adjacent contour lines a substantial amount around their entire boarders. Such wide spacing corresponds to a substantial amount of rise or fall distances between adjacent contour lines, as discussed above with respect to FIG. 33B. Thus, such contour lines would likely fail to meet the angular criterion $\theta_c$ and be subject to the overestimation process such that jig surfaces corresponding to the contour lines 3810-3812 would not contact the corresponding surfaces of the arthroplasty target areas.

As can be understood from FIG. 38, in the distal portion of the femoral condyle, the contour lines 3802-3809 in the region 3814 converge such that there is little, if any, amount of rise or fall distance between adjacent contour lines. Thus, such contour lines 3802-3809 in the region 3814 would likely meet the first angular criterion $\theta_c$.

As can be understood from the arrows in region 3814, the angular differences between normal vectors for the contour line portions within the region 3814 would be minimal, likely meeting the second angular criterion $\varphi_c$. Thus, as the portions of the contour lines 3802-3809 within region 3814 likely meet both angular criterion $\theta_c$ and $\varphi_c$, the portions of the contour lines 3802-3809 within the region 3814 represent an optimal contact area 3814 for mating contact with the jig's bone mating surface 40. In one embodiment, as can be understood from FIG. 39A discussed below, the optimal contact area 3814 may be the medial half of the surface of the medial condyle that displaces against the recess of the medial tibia plateau.

In one embodiment, the optimal contact area 3814 matingly corresponds to the jig's bone mating surface 40 such that the portions of the contour lines 3408 indicated by region 3814 may be used to generate the jig's bone mating surface 40, per the algorithm 2500 of FIG. 25. Conversely, per the algorithm 2500, the portions of the contour lines 3408 outside region 3814 may be subjected to the overestimation process discussed above such that the jig's surfaces created from the overestimated contour line portions results in jig surfaces that do not contact the corresponding portions of the patient's arthroplasty target regions.

As can be understood from the preceding discussion, the overestimation process disclosed herein can be used to identifying optimal target areas (e.g., optimal target areas 3510, 3614, 3616, 3714, 3716 and 3814 as discussed with respect to FIGS. 35-38). More specifically, the overestimation process disclosed herein can employ these optimal target areas to generate the bone mating surfaces 40 of the jigs 2 while causing the other surface areas of the jigs to be configured such that these other jig surface areas will not contact the surfaces of the arthroplasty target areas when the jig's bone mating surfaces 40 have matingly received and contacted the arthroplasty target areas. The result is a jig that has bone mating surfaces 40 that are based on the regions of the arthroplasty target region that are most accurately represented via 3D computer modeling and most likely to be machinable into the jig. Such a jig provides an increased accuracy of fit between the jig's mating surface 40 and the arthroplasty target areas of the patient's bone.

For most patients, it is common that the overestimation process outlined in FIG. 25 will result in certain areas of the femoral arthroplasty target region being identified as the optimal target areas discussed above with respect to FIGS. 35-38. For example, as depicted in FIG. 39A, which is distal-sagittal isometric view of a femoral distal end 3900, a commonly encountered, healthy, non-deformed femoral distal end 3900 may have an arthroplasty target region 3902 with certain optimal target regions 3904, 3906 and 3908. These optimal target regions 3904, 3906 and 3908 commonly identified on most patients via the overestimation process of FIG. 25 are indicated in FIG. 39A by the cross-hatched regions. It has been found that these optimal target regions 3904, 3906 and 3908 are the regions of the arthroplasty target region 3902 that are most likely to satisfy the criterion $w_i$, $\theta_c$ and $\varphi_c$ of blocks 2508 and 2514 of FIG. 25. Therefore, these target regions 3904, 3906 and 3908 may be used to generate the jig's bone mating surfaces 40.

Figure 39A:
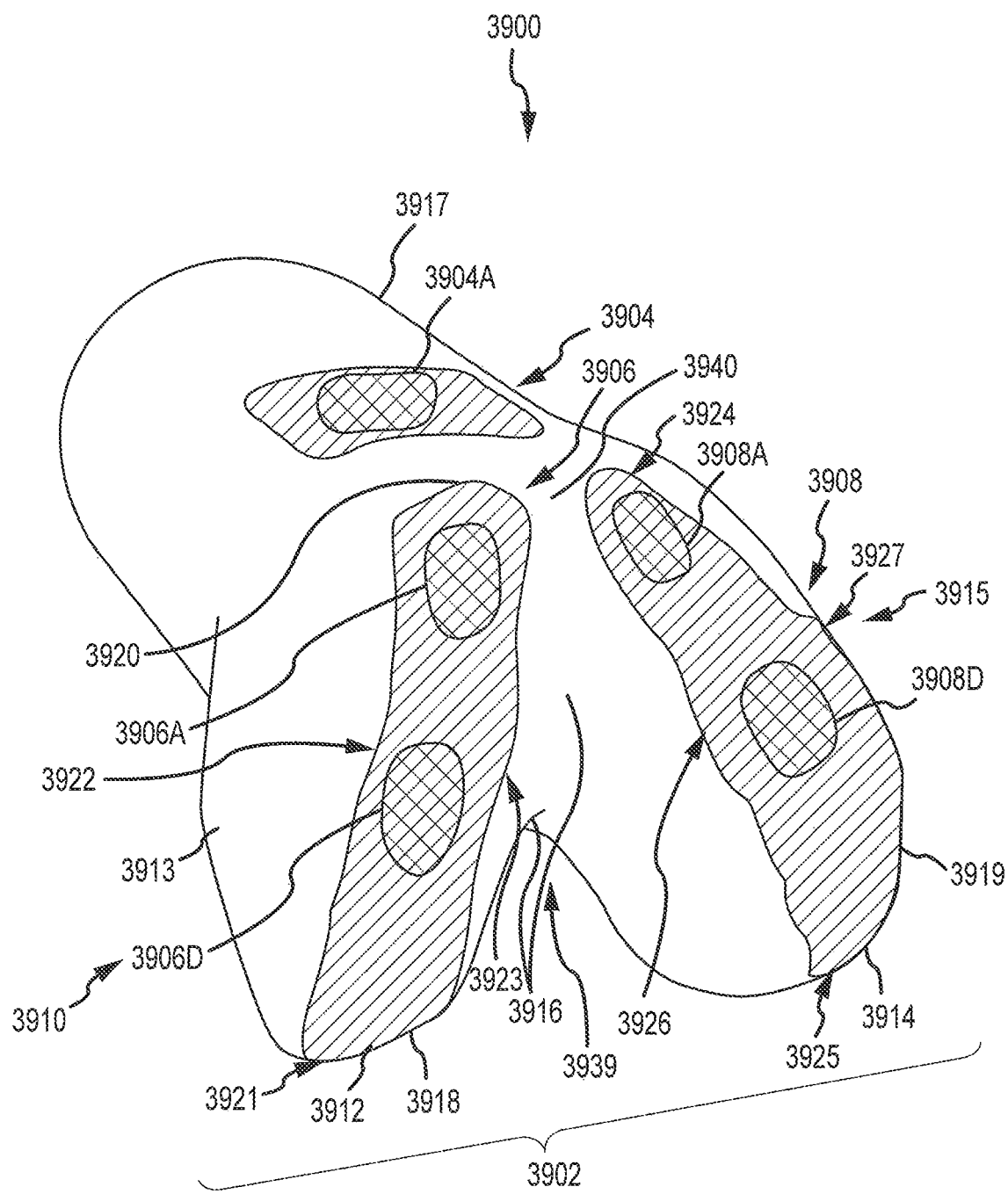
FIG. 39A is distal-sagittal isometric view of a femoral distal end.

While, in one embodiment, the overestimation process of FIG. 25 is likely to result in optimal target regions such as those indicated via the cross-hatching 3904, 3906 and 3908, in other embodiments, the optimal target regions may result in target regions in other locations on the femoral distal end 3900 that are in addition to, or in place of, those regions 3904, 3906 and 3908 depicted in FIG. 39A.

One of the benefits of the overestimation process of FIG. 25 is that it identifies two types of contour lines 210, the first type being those contour lines that are most likely to be unacceptable for the generation a jig's bone mating surfaces 40, and the second type being those contour lines that are most likely to be acceptable for the generation of a jig's bone mating surfaces 40. The first type of contour lines are unlikely to be acceptable for the generation of a jig's bone mating surfaces 40 because they pertain to bone surfaces that are too varied to be accurately 3D computer modeled and/or are such that they are not readily machinable into the jig blank. Conversely, the second type of contour lines are likely to be acceptable for the generation of a jig's bone mating surfaces 40 because they pertain to bone surfaces that vary such an insubstantial amount that they can be accurately 3D computer modeled and are such that they are readily machinable into the jig blank. While optimal target regions 3904, 3906 and 3908 represent regions likely corresponding to contour lines of the second type for most commonly encountered patients, the overestimation processes disclosed herein may be adapted to result in other or additional optimal target regions.

In some instances the entirety of the target regions 3904, 3906 and 3908 may correspond to the second type of contour lines, namely those type of contour lines that satisfy the criterion $w_i$, $\theta_c$ and $\varphi_c$ of blocks 2508 and 2514 of FIG. 25. In such instances, the entirety of the target regions 3904, 3906 and 3908 are matingly contacted by the jig's bone mating surface 40.

However, in some instances one or more portions of one or more of the target regions 3904, 3906 and 3908 may be subjected to overestimation so that the jig's bone mating surface 40 does not contact such portions of the target regions 3904, 3906 and 3908, although the jig's bone mating surface 40 still matingly contacts the other portions of the target regions 3904, 3906 and 3908 corresponding to the second type of contour lines. Such a situation may arise, for example, where a substantial surface variation (e.g., a hole, deformity or osteophyte) exists on a condyle articular surface 3918, 3919 that meets the criterion $w_i$, $\theta_c$ and $\varphi_c$ of blocks 2508 and 2514 for the rest of its surface.

The overestimation process disclosed herein may result in the identification of target regions 3904, 3906, 3908 that are most likely to result in bone mating surfaces 40 of jigs 2 that are readily machinable into the jigs 2 and most likely to facilitate reliable and accurate mating of the jigs to the arthroplasty target regions. The overestimation process results in such accurate and reliable bone mating surfaces 40 while causing other surfaces of the jigs 2 corresponding to less predictable bone surfaces to not contact the bone surfaces when the bone mating surfaces 40 matingly receive the target regions 3904, 3906, 3908 of the actual arthroplasty target region.

As indicated in FIG. 39A by the cross-hatched regions, optimal target regions 3904, 3906 and 3908 may include three general areas of the femoral condyle 3910. For example, the anterior optimal target region 3904 may include the anterior portion of the femoral distal end 3900 just proximal of the condyle 3910 region, the lateral optimal target region 3906 may include the distal portion of the lateral condyle 3912, and the medial optimal target region 3908 may include the distal portion of the medial condyle 3914.

As indicated in FIG. 39A, the femoral distal end 3900 may include a lateral condyle 3912 and a lateral epicondyle 3913, a medial condyle 3914 and a medial epicondyle 3915, a intercondylar notch 3939 and a trochlear groove 3916 of the patellar surface separating the two condyles 3912 and 3914, and a femoral shaft 3917 extending distally from the condyle region 3910. Each condyle 3912 and 3914 includes an articular surface 3918 and 3919 that articulates against corresponding articular surfaces of the tibia plateau.

Figure 39B:
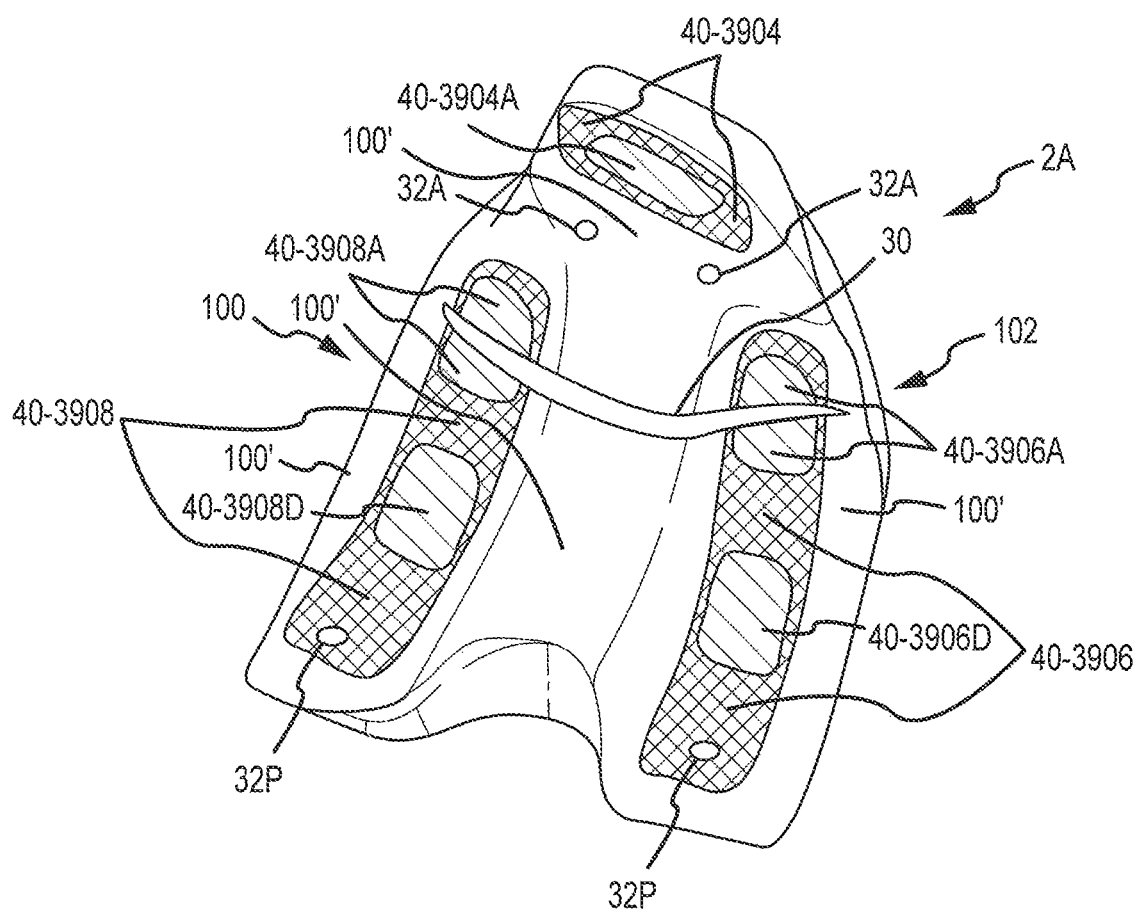
FIG. 39B is a bottom perspective view of an example customized arthroplasty femur jig that has been generated via the overestimation process disclosed herein.
Figure 39C:
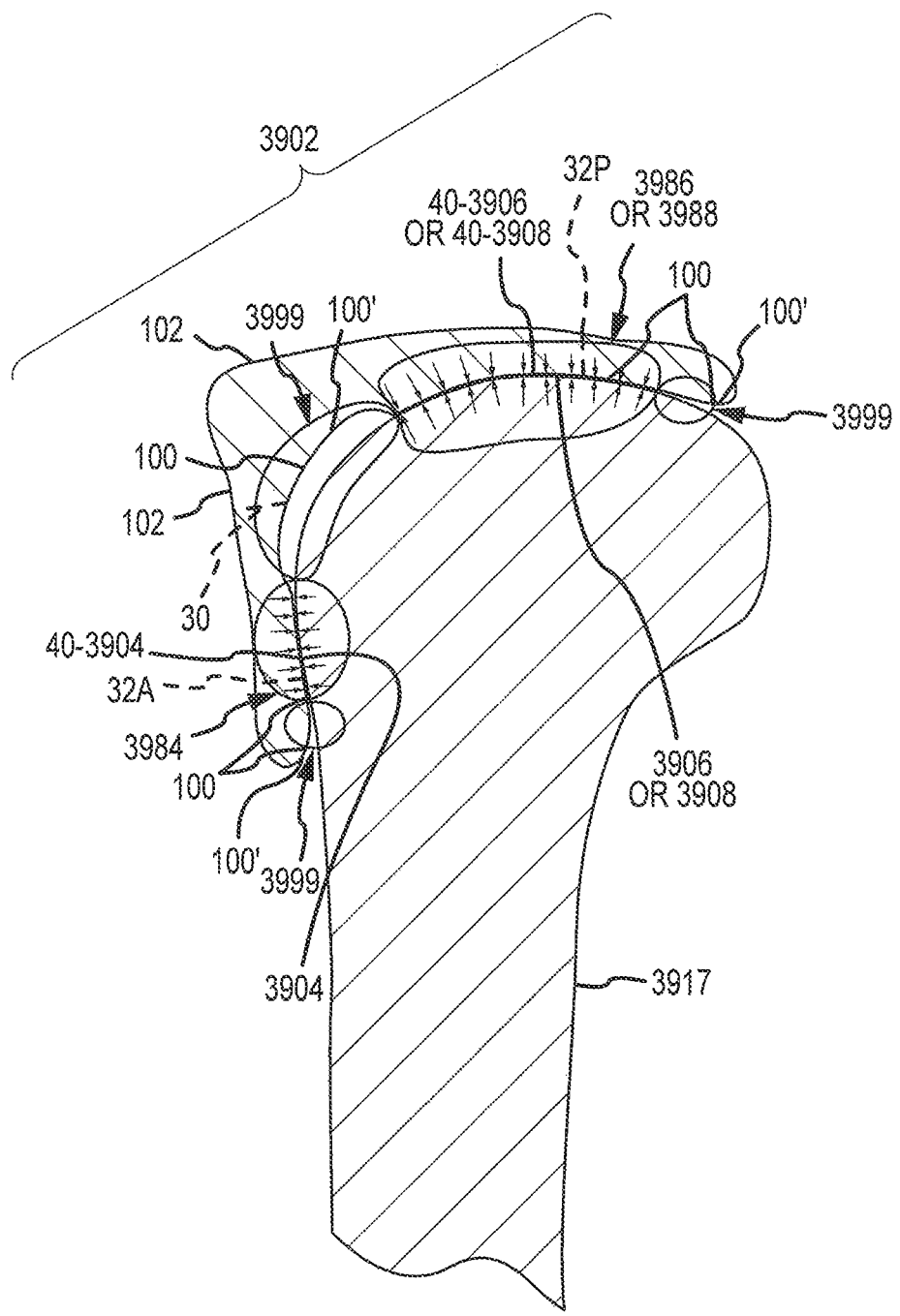
FIG. 39C is an anterior-posterior cross-section of the femur jig of FIG. 39B mounted on the femur distal end of FIG. 39A.
Figure 39D:
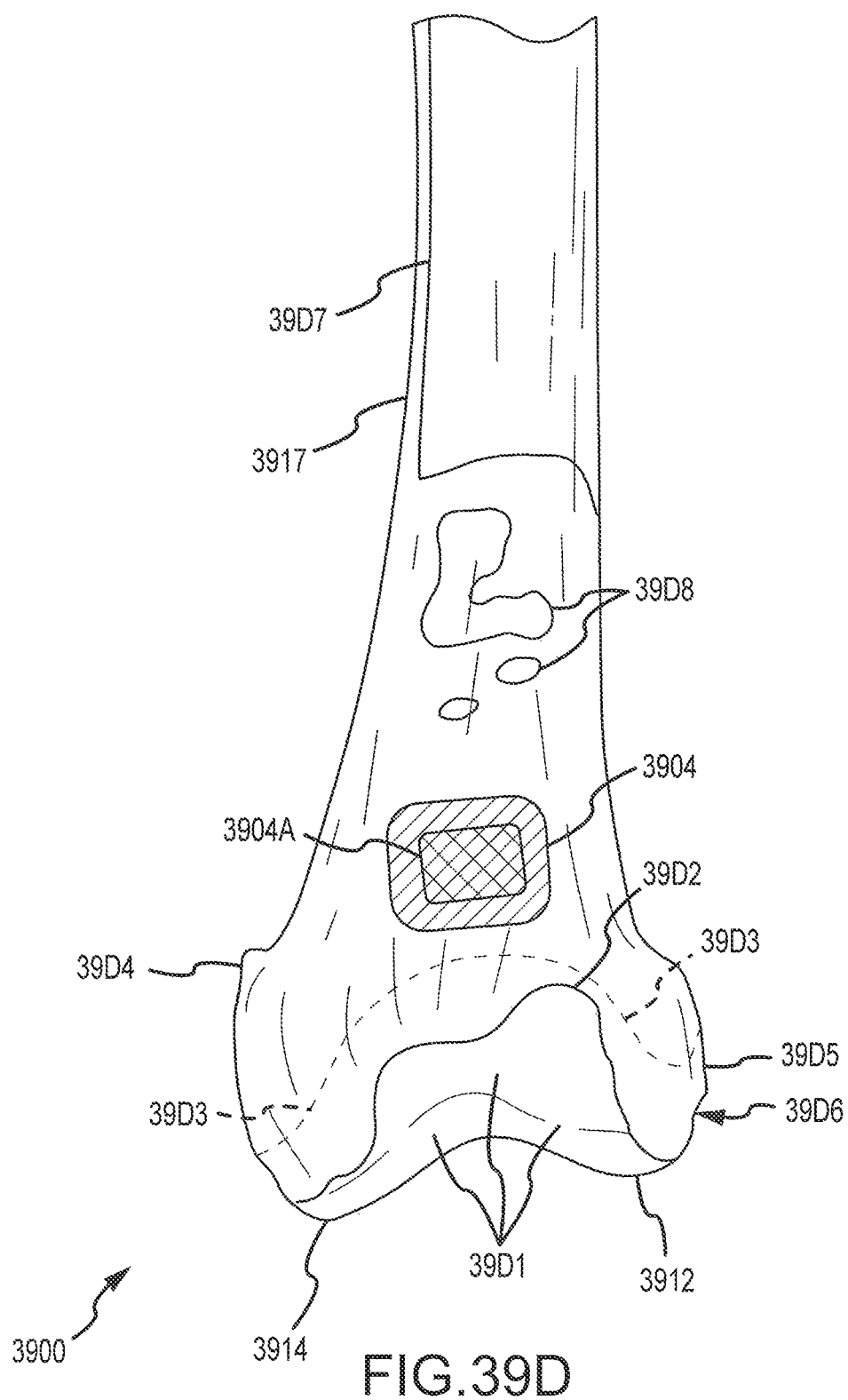
FIG. 39D is a coronal view of the anterior side of the femoral distal end.

As indicated in FIG. 39D, which is a coronal view of the anterior side of the femoral distal end 3900, the articular surfaces of the condyles 3914, 3912 and the trochlear groove 3916 transition into each other to form a patellar facet 39D1 that has an anterior boarder or seam 39D2. Proximal of the patellar facet boarder 39D2 and identified by a dashed line is the capsular line 39D3 extending medial-lateral in an arc. The adductor tubercle is indicated at 39D4, the fibular lateral ligament at 39D5, the popliteus at 39D6, the vastus intermedius at 39D7, and the articular genu at 39D8.

As indicated in FIG. 39A by the cross-hatching, in one embodiment, the lateral optimal target region 3906 may be generally coextensive with the lateral condyle articular surface 3918 that articulates against the respective articulate surface of the tibia plateau. In one embodiment, the lateral optimal target region 3906 may extend: anterior-posterior between the anterior end 3920 and posterior end 3921 of the lateral articular condyle surface 3918; and lateral-medial between the lateral side 3922 and medial side 3923 of the lateral articular condyle surface 3918. In one embodiment, the lateral optimal target region 3906 generally begins near the anterior-distal end 3920 of the lateral condyle 3912 outside the trochlear groove 3916 of the patellar surface and ends near the posterior-distal end 3921 of the lateral condyle 3912. In one embodiment as can be understood from FIG. 39A, the lateral optimal target region 3906 may be the entire cross-hatched region 3906 or any one or more portions of the cross-hatched region 3906.

In one embodiment as indicated in FIG. 39A by the double cross-hatching, an anterior target area 3906A and a distal target area 3906D may be identified within the lateral optimal target region 3906 via the overestimation process disclosed herein. Thus, although the lateral optimal target region 3906 may be generally coextensive with the lateral condyle articular surface 3918, the actual areas within the lateral optimal target region 3906 identified as being reliable surfaces for the generation of the mating surfaces of arthroplasty jigs may be limited to an anterior target area 3906A and a distal target area 3906D, the remainder of the lateral optimal target region 3906 being subjected to the overestimation process. The anterior target area 3906A may be located in the anterior third of the lateral optimal target region 3906, and the distal target area 3906D may be located near a most distal point of the lateral optimal target region 3906.

As indicated in FIG. 39A by the cross-hatching, in one embodiment, the medial optimal target region 3908 may be generally coextensive with the medial condyle articular surface 3919 that articulates against the respective articulate surface of the tibia plateau. Specifically, in one embodiment, the medial optimal target region 3908 may extend: anterior-posterior between the anterior end 3924 and posterior end 3925 of the medial articular condyle surface 3919; and lateral-medial between the lateral side 3926 and medial side 3927 of the medial articular condyle surface 3919. In one embodiment, the medial optimal target region 3908 generally begins near the anterior-distal end 3924 of the medial condyle 3914 outside the trochlear groove 3916 of the patellar surface and ends near the posterior-distal end 3925 of the medial condyle 3914. In one embodiment as can be understood from FIG. 39A, the medial optimal target region 3908 may be the entire cross-hatched region 3908 or any one or more portions of the cross-hatched region 3908.

In one embodiment as indicated in FIG. 39A by the double cross-hatching, an anterior target area 3908A and a distal target area 3908D may be identified within the medial optimal target region 3908 via the overestimation process disclosed herein. Thus, although the medial optimal target region 3908 may be generally coextensive with the medial condyle articular surface 3919, the actual areas within the medial optimal target region 3908 identified as being reliable surfaces for the generation of the mating surfaces of arthroplasty jigs may be limited to an anterior target area 3908A and a distal target area 3908D, the remainder of the medial optimal target region 3908 being subjected to the overestimation process. The anterior target area 3908A may be located in the anterior third of the medial optimal target region 3908, and the distal target area 3908D may be located near a most distal point of the medial optimal target region 3908.

As indicated in FIG. 39A by the cross-hatching, in one embodiment, the anterior optimal target region 3904 may be a generally planar area of the anterior side of the femoral shaft 3917 proximally adjacent the condyle portion 3910 of the femoral distal end 3900. In other words, the anterior optimal target region 3904 may be a generally planar area of the anterior side of the femoral shaft 3917 proximally adjacent the anterior end 3940 of the trochlear groove 3916.

As shown in FIG. 39D by the cross-hatching, in one embodiment, the anterior optimal target region 3904 may be located in a generally planar surface region of the anterior side of the femoral shaft 3917 generally distal of the articularis genu 39D8 and generally proximal of the patellar facet boarder 39D2. In one embodiment, the anterior optimal target region 3904 may be located in a generally planar surface region of the anterior side of the femoral shaft 3917 generally distal of the articularis genu 39D8 and generally proximal of the capsular line 39D3. In either case, the anterior optimal target region 3904 may be generally centered medial-lateral on the anterior side of the femoral shaft 3917.

As can be understood from FIG. 39A, in one embodiment, the anterior target region 3904 may have a lateral-medial dimension of approximately one centimeter to approximately seven centimeters. In one embodiment, the anterior optimal target region 3904 may be approximately centered on a line that: is generally parallel to the femoral anatomical axis; and extends from the center of the trochlear groove 3916. In one embodiment, the medial-lateral width of the anterior optimal target region 3904 may be medially-laterally bounded by lines extending generally parallel to the femoral anatomical axis from the most medial and most lateral boundaries of the trochlear groove 3916. In one embodiment as can be understood from FIG. 39A, the anterior target region 3904 may be the entire cross-hatched region 3904 or any one or more portions of the cross-hatched region 3904.

In one embodiment as indicated in FIGS. 39A and 39D by the double cross-hatching, an anterior target area 3904A may be identified within the anterior optimal target region 3904 via the overestimation process disclosed herein. Thus, although the anterior optimal target region 3904 may be generally coextensive with the generally planar surface area between the articularis genu 39D8 and the capsular line 39D3, the actual areas within the anterior optimal target region 3904 identified as being a reliable surface for the generation of the mating surfaces of arthroplasty jigs may be limited to an anterior target area 3904A, the remainder of the anterior optimal target region 3904 being subjected to the overestimation process. The anterior target area 3904A may be located any where within the anterior optimal target region 3904.

FIG. 39B is bottom perspective view of an example customized arthroplasty femoral jig 2A that has been generated via the overestimation process disclosed herein. Similar to the femoral jig 2A depicted in FIGS. 1G and 1F, the femoral jig 2A of FIG. 39B includes an interior or bone-facing side 100 and an exterior side 102. When the jig 2A is mounted on the arthroplasty target region during a surgical procedure, the bone-facing side 100 faces the surface of the arthroplasty target region while the exterior side 102 faces in the opposite direction.

The interior or bone-facing side 100 of the femur cutting jig 2A includes bone mating surfaces 40-3904, 40-3906 and 40-3908 that: are machined into the jig interior or bone-facing side 100 based on contour lines that met the criterion of blocks 2508 and 2514 of FIG. 25; and respectively correspond to the optimal target regions 3904, 3906 and 3908 of FIG. 39A. The rest 100' of the interior or bone-facing side 100 (i.e., the regions 100' of the interior or bone facing sides 100 outside the bounds of bone mating surfaces 40-3904, 40-3906 and 40-3908) are the result of the over-estimation process wherein the corresponding contour lines failed to meet one or more of the criterion of blocks 2508 and 2514 of FIG. 25 and, consequently, were moved away from the bone surface. As a result, the interior side surface 100' is machined to be spaced away from the bone surfaces of the arthroplasty target region so as to not contact the bone surfaces when the bone mating surfaces 40-3904, 40-3906 and 40-3908 matingly receive and contact the bone surfaces of the arthroplasty target region corresponding to regions 3904, 3906 and 3908.

As can be understood from FIG. 39B, depending on the patient's bone topography, the overestimation process disclosed herein may result in bone mating surfaces 40-3904, 40-3906 and 40-3908 that are actually multiple bone mating surfaces and/or substantially smaller than depicted in FIG. 39B. For example, the lateral condyle bone mating surface 40-3906 may actually be an anterior lateral condyle bone mating surface 40-3906A and a distal lateral condyle bone mating surface 40-3906D, with the areas of the lateral condyle bone mating surface 40-3906 outside the anterior and distal bone mating surfaces 40-3906A and 40-3906D being the result of the overestimation process so as to not contact the corresponding bone surfaces when the anterior and distal mating surfaces 40-3906A and 40-3906D matingly receive and contact their respective corresponding bone surfaces. The anterior and distal bone mating surfaces 40-3906A and 40-3906D may be configured and positioned in the jig inner surface 100 to matingly receive and contact the anterior and distal optimal target areas 3906A and 3906D discussed above with respect to FIG. 39A.

As can be understood from FIG. 39B, the medial condyle bone mating surface 40-3908 may actually be an anterior medial condyle bone mating surface 40-3908A and a distal medial condyle bone mating surface 40-3908D, with the areas of the medial condyle bone mating surface 40-3908 outside the anterior and distal mating surfaces 40-3908A and 40-3908D being the result of the overestimation process so as to not contact the corresponding bone surfaces when the anterior and distal bone mating surfaces 40-3908A and 40-3908D matingly receive and contact their respective corresponding bone surfaces. The anterior and distal bone mating surfaces 40-3908A and 40-3908D may be configured and positioned in the jig inner surface 100 to matingly receive and contact the anterior and distal optimal target areas 3908A and 3908D discussed above with respect to FIG. 39A.

As can be understood from FIG. 39B, the anterior shaft bone mating surface 40-3904 may actually be a smaller anterior shaft bone mating surface 40-3904A, with the area of the anterior shaft bone mating surface 40-3904 outside the smaller anterior mating surface 40-3904A being the result of the overestimation process so as to not contact the corresponding bone surface when the smaller anterior mating surface 40-3904A matingly receives and contacts its corresponding bone surface. The smaller anterior bone mating surface 40-3904A may be configured and positioned in the jig inner surface 100 to matingly receive and contact the anterior optimal target area 3904A discussed above with respect to FIGS. 39A and 39D.

As can be understood from FIG. 39C, which is a anterior-posterior cross-section of the femur jig 2A of FIG. 39B mounted on the femur distal end 3900 of FIG. 39A, the interior or bone-facing side 100 is formed of bone mating surfaces 40-3904, 40-3906 and 40-3908 and spaced-apart surfaces 100' (i.e., bone-facing surfaces 100 that are a product of the overestimation process and are spaced-apart from the corresponding bone surfaces of the arthroplasty target region 3902). As indicated by the plurality of opposed arrows in regions 3984, 3986 and 3988, the bone mating surfaces 40-3904, 40-3906 and 40-3908 matingly receive and contact the corresponding bone surfaces 3904, 3906 and 3908 to form mating surface contact regions 3984, 3986 and 3988. Conversely, the spaced-apart surfaces 100' are spaced apart from the corresponding bone surfaces to form spaced-apart non-contact regions 3999, wherein the spaced-apart surfaces 100' do not contact their corresponding bone surfaces. In addition to having the mating surfaces 40-3904, 40-3906 and 40-3908 and the spaced-apart surfaces 100', the femur jigs 2A may also have a saw cutting guide slot 30 and anterior and posterior drill holes 32A and 32P, as discussed above.

The arrows in FIG. 39C represent a situation where the patient's bone topography and the resulting overestimation process has generated bone mating surfaces 40-3904, 40-3906 and 40-3908 that match the target regions 3904, 3906 and 3908, which are generally coextensive with the entirety of their respective potential regions as discussed above. Of course, where the patient's bone topography and the resulting overestimation process generates bone mating surfaces 40-3904A, 40-3906A, 40-3906D, 40-3908A and 40-3908D that match the target areas 3904A, 3906A, 3906D, 3908A and 3908D, which are substantially smaller than their respective target regions 3904, 3906 and 3908, the mating surface contact regions 3984, 3986 and 3988 may be smaller and/or segmented as compared to what is depicted in FIG. 39C.

Figure 40:
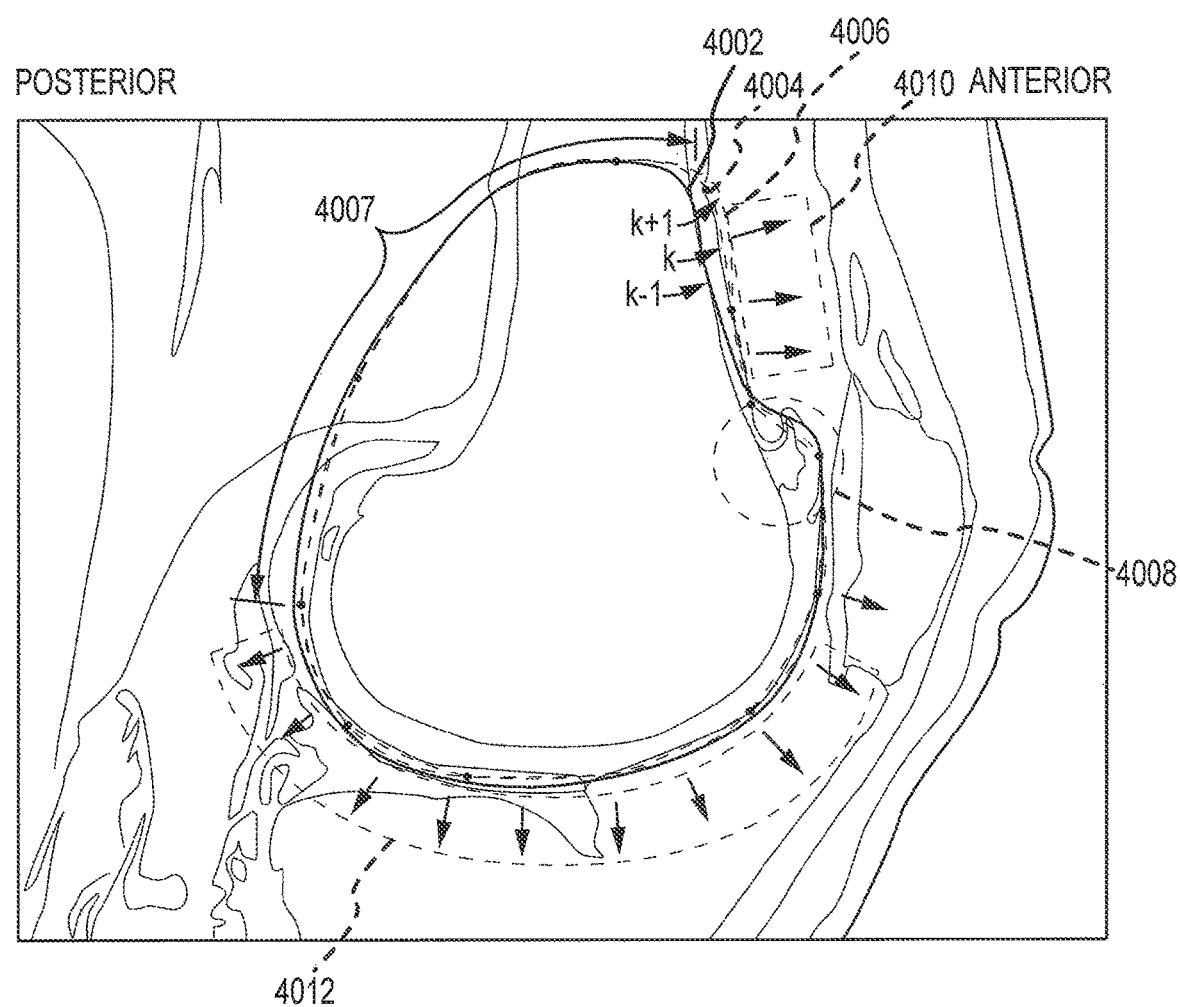
FIG. 40 depicts closed-loop contour lines that are image segmented from image slices, wherein the contour lines outline the cortical bone surface of the lower end of the femur.

FIG. 40 depicts closed-loop contour lines 4002, 4004, and 4006 that are image segmented from image slices, wherein the contour lines outline the cortical bone surface of the lower end of the femur. These contour lines 4002, 4004, and 4006 may be identified via image segmentation techniques from medical imaging slices generated via, e.g., MRI or CT.

As shown in FIG. 40, there are posterior portions of the contour lines (indicated as 4007) that may be of no interest during overestimation because the contour line region 4007 corresponds to a region of the knee that may be inaccessible during surgery and may not correspond to a jig surface because no part of the jig may access the region 4007 during surgery. An osteophyte in contour line region 4008 may be identified based on the algorithm 2500. The contour lines in region 4008 may be subsequently overestimated (based on the algorithm 2500) such that the resulting jig surface does not come into contact with the osteophyte (i.e., with the osteophyte bone surface represented by contour line region 4008) when the jig's bone mating surface 40 matingly receives and contacts the bone surfaces of the arthroplasty target region. Additionally, optimal contour line regions 4010 and 4012 may be identified during execution of the algorithm 2500 as areas of the patient's bone anatomy that have surface variations within the angular criteria of the algorithm 2500 and, therefore, are used to generate the jig's bone mating surface 40 that matingly receives and contacts the bone surfaces of the arthroplasty target region.

Contour line region 4010 may pertain to region 3904 of FIG. 39A and femur jig region 40-3904 of FIG. 39B. Contour line region 4012 may pertain to either region 3906 or 3908 of FIG. 39A and either femur jig region 40-3906 or 40-3908 of FIG. 39B. Utilizing the optimal areas 4010 and 4012 as jig bone mating surfaces 40 allows irregular areas of the patient's bone anatomy to be accommodated without affecting the fit of the jig 2 to the patient's bone anatomy. In fact, an accurate and custom fit between the jig 2 and the patient's bone anatomy can be made by using only a few of such optimal areas. This allows substantial overestimation of the jig surface in regions corresponding to irregularities, thereby preventing the irregularities from interfering with an accurate and reliable fit between the jig's bone mating surfaces and those bone surfaces of the arthroplasty target region corresponding to those bone mating surfaces. The result of the overestimation process is a jig with bone mating surfaces that offer a reliable and accurate custom fit with the arthroplasty target region. This may result in an increased success rate for TKR or partial knee replacement surgery because the jig may custom fit to the most reliable bone surfaces and be deliberately spaced from the bone surfaces that may be unreliable, for example, because of imaging or tool machinery limitations.

2. Overestimating the 3D Tibia Surface Models

As described above with regard to block 140 of FIG. 1D, the "jig data" 46 is used to produce a jigs having bone mating surfaces customized to matingly receive the target areas 42 of the respective bones of the patent's joint. Data for the target areas 42 may be based, at least in part, on the 3D computer generated surface models 40 of the patient's joint bones. Furthermore, as described above with regard to FIG. 1A and [blocks 100-105] of FIG. 1B, these 3D computer generated surface models 40 may be based on the plurality of 2D scan image slices 16 taken from the imaging machine 8 and, more precisely, from the contour lines derived from those 2D scan image slices via image segmentation processes known in the art or, alternatively, as disclosed in U.S. Provisional Patent Application 61/126,102, which was filed Apr. 30, 2008 and is incorporated by reference herein in its entirety.

Figure 41B:
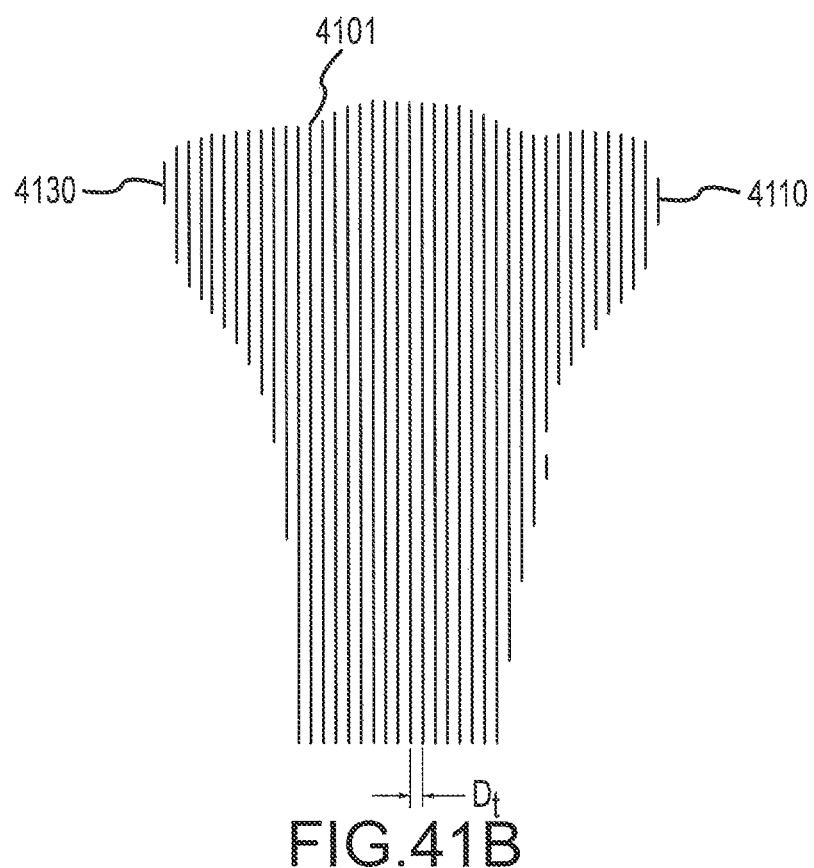
FIG. 41B represents a coronal view of a 3D model of the patient's tibia with the contour lines of the image slices shown and spaced apart by the thickness $D_T$ of the slices.
Figure 41A:
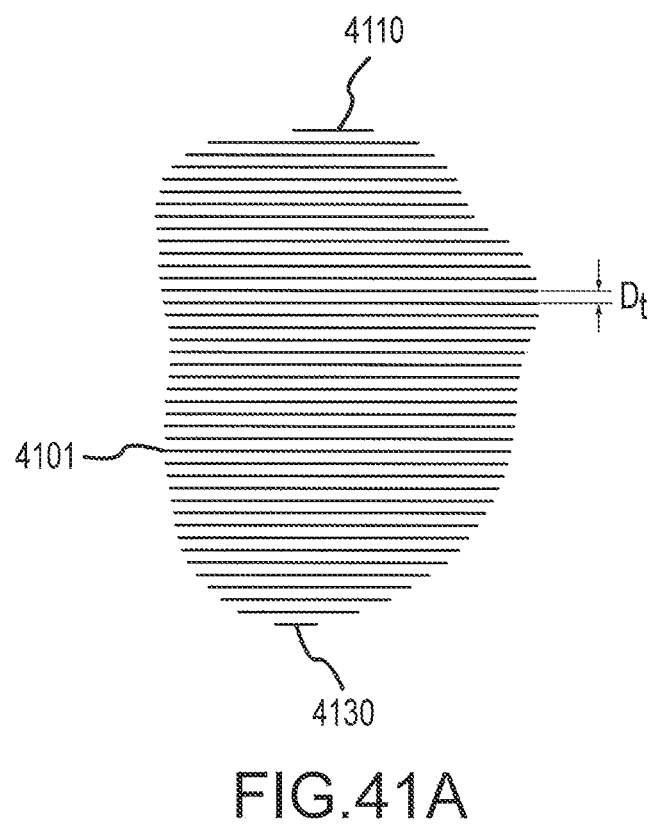
FIG. 41A illustrates the proximal axial view of the 3D model of the patient's tibia shown in FIG. 15 with the contour lines of the image slices shown and spaced apart by the thickness $D_T$ of the slices.

Each scan image slice 16 represents a thin slice of the desired bones. FIG. 41A illustrates the proximal axial view of the 3D model of the patient's tibia shown in FIG. 15 with the contour lines 4101 of the image slices shown and spaced apart by the thickness $D_T$ of the slices. FIG. 41B represents a coronal view of a 3D model of the patient's tibia with the contour lines 4101 of the image slices shown and spaced apart by the thickness $D_T$ of the slices.

The slices shown in FIGS. 41A-B have contour lines 4101 similar to the open and closed loop contour line segments 210, 210' depicted in FIGS. 2B and 2E. The contour lines 4101 of each respective image slice 16 are compiled together to form the 3D model of the patient's tibia. The overall resolution or preciseness of the 3D models 40 (shown in FIG. 12C) resulting from compiling together the contour lines of each of these slices (shown in [block 1010]) may be impacted by the thickness $D_T$ of the slices shown in FIGS. 41A-B. Specifically, the greater the thickness $D_T$ of the slices, the lower the resolution/preciseness of the resulting 3D models, and the smaller the thickness $D_T$ of the slices, the higher the resolution/preciseness of the resulting 3D models.

As the resolution/preciseness of the 3D models increases, more accurate customized arthroplasty jigs 2 may be generated. Thus, the general impetus is to have thinner slices rather than thicker slices. However, depending upon the imaging technology used, the feasible thickness $D_T$ of the image slices may vary and may be limited due a variety of reasons. For example, an imaging thickness $D_T$ that is sufficiently precise to provide the desired imaging resolution may also need to be balanced with an imaging duration that is sufficiently brief to allow a patient to remain still for the entire imaging duration.

In embodiments utilizing MRI technology, the range of slice thickness $D_T$ may be from approximately 0.8 mm to approximately 5 mm. MRI slice thicknesses $D_T$ below this range may be unfeasible because they have associated imaging durations that are too long for most patient's to remain still. Also, MRI slice thicknesses $D_T$ below this range may be unfeasible because they may result in higher levels of noise with regard to actual signals present, residuals left between slices, and volume averaging limitations of the MRI machine. MRI slice thicknesses above this range may not provide sufficient image resolution/preciseness. In one embodiment, the MRI slice thicknesses $D_T$ is approximately 2 mm.

While embodiments utilizing CT technology may have a range of slice thicknesses $D_T$ from approximately 0.3 mm to approximately 5 mm, CT imaging may not capture the cartilage present in the patient's joints to generate the arthritic models mentioned above.

Regardless of the imaging technology used and the resulting resolution/preciseness of the 3D models, the CNC machine 10 may be incapable of producing the customized arthroplasty jigs 2 due to mechanical limitations, especially where irregularities in the bone surface are present. This, for example, may result where a milling tool bit has dimensions that exceed those of the feature to be milled.

Figure 42:
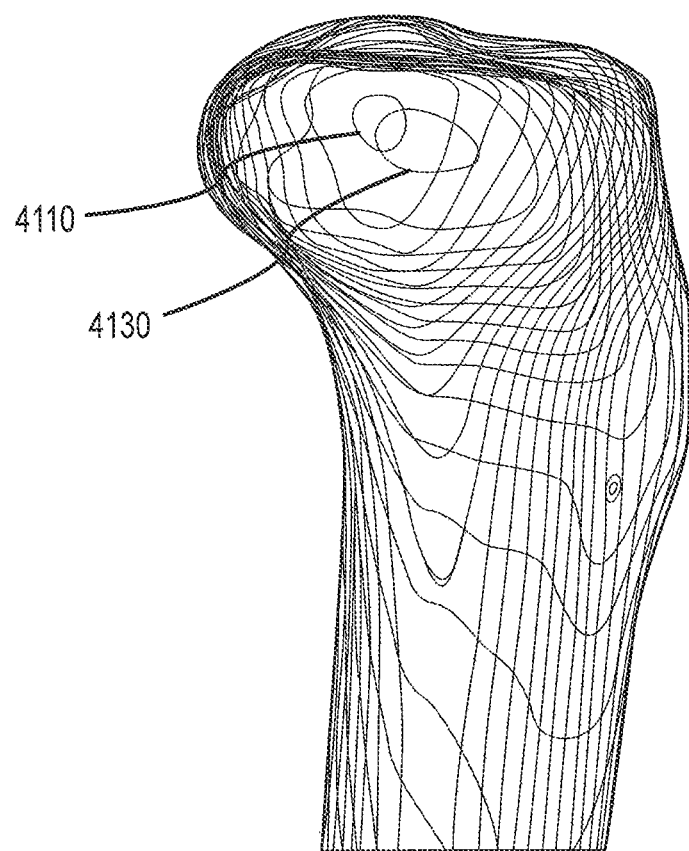
FIG. 42 illustrates an example sagittal view of compiled contour lines of successive sagittal 2D MRI images based on the slices shown in FIGS. 41A-B with a slice thickness $D_T$ of 2 mm.

FIG. 42 illustrates an example sagittal view of compiled contour lines of successive sagittal 2D MRI images based on the slices shown in FIGS. 41A-B with a slice thickness $D_T$ of 2 mm. As can be understood from FIGS. 41A-42, the contour lines shown begin on the medial side of the knee at the image slice corresponding to contour line 4110 and conclude on the lateral side of the knee at the image slice corresponding to contour line 4130. Thus, in one embodiment, contour lines 4110 and 4130 represent the contour lines of the first and last images slices taken of the tibia, with the other contour lines between contour lines 4110, 4130 representing the contour lines of the intermediate image slices taken of the tibia. Each of the contour lines is unique is size and shape, may be either open-loop or closed-loop, and corresponds to a unique image slice 16.

Figure 43:
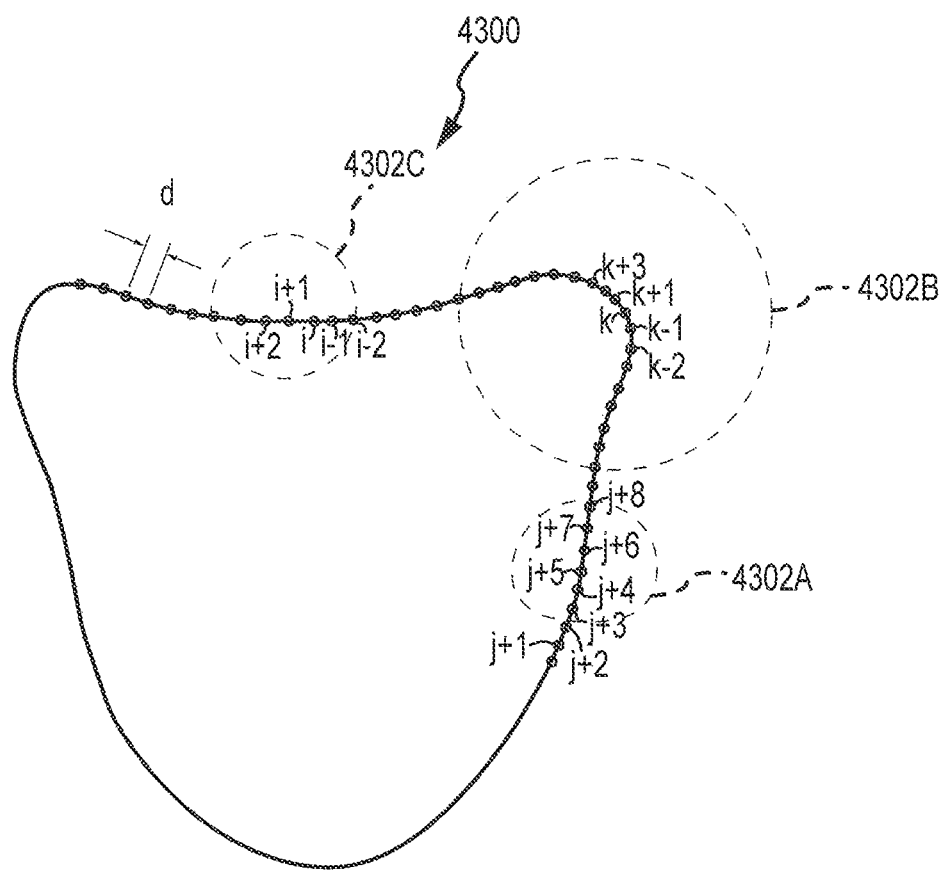
FIG. 43 illustrates an example contour line of one of the contour lines depicted in FIGS. 41A-42, wherein the contour line is depicted in a sagittal view and is associated with an image slice of the tibia plateau.

FIG. 43 illustrates an example contour line 4300 of one of the contour lines depicted in FIGS. 41A-42, wherein the contour line 4300 is depicted in a sagittal view and is associated with an image slice 16 of the tibia plateau. As shown, the contour line 2400 includes a plurality of surface coordinate points (e.g., i.e., i−n, . . . , i−3, i−2, i−1, i, i+1, i+2, i+3, . . . , i+n; j−n, . . . , j−3, j−2, j−1, j, j+1, j+2, j+3, . . . , j+n; and k−n, . . . , k−3, k−2, k−1, k, k+1, k+2, k+3, . . . , k+n). The contour line and associated points may be generated by imaging technology, for example, via an image segmentation process that may employ, for example, a shape recognition process and/or an pixel intensity recognition process. In one embodiment, the contour line 4300 may represent the boundary line along the cortical-cancellous bone edge. In one embodiment, the boundary line may represent the outer boundary line of the cartilage surface.

Each of the surface contour points in the plurality may be separated by a distance "d". In one embodiment, distance "d" may be a function of the minimum imaging resolution. In some embodiments, distance "d" may be function of, or associated with, the size of the milling tool used to manufacture the jig. For example, the distance "d" may be set to be approximately 10 times smaller than the diameter of the milling tool. In other words, the distance "d" may be set to be approximately $1/10^{th}$ or less of the diameter of the milling tool. In other embodiments, the distance "d" may be in the range of between approximately equal to the diameter of the milling tool to approximately $1/100^{th}$ or less of the diameter of the milling tool.

Depending on the embodiment, the separation distance d may be either uniform along the contour line 4300, or may be non-uniform. For example, in some embodiments, areas of bone irregularities may have points that are closer together than areas where no irregularities are present. In one embodiment, the points shown along the example contour line 4300 may have a separation distance d of approximately 2 mm. In other embodiments, distance d may be in the range of approximately 0.8 mm to approximately 5 mm.

The bone surface of the example contour line 4300 includes a region 4302A on the anterior portion of the tibia plateau, a region 4302B on the tibia plateau that is representative of an irregularity, and a region 4302C on the articular surface of the tibia plateau. The irregularity of region 4302B may be due to a variety of patient specific factors. For example, irregular region 4302B illustrates a type of bone irregularity, referred to as an "osteophyte", where a bony outgrowth has occurred in the tibia plateau. Osteophytes may be present in patients that have undergone trauma to the bone or who have experienced degenerative joint disease.

Irregularities may be due to other factors, such as cartilage damage, which may appear as notches in the contour line 4300. Regardless of the cause of the irregularities, the presence of irregularities in the contour line 4300 may adversely impact the ability to generate a mating surface in the actual arthroplasty jig that accurately and reliably mates with the corresponding bone surface of the patient during the arthroplasty procedure. This may be the result of the imaging impreciseness in the vicinity of the contour irregular region 4302B or because the contour irregular region 4302B represents a surface contour that is too small for the tooling of the CNC machine 10 to generate. To account for contour line regions associated with imaging impreciseness and/or features too small to be milled via the tooling of the CNC machine, in some embodiments, such contour line regions may be identified and corrected or adjusted via the overestimation process prior to being compiled to form the 3D models 40.

As discussed above, FIG. 25 represents an example overestimation algorithm 2500 that may be used to identify and adjust for irregular region 4302B when forming the 3D models 40. In block 2502, medical imaging may be performed on the damaged bone at desired slice thicknesses $D_T$, which in some embodiments may be equal to those slice thicknesses $D_T$ mentioned above with regard to FIGS. 41A-B. For example, MRI and/or CT scans may be performed at predetermined thicknesses $D_T$ as shown in FIGS. 41A-B. In some embodiments, the desired thickness $D_T$ used in block 2502 is set at 2 mm or any other thickness $D_T$ within the range of thicknesses $D_T$ mentioned above.

From this medical imaging, a series of slices 16 may be produced and image segmentation processes can be used to generate the contour lines 210, 210', 4101, 4110, 4130, 4300 discussed with respect to FIGS. 2, 41A-B, and 43 (see block 2504). Also in block 2504, a plurality of surface coordinate points along each contour line segment 4302A-C may be identified as shown in FIG. 43 with respect to contour line 4300. For example, the points in the irregular region corresponding to contour line segment 4302B may be identified and indexed as k−n, . . . , k−3, k−2, k−1, k, k+1, k+2, k+3, . . . , k+n.

With the surface coordinate points along the contour 4300 defined, an analysis may be performed on two or more of the points (e.g., k and k+1) to determine if an irregularity exists in the contour line segment per block 2506.

Figure 44:
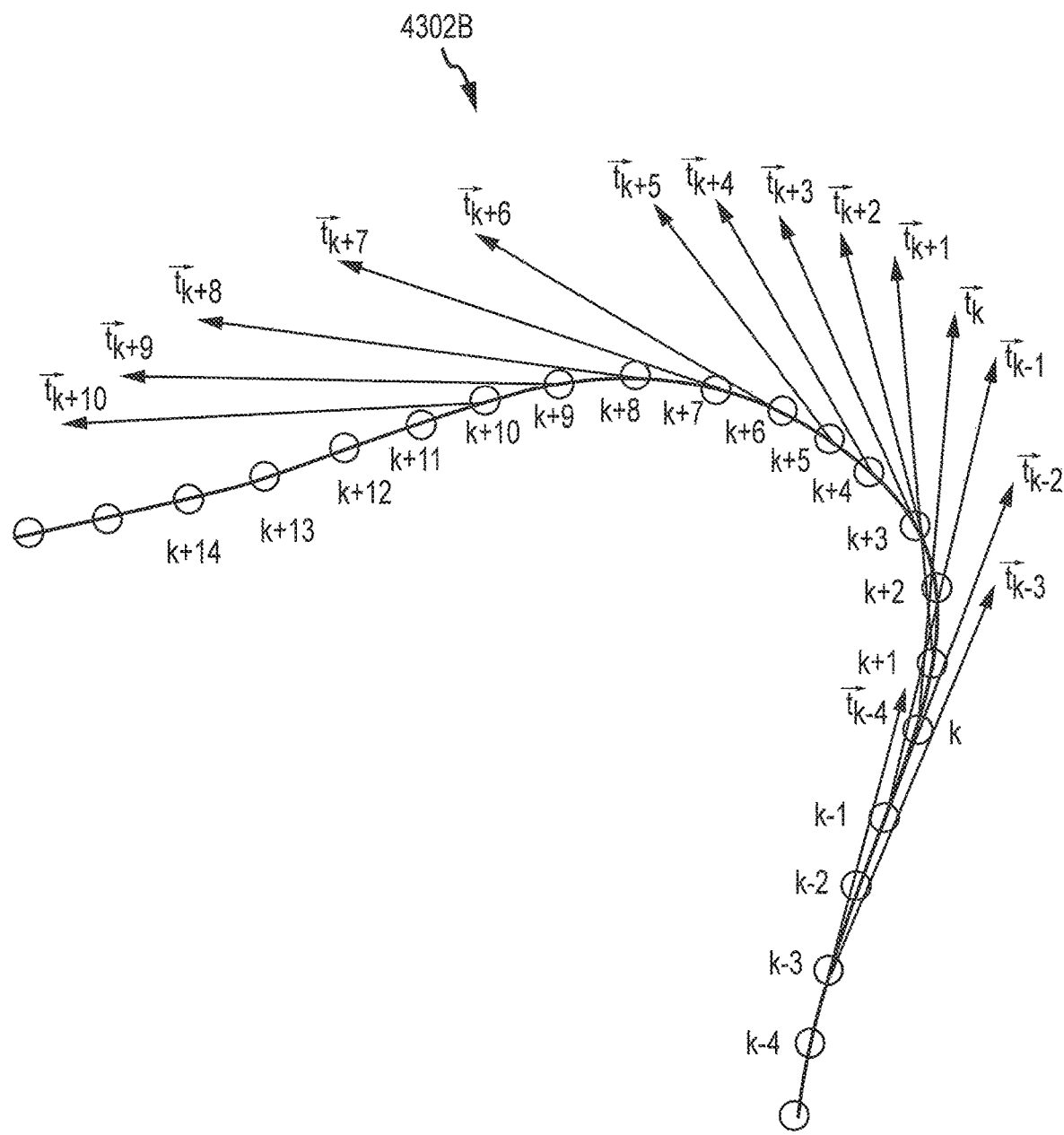
FIG. 44 depicts implementing an example analysis scheme (according to block 2506) on the irregular contour line region 4302B of FIG. 43.

FIG. 44 depicts implementing an example analysis scheme (according to block 2506) on the irregular contour line region 4302B of FIG. 43. As shown, the analysis may include constructing one or more tangent lines (labeled as $t_{k-1}, t_k, t_{k+1}, t_{k+2}, t_{k+3}, t_{k+4}$, etc.), corresponding to the points in the irregular region 4302B. The analysis of block 2506 may further include calculating differences between the angles formed by one or more of the tangent lines. For example, the difference between the angles formed by the tangent lines $t_k$ and $t_{k+1}$ may be defined as $w_k$, where $$w_k = \cos^{-1}\left(\frac{t_{k+1} \cdot t_k}{|t_{k+1}||t_k|}\right).$$

In some embodiments, the operations of block 2506 may be performed repetitively on each point within the contour segment.

The operations of block 2506 may be calculated on subsequent points (e.g., between $t_k$ and $t_{k+1}$) in some embodiments, and on non-subsequent points in other embodiments (e.g., $t_{k+2}$ and $t_{k+4}$).

The angular difference w may indicate whether portions of the contour line segment are too eccentric for use in constructing the 3D models 40. In block 2508, the angular difference w may be compared to a predetermined angular criterion $w_c$. The angular criterion $w_c$ may be determined based on several factors, including the physical dimensions and characteristics of the CNC machine 10. In some embodiments, the predetermined angular criterion $w_c$ is set at approximately 5 degrees. In other embodiments, the predetermined angular criterion $w_c$ is set at between approximately 5 degrees and approximately 20 degrees.

For the sake of discussing the example irregular region 4302B shown in FIG. 44, the angular criterion $w_c$ is set to 5 degrees in one embodiment. The angular differences between tangent lines associated with adjacent points k−4, k−3, k−2 and k+12, k+13, and k+14 are within the predetermined angular criterion $w_c$ of 5 degrees, but the differences between tangent lines associated with adjacent points k−3, k−2, k−1, ki, k+1, k+2, . . . , k+10 exceeds the predetermined angular criterion $w_c$ of 5 degrees and therefore indicates an irregular region of the contour line. As mentioned above, these irregularities may result from conditions of the patient's bone such as arthritis or osteoarthritis and generally result in a contour line segment being unsuitable for using when forming the 3D models 40. Accordingly, if the comparison from block 2508 indicates that the angular difference w is greater than the predetermined criterion $w_c$, then the data associated with the irregular contour line segment may be modified by overestimating (e.g., adjusting the irregular contour line segment outward or away from the bone portion of the image slice 16) as discussed in greater detail below with respect to FIG. 45 (see block 2510).

Figure 45:
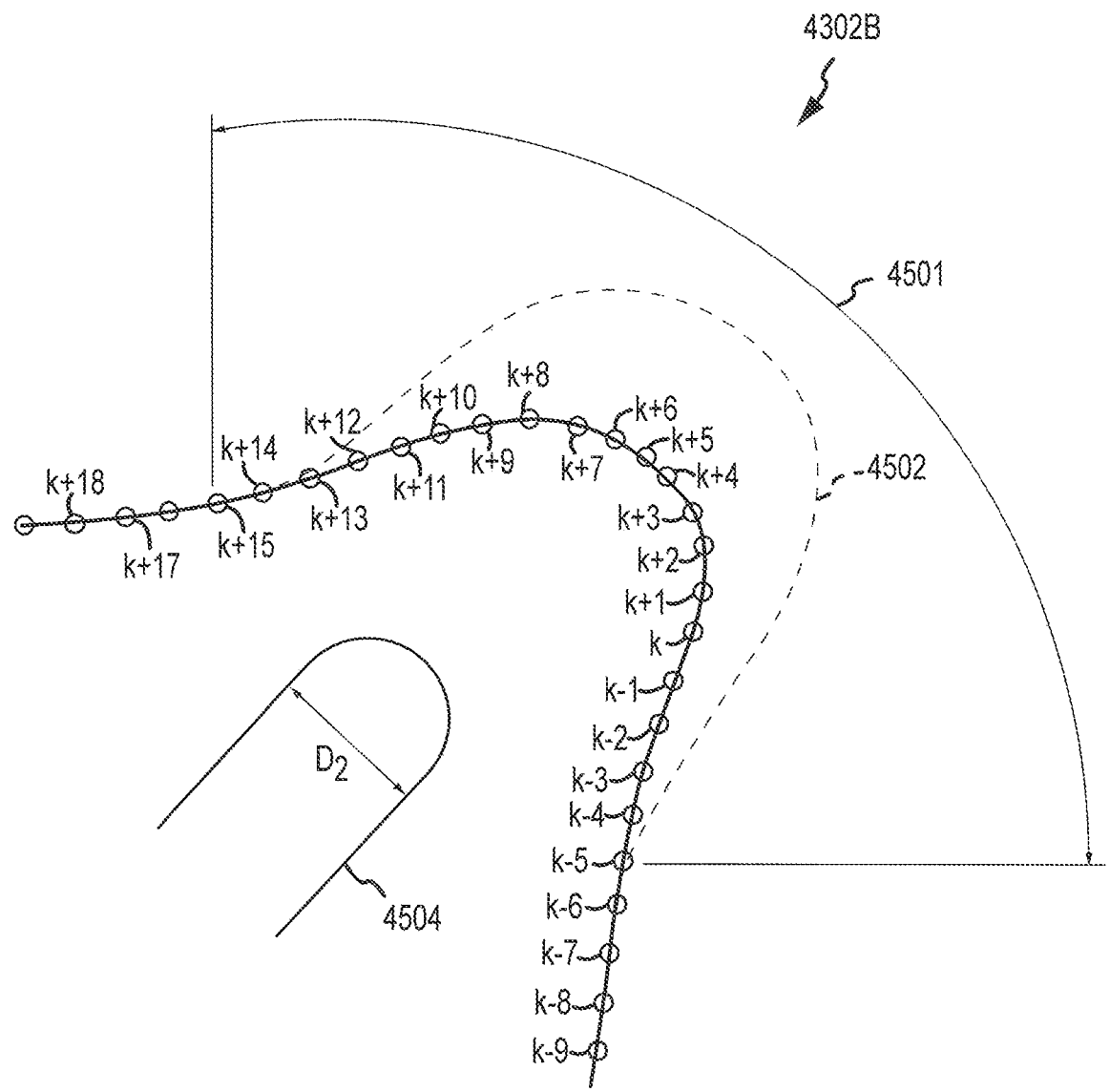
FIG. 45 depicts the irregular region 4302B from FIG. 44 including a proposed area of overestimation, wherein an overestimation procedure creates an adjusted contour line and positionally deviates the adjusted contour line from the original surface profile contour line.

FIG. 45 depicts the irregular region 4302B from FIG. 44 including a proposed area of overestimation 4501, wherein an overestimation procedure creates an adjusted contour line 4502 and positionally deviates the adjusted contour line 4502 from the original surface profile contour line 4302B. In the event that the comparison performed in block 2508 indicates that the angular differences between any of the points k−3 through k+10 exceed the predetermined angular criterion $w_c$, then the contour line segment may be overestimated between these points as shown by the dashed line 4502. As can be understood from a comparison of contour line 4302B to the overestimated or adjusted line 4502, the adjusted line 4502 is adjusted or moved outward or away from the location of the contour line 4502B by an offset distance. Depending on the embodiment, the offset distance between the contour line 4302B and the adjusted line 4502 may range between a few millimeters to a few centimeters. This overestimation may be built into the data used to construct 3D surface models 40 and result in a gap between the respective region of the bone mating surface of the jig 2 and the corresponding portion of the patient's bone surface, thereby avoiding contact between these respective areas of the jig and bone surface. The other areas, such as k−6, k−7, k−8, k−9 and k+15, k+16, k+17, and k+18, need not be overestimated, per block 2510, because the differences between their tangent lines fall within the angular difference criterion $w_c$. These areas may be designated as potential target areas that may later be used as the 3D surface models 40 if other angular criteria (described below) are satisfied.

By building overestimation data into the 3D surface models 40, deliberate spaces may be created in regions of the custom arthroplasty jig 2 corresponding to irregularities in the patient's bone, where it is often difficult to predict the size and shape of these irregularities from 2D MRI or where it is difficult to accurately machine the contour line into the jig's bone mating surface because of the largeness of the milling tool relative to the changes in contour. Thus, the jig 2 may include one or more deliberate spaces to accommodate these irregularities or inability to machine. Without these deliberate spaces, the jig 2 may be potentially misaligned during the TKR surgery and may reduce the chances of the surgery's success.

As described above with respect to FIGS. 28 and 30, the image generation, analysis and overestimation of blocks 2506, 2508 and 2510 may be performed on other irregularities of contour line 4300, if such additional irregularities were present in FIG. 43.

As shown in FIG. 45, a tool 4504 having diameter $D_2$ may be employed to machine the contour line 4302 into the jig blank. As described above with respect to FIG. 29A, in some embodiments, to allow for an adequate transition from the non-overestimated regions to the overestimated regions 4501 in view of the diameter $D_2$ of the tool 4504 to be used, the overestimation may include additional points to either side of the points falling outside of the predetermined criterion $w_c$ (i.e., points k−3, k−4, and k−5 as well as at points k+12, k+13, and k+14). Thus, the overestimation in region 4302B may extend from k−5 through k+14. Furthermore, since the comparison performed in block 2508 indicates that the angular difference $w_k$ is less than the predetermined criterion $w_e$ at points k−3, k−4, k−5, k−6, k−7, k−8, k−9 and k+12, k+13, k+14, k+15, k+16, k+17, and k+18, these points k−6, k−7, k−8, k−9 and k+15, k+16, k+17, and k+18 (adjusting for the addition of points k−3, k−4, and k−5 as well as at points k+12, k+13 to the overestimation transition regions 4501) may be used in constructing the 3D models 40 as long as other criteria (described below in the context of blocks 2514-2520) are met.

A tool 4504 may be used to form the surface of the jig's bone mating surface from the 3D models 40 formed from the compiled contour lines, some of which may have been modified via the overestimation process. The tool 4504 may be part of the CNC machine 10 or any other type of machining or manufacturing device having any type of tool or device for forming a surface in a jig blank. Regardless of the type of the device used to mill or form the jigs 2, the tool 4504 may have certain attributes associated with jig machining process that are taken into account when performing the overestimating per block 2510. The associated attributes may include the accessible space for the machining tools to reach and machine the jig's bone mating surface. Examples of such attributes may include the collar diameter of the drilling cutter device, the allowable angle the drilling device can make with the surface to be drilled (e.g., 45 degrees±10%), and/or the overall length of the drilling cutter head.

For example, as indicated in FIG. 45, if the minimum diameter of the overestimated region 4501 is larger than the diameter $D_2$ of the tool 4504, then overestimation of block 2510 may not need to account for the dimensions of the tool 4504, except to provide adequate transitions leading to the overestimated region 4501 as illustrated above by the addition of a single or few points (e.g., points k−3, k−4, and k−5 as well as at points k+12, k+13) to either side of the points outside predetermined criterion $w_c$.

If, on the other hand, the tool 4504 has a diameter $D_2$ that is greater than the diameter of the overestimated region, then the overestimated region may be increased in diameter to account for the large tool diameter, as described above with respect to FIGS. 29B-29C. With the curves overestimated to account for factors related to the tool 4504, the resulting overestimated surface profile or contour may be saved for generating the 3D model 40 as long as other criteria (described below in the context of block 2514-2520) are met.

Figure 46A:
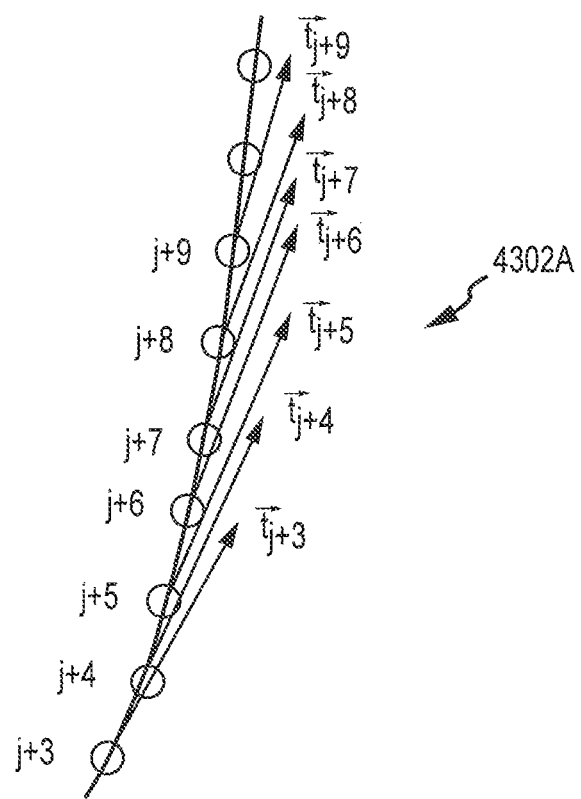
FIGS. 46A and 46B show an analysis of the regular regions 4302A and 4302C from FIG. 43.
Figure 46B:
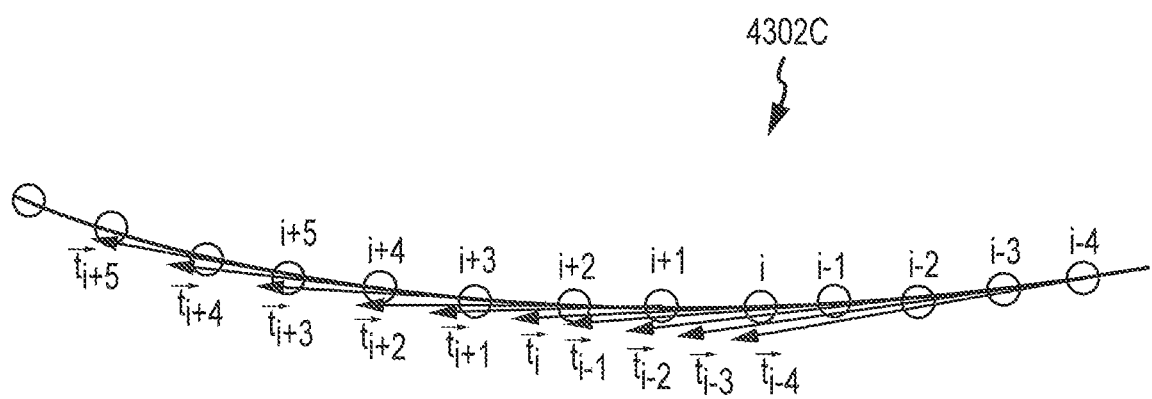

FIGS. 46A-B show similar analyses of the regular regions 4302A and 4302C (from FIG. 43). As was the case with the irregular region 4302B, points i+1, i+2, i+3, . . . , i+n and j+1, j+2, j+3, j+n along the contour line 4300 may be identified for regions 4302A and 4302C and then tangent lines (labeled as $t_{j+1}$, $t_{j+2}$, $t_{j+3}$, etc. and $t_{i+1}$, $t_{i+2}$, $t_{i+3}$, etc.) may be constructed per block 2506. Per block 2508, comparing the angular differences w between these tangent lines using the formulas $$w_j = \cos^{-1}\left(\frac{t_{j+1} \cdot t_j}{|t_{j+1}||t_j|}\right) \text{ and } w_i = \cos^{-1}\left(\frac{t_{i+1} \cdot t_i}{|t_{i+1}||t_i|}\right)$$

shows that they $w_j$, $w_i$ are within the angular criterion $w_c$, which in this example is 5 degrees. Thus, the points of the regions 4302A and 4302C shown in FIGS. 46A-B may be saved and used as potential surface profiles for the mating surface of the tibial jig if the surface variations between these points and points on contour lines of adjacent slices are not too extreme. That is, if the angular differences associated with a contour line of a particular slice fall within the angular criterion $w_c$, and the points are used as a potential jig surface, then surface variation between contour lines of adjacent slices may be checked in block 2514. This approach may help to identify certain areas where no cartilage damage or osteophyte is observed in the imaging, yet there is a need to overestimate because the surface variation, between the adjacent slices shown in FIGS. 41A-B, may be too great to be used as an accurate representation of the actual bone surface to be a potential tibial jig surface. Example areas falling within this category for the proximal tibia plateau include the areas near the medial and lateral tibial plateaus adjacent to, and including, the spine portion to name a few examples.

Once it is determined that a specific portion of a contour line has satisfied the criterion $w_c$ of block 2508 of FIG. 25, that contour line portion may be further analyzed to determine if the contour line portion also satisfies both of the criterion $\theta_c$ and $\varphi_c$ of block 2514, as discussed above with respect to FIGS. 25 and 32A-33B. More specifically, corresponding coordinate points are determined via any of the three methods discussed above with respect to FIGS. 33A-33F. The surface variation between the corresponding coordinate points is analyzed as discussed with above with respect to FIGS. 33A-33F with respect to: (1) angular deviation $\theta$ between corresponding coordinate points of contour lines of adjacent image slices; and (2) the angular differences $\varphi$ of normal vectors associated with corresponding coordinate points of contour lines of adjacent image slices. If the contour line portion meets all of the criterion $w_i$, $\theta_c$ and $\varphi_c$ of blocks 2508 and 2514 of FIG. 25, then, as discussed above and indicated in block 2520 of FIG. 25, the contour line portion may be recorded and employed in generating the jig's bone mating surfaces. Alternatively, if the contour portion line fails to meet any one or more of the criterion $w_i$, $\theta_c$ and $\varphi_c$ of blocks 2508 and 2514, then as indicated in FIG. 25 and discussed above, the contour line portion may be modified per the overestimation process (block 2510) or, in some instances, the image slice thickness $D_T$ may be reset to a more narrow thickness $D_T$ and the entire process repeated beginning at block 2502 of FIG. 25.

Figure 47:
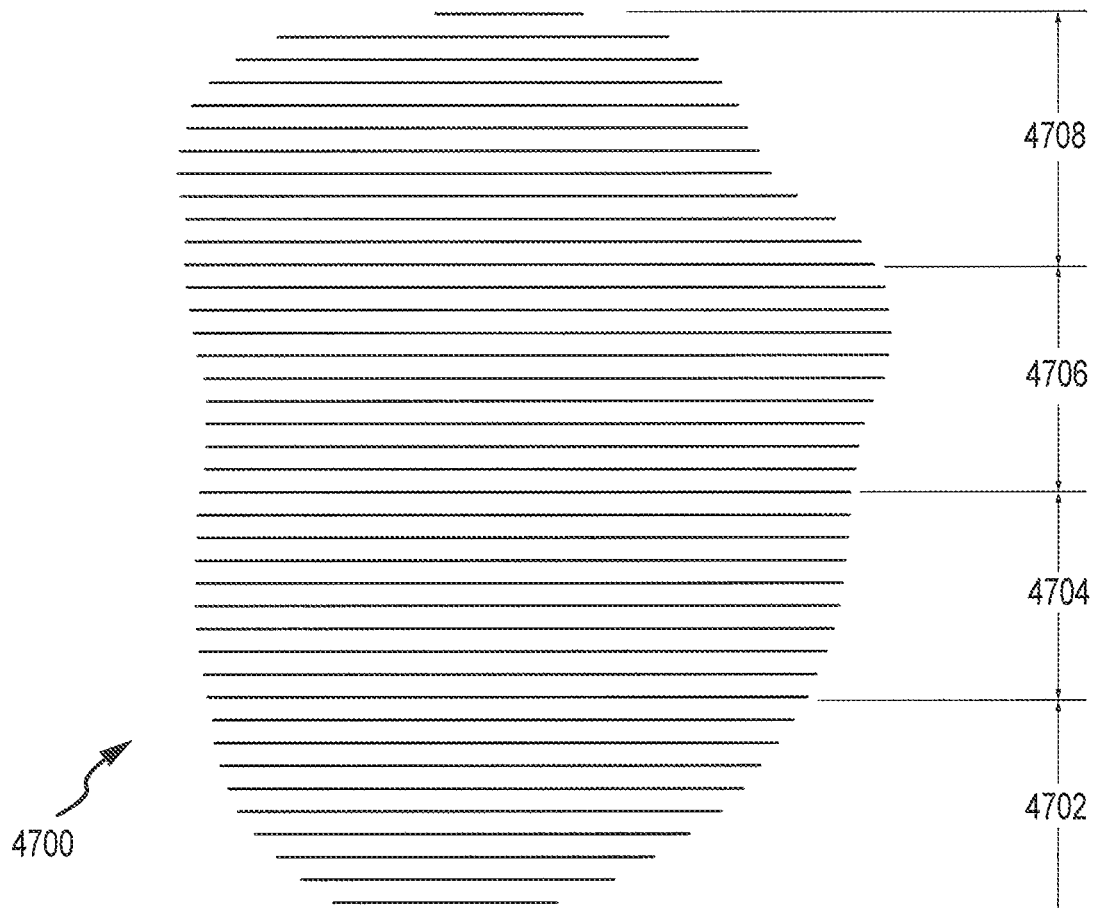
FIG. 47 is a distal view similar to that of FIG. 15 depicting contour lines produced by imaging the left tibia at an image spacing $D_T$ of, for example, 2 mm.

FIG. 47 is a proximal view of the tibia plateau similar to that of FIG. 15 depicting contour lines 4700 produced by imaging the left tibia at an image spacing $D_T$ of, for example, 2 mm. As shown, the contour lines 4700 may be grouped into multiple regions in the lateral-medial direction 4702-4708 for the sake of discussion. The region 4702 includes the contour lines 4700 of the most medial half of the medial tibial plateau and extends laterally from the most medial side of the medial tibial plateau to the medial-lateral middle of the medial tibial plateau. The region 4704 includes the contour lines 4700 of the most lateral half of the medial tibial plateau and extends laterally from the middle of the medial tibial plateau to the medial-lateral point near the tibial spine. The region 4706 includes the contour lines 4700 of the most medial half of the lateral tibial plateau and extends laterally from the medial-lateral point near the tibial spine to the medial-lateral middle of the lateral tibial plateau. The region 4708 includes the contour lines 4700 of the most lateral half of the lateral tibial plateau and extends laterally from the medial-lateral middle of the lateral tibial plateau to the most lateral side of the lateral tibial plateau.

Figure 48:
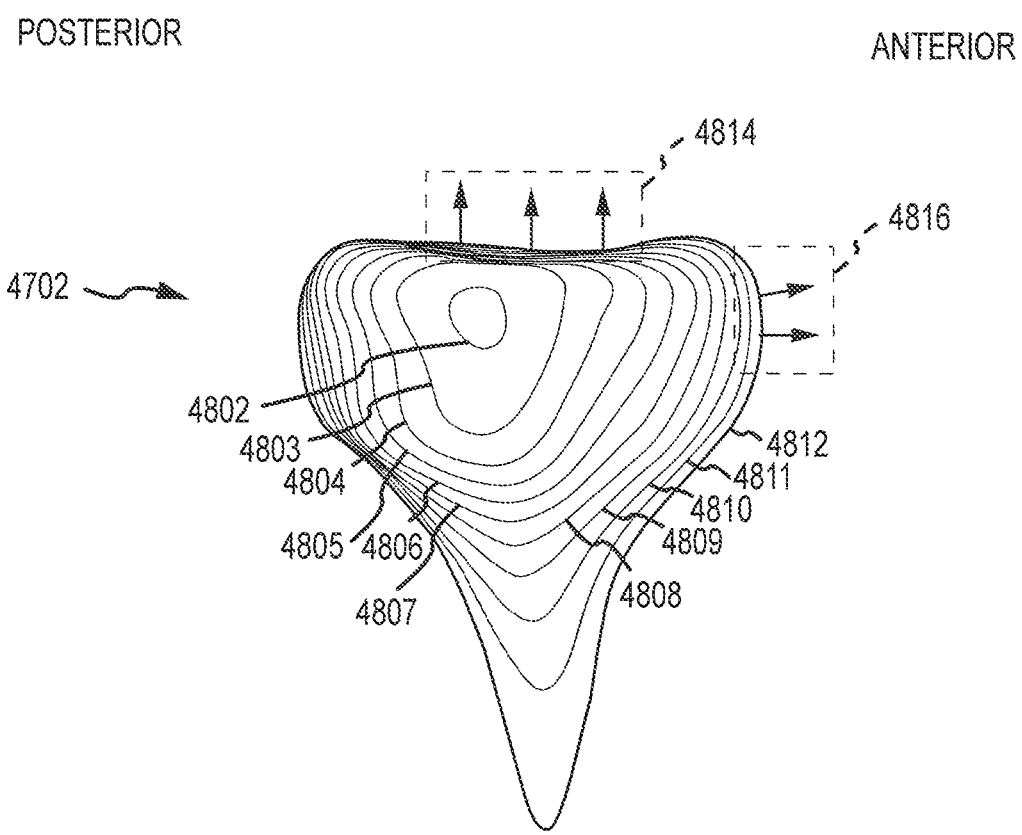
FIGS. 48-51 are sagittal views of the contour lines of respective regions of FIG. 47.

FIG. 48 is a sagittal view of the contour lines 4700 of region 4702 of FIG. 47. The contour lines 4700 of region 4702 include contour lines 4802-4812, with the most medial portion of the medial tibial plateau being indicated by contour line 4802. The size of each successive contour line 4700 of region 4702 increases moving laterally from the most medial contour line 4802 of region 4702 to the most lateral contour line 4812 of region 4702, which is near the medial-lateral middle of the medial tibial plateau.

As can be understood from FIG. 48, the contour lines 4802-4803 are spaced apart from their respective adjacent contour lines a substantial amount around their entire boarders. Such wide spacing corresponds to a substantial amount of rise or fall distances between adjacent contour lines, as discussed above with respect to FIG. 33B. Thus, such contour lines would likely fail to meet the angular criterion $\theta_c$ and be subject to the overestimation process such that jig surfaces corresponding to the contour lines 4802-4803 would not contact the corresponding surfaces of the arthroplasty target areas.

As can be understood from FIG. 48, in the proximal portion of the medial tibial plateau, the contour lines 4804-4812 in the region 4814 converge such that there is little, if any, amount of rise or fall distance between adjacent contour lines. Thus, such contour lines 4804-4812 in the region 4814 would likely meet the first angular criterion $\theta_c$. Similarly, in the anterior tibial plateau portion of the proximal tibia, the contour lines 4811-4812 in region 4816 converge such that there is little, if any, amount of rise or fall distance between adjacent contour lines. Thus, such contour lines 4804-4812 in region 4814 and contour lines 4811-4812 in region 4816 would likely meet the first angular criterion $\theta_c$.

As can be understood from the arrows in regions 4814 and 4816, the angular differences between normal vectors for the contour line portions within regions 4814 and 4816 would be minimal, likely meeting the second angular criterion $\varphi_c$. Thus, as the portions of the contour lines 4804-4812 within region 4814 and the portions of the contour lines 4811-4812 within region 4816 likely meet both angular criterion $\theta_c$ and $\varphi_c$, the portions of the contour lines 4804-4812 within the region 4814 and the portions of the contour lines 4811-4812 within region 4816 represent optimal contact areas 4814 and 4816 for mating contact with the jig's bone mating surface 40.

In one embodiment, as can be understood from FIG. 52A discussed below, the optimal contact area 4814 may be the surface of the medial tibial plateau that displaces against the corresponding articular surface of the medial femoral condyle, and the optimal contact area 4816 may be the medial anterior region of the proximal tibia just distal of the tibial plateau edge and medial of the tuberosity of the tibia.

In one embodiment, the optimal contact areas 4814 and 4816 matingly corresponds to the jig's bone mating surface 40 such that the portions of the contour lines 4702 indicated by regions 4814 and 4816 may be used to generate the jig's bone mating surface 40, per the algorithm 2500 of FIG. 25. Conversely, per the algorithm 2500, the portions of the contour lines 4702 outside regions 4814 and 4816 may be subjected to the overestimation process discussed above such that the jig's surfaces created from the overestimated contour line portions results in jig surfaces that do not contact the corresponding portions of the patient's arthroplasty target regions.

Figure 49:
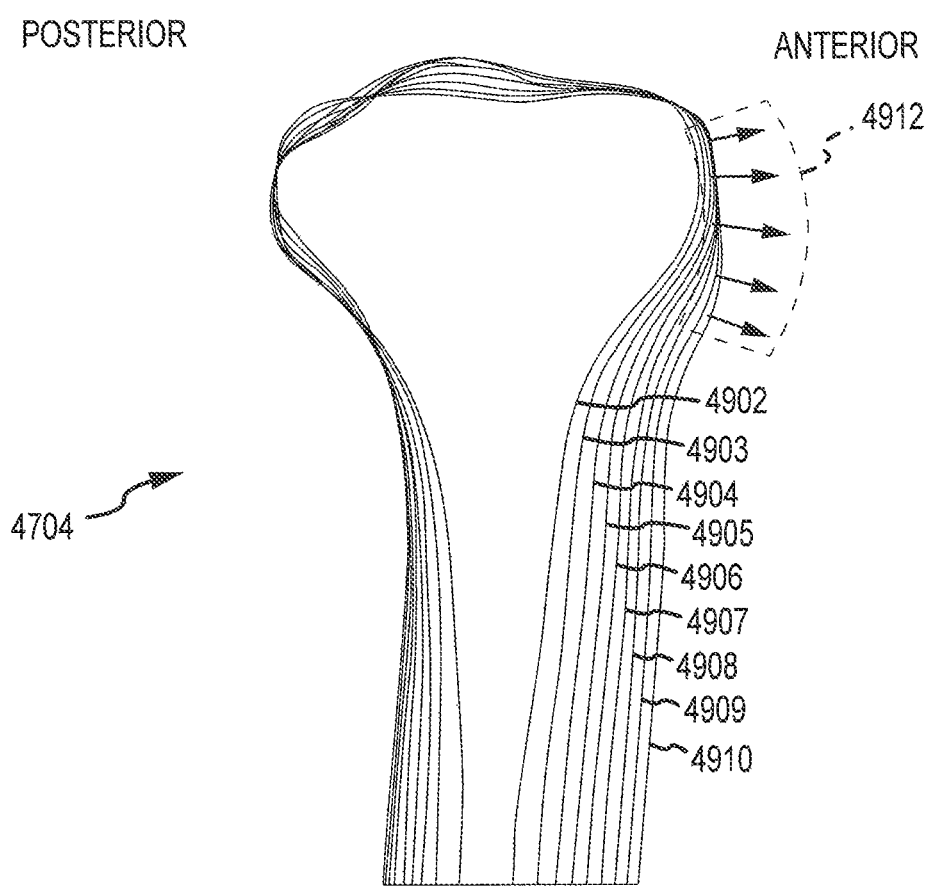

FIG. 49 is a sagittal view of the contour lines 4700 of region 4704 of FIG. 47. The contour lines 4700 of region 4704 include contour lines 4902, 4903, 4904, 4905, 4906, 4907, 4908, 4909 and 4910 with the most medial portion of region 4704 being indicated by contour line 4802, which is near the medial-lateral middle of the medial tibial plateau, and the most lateral portion of region 4704 being indicated by contour line 4810, which is a medial-lateral point near the tibial spine. The size of each successive contour line 4700 of region 4704 increases moving laterally from the most medial contour line 4902 to the most lateral contour line 4910.

As can be understood from FIG. 49, the contour lines 4902-4910 are spaced apart from their respective adjacent contour lines a substantial amount in their posterior and anterior portions along the shaft of the tibia, and to a lesser extent in their tibia spine portions. Such wide spacing corresponds to a substantial amount of rise or fall distances between adjacent contour lines, as discussed above with respect to FIG. 33B. Thus, such contour lines would likely fail to meet the angular criterion $\theta_c$ and be subject to the overestimation process such that jig surfaces corresponding to the contour lines 4902-4910 would not contact the corresponding surfaces of the arthroplasty target areas.

As can be understood from FIG. 49, in the anterior tibial plateau portion of the proximal tibia, the contour lines 4902-4910 in the region 4912 converge such that there is little, if any, amount of rise or fall distance between adjacent contour lines. Thus, such contour lines 4902-4910 in the region 4912 would likely meet the first angular criterion $\theta_c$.

As can be understood from the arrows in region 4912, the angular differences between normal vectors for the contour line portions within the region 4912 would be minimal, likely meeting the second angular criterion $\varphi_c$. Thus, as the portions of the contour lines 4902-4910 within region 4912 likely meet both angular criterion $\theta_c$ and $\varphi_c$, the portions of the contour lines 4902-4910 within the region 4912 represent an optimal contact area 4912 for mating contact with the jig's bone mating surface 40.

In one embodiment, the optimal contact area 4912 matingly corresponds to the jig's bone mating surface 40 such that the portions of the contour lines 4902-4910 indicated by region 4912 may be used to generate the jig's bone mating surface 40, per the algorithm 2500 of FIG. 25. Conversely, per the algorithm 2500, the portions of the contour lines 4902-4910 outside region 4912 may be subjected to the overestimation process discussed above such that the jig's surfaces created from the overestimated contour line portions results in jig surfaces that do not contact the corresponding portions of the patient's arthroplasty target regions.

In one embodiment, as can be understood from FIG. 52A discussed below, the optimal contact area 4912 may be the anterior region of the proximal tibia just distal of the tibial plateau edge and just distal of the tuberosity of the tibia, extending medial-lateral from just medial of the tuberosity of the tibia to generally centered medial-lateral relative to the tuberosity of the tibia.

Figure 50:
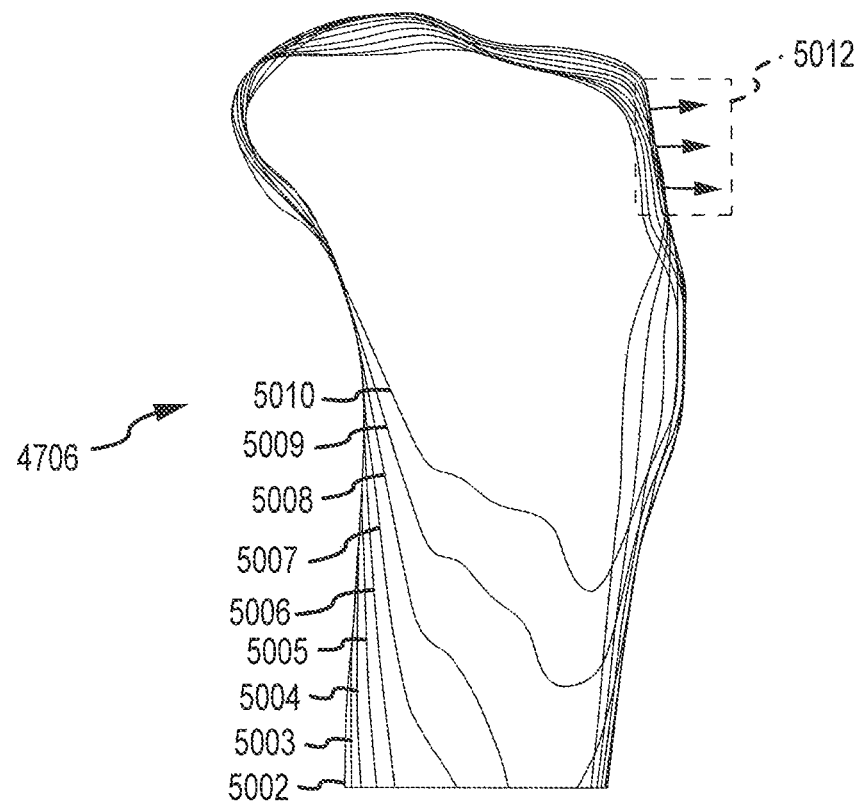

FIG. 50 is a sagittal view of the contour lines 4700 of region 4706 of FIG. 47. The contour lines 4700 of region 4706 include contour lines 5002, 5003, 5004, 5005, 5006, 5007, 5008, 5009 and 5010 with the most medial portion of region 4706 being indicated by contour line 5002, which is a medial-lateral point near the tibial spine, and the most lateral portion of region 4704 being indicated by contour line 5010, which is near the medial-lateral middle of the lateral tibial plateau. The size of each successive contour line 4700 of region 4704 decreases moving laterally from the most medial contour line 5002 to the most lateral contour line 5010.

As can be understood from FIG. 50, the contour lines 5002-5010 are spaced apart from their respective adjacent contour lines a substantial amount in their posterior and anterior portions along the shaft of the tibia, and to a lesser extent in their tibia spine and tibia tuberosity portions. Such wide spacing corresponds to a substantial amount of rise or fall distances between adjacent contour lines, as discussed above with respect to FIG. 33B. Thus, such contour lines would likely fail to meet the angular criterion $\theta_c$ and be subject to the overestimation process such that jig surfaces corresponding to the contour lines 5002-5010 would not contact the corresponding surfaces of the arthroplasty target areas.

As can be understood from FIG. 50, in the anterior tibial plateau portion of the proximal tibia, the contour lines 5002-5010 in the region 5012 converge such that there is little, if any, amount of rise or fall distance between adjacent contour lines. Thus, such contour lines 5002-5010 in the region 5012 would likely meet the first angular criterion $\theta_c$.

As can be understood from the arrows in region 5012, the angular differences between normal vectors for the contour line portions within the region 5012 would be minimal, likely meeting the second angular criterion $\varphi_c$. Thus, as the portions of the contour lines 5002-5010 within region 5012 likely meet both angular criterion $\theta_c$ and $\varphi_c$, the portions of the contour lines 5002-5010 within the region 5012 represent an optimal contact area 5012 for mating contact with the jig's bone mating surface 40.

In one embodiment, the optimal contact area 5012 matingly corresponds to the jig's bone mating surface 40 such that the portions of the contour lines 5002-5010 indicated by region 5012 may be used to generate the jig's bone mating surface 40, per the algorithm 2500 of FIG. 25. Conversely, per the algorithm 2500, the portions of the contour lines 5002-5010 outside region 5012 may be subjected to the overestimation process discussed above such that the jig's surfaces created from the overestimated contour line portions results in jig surfaces that do not contact the corresponding portions of the patient's arthroplasty target regions.

In one embodiment, as can be understood from FIG. 52A discussed below, the optimal contact area 5012 may be the anterior region of the proximal tibia just distal of the tibial plateau edge and just distal of the tuberosity of the tibia, extending medial-lateral from just lateral of the tuberosity of the tibia to generally centered medial-lateral relative to the tuberosity of the tibia.

Figure 51:
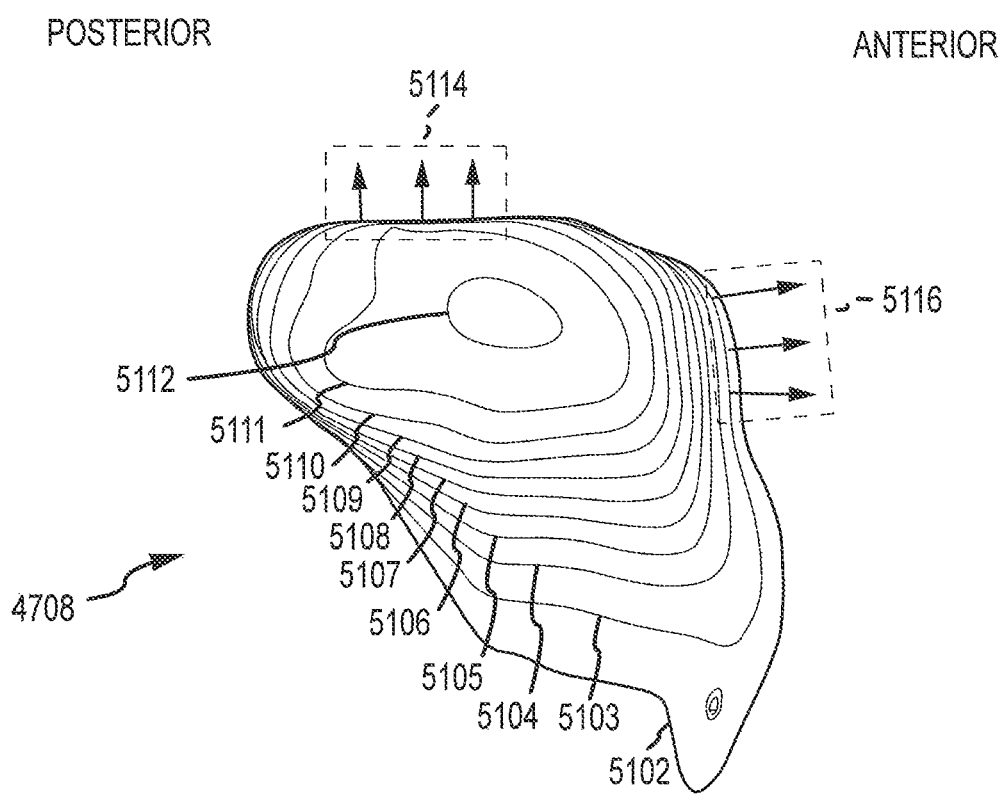

FIG. 51 is a sagittal view of the contour lines 4700 of region 4708 of FIG. 47. The contour lines 4700 of region 4708 include contour lines 5102-5112, with the most lateral portion of the lateral tibial plateau being indicated by contour line 5102. The size of each successive contour line 4700 of region 4708 increases moving laterally from the most medial contour line 5102 of region 4708, which is near the medial-lateral middle of the medial tibial plateau, to the most lateral contour line 5110 of region 4708, which is the most lateral portion of the lateral tibial plateau.

As can be understood from FIG. 51, the contour lines 5110-5112 are spaced apart from their respective adjacent contour lines a substantial amount around their entire boarders. Such wide spacing corresponds to a substantial amount of rise or fall distances between adjacent contour lines, as discussed above with respect to FIG. 33B. Thus, such contour lines would likely fail to meet the angular criterion $\theta_c$ and be subject to the overestimation process such that jig surfaces corresponding to the contour lines 5110-5112 would not contact the corresponding surfaces of the arthroplasty target areas.

As can be understood from FIG. 51, in the proximal portion of the lateral tibial plateau, the contour lines 5102-5109 in the region 5114 converge such that there is little, if any, amount of rise or fall distance between adjacent contour lines. Thus, such contour lines 5102-5109 in the region 5114 would likely meet the first angular criterion $\theta_c$. Similarly, in the anterior tibial plateau portion of the proximal tibia, the contour lines 5102-5105 in region 5116 converge such that there is little, if any, amount of rise or fall distance between adjacent contour lines. Thus, such contour lines 5102-5109 in region 5114 and contour lines 5102-5105 in region 5116 would likely meet the first angular criterion $\theta_c$.

As can be understood from the arrows in regions 5114 and 5116, the angular differences between normal vectors for the contour line portions within regions 5114 and 5116 would be minimal, likely meeting the second angular criterion $\varphi_c$. Thus, as the portions of the contour lines 5102-5109 within region 5114 and the portions of the contour lines 5102-5105 within region 4816 likely meet both angular criterion $\theta_c$ and $\varphi_c$, the portions of the contour lines 5102-5109 within the region 5114 and the portions of the contour lines 5102-5105 within region 5116 represent optimal contact areas 5114 and 5116 for mating contact with the jig's bone mating surface 40.

In one embodiment, as can be understood from FIG. 52A discussed below, the optimal contact area 5114 may be the surface of the lateral tibial plateau that displaces against the corresponding articular surface of the lateral femoral condyle, and the optimal contact area 5116 may be the lateral anterior region of the proximal tibia just distal of the tibial plateau edge and lateral of the tuberosity of the tibia.

In one embodiment, the optimal contact areas 5114 and 5116 matingly corresponds to the jig's bone mating surface 40 such that the portions of the contour lines 4708 indicated by regions 5114 and 5116 may be used to generate the jig's bone mating surface 40, per the algorithm 2500 of FIG. 25. Conversely, per the algorithm 2500, the portions of the contour lines 4708 outside regions 5114 and 5116 may be subjected to the overestimation process discussed above such that the jig's surfaces created from the overestimated contour line portions results in jig surfaces that do not contact the corresponding portions of the patient's arthroplasty target regions.

As can be understood from the preceding discussion, the overestimation process disclosed herein can be used to identifying optimal target areas (e.g., optimal target areas 4814, 4816, 4912, 5012, 5114, 5116 as discussed with respect to FIGS. 47-51). More specifically, the overestimation process disclosed herein can employ these optimal target areas to generate the bone mating surfaces 40 of the jigs 2 while causing the other surface areas of the jigs to be configured such that these other jig surface areas will not contact the surfaces of the arthroplasty target areas when the jig's bone mating surfaces 40 have matingly received and contacted the arthroplasty target areas. The result is a jig that has bone mating surfaces 40 that are based on the regions of the arthroplasty target region that are most accurately represented via 3D computer modeling and most likely to be machinable into the jig. Such a jig provides an increased accuracy of fit between the jig's mating surface 40 and the arthroplasty target areas of the patient's bone.

For most patients, it is common that the overestimation process outlined in FIG. 25 will result in certain areas of the tibial arthroplasty target region being identified as the optimal target areas discussed above with respect to FIGS. 47-51. For example, as depicted in FIG. 52A, which is proximal-sagittal isometric view of a tibial proximal end 5200, a commonly encountered, healthy, non-deformed tibial proximal end 5200 may have an arthroplasty target region 5202 with certain optimal target regions 5204, 5206 and 5208. These optimal target regions 5204, 5206 and 5208 commonly identified on most patients via the overestimation process of FIG. 25 are indicated in FIG. 52A by the cross-hatched regions. It has been found that these optimal target regions 5204, 5206 and 5208 are the regions of the arthroplasty target region 5202 that are most likely to satisfy the criterion $w_i$, $\theta_c$ and $\varphi_c$ of blocks 2508 and 2514 of FIG. 25. Therefore, these target regions 5204, 5206 and 5208 may be used to generate the jig's bone mating surfaces 40.

Figure 52A:
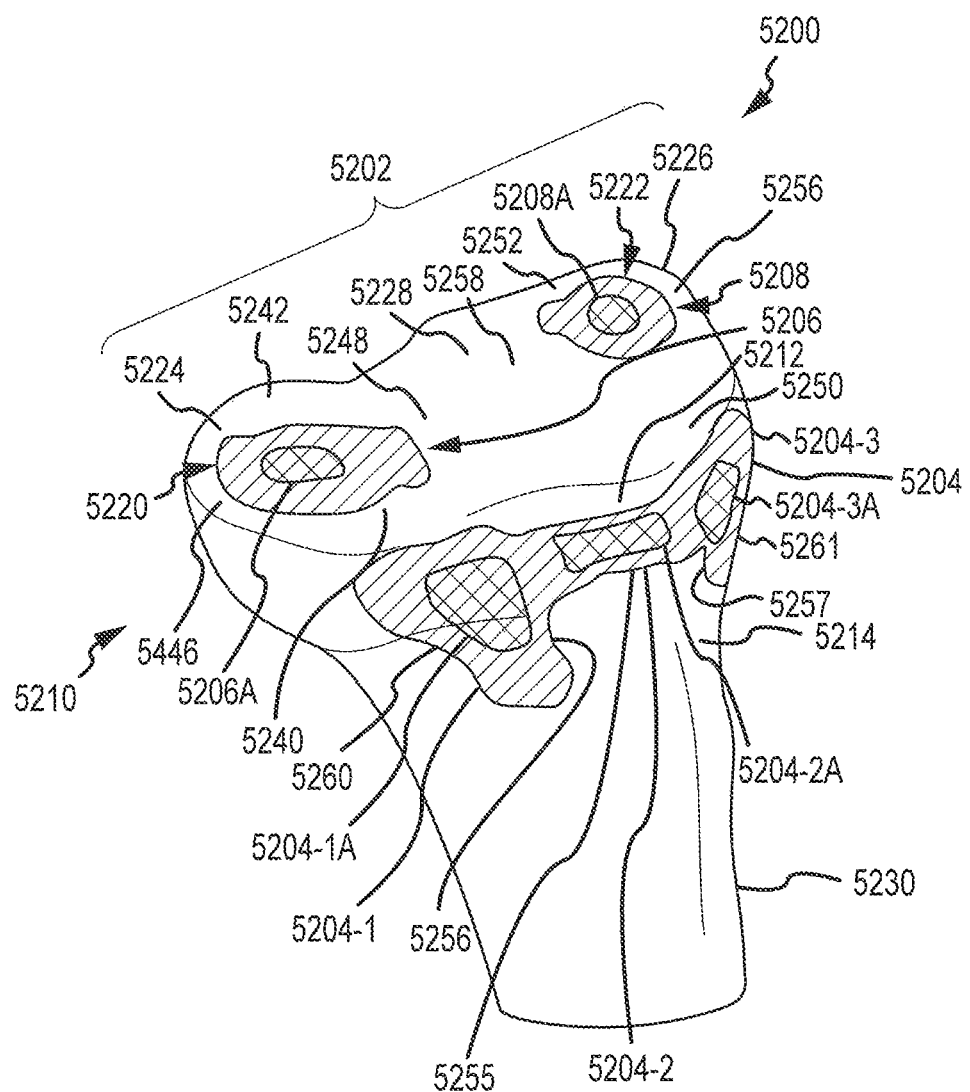
FIG. 52A is distal-sagittal isometric view of a tibial proximal end.

While, in one embodiment, the overestimation process of FIG. 25 is likely to result in optimal target regions such as those indicated via the cross-hatching regions 5204, 5206 and 5208, in other embodiments, the optimal target regions may result in target regions in other locations on the tibial proximal end 5200 that are in addition to, or in place of, those regions 5204, 5206 and 5208 depicted in FIG. 52A.

One of the benefits of the overestimation process of FIG. 25 is that it identifies two types of contour lines 210, the first type being those contour lines that are most likely to be unacceptable for the generation a jig's bone mating surfaces 40, and the second type being those contour lines that are most likely to be acceptable for the generation of a jig's bone mating surfaces 40. The first type of contour lines are unlikely to be acceptable for the generation of a jig's bone mating surfaces 40 because they pertain to bone surfaces that are too varied to be accurately 3D computer modeled and/or are such that they are not readily machinable into the jig blank. Conversely, the second type of contour lines are likely to be acceptable for the generation of a jig's bone mating surfaces 40 because they pertain to bone surfaces that vary such an insubstantial amount that they can be accurately 3D computer modeled and are such that they are readily machinable into the jig blank. While optimal target regions 5204, 5206 and 5208 represent regions likely corresponding to contour lines of the second type for most commonly encountered patients, the overestimation processes disclosed herein may be adapted to result in other or additional optimal target regions.

In some instances the entirety of the target regions 5204, 5206 and 5208 may correspond to the second type of contour lines, namely those type of contour lines that satisfy the criterion $w_i$, $\theta_c$ and $\varphi_c$ of blocks 2508 and 2514 of FIG. 25. In such instances, the entirety of the target regions 5204, 5206 and 5208 are matingly contacted by the jig's bone mating surface 40.

However, in some instances one or more portions of one or more of the target regions 5204, 5206 and 5208 may be subjected to overestimation so that the jig's bone mating surface 40 does not contact such portions of the target regions 5204, 5206 and 5208, although the jig's bone mating surface 40 still matingly contacts the other portions of the target regions 5204, 5206 and 5208 corresponding to the second type of contour lines. Such a situation may arise, for example, where a substantial surface variation (e.g., a hole, deformity or osteophyte) exists on a tibial plateau articular surface 5218, 5219 that meets the criterion $w_i$, $\theta_c$ and $\varphi_c$ of blocks 2508 and 2514 for the rest of its surface.

The overestimation process disclosed herein may result in the identification of target regions 5204, 5206 and 5208 that are most likely to result in bone mating surfaces 40 of jigs 2 that are readily machinable into the jigs 2 and most likely to facilitate reliable and accurate mating of the jigs to the arthroplasty target regions. The overestimation process results in such accurate and reliable bone mating surfaces 40 while causing other surfaces of the jigs 2 corresponding to less predictable bone surfaces to not contact the bone surfaces when the bone mating surfaces 40 matingly receive the target regions 5204, 5206 and 5208 of the actual arthroplasty target region.

As indicated in FIG. 52A by the cross-hatched regions, optimal target regions 5204, 5206 and 5208 may include three general areas of the tibial plateau 5210. For example, the anterior optimal target region 5204 may include the anterior portion of the tibial proximal end 5200 just distal of the anterior edge 5212 of the tibia plateau 5210 and just proximal of the tibial tuberosity 5214, the anterior optimal target region 5204 extending both medial and lateral of the tuberosity. Also, for example, the medial optimal target region 5206 may include the articular portion of the medial tibial plateau 5220 (i.e., the portion of the medial tibial plateau 5224 that articulates against the articulate surface of the medial femoral condyle), and the lateral optimal target region 5208 may include the articular portion of the lateral tibial plateau 5222 (i.e., the portion of the lateral tibial plateau 5226 that articulates against the articulate surface of the lateral femoral condyle).

As indicated in FIG. 52A, the tibial proximal end 5200 may include a medial tibial plateau 5224, a lateral tibial plateau 5226, a tibial spine 5228 separating the two plateaus 5224, 5226, a tibial tuberosity 5214, and a tibial shaft 5230 extending distally from the tibial plateau region 5210. Each plateau 5224 and 5226 includes an articular surface 5220 and 5222 that articulates against corresponding articular surfaces of the femoral condyles.

Figure 52B:
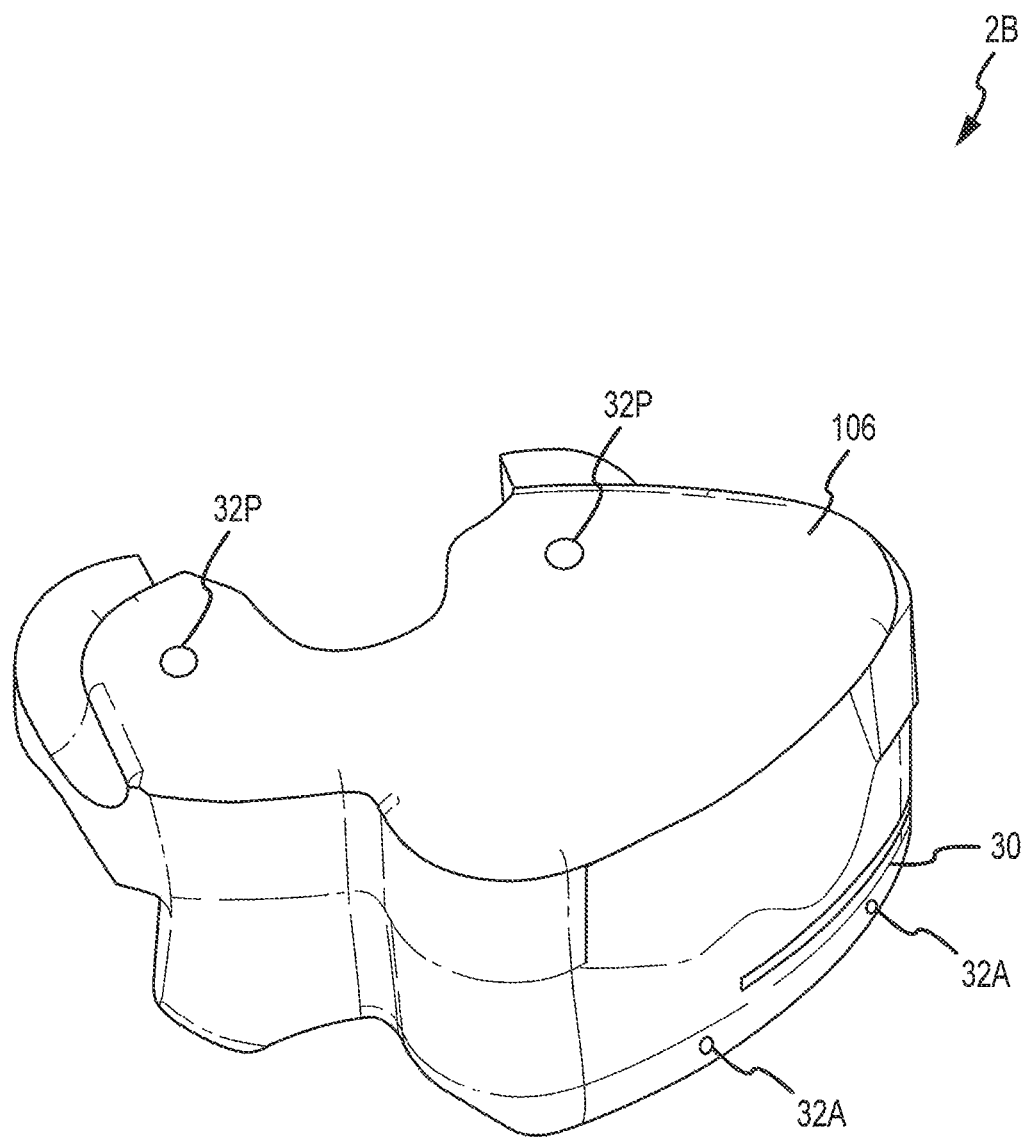
FIGS. 52B-C are, respectively, top and bottom perspective views of an example customized arthroplasty tibia jig that has been generated via the overestimation process disclosed herein.
Figure 52C:
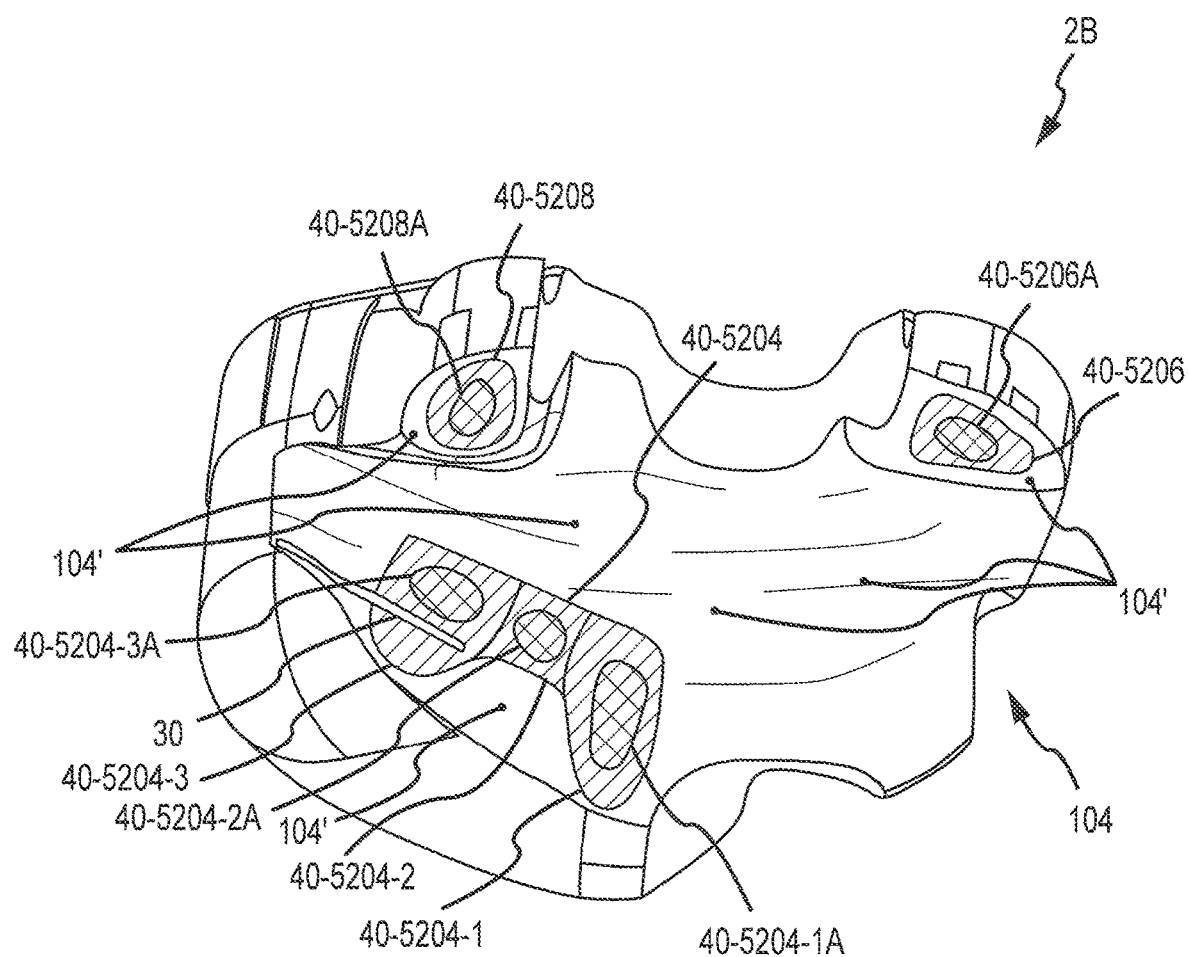
Figure 52D:
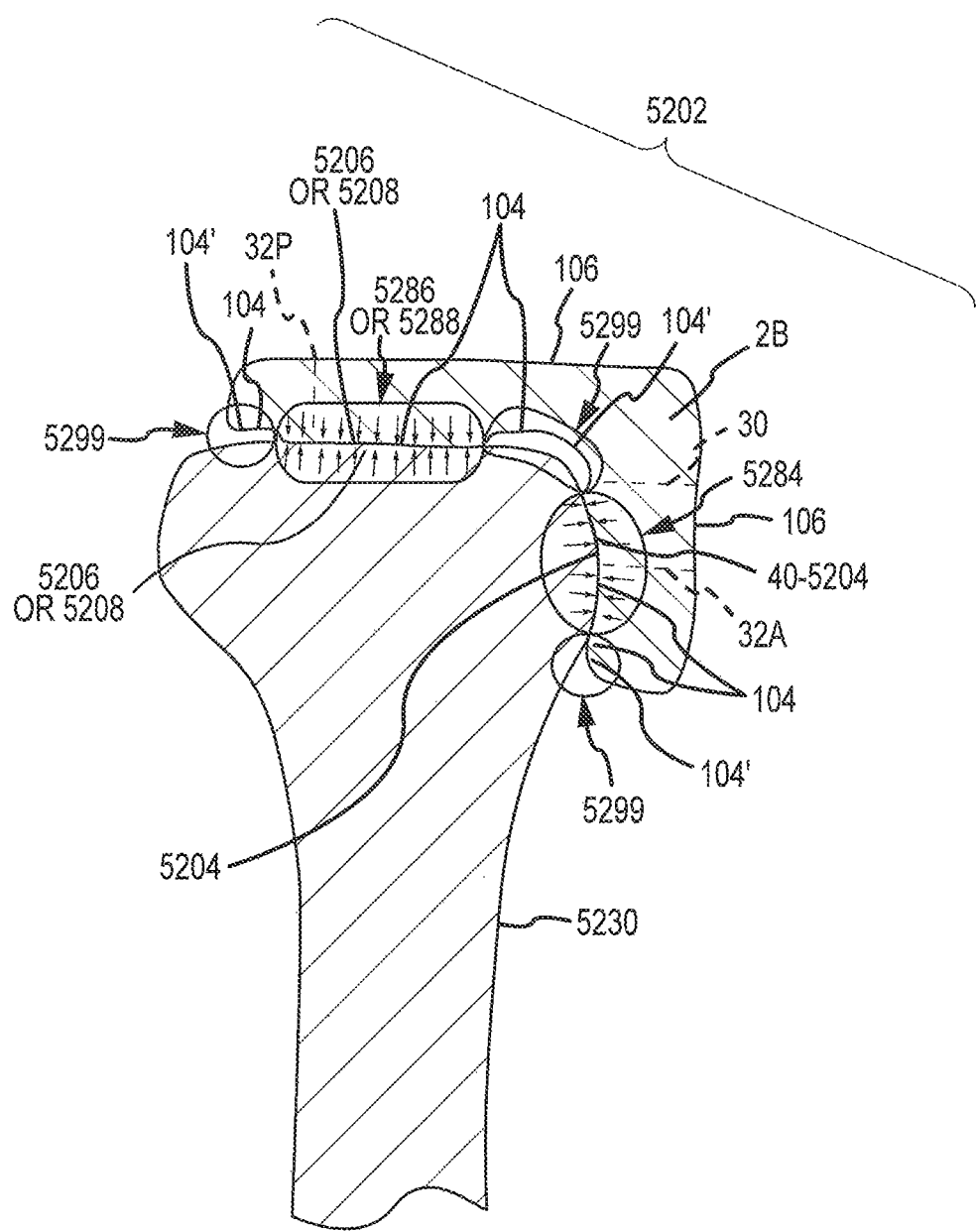
FIG. 52D is an anterior-posterior cross-section of the tibia jig of FIGS. 52B-C mounted on the tibia proximal end of FIG. 52A.
Figure 52E:
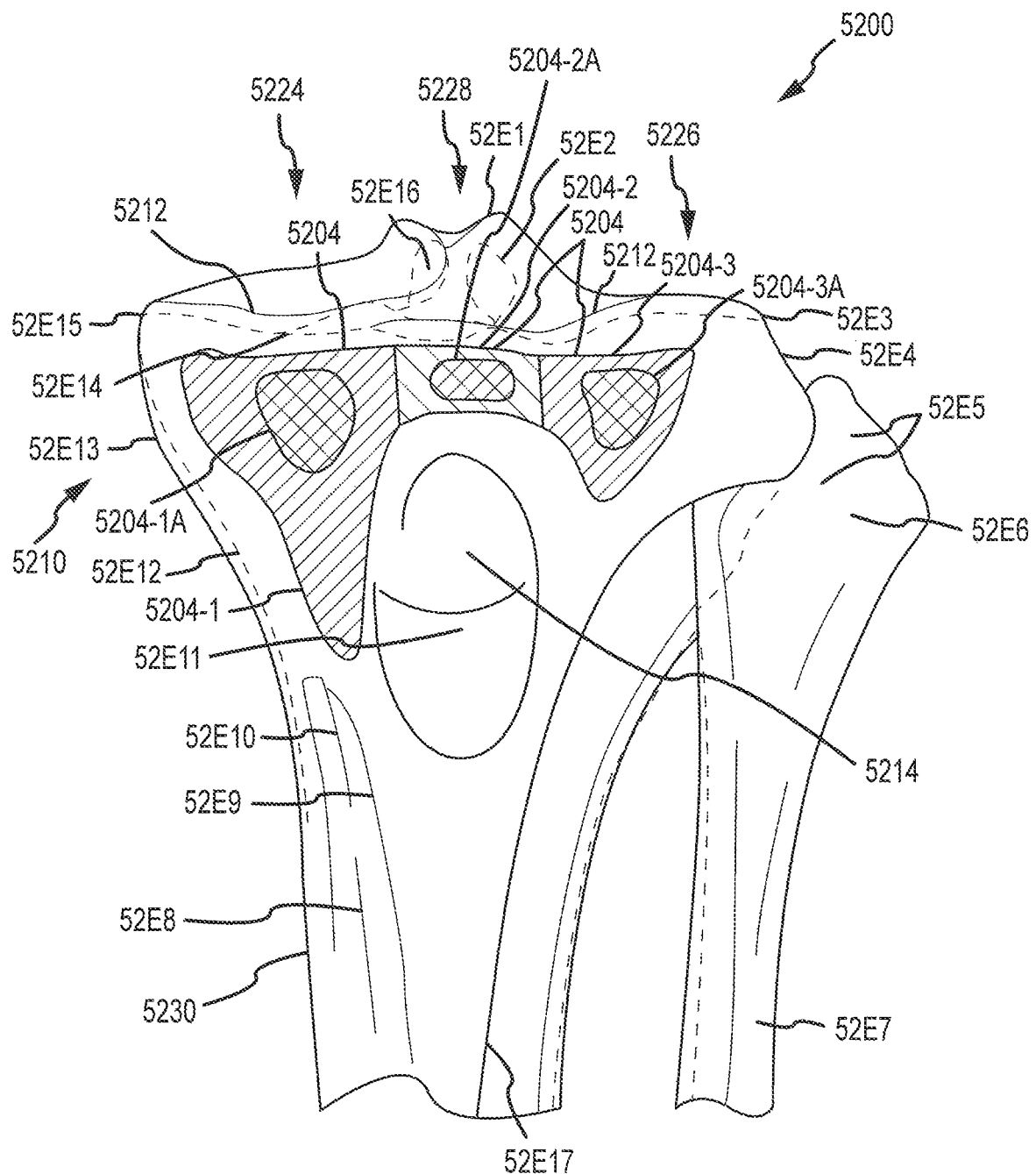
FIG. 52E is a coronal view of the anterior side of the tibial proximal end.

As indicated in FIG. 52E, which is a coronal view of the anterior side of the tibial proximal end 5200, the medial tibial plateau 5224 and lateral tibial plateau 5226 converge to form the tibial spine 5228, which separates the two plateaus 5224, 5226 and forms the intercondyloid eminence 52E1. The tibial shaft 5230 distally extends from the tibial plateau region 5210, and the tibial tuberosity 5214 is located on a proximal region of the shaft 5230. The lateral meniscus is indicated at 52E2, the capsule is indicated at the dashed line at 52E3, the lateral condyle is located at 52E4, the biceps and the anterior tibio-fibular ligament are indicated at 52E5, the fibular lateral ligament is indicated at 52E6, the lateral digitorum longus is indicated at 52E7, the lateral surface of the tibia shaft or tibialis anterior is indicated at 52E17, the semitendinosus is indicated at 52E8, the sartorius is indicated at 52E9, the graoilis is indicated at 52E10, the distal portion of the ligamentum patella is indicated at 52E11, the tibial lateral ligament is indicated at 52E12, the medial condyle is indicated at 52E13, the anterior crucial ligament is indicated at 52E14, the coronary ligament is indicated at 52E15, and the medial meniscus is indicated at 52E16.

As indicated in FIG. 52A by the cross-hatching, in one embodiment, the medial optimal target region 5206 may be generally coextensive with the medial articular surface 5220 that articulates against the respective articulate surface of the medial femoral condyle. In one embodiment, the medial optimal target region 5220 may extend: anterior-posterior between the anterior edge 5240 and posterior edge 5242 of the medial tibial plateau 5224; and lateral-medial between the medial side 5446 of the medial tibial plateau 5224 and the medial base 5248 of the medial tibial spine. In one embodiment as can be understood from FIG. 52A, the medial optimal target region 5206 may be the entire cross-hatched region 5206 or any one or more portions of the cross-hatched region 5206.

In one embodiment as indicated in FIG. 52A by the double cross-hatching, a medial target area 5206A may be identified within the medial optimal target region 5206 via the overestimation process disclosed herein. Thus, although the medial optimal target region 5206 may be generally coextensive with the medial articular surface 5220, the actual area within the medial optimal target region 5206 identified as being a reliable surface for the generation of the mating surfaces of arthroplasty jigs may be limited to a medial target area 5206A, the remainder of the medial optimal target region 5206 being subjected to the overestimation process. The medial target area 5206A may be located near a central portion of the optimal target region 5206.

As indicated in FIG. 52A by the cross-hatching, in one embodiment, the lateral optimal target region 5208 may be generally coextensive with the lateral articular surface 5222 that articulates against the respective articulate surface of the lateral femoral condyle. In one embodiment, the lateral optimal target region 5222 may extend: anterior-posterior between the anterior edge 5250 and posterior edge 5252 of the lateral tibial plateau 5226; and lateral-medial between the lateral side 5256 of the lateral tibial plateau 5226 and the lateral base 5258 of the lateral tibial spine. In one embodiment as can be understood from FIG. 52A, the lateral optimal target region 5208 may be the entire cross-hatched region 5208 or any one or more portions of the cross-hatched region 5208.

In one embodiment as indicated in FIG. 52A by the double cross-hatching, a lateral target area 5208A may be identified within the lateral optimal target region 5208 via the overestimation process disclosed herein. Thus, although the lateral optimal target region 5208 may be generally coextensive with the lateral articular surface 5222, the actual area within the lateral optimal target region 5208 identified as being a reliable surface for the generation of the mating surfaces of arthroplasty jigs may be limited to a lateral target area 5208A, the remainder of the lateral optimal target region 5208 being subjected to the overestimation process. The lateral target area 5208A may be located near a central portion of the optimal target region 5208.

As indicated in FIG. 52A by the cross-hatching, in one embodiment, the anterior optimal target region 5204 may be an anterior surface of the tibia plateau region 5202 distal of the joint line or, more specifically, distal of the anterior tibia plateau edge 5212. The anterior optimal target region 5204 may be the anterior region of the proximal end of the tibia extending between the plateau edge 5212 and the proximal edge 5255 of the tibia tuberosity 5214. The anterior target region 5204 may extend distally along the tibia adjacent to the medial and lateral edges 5256, 5257 of the tibia tuberosity 5214. The anterior target region 5204 may extend medially to the anterior medial edge 5260 of the tibia, and laterally to the anterior lateral edge 5261 of the tibia.

As shown in FIG. 52E by the cross-hatching, the anterior optimal target region 5204 may be divided into three sub-regions 5204-1, 5204-2 and 5204-3. The first or medial sub-region 5204-1 may be a generally planar surface region that extends distally from generally the plateau edge 5212 or capsule line 52E3 to a point generally even with the beginning of the distal half to distal third of the tibial tuberosity 5214. The medial sub-region 5204-1 may extend medial-lateral from the medial edge of the medial tibia condyle to a point generally even with a medial edge of the tibial tuberosity 5214. The medial sub-region 5204-1 may generally taper is the distal direction to be generally triangular.

The second or middle sub-region 5204-2 may be a generally planar surface region that extends distally from generally the plateau edge 5212 or capsule line 52E3 to a point near the proximal boundary of the tibial tuberosity 5214. The middle sub-region 5204-2 may extend medial-lateral from the lateral edge of the medial sub-region 5204-1 to a point generally even with a lateral edge of the tibial tuberosity 5214. The first sub-region 5204-1 may be generally rectangular, with the long length extending medial-lateral.

The third or lateral sub-region 5204-3 may be a generally planar surface region that extends distally from generally the plateau edge 5212 or capsule line 52E3 to a point generally even with the beginning of the distal two-thirds to distal three-quarters of the tibial tuberosity 5214. The lateral sub-region 5204-3 may extend medial-lateral from the lateral edge of the middle sub-region 5204-2 to a lateral edge of the lateral tibia condyle. The lateral sub-region 5204-3 may generally taper is the distal direction to be generally triangular.

In one embodiment as can be understood from FIGS. 52A and 52E, the anterior target region 5204 may be the entire cross-hatched region 5204 or any one or more sub-regions 5204-1, 5204-2, 5204-3 of the cross-hatched region 5204 or any one or more portions of the sub-regions 5204-1, 5204-2, 5204-3. For example, as indicated by the double cross-hatching, each sub-region 5204-1, 5204-2 and 5204-3 may have a respective target area 5204-1A, 5204-2A and 5204-3A therein that may be identified via the overestimation process disclosed herein. Thus, although the anterior optimal target region 5204, or more specifically, its sub-regions 5204-1, 5204-2, 5204-3 may be generally coextensive with the three generally planar surface areas identified above with respect to FIG. 52E, the actual areas within the anterior optimal target region 5204 identified as being a reliable surface for the generation of the mating surfaces of arthroplasty jigs may be limited to an target areas 5204-1A, 5204-2A and 5204-3A, the remainder of the sub-regions 5204-1, 5204-2, 5204-3 being subjected to the overestimation process. The anterior target areas 5204-1A, 5204-2A and 5204-3A may be located any where within the respective sub-regions 5204-1, 5204-2, 5204-3.

FIGS. 52B-C and are, respectively, top and bottom perspective views of an example customized arthroplasty tibial jig 2B that has been generated via the overestimation process disclosed herein. Similar to the femoral jig 2A depicted in FIGS. 1H and 1I, the tibia jig 2B of FIGS. 52B-C includes an interior or bone-facing side 104 and an exterior side 106. When the jig 2B is mounted on the arthroplasty target region during a surgical procedure, the bone-facing side 104 faces the surface of the arthroplasty target region while the exterior side 106 faces in the opposite direction.

The interior or bone-facing side 104 of the tibia cutting jig 2B includes bone mating surfaces 40-5204, 40-5206 and 40-5208 that: are machined into the jig interior or bone-facing side 104 based on contour lines that met the criterion of blocks 2508 and 2514 of FIG. 25; and respectively correspond to the optimal target regions 5204, 5206 and 5208 of FIG. 52A. The rest 104' of the interior or bone-facing side 104 (i.e., the regions 104' of the interior or bone facing sides 104 outside the bounds of bone mating surfaces 40-5204, 40-5206 and 40-5208) are the result of the overestimation process wherein the corresponding contour lines failed to meet one or more of the criterion of blocks 2508 and 2514 of FIG. 25 and, consequently, were moved away from the bone surface. As a result, the interior side surface 104' is machined to be spaced away from the bone surfaces of the arthroplasty target region so as to not contact the bone surfaces when the bone mating surfaces 40-5204, 40-5206 and 40-5208 matingly receive and contact the bone surfaces of the arthroplasty target region corresponding to regions 5204, 5206 and 5208.

As can be understood from FIG. 52C, the medial bone mating surface 40-5206 may include a smaller sub region bone mating surface 40-5206A, with the area of the medial bone mating surface 40-5206 outside the smaller sub region mating surface 40-5206A being the result of the overestimation process so as to not contact the corresponding bone surface when the smaller sub region mating surface 40-5206A matingly receives and contacts its corresponding bone surface. The smaller sub region bone mating surface 40-5206A may be configured and positioned in the jig inner surface 100 to matingly receive and contact the optimal target area 5206A discussed above with respect to FIGS. 52A and 52E.

As can be understood from FIG. 52C, the lateral bone mating surface 40-5208 may include a smaller sub region bone mating surface 40-5208A, with the area of the lateral bone mating surface 40-5208 outside the smaller sub region mating surface 40-5208A being the result of the overestimation process so as to not contact the corresponding bone surface when the smaller sub region mating surface 40-5208A matingly receives and contacts its corresponding bone surface. The smaller sub region bone mating surface 40-5208A may be configured and positioned in the jig inner surface 100 to matingly receive and contact the optimal target area 5208A discussed above with respect to FIGS. 52A and 52E.

As can be understood from FIG. 52C, depending on the patient's bone topography, the overestimation process disclosed herein may result in an anterior bone mating surface 40-5204 that is actually multiple bone mating surfaces have sub region mating surfaces that may be substantially smaller than surface 5204 depicted in FIGS. 52A and 52E. For example, the anterior bone mating surface 40-5204 may actually be made of an anterior medial bone mating surface 40-5204-1, an anterior middle bone mating surface 40-5204-2 and an anterior lateral bone mating surface 40-5204-3. These mating surfaces 40-5204-1, 40-5204-2, 40-5204-3 may have respective sub region bone mating surfaces 40-5204-1A, 40-5204-2A, 40-5204-3A, with the areas of the mating surfaces 40-5204-1, 40-5204-2, 40-5204-3 outside the respective sub region bone mating surfaces 40-5204-1A, 40-5204-2A, 40-5204-3A being the result of the overestimation process so as to not contact the corresponding bone surfaces when the respective sub region bone mating surfaces 40-5204-1A, 40-5204-2A, 40-5204-3A matingly receive and contact their respective corresponding bone surfaces. The sub region bone mating surfaces 40-5204-1A, 40-5204-2A, 40-5204-3A may be configured and positioned in the jig inner surface 100 to matingly receive and contact the respective optimal target areas 5204-1A, 5204-2A, 5204-3A discussed above with respect to FIGS. 52A and 52E.

As can be understood from FIG. 52D, which is a anterior-posterior cross-section of the tibia jig 2B of FIGS. 52B-C mounted on the tibial proximal end 5200 of FIG. 52A, the interior or bone-facing side 104 is formed of bone mating surfaces 40-5204, 40-5206 and 40-5208 and spaced-apart surfaces 104' (i.e., bone-facing surfaces 104 that are a product of the overestimation process and are spaced-apart from the corresponding bone surfaces of the arthroplasty target region 5202). As indicated by the plurality of opposed arrows in regions 5284, 5286 and 5288, the bone mating surfaces 40-5204, 40-5206 and 40-5208 matingly receive and contact the corresponding bone surfaces 5204, 5206 and 5208 to form mating surface contact regions 5284, 5286 and 5288. Conversely, the spaced-apart surfaces 104' are spaced apart from the corresponding bone surfaces to form spaced-apart non-contact regions 5299, wherein the spaced-apart surfaces 104' do not contact their corresponding bone surfaces. In addition to having the mating surfaces 40-5204, 40-5206 and 40-5208 and the spaced-apart surfaces 104', the tibia jigs 2B may also have a saw cutting guide slot 30 and anterior and posterior drill holes 32A and 32P, as discussed above.

The arrows in FIG. 52D represent a situation where the patient's bone topography and the resulting overestimation process has generated bone mating surfaces 40-5204, 40-5206 and 40-5208 that match the target regions 5204, 5206 and 5208, which are generally coextensive with the entirety of their respective potential regions as discussed above. Of course, where the patient's bone topography and the resulting overestimation process generates bone mating surfaces 40-5204-1A, 40-5204-2A, 40-5204-3A, 40-5206A and 40-5208A that match the target areas 5204-1A, 5204-2A, 5204-3A, 5206A and 5208A, which may be substantially smaller than their respective target regions 5204-1, 5204-2, 5204-3, 5206 and 5208, the mating surface contact regions 5284, 5286 and 5288 may be smaller and/or segmented as compared to what is depicted in FIG. 52D.

Figure 53:
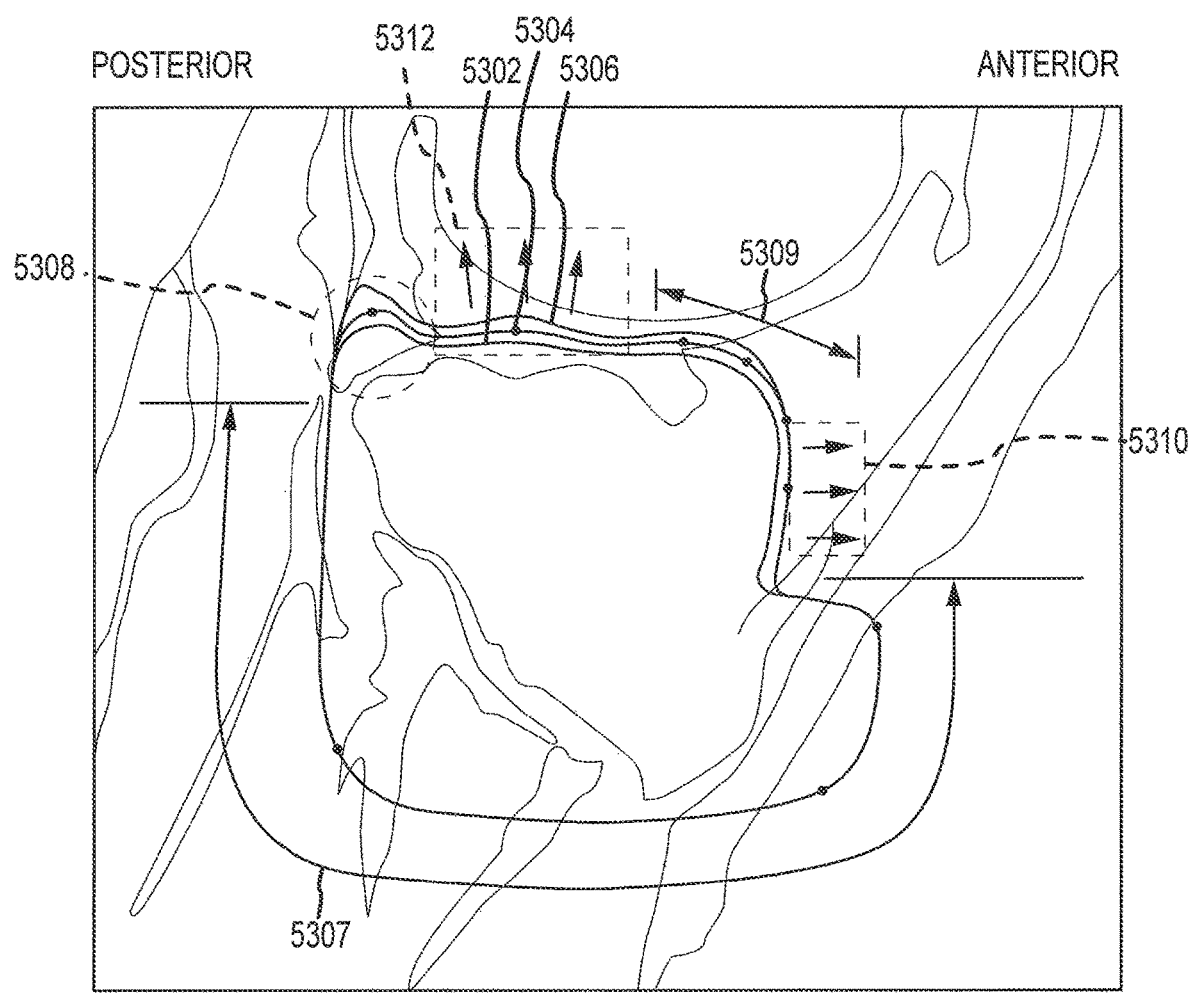
FIG. 53 depicts closed-loop contour lines that are image segmented from image slices, wherein the contour lines outline the cortical bone surface of the upper end of the tibia.

FIG. 53 depicts closed-loop contour lines 5302, 5304, and 5306 that are image segmented from image slices, wherein the contour lines outline the cortical bone surface of the upper end of the tibia. These contour lines 5302, 5304, and 5306 may be identified via image segmentation techniques from medical imaging slices generated via, e.g., MRI or CT.

As shown in FIG. 53, there are posterior portions of the contour lines (indicated as 5307) that may be of no interest during overestimation because the contour line region 5307 corresponds to a region of the knee that may be inaccessible during surgery and may not correspond to a jig surface because no part of the jig may access the region 5307 during surgery. There are also portions of the contour lines (indicated as 5309) which may correspond generally to the plateau edge 5212 and may not correspond to a jig surface because no part of the jig may abut against or matingly engage this contour line region 5309. An osteophyte in contour line region 5308 may be identified based on the algorithm 2500. The contour lines in region 5308 may be subsequently overestimated (based on the algorithm 2500) such that the resulting jig surface does not come into contact with the osteophyte (i.e., with the osteophyte bone surface represented by contour line region 5308) when the jig's bone mating surface 40 matingly receives and contacts the bone surfaces of the arthroplasty target region. Additionally, optimal contour line regions 5310 and 5312 may be identified during execution of the algorithm 2500 as areas of the patient's bone anatomy that have surface variations within the angular criteria of the algorithm 2500 and, therefore, are used to generate the jig's bone mating surface 40 that matingly receives and contacts the bone surfaces of the arthroplasty target region.

Contour line region 5310 may pertain to region 5204 of FIG. 52A and tibia jig region 40-5204 of FIG. 52B. Contour line region 5312 may pertain to either region 5206 or 5208 of FIG. 52A and either tibia jig region 40-5206 or 40-5208 of FIG. 52C.

Utilizing the optimal areas 4310 and 4312 as jig bone mating surfaces 40 allows irregular areas of the patient's bone anatomy to be accommodated without affecting the fit of the jig 2 to the patient's bone anatomy. In fact, an accurate and custom fit between the jig 2 and the patient's bone anatomy can be made by using only a few of such optimal areas. This allows substantial overestimation of the jig surface in regions corresponding to irregularities, thereby preventing the irregularities from interfering with an accurate and reliable fit between the jig's bone mating surfaces and those bone surfaces of the arthroplasty target region corresponding to those bone mating surfaces. The result of the overestimation process is a jig with bone mating surfaces that offer a reliable and accurate custom fit with the arthroplasty target region. This may result in an increased success rate for TKR or partial knee replacement surgery because the jig may custom fit to the most reliable bone surfaces and be deliberately spaced from the bone surfaces that may be unreliable, for example, because of imaging or tool machinery limitations.

Figure 54:
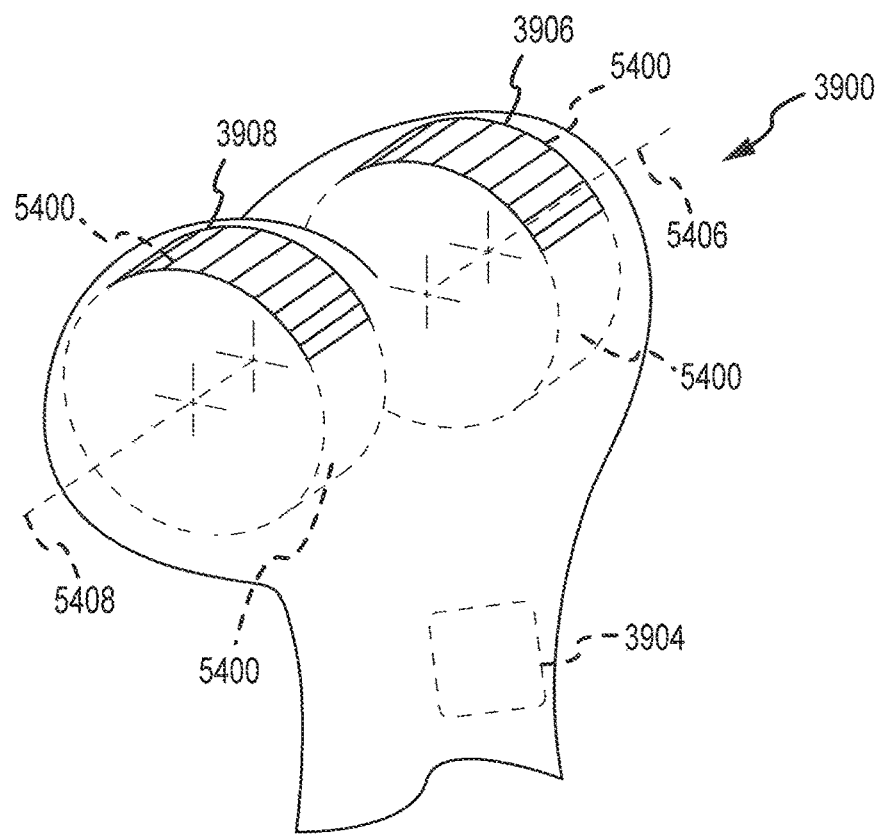
FIG. 54 is an anterior isometric view of the femur distal end.
Figure 55:
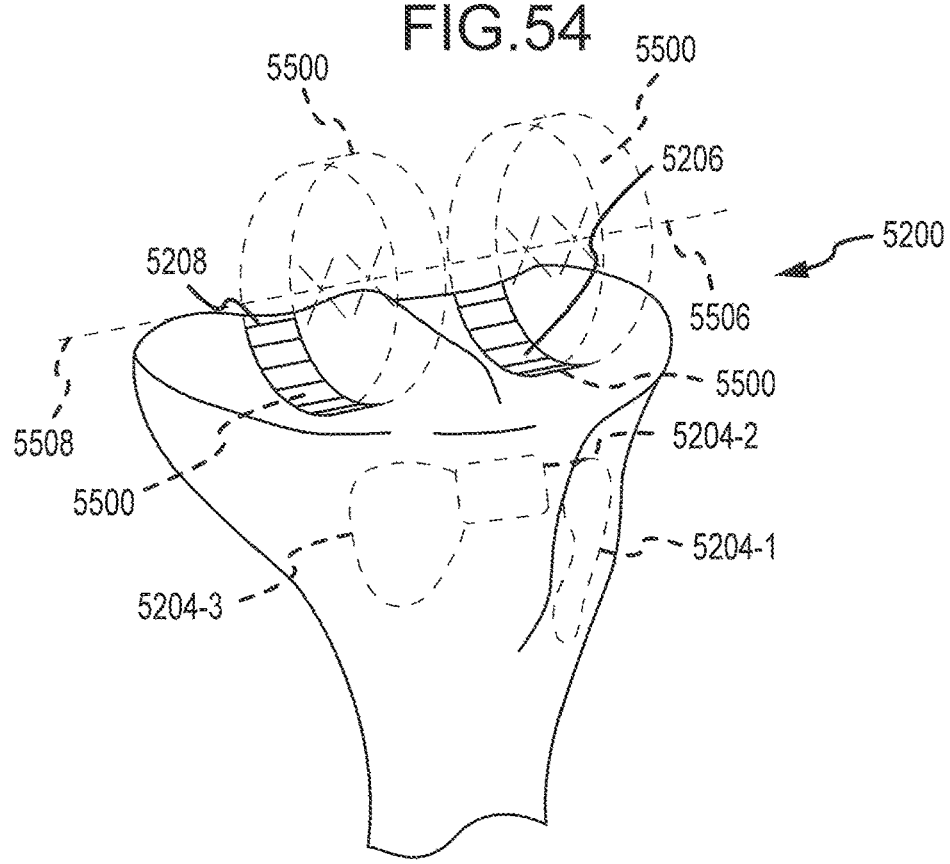
FIG. 55 is an anterior isometric view of the tibia proximal end.

As can be understood from FIGS. 54 and 55, which are respectively anterior isometric views of the femur 3900 and tibia 5200, a patient's bones 3900, 5200 may have regions that are more likely to be accurately computer modeled from two dimensional medical image slices than other regions of the patient's bones. Examples of such regions 3904, 3906, 3908, 5204-1, 5204-2, 5204-3, 5206, and 5208 and how to determine such regions are provided in the preceding discussion and also indicated in FIGS. 54 and 55.

With respect to the articular regions 3906, 3908, 5206 and 5208 of the femur 3900 and tibia 5200, in one embodiment, where the analysis of blocks 2508 and 2514 of FIG. 25 indicate that there is little, if any contour line variation along a specific contour line or between adjacent contour lines, these regions 3906, 3908, 5206 and 5208 of the femur 3900 and tibia 5200 may be understood to most closely approximate circumferential surfaces 5400, 5500 of cylinders 5402, 5504 each having an axis 5406, 5408, 5506, 5508 extending medial-lateral and having their respective circumferential surfaces 5400, 5500 superimposed onto the articular regions 3906, 3908, 5206, 5208. Accordingly, such regions 3906, 3908, 5206, 5208 may be likely to be readily accurately computer modeled.

In one embodiment, the circumferential surfaces 5400, 5500 may be correspond to an elliptical cylinder having an elliptical cross section transverse to its axis 5406, 5408, 5506, 5508 and having its elliptical major axis extending generally anterior-posterior and is elliptical minor axis extending generally proximal-distal. In one embodiment, the circumferential surfaces 5400, 5500 may be correspond to an circular cylinder having an circular cross section transverse to its axis 5406, 5408, 5506, 5508.

It should be noted that the overestimation process discussed above with respect to FIGS. 22A-55 is useful for the generation of customized arthroplasty jigs, regardless of whether the arthroplasty jigs are configured to produce natural alignment or zero degree or mechanical axis alignment for the patient's knee undergoing the arthroplasty procedure. Also, the overestimation process discussed above may be employed for both the generation of jigs for total knee arthroplasty and partial or uni-compartmental knee arthroplasty. Furthermore, while the overestimation process is discussed in the context of knee arthroplasty, those skilled in the art will readily recognize that the concepts taught herein may be employed for the production of jigs for other types of joint arthroplasty, including, for example, arthroplasty for hip, ankle, elbow, shoulder, wrist, toe joint, finger joint, vertebra-vertebra interfaces, vertebra-pelvis interfaces, vertebra-skull interfaces, etc. Accordingly, the overestimation processes and resulting jigs disclosed herein should be considered as being for all types of arthroplasty procedures.

Although the present invention has been described with reference to preferred embodiments, persons skilled in the art will recognize that changes may be made in form and detail without departing from the spirit and scope of the invention.

What is claimed is:

1. A method of generating manufacturing instructions for the manufacture of a patient-specific surgical guide having a mating surface and a saw slot for treating an anatomical structure of a patient, the method comprising:
   receiving medical images of the anatomical structure of the patient;
   identifying, within the medical images, target areas including a portion of an external surface of the anatomical structure intended to match the mating surface of the patient-specific surgical guide;
   segmenting the medical images only in the target areas;
   generating a three-dimensional model of the target area from the segmented medical images;
   defining a position of a resection relative to the three-dimensional model of the target area; and
   generating manufacturing instructions for the manufacture of the patient-specific surgical guide including the mating surface and the saw slot.

2. The method of claim 1, further comprising manufacturing the patient-specific surgical guide using the manufacturing instructions.

3. The method of claim 2, wherein the patient-specific surgical guide is manufactured by a computer numeric control (CNC) machine.

4. The method of claim 1, wherein the saw slot is configured to facilitate a bone cut on the anatomical structure of the patient in a position that matches the position of the resection relative to the three-dimensional model of the target area.

5. The method of claim 1, wherein the identifying, within the medical images, target areas is carried out automatically.

6. The method of claim 1, wherein the patient-specific surgical guide is manufactured by a rapid production machine utilizing an additive manufacturing process.

7. The method of claim 1, wherein the target area is an articulating contact surface of the anatomical structure of the patient.

8. The method of claim 7, wherein the articulating contact surface comprises a femoral condyle surface.

9. The method of claim 7, wherein the articulating contact surface comprises a tibial plateau surface.

10. The method of claim 1, wherein segmenting the medical images only in the target areas is via an open-loop process that does not outline an entirety of a bone of the anatomical structure of the patient.

11. The method of claim 1, wherein the three-dimensional model comprises at least two separate regions intended to match the mating surface of the patient-specific surgical guide, the at least two separate regions being non-joined with each other.

12. The method of claim 1, further comprising:
    defining a plurality of surface coordinate points on at least one of the segmented medical images;
    identifying particular coordinate points of the plurality of surface coordinate points that impact the ability to generate a reliable mating surface; and
    adjusting a position of the particular coordinate points of the plurality of surface coordinate points such that the particular coordinate points are excluded from being part of the external surface of the anatomical structure intended to match the mating surface of the patient-specific surgical guide.

13. The method of claim 12, wherein the particular coordinate points of the plurality of surface coordinate points impact the ability to generate the reliable mating surface based on a mathematical relationship between adjacent points in the plurality of surface coordinate points.

14. The method of claim 12, wherein the mathematical relationship is an angular relationship.

15. The method of claim 1, wherein the medical images comprise two-dimensional medical images.

16. The method of claim 1, wherein the medical images comprises computed tomography images.

17. The method of claim 1, wherein the medical images comprises magnetic resonance images.

18. A method of generating manufacturing instructions for the manufacture of a patient-specific surgical guide having a mating surface and a saw slot for treating an anatomical structure of a patient, the method comprising:
    receiving medical images of the anatomical structure of the patient;
    identifying, within the medical images, target areas including a portion of an external surface of the anatomical structure intended to match the mating surface of the patient-specific surgical guide;
    segmenting the medical images in the target areas;
    identifying regions within the segmented medical images that impact the generation of the mating surface in a reliable fashion;
    altering the segmented medical images in the identified regions so as to be non-anatomical;
    generating a three-dimensional model of the target area from the altered segmented medical images;
    defining a position of a resection relative to the three-dimensional model of the target area; and
    generating manufacturing instructions for the manufacture of the patient-specific surgical guide including the mating surface and the saw slot.

19. The method of claim 18, further comprising manufacturing the patient-specific surgical guide using the manufacturing instructions.

20. The method of claim 19, wherein the patient-specific surgical guide is manufactured by a computer numeric control (CNC) machine.

21. The method of claim 18, wherein the saw slot is configured to facilitate a bone cut on the anatomical structure of the patient in a position that matches the position of the resection relative to the three-dimensional model of the target area.

22. The method of claim 18, wherein the identifying, within the medical images, target areas is carried out automatically.

23. The method of claim 18, wherein the patient-specific surgical guide is manufactured by a rapid production machine utilizing an additive manufacturing process.

24. The method of claim 18, wherein the target area is an articulating contact surface of the anatomical structure of the patient.

25. The method of claim 24, wherein the articulating contact surface comprises a femoral condyle surface.

26. The method of claim 24, wherein the articulating contact surface comprises a tibial plateau surface.

27. The method of claim 18, wherein the medical images are segmented only in the target areas.

28. The method of claim 18, wherein identifying regions within the segmented medical images comprise:
    defining a plurality of surface coordinate points on at least one of the segmented medical images; and
    identifying particular coordinate points of the plurality of surface coordinate points that impact the ability to generate a reliable mating surface.

29. The method of claim 28, wherein altering the segmented medical images in the identified regions so as to be non-anatomical comprises:
    adjusting a position of the particular coordinate points of the plurality of surface coordinate points such that the particular coordinate points are excluded from being part of the external surface of the anatomical structure intended to match the mating surface of the patient-specific surgical guide.

30. The method of claim 18, wherein the medical images comprise two-dimensional medical images.

* * * * *